US012655190B2

(12) United States Patent (10) Patent No.: US 12,655,190 B2
Delaney et al. (45) Date of Patent: Jun. 16, 2026

(54) NK CELL COMPOSITIONS AND PREPARATIONS FOR IMMUNOTHERAPY AND METHODS FOR THEIR PRODUCTION

(71) Applicant: Deverra Therapeutics Inc., Seattle, WA (US)

(72) Inventors: Colleen Delaney, Seattle, WA (US); Carrie Stoltzman, Seattle, WA (US); Elizabeth Dam, Seattle, WA (US); Mary Prieve, Seattle, WA (US)

(73) Assignee: Deverra Therapeutics Inc., Seattle, WA (US)

( * ) Notice: Subject to any disclaimer, the term of this patent is extended or adjusted under 35 U.S.C. 154(b) by 972 days.

(21) Appl. No.: 17/631,035

(22) PCT Filed: Jul. 29, 2020

(86) PCT No.: PCT/US2020/044117
§ 371 (c)(1),
(2) Date: Jan. 28, 2022

(87) PCT Pub. No.: WO2021/021963
PCT Pub. Date: Feb. 4, 2021

(65) Prior Publication Data
US 2022/0275334 A1 Sep. 1, 2022

Related U.S. Application Data

(60) Provisional application No. 62/960,507, filed on Jan. 13, 2020, provisional application No. 62/892,779, filed on Aug. 28, 2019, provisional application No. 62/880,044, filed on Jul. 29, 2019.

(51) Int. Cl.
| | |
|---|---|
| *A61K 40/15* | (2025.01) |
| *A61K 40/31* | (2025.01) |
| *A61K 40/42* | (2025.01) |
| *C07K 14/705* | (2006.01) |
| *C07K 16/28* | (2006.01) |
| *C12N 5/0783* | (2010.01) |

(52) U.S. Cl.
CPC .......... *C07K 14/7051* (2013.01); *A61K 40/15* (2025.01); *A61K 40/31* (2025.01); *A61K 40/4211* (2025.01); *A61K 40/4255* (2025.01); *C07K 14/70521* (2013.01); *C07K 14/70578* (2013.01); *C07K 16/2803* (2013.01); *C12N 5/0646* (2013.01); *A61K 2239/31* (2023.05); *A61K 2239/38* (2023.05); *A61K 2239/47* (2023.05); *A61K 2239/48* (2023.05); *C07K 2317/53* (2013.01); *C07K 2317/622* (2013.01); *C12N 2501/145* (2013.01); *C12N 2501/2302* (2013.01); *C12N 2501/2303* (2013.01); *C12N 2501/2306* (2013.01); *C12N 2501/2315* (2013.01); *C12N 2501/26* (2013.01); *C12N 2501/42* (2013.01); *C12N 2506/03* (2013.01)

(58) Field of Classification Search
None
See application file for complete search history.

(56) References Cited

U.S. PATENT DOCUMENTS

| | | | | |
|---|---|---|---|---|
| 2018/0085406 A1* | 3/2018 | Bernstein | ............... | G16H 20/40 |
| 2018/0346877 A1* | 12/2018 | Zhang | ...................... | A61P 1/04 |

OTHER PUBLICATIONS

Della Chiesa, Mariella, et al. Blood, The Journal of the American Society of Hematology 119.2 (2012): 399-410. (Year: 2012).*

Hermanson, David L., and Dan S. Kaufman. Frontiers in immunology 6 (2015): 195. (Year: 2015).*

Beck, R.C., et al., "The Notch Ligands Jagged2, Delta1, and Delta4 Induce Differentiation and Expansion of Functional Human NK Cells from CD34+ Cord Blood Hematopoietic Progenitor Cells," Biology of Blood and Marrow Transplantation: Journal of the American Society for Blood and Marrow Transplantation 15(9):1026-1037, Sep. 2009.

Shi, P.A., et al., "Umbilical Cord Blood: An Undervalued and Underutilized Resource in Allogeneic Hematopoietic Stem Cell Transplant and Novel Cell Therapy Applications," Current Opinion in Hematology 29(6):317-326, Nov. 2022.

Spanholtz, J., et al., "Clinical-Grade Generation of Active NK Cells From Cord Blood Hematopoietic Progenitor Cells for Immunotherapy Using a Closed-System Culture Process," 6(6):e20740, Jun. 2011.

Spanholtz, J., et al., "High Log-Scale Expansion of Functional Human Natural Killer Cells From Umbilical Cord Blood CD34-Positive Cells for Adoptive Cancer Immunotherapy," PLoS One (Public Library of Science) 5(2):e9221, Feb. 2010.

Extended European Search Report and Supplemental Search Report mailed Feb. 20, 2024, issued in EP Application No. 20848443.6, filed Jul. 29, 2020, 5 pages.

International Search Report and Written Opinion mailed Nov. 9, 2020, issued in International Patent Application No. PCT/US2020/044117, filed Jul. 29, 2020, 11 pages.

International Preliminary Report on Patentability mailed Feb. 1, 2022, issued in International Patent Application No. PCT/US2020/044117, filed Jul. 29, 2020, 7 pages.

Tang, S.Y., "IPSC-Derived Immune Cells for Cancer Immunology," PhD Thesis, National University of Singapore, May 2018, 242 pages.

(Continued)

*Primary Examiner* — Maria G Leavitt
*Assistant Examiner* — Brendan Thomas Tinsley
(74) *Attorney, Agent, or Firm* — Christensen O'Connor Johnson Kindness PLLC

(57) ABSTRACT

The present invention provides NK cell compositions and/or preparations and methods of using such NK cell compositions and/or preparations for immunotherapy. The NK cell compositions and/or preparations can be used in therapies of a broad range of viral infections, bacterial infections, cancer and leukemia malignancies, and other diseases.

14 Claims, 24 Drawing Sheets
Specification includes a Sequence Listing.

(56)                          References Cited

OTHER PUBLICATIONS

Zeng, J., et al., "Generation of "Off-the-Shelf" Natural Killer Cells
From Peripheral Blood Cell-Derived Induce Pluripotent Stem Cells,"
Stem Cell Reports 9(6):1796-1812, Dec. 2017.
Examination Report mailed Aug. 21, 2025, issued in related EP
Application No. 20848443.6, filed Jul. 29, 2020, 5 pages.

* cited by examiner

% NK Cells Generated in 20 Separate Batches

4 hr cytotoxicity assay

24 hr cytotoxicity assay

NK CELL COMPOSITIONS AND PREPARATIONS FOR IMMUNOTHERAPY AND METHODS FOR THEIR PRODUCTION

CROSS-REFERENCES TO RELATED APPLICATIONS

This application is a National Stage of International Application No. PCT/US2020/044117, filed Jul. 29, 2020, which claims the benefit of U.S. Provisional Application No. 62/880,044, filed Jul. 29, 2019, U.S. Provisional Application No. 62/892,779, filed Aug. 28, 2019, and U.S. Provisional Application No. 62/960,507, filed Jan. 13, 2020, the disclosures of which are incorporated herein by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is 72246_Sequence_Final_2020-07-28.txt. The text file is 144 KB; was created on Jul. 28, 2020; and is being submitted via EFS-Web with the filing of the specification.

FIELD OF THE INVENTION

The present disclosure provides natural killer (NK) cell compositions and/or preparations, and methods of making and using such NK cell compositions and/or preparations for non-autologous immunotherapy. The NK cell compositions and/or preparations can be used in therapies for a broad range of viral and bacterial infections, cancer, including solid tumors and hematologic malignancies (leukemia, lymphoma), and other diseases.

BACKGROUND OF THE INVENTION

Natural Killer (NK) cells are components of the innate immune system that exhibit a variety of cytotoxic activities against transformed target cells, such as production of certain cytokines, direct cytotoxicity, and mediation of antibody-dependent cell-mediated cytotoxicity (ADCC). NK cells play a key role in host defense against essentially any virus infected or cancer transformed cells and the clearance of these cells. In addition, NK cells have been proposed as effectors for immunotherapy of various conditions including, for example, clearing transformed cancer cells. Various methods have been described for producing NK cells, such as generation from induced pluripotent stem cells, peripheral blood mononuclear cells, peripheral blood stem or progenitor cells, or umbilical cord blood stem or progenitor cells. For each source, the properties of the NK cells depend on their method of generation. Such methods have traditionally relied on many rounds of ex vivo cell division to produce adequate numbers of NK cells for therapeutic purposes. NK cells resulting from such processes tend to be more mature and/or are more likely to exhibit exhaustion following administration to a patient. NK cell exhaustion can be exhibited by reduced production of, for example, interferon gamma (IFNγ), CD107a, granzyme B and/or perforin, decreased cytolytic activity, and the like. Such NK cells are likely to be less active or persistent when administered in vivo. Therefore, there remains a need for NK cell populations and compositions comprising said NK cell populations for therapeutic purposes which exhibit and retain higher levels of activity and/or persistence after administration to patients, as well as methods for producing such NK cell populations and/or compositions.

SUMMARY OF THE DISCLOSURE

The present disclosure provides compositions of NK cell preparations and methods of making and using such NK cell compositions and/or preparations for immunotherapy. The NK cell compositions and/or preparations can be used in therapies for a broad range of viral infections, malignancies, and other diseases. The NK cell compositions and/or preparations can be comprised of $CD56^+$ (mainly NK) cells derived from multiple human donors, with typically at least two or at least four human donors, or from fully matched or partially matched (mismatched) donors. The NK cell compositions and/or preparations can be prepared from pooled, non-HLA matched (unmatched), $CD34^+$ hematopoietic stem and progenitor cells (HSPCs), from immunologically matched, or from partially immunologically matched (mismatched) HSPCs by expansion of the HSPCs in vitro or ex vivo, followed by differentiation into $CD56^+$ (mainly NK) cells. Significantly, the resulting NK cell compositions and/or preparations whether immunologically unmatched, matched or mismatched, comprise a mixture of $CD56^+$ (largely NK) cells and $CD56^-$ (non-NK) cells. The $CD56^+$ (NK) cells produced by the disclosed methods are highly potent, but less mature than, comparable NK cells in the prior art that are typically derived from adult human donors, and thus may exhibit more cytolytic activity and/or persistence in vivo. The non-NK cells present in the herein described compositions and/or preparations are typically of myeloid origin and support NK cell differentiation and activation, eliminating the need for an exogenous feeder cell layer.

In some embodiments, an NK cell composition and/or preparation of the present disclosure comprises from about 50% up to about 80% $CD56^+$ cells and about 50% to about 20% $CD56^-$ myeloid-derived cells, such as dendritic cells, macrophages, and granulocytes. The $CD56^-$ cells produced during the generation of the $CD56^+$ are considered endogenous to the $CD56^+$ cells. In some embodiments, the NK cell composition and/or preparation comprises from about 50% up to about 85% $CD56^+$ cells and about 50% to about 15% $CD56^-$ myeloid-derived cells, such as dendritic cells, macrophages, and granulocytes. In some embodiments, the NK cell composition and/or preparation produced by the disclosed methods comprises from about 55% up to about 65% $CD56^+$ cells and about 45% to about 35% $CD56^-$, myeloid-derived cells, such as dendritic cells, macrophages, and granulocytes. In some embodiments, the NK cell composition and/or preparation produced comprises from about 70% up to about 85% $CD56^+$ cells and about 30% to about 15% $CD56^-$, myeloid-derived cells, such as dendritic cells, macrophages, and granulocytes.

The above described $CD56^+$ subpopulation is mainly comprised of NK cells. In addition to CD56, the $CD56^+$ cells can express a high frequency of NKp30, NKp46, NKp44, NKG2A, and/or granzyme B, moderate to a high frequency of perforin and/or CD107a, a low to moderate frequency of NKG2D, and substantially no killer cell immunoglobulin-like receptors (KIRs). In some embodiments the $CD56^+$ cells are $KIR^-$. (As used herein, "$KIR^-$" refers to KIR family members KIR2DL1, KIR2DS1, KIR2DS3, KIR2DS5, KIR2DL2, KIR2DL3, KIR2DS2, KIR2DS4, KIR3DL1, and KIR3DS1.) CD16 (also known as Fc gamma receptor III (FcγRIII)) can be expressed at a low or moderate frequency on NK cells induced to differentiate in in vitro by the methods described herein. In some embodiments, the CD56⁻ cells express a moderate to high frequency of granzyme B, a high frequency of CD107a, and a low frequency of perforin. In some embodiments an expanded NK cell composition and/or preparation comprises cells derived from at least two human donors, without matching to the HLA type of the other donors and without matching to the HLA type of the patient who will receive the NK cells. In other embodiments the expanded NK cell composition and/or preparation comprises cells immunologically matched to the HLA type to the subject. In still other embodiments the expanded NK cell composition and/or preparation comprises cells that are at least partially immunologically matched (mismatched) to the subject.

In some embodiments, in vitro or ex vivo methods for preparing an NK cell composition and/or preparation are provided. The methods typically include selecting a plurality of umbilical cord blood and/or placental blood units without immunological matching to each other; lysing or otherwise depleting red blood cells; depleting the T cells; enriching for CD34⁺ hematopoietic stem and progenitor cells (HSPCs); followed by culturing the CD34⁺ enriched HSPCs in an expansion culture medium and in the absence of feeder cells for a sufficient time to produce an expanded HSPC cell population, wherein the expanded HSPCs do not substantially differentiate into CD56⁺ (mainly NK) cells during the expansion; and then culturing the expanded HSPC cell population in a differentiation culture medium with cytokines and in the absence of feeder cells for a sufficient time to produce an NK cell composition and/or preparation comprising about 50 to about 80% CD56⁺ cells and about 50 to about 20% endogenous CD56⁻ cells. In some embodiments, an NK cell composition and/or preparation comprises from about 50% up to about 85% CD56⁺ cells and about 50% to about 15% CD56⁻, endogenous myeloid-derived cells, such as dendritic cells, macrophages, and granulocytes. In some embodiments, an NK cell composition and/or preparation comprises from about 55% up to about 65% CD56⁺ cells and about 45% to about 35% CD56⁻, endogenous myeloid-derived cells, such as dendritic cells, macrophages, and granulocytes. In some embodiments, an NK cell composition and/or preparation comprises from about 70% up to about 85% CD56⁺ cells and about 30% to about 15% CD56⁻, myeloid-derived cells, such as dendritic cells, macrophages, and granulocytes. The CD56⁺ subpopulation is mainly comprised of NK cells. In addition to CD56, the CD56⁺ cells express a high frequency of NKp30, NKp46, NKp44, NKG2A, and granzyme B, moderate to a high frequency of perforin and CD107a, a low to moderate frequency of NKG2D, and substantially no KIRs. In some embodiments the CD56⁺ cells are KIR⁻. (As used herein, "KIR⁻" refers to KIR2DL1, KIR2DS1, KIR2DS3, KIR2DS5, KIR2DL2, KIR2DL3, KIR2DS2, KIR2DS4, KIR3DL1, and KIR3DS1.) CD16 is expressed at a low or moderate frequency. In some embodiments, the CD56⁻ cells express a moderate to high frequency of granzyme B, a high frequency of CD107a, and a low frequency of perforin.

In other embodiments, the in vitro or ex vivo methods for preparing an NK cell composition and/or preparation comprise selecting fully immunologically matched or mismatched units of umbilical cord blood and/or placental blood units Immunological matching can be carried out by any method known in the art. Subsequent to selecting the umbilical cord blood and/or placental blood unit(s), the method comprises lysing or otherwise depleting red blood cells; depleting the T cells; enriching for CD34⁺ hematopoietic stem and progenitor cells (HSPCs); followed by culturing the CD34⁺ enriched HSPCs in an expansion culture medium and in the absence of feeder cells for a sufficient time to produce an expanded HSPC cell population, wherein the expanded HSPCs do not substantially differentiate into CD56⁺ (mainly NK) cells during the expansion; and then culturing the expanded HSPC cell population in a differentiation culture medium with cytokines and in the absence of feeder cells for a sufficient time to produce an NK cell composition and/or preparation comprising about 50 to about 80% CD56⁺ cells and about 50 to about 20% endogenous CD56⁻ cells. In some embodiments, the NK cell composition and/or preparation comprises from about 50% up to about 85% CD56⁺ cells and about 50% to about 15% CD56⁻, endogenous myeloid-derived cells, such as dendritic cells, macrophages, and granulocytes. In some embodiments, the NK cell composition and/or preparation comprises from about 55% up to about 65% CD56⁺ cells and about 45% to about 35% CD56⁻, endogenous myeloid-derived cells, such as dendritic cells, macrophages, and granulocytes. In other embodiments, the NK cell composition and/or preparation comprises from about 70% up to about 85% CD56⁺ cells and about 30% to about 15% CD56⁻, endogenous myeloid-derived cells, such as dendritic cells, macrophages, and granulocytes. The CD56⁺ subpopulation is mainly comprised of NK cells. In addition to CD56, the CD56⁺ cells express a high frequency of NKp30, NKp46, NKp44, NKG2A, and granzyme B, moderate to a high frequency of perforin and CD107a, a low to moderate frequency of NKG2D and substantially no KIRs. In some embodiments the CD56⁺ cells are KIR⁻. (As used herein, "KIR⁻" refers to KIR2DL1, KIR2DS1, KIR2DS3, KIR2DS5, KIR2DL2, KIR2DL3, KIR2DS2, KIR2DS4, KIR3DL1, and KIR3DS1.) CD16 can also be expressed at a low or moderate frequency. In some embodiments, the CD56⁻ cells can express a moderate to high frequency of granzyme B, a high frequency of CD107a, and a low frequency of perforin.

In some embodiments, regardless of whether the HSPCs originate from unmatched, matched, or mismatched cord blood units, the HSPC expansion culture medium comprises interleukin-3 (IL-3), interleukin-6 (IL-6), thrombopoietin (TPO), Flt-3 ligand (Flt-3L), stem cell factor (SCF) in a solid phase tissue culture substrate coated with a Notch ligand and fibronectin or fragments thereof. In some embodiments, the only growth factors added to the HSPC in vitro or ex vivo expansion culture medium are IL-3, IL-6, TPO, Flt-3L, and SCF. In some embodiments, the Notch ligand in the HSPC expansion culture medium is Delta1$^{ext-IgG}$. In some embodiments, the fibronectin or fragments thereof are recombinant human fibronectin or fragments thereof.

Differentiation of the now expanded HSPCs comprises their isolation and in vitro or ex vivo culture of the isolated HSPCs in a cell culture media supplemented with IL-2 and IL-15 to induce differentiation. In some embodiments, the only cytokines added to the in vitro or ex vivo differentiation culture medium are IL-2 and IL-15. In some embodiments, the amount of IL-2 and IL-15 in the differentiation culture medium is from about 25 U/ml to about 100 U/ml of IL-2 and from about 25 ng/ml to about 50 ng/ml of IL-15. In other embodiments, the amount of IL-2 and IL-15 in the differentiation culture medium can be about 50 U/ml for IL-2 and about 40 ng/ml for IL-15. In some embodiments, the cytokines in the differentiation culture comprise IL-2 and IL-15, wherein other cytokines, such as Flt-3L, fibroblast growth factor 2 (FGF-2), IL-6, IL-7, IL-12, IL-3, GM-CSF, granulocyte-colony stimulating factor (G-CSF), leukemia inhibitory factor (LIF), macrophage inhibitory protein 1 alpha (MIP-1α), SCF, IL-21, IL-18, and 4-1BBL (4-1BB ligand), are not added to the differentiation culture medium. In some embodiments, the differentiation culture medium does not contain added cytokines other than the added IL-2 and IL-15 used to induce differentiation of the NK cells.

In certain embodiments of the disclosure, IL-15 is added during the expansion of the CD34$^+$ enriched HSPCs to prime the differentiation of the NK cell compositions and/or preparations. The IL-15 can be added during the last 4 to 7 days of the expansion phase. If the expansion phase is reduced to 7 days, the priming with IL-15 can be during the last about 4 days. Differentiation of the now expanded and primed HSPCs comprises their isolation and in vitro or ex vivo culture of the isolated HSPCs in a cell culture media supplemented with IL-2 and IL-15 to induce differentiation. In some embodiments, the only cytokines added to the in vitro or ex vivo differentiation culture medium are IL-2 and IL-15. In some embodiments, the amount of IL-2 and IL-15 in the differentiation culture medium is from about 25 U/ml to about 100 U/ml of IL-2 and from about 25 ng/ml to about 50 ng/ml of IL-15. In other embodiments, the amount of IL-2 and IL-15 in the differentiation culture medium can be about 50 U/ml for IL-2 and about 40 ng/ml for IL-15. In some embodiments, the cytokines in the differentiation culture comprise IL-2 and IL-15, wherein other cytokines, such as Flt-3L, fibroblast growth factor 2 (FGF-2), IL-6, IL-7, IL-12, IL-3, GM-CSF, granulocyte-colony stimulating factor (G-CSF), leukemia inhibitory factor (LIF), macrophage inhibitory protein 1 alpha (MIP-1α), SCF, IL-21, IL-18, and 4-1BBL (4-1BB ligand), are not added to the differentiation culture medium. In some embodiments, the differentiation culture medium does not contain added cytokines other than the added IL-2 and IL-15 used to induce differentiation of the NK cells.

In certain embodiments of the present methods the non-animal sourced protein used to supplement the differentiation medium is human AB serum, fresh frozen human plasma, or human platelet lysate. Still further, in certain embodiments the HSPCs are not derived from somatic cells embryonic stem cells, peripheral blood mononuclear cell, or induced pluripotent stem cells.

In certain embodiments of the disclosure the methods produce NK cell compositions and/or preparations that comprise less than 2% CD3+ cells, less than 2% CD19+ cells, and/or less than 2% CD34+ cells. The CD56$^+$ cells of the compositions and or preparations further express a high frequency of KIR2DL4. In some embodiments the method comprises the use of a Notch ligand that is DXI or an antibody specific for Notch.

In certain embodiments the methods comprise the genetic modification the NK cell compositions and/or preparations. In certain specific embodiments the genetic modification is done during the expansion phase and in other the genetic modification is done subsequent to differentiation of the NK cells. The cells of the NK cell composition and/or preparation can be genetically modified to express an antigen recognizing receptor. In certain specific embodiments the genetic modification is the introduction of a polynucleotide expressing a T cell receptor (TCR) or a chimeric antigen receptor (CAR). The TCR or the CAR can be designed to specifically binds to a viral antigen, a bacterial antigen, or a tumor specific or tumor associate antigen.

In certain embodiments of the disclosed methods the viral antigen is present in Cytomegalovirus (CMV), Epstein Barr Virus (EBV), Human Immunodeficiency Virus (HIV), Herpes simplex virus (HSV), Hepatitis virus, zika virus, influenza virus, or coronavirus. In specific embodiments, the Herpes virus is HSV 1 or HSV2, the Hepatitis virus is Hepatitis A, B or C, and the coronavirus is SARS-CoV or SARS-CoV-2.

In certain other embodiments the where the CAR is directed to a tumor specific or tumor associated antigen the antigen can be CD19, ROR1, Her2, PSMA, PSCA, mesothelin, or CD20.

The polynucleotide encoding the CAR can comprise an intracellular signaling domain comprising a signaling domain of CD3zeta, CD28, and 4-1BB; at least one co-stimulatory domain comprising a co-stimulatory domain of CD27, CD28, 4-1BB, 2B4, DAP10, DAP12, OX40, CD30, CD40, lymphocyte function-associated antigen-1 (LFA-1), CD2, CD7, LIGHT, NKG2C, or B7-H3; a transmembrane domain comprising a transmembrane domain of CD8, CD28, CD3zeta, CD4, 4-1BB, OX40, ICOS, or NKG2D; and a spacer region comprising a hinge region of IgG$_1$, the CH$_2$CH$_3$ region of an immunoglobulin, a portion of CD3, a portion of CD28, or a portion of CD8. In some embodiments the CAR can comprise a single chain Fv (scFv) having the CDRs of monoclonal antibody FMC63.

In certain embodiments the NK cell compositions and preparations produced by a method disclosed herein can be formulated for infusion into a subject.

In certain embodiments disclosed herein natural killer (NK) cell compositions are produced for use in immunotherapy. The compositions can comprise about 50 to about 80% CD56$^+$ cells and about 50 to about 20% endogenous CD56$^-$ cells, or about 50 to about 85% CD56$^+$ cells and about 50 to about 15% endogenous CD56$^-$ cells, wherein the CD56$^+$ cells express a high frequency of NKp30, NKp46, NKp44, NKG2A, NKG2D, and granzyme B, a moderate to a high frequency of perforin and CD107a, a low to moderate frequency of CD16 and substantially no KIRs; and wherein the CD56$^-$ cells express a moderate to high frequency of granzyme B, a high frequency of CD107a, and a low frequency of perforin, and a pharmaceutically acceptable carrier. In specific embodiments the NK cell composition does not contain exogenous feeder cells.

In certain embodiments, the NK cell composition comprises less than 2% CD3$^+$ cells, and/or less than 2% CD19$^+$ cells, and/or less than 2% CD34$^+$ cells. In specific embodiments the NK cell compositions comprise CD56$^+$ cells that further express a high frequency of KIR2DL4.

The NK cell compositions described herein can comprise cells that are genetically modified. The genetically modified cells of the composition can be genetically modified to express an antigen recognizing receptor. These antigen recognizing receptors can be encoded by an introduced polynucleotide expressing a TCR or a CAR. In certain specific embodiments the TCR or the CAR can specifically bind to a viral antigen, a bacterial antigen, or a tumor associated or tumor specific antigen. In more specific embodiments, the viral antigen is present in Cytomegalovirus (CMV), Epstein Barr Virus (EBV), Human Immunodeficiency Virus (HIV), Herpes simplex virus (HSV), Hepatitis virus, zika virus, influenza virus, or coronavirus. In more preferred embodiments the Herpes virus is HSV 1 or HSV 2, the Hepatitis virus is Hepatitis A, B or C, and the coronavirus is SARS-CoV or SARS-CoV-2.

In certain embodiments the NK cell composition and/or preparation comprising a TCR or a CAR, the TCR or CAR is specific for a tumor associated or tumor specific antigen is specific for carbonic anhydrase IX (CA1X), carcinoembryonic antigen (CEA), CD8, CD7, CD10, CD19, CD20, CD22, CD30, CD33, CLL1, CD34, CD38, CD41, CD44, CD49c, CD49f, CD56, CD66c, CD73, CD74, CD104, CD133, CD138, CD123, CD142, CD44V6, an antigen of a cytomegalovirus (CMV) infected cell (e.g., a cell surface antigen), cutaneous lymphocyte-associated antigen (CLA; a specialized glycoform of P-selectin glycoprotein ligand-1 (PSGL-1)), epithelial glycoprotein-2 (EGP-2), epithelial glycoprotein-40 (EGP-40), epithelial cell adhesion molecule (EpCAM), receptor tyrosine-protein kinases erb-B2,3,4 (erb-B2,3,4), folate-binding protein (FBP), fetal acetylcholine receptor (AChR), folate receptor-alpha, Ganglioside G2 (GD2), Ganglioside G3 (GD3), human Epidermal Growth Factor Receptor 2 (HER2), human telomerase reverse transcriptase (hTERT), Interleukin-13 receptor subunit alpha-2 (IL-13Ralpha2), kappa-light chain, kinase insert domain receptor (KDR), Lewis Y (LeY), L1 cell adhesion molecule (L1CAM), melanoma antigen family A, 1 (MAGE-A1), Mucin 16 (MUC16), Mucin 1 (MUC1), Mesothelin (MSLN), ERBB2, MAGEA3, p53, MART1, GP100, Proteinase3 (PR1), Tyrosinase, Survivin, hTERT, EphA2, an NKG2D ligand, cancer-testis antigen NY-ES0-1, oncofetal antigen (h5T4), prostate stem cell antigen (PSCA), prostate-specific membrane antigen (PSMA), ROR1, tetraspanin 8 (TSPAN8), tumor-associated glycoprotein 72 (TAG-72), vascular endothelial growth factor R2 (VEGF-R2), Wilms tumor protein (WT-1), BCMA, GPC3, NKCS1, EGF1R, EGFR-VIII, CRLF2, and ERBB. In more specific embodiments, the tumor associated or tumor specific antigen is CD19, ROR1, Her2, PSMA, PSCA, mesothelin, CRLF2, or CD20.

In certain embodiments where the NK cell comprises an antigen recognizing receptor, the antigen recognizing receptor can be a CAR. In more specific embodiments the CAR can comprise an intracellular signaling domain of CD3zeta, CD28, and 4-1BB; at least one co-stimulatory domain of CD27, CD28, 4-1BB, 2B4, DAP10, DAP12, OX40, CD30, CD40, lymphocyte function-associated antigen-1 (LFA-1), CD2, CD7, LIGHT, NKG2C, or B7-H3 costimulatory domain; a transmembrane domain of CD8, CD28, CD3zeta, CD4, 4-1BB, OX40, ICOS, or NKG2D; and a spacer region of IgG 1, the $CH_2CH_3$ region of an immunoglobulin, a portion of CD3, a portion of CD28, or a portion of CD8. In certain embodiments the In certain embodiments the NK cell composition can further comprise a cryoprotective agent and the NK cell composition is frozen for future use. In certain specific embodiments the NK cell composition is formulated for infusion into a subject. The formulation can comprise the cryoprotective agent used to store the composition. The NK cell composition can comprise from about 50 million to about 2 billion viable cells. In certain embodiments the NK cell composition comprises from about 50 million to about 2 billion viable $CD56^+$ cells.

The present disclosure also provides methods of treating a subject in need thereof, comprising administering a therapeutically effective amount of the NK cell composition described above to the subject. The subject can have for example a cancer expressing a tumor antigen and the NK cells of the composition express an antigen recognizing receptor that binds to the tumor antigen. In other embodiments the subject has a viral or bacterial infection. In certain embodiments, the NK cell composition expresses a chimeric antigen receptor that is specific for a tumor specific or associated antigen, a viral antigen, or a bacterial antigen.

DESCRIPTION OF THE DRAWINGS

The foregoing aspects and many of the attendant advantages of this methods and compositions and/or preparations will become more readily appreciated as the same become better understood by reference to the following detailed description, when taken in conjunction with the accompanying drawings, wherein:

FIG. 1A shows the increase in $CD56^+$ cells/starting $CD34^+$ cells over the course of a 28-day culture (phases 1 and 2). FIG. 1B demonstrates reproducibility of $CD56^+$ cell generation over a 28-day cell culture process.

FIG. 11 A is a graph of the tumor size for the untreated control (line with circles) and for the NK cell composition and/or preparation (line with squares) over time for this study. The NK cell composition was able to cause a significant delay in tumor progression. FIG. 11B shows the NK cell composition persisted and was detectable 37 days post injection, as measured by detecting human $CD45^+$ cells in the tumor.

FIG. 17A shows the increase in CD56+ cells/starting CD34+ cells over the course of a 24-day culture (phases 1 and 2). FIG. 17B demonstrates the reproducibility of CD56+ cell generation over a 24-day cell culture process.

FIG. 18A is a fresh NK cell preparation. FIG. 18B is a cryopreserved and thawed NK cell preparation, and FIG. 18C is an assay where a fresh NK cell preparation received repeat doses of target cells every 3 days for a total of 10 days.

DETAILED DESCRIPTION OF SPECIFIC EMBODIMENTS

Figure 1A:
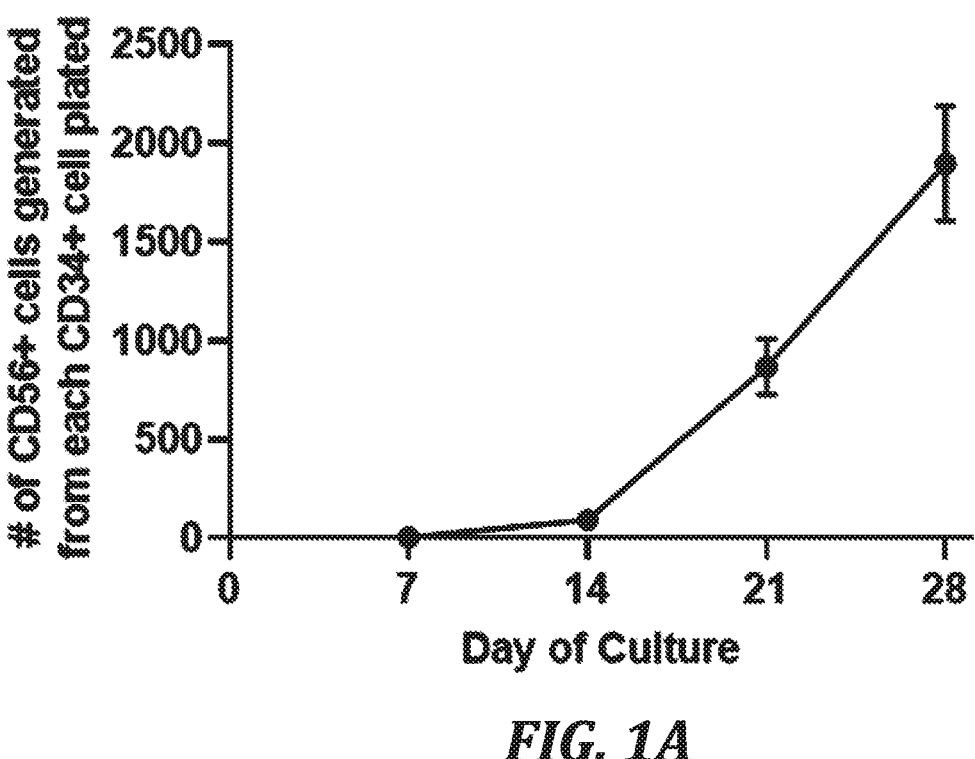
FIGS. 1A and 1B show the results from 20 batches of NK cell compositions and/or preparations produced following the process described in Example 1.

Although any methods and materials similar or equivalent to those described herein can be used in the practice or testing of the present cell compositions and/or preparations, certain preferred methods and materials are described. For purposes of the present disclosure, the following terms are defined below.

As used herein, "expanded HSPCs" refers to hematopoietic stem cells or stem and progenitor cells that have been subjected to a technique for expanding the hematopoietic stem cells, or hematopoietic stem and progenitor cells ex vivo, which technique has been shown to result in (i) an increase in the number of hematopoietic stem cells, or hematopoietic stem and progenitor cells, in an aliquot of the cells thus expanded, or (ii) an increased number of severe combined immunodeficiency (SCID) repopulating cells determined by limiting-dilution analysis as shown by enhanced engraftment in non-obese diabetic (NOD)/SCID mice infused with an aliquot of the cells thus expanded. These are relative to that seen with an aliquot of the cells not subjected to the expansion technique. (See US Patent Application Publication No. 2013/0095079; Delaney et al., *Nature Med.* 16(2):232-236, 2010). Typically, the hematopoietic stem cells, or stem and progenitor cells, are CD34$^+$. In some embodiments, the hematopoietic stem cells, or hematopoietic stem and progenitor cells, are derived from human umbilical cord blood and/or human placental blood. In some embodiments, the expanded stem cells are prepared using a Notch-agonist expansion method. In some embodiments, the expanded stem cells are prepared using a Delta1$^{ext-IgG}$ (DXI) expansion method.

As used herein, a "chemotherapy regimen" refers to a regimen for chemotherapy, defining the drugs to be used, their dosage, the frequency and duration of treatments, and other considerations. Such regimens can combine several chemotherapy drugs in combination with chemotherapy. The majority of drugs used today in chemotherapy are cytostatic or cytotoxic.

The present disclosure provides compositions comprising a natural killer (NK) cell preparation and methods of using such NK cell compositions and/or preparations for immunotherapy. The NK cell compositions and/or preparations can be used in therapies for a broad range of viral infections, malignancies, and other diseases, including hematologic and non-hematologic malignancies. An NK cell composition and/or preparation is produced from pooled, expanded CD34$^+$ hematopoietic stem and progenitor cells (HSPCs). Typically, HSPCs from at least two or more, or up to at least four, different human donors are combined or pooled, before or after ex vivo expansion, to generate an expanded HSPC cell population. The expanded cell population is then differentiated ex vivo to generate an NK cell composition and/or preparation comprising a mixture of CD56⁺ and CD56⁻ cells. The CD56⁺ cells are predominantly NK cells. The CD56⁻ cells that make up a portion of the cell composition and/or preparation are typically of myeloid origin and support NK cell differentiation and activation during differentiation. The CD56⁻ cells produced during the ex vivo generation of the CD56⁺ are considered endogenous to the CD56⁺ cells.

In some embodiments, the NK cell composition and/or preparation comprises from about 50% up to about 80% CD56⁺ cells and about 50% to about 20% CD56⁻, endogenous myeloid-derived cells, such as dendritic cells, macrophages, and granulocytes. In some embodiments, the NK cell composition and/or preparation comprises from about 50% up to about 85% CD56⁺ cells and about 50% to about 15% CD56⁻, endogenous myeloid-derived cells, such as dendritic cells, macrophages, and granulocytes. In some embodiments, the NK cell composition and/or preparation comprises from about 55% up to about 65% CD56⁺ cells and about 45% to about 35% CD56⁻, endogenous myeloid-derived cells, such as dendritic cells, macrophages, and granulocytes. In some embodiments, the NK cell composition and/or preparation comprises from about 70% up to about 85% CD56⁺ cells and about 30% to about 15% CD56⁻, endogenous myeloid-derived cells, such as dendritic cells, macrophages, and granulocytes.

In addition to CD56, the CD56⁺ cells can express a high frequency of natural killer cell proteins NKp30, NKp46, NKp44, and NKG2A, and granzyme B; a moderate to high frequency of perforin and CD107a; a low to moderate frequency of NKG2D; and substantially no KIRs. In some embodiments the CD56⁺ cells are KIR⁻. (As used herein, "KIR⁻" refers to KIR2DL1, KIR2DS1, KIR2DS3, KIR2DS5, KIR2DL2, KIR2DL3, KIR2DS2, KIR2DS4, KIR3DL1, and KIR3DS1). In some embodiments, CD16 is expressed at a low frequency. In some embodiments, CD16 is expressed at a moderate frequency. In some embodiments, the CD56⁻ cells express a moderate to high frequency of granzyme B, a high frequency of CD107a, and a low frequency of perforin.

In some embodiments, an NK cell composition and/or preparation produced by the methods described herein has the following characteristics.

The frequency of expression of the various NK markers is shown in the following Table.

TABLE 1

| Frequency of NK Cell Marker Expression | | | |
|---|---|---|---|
| CD56⁺ Cells | | CD56⁻ Cells | |
| Granzyme B+ | High | Granzyme B⁺ | Moderate to high |
| Perforin⁺ | Moderate to high | Perforin⁺ | Low |
| CD107a⁺ | Moderate | CD107a⁺ | High |
| CD16⁺ | Low to moderate | CD15⁺CD14⁺ | Moderate |
| NKp30⁺ | High | CD15⁺CD14⁻ | Low to moderate |
| NKp44⁺ | High | CD15⁻CD14⁺ | Low to moderate |
| NKp46⁺ | High | CD11b⁺CD11V⁺ | High |
| NKG2A⁺ | High | of the CD15⁻CD14⁻ | |
| NKG2D⁺ | Low to moderate | | |
| KIR | Substantially no | | |

High expression refers to a frequency of about 60 to about 100%. Moderate expression refers to a frequency of about 20 to about 60%. Low expression refers to a frequency of about 1 to about 20%. Substantially no refers to a frequency of expression of less than 1%. As used herein, "KIR⁻" refers to KIR2DL1, KIR2DS1, KIR2DS3, KIR2DS5, KIR2DL2, KIR2DL3, KIR2DS2, KIR2DS4, KIR3DL1, and KIR3DS1.

In some embodiments, the ranges of the markers for the CD56⁺ and CD56⁻ cells are as recited in Tables 2 and 3:

TABLE 2

| Range of NK Cell Markers for CD56⁺ Cells | | |
|---|---|---|
| CD56⁺ Cells | Frequency (Mean ± SD) | Range |
| CD56⁺ population | 60.7 ± 14.7 | 27.0-80.0 |
| Subsets within CD56⁺ Cells | | |
| Granzyme B⁺ | 89.6 ± 7.1 | 79.1-98 |
| Perforin⁺ | 61.0 ± 12.3 | 51.9-81.5 |
| CD107a⁺ | 49.7 ± 5.7 | 42.9-58.8 |
| CD16⁺ | 18.4 ± 12.9 | 4.0-30.0 |
| NKp30⁺ | 84.1 ± 10.9 | 68.7-92.8 |
| NKp44⁺ | 80.0 ± 7.1 | 81.1-88.9 |
| NKp46⁺ | 85.4 ± 3.2 | 81.6-8.8 |
| NKG2A⁺ | 73.6 ± 2.0 | 70.4-85.4 |
| NKG2D⁺ | 7.3 ± 1.2 | 6.3-8.1 |
| KIR⁺ | 0.14 ± 0.04 | 0.10-0.16 |

TABLE 3

| Range of NK Cell Markers for CD56⁻ Cells | | |
|---|---|---|
| CD56⁻ Cells | Frequency (Mean ± SD) | Range |
| CD56⁻ population | 39.3 ± 14.7 | 20.0-73.0 |
| Subsets within CD56⁻ population | | |
| Granzyme B⁺ | 64.4 ± 21.6 | 27.4-82.3 |
| Perforin⁺ | 1.5 ± 0.3 | 1.2-2.0 |
| CD107a⁺ | 89.3 ± 4.6 | 82.7-95.0 |
| CD15⁺CD14⁺ | 28.7 ± 3.7 | 24.3-33.7 |
| CD15⁺CD14⁻ | 19.8 ± 5.4 | 15.3-28.9 |
| CD15⁻CD14⁺ | 18.3 ± 9.0 | 21.4-2.9 |
| CD11b⁺CD11c⁺ (within the CD15⁻CD14⁻ population) | 76.6 ± 6.4 | 70.3-81.4 |

In some embodiments, an NK cell composition and/or preparation contains less than 2% CD3⁺ cells (T cells). In some embodiments, the NK cell composition and/or preparation contains less than 1% CD3⁺ cells (T cells). In some embodiments, the NK cell composition and/or preparation contains less than 2% CD19⁺ cells (B cells). In some embodiments, the NK cell composition and/or preparation contains less than 1% CD19⁺ cells (B cells). In some embodiments, the NK cell composition and/or preparation contains less than 2% CD34⁺ cells. In some embodiments, the NK cell composition and/or preparation contains less than 1% CD34⁺ cells (HSPCs). In some embodiments, the NK cell composition and/or preparation contains less than 2% CD19⁺ cells (B cells), less than 2% CD3⁺ (T cells) and less than 2% CD34⁺ cells (HSPCs). In some embodiments, the NK cell composition and/or preparation contains less than 1% CD19⁺ cells, less than 1% CD3⁺ (T cells) and less than 1% CD34⁺ cells (HSPCs).

In humans, NK cells are regulated by clonally distributed killer immunoglobulin-like receptors (KIRs) that recognize allotypic determinants displayed by different human leukocyte antigen (HLA) class I alleles. Inhibitory KIRs are generally dominant and prevent NK cells from killing autologous cells. The NK cell compositions and/or preparations prepared by the present methods lack MHC class I inhibitory signals. While expressing high levels of NKG2A, the NK cell composition and/or preparation can be more active in vitro than adult NK cells.

The receptor phenotype of the NK cell compositions and/or preparations produced by the methods disclosed herein can further include a high frequency of expression of the natural cytotoxicity receptors NKp30, NKp44, NKp46, while having a low to moderate frequency of expression of NKG2D by the $CD56^+$ cells. The $CD56^+$ cells of the instant NK cell compositions and/or preparations can further be identified by low to moderate CD16 expression.

The differentiated NK cells of the present disclosure are further identified by their capability to lyse various tumor cells lines at levels similar to or greater than activated peripheral blood NK cells (as further described in the Examples). The cytotoxic capabilities of the cells in culture can therefore be measured to verify the characteristics of an NK cell composition and/or preparation.

Preparation of differentiated NK cells ex vivo as described in the methods of the present disclosure comprises two separate phases, wherein there is a first phase involving expansion of HSPCs to generate expanded HSPCs, and wherein the first phase is followed by a second phase during which the expanded HSPCs are differentiated to form an NK cell composition and/or preparation. In contrast to the prior art, feeder cells are not used in either phase.

The expanded HSPCs comprise hematopoietic stem cells or stem and progenitor cells that have been expanded ex vivo (e.g., with a Notch ligand) and depleted of both T cells and red blood cells. The expanded HSPCs are typically $CD34^+$ hematopoietic stem cells or stem and progenitor cells and are typically derived from different human sources which are not HLA-matched. In some embodiments, the expanded HSPCs are $CD34^+$ hematopoietic stem or stem and progenitor cells from different human umbilical cord blood sources and/or placental blood sources. The hematopoietic stem or stem and progenitor cells comprise multiple HLA-types because the HSPCs are not matched to each other prior to pooling. As used herein, depleted of T cells refers to less than 2% $CD3^+$ cells (T cells), or less than 1% $CD3^+$ (T cells), or less than 0.5% $CD3^+$ cells (T cells), or less than 0.1% $CD3^+$ cells (T cells), in the expanded HSPCs.

In certain embodiments the hematopoietic stem cells or hematopoietic stem and progenitor cells have been immunologically matched to the patient that is to receive the NK cell composition and/or preparation as an immunotherapy. The immunological matching can be a full match or a partial mismatch of up to 2, 3, or sometimes 4 immunotypes. In the majority of compositions comprising the hematopoietic stem cells or hematopoietic stem and progenitor cells have been matched at the most common HLA antigens, such as, for example, HLA A-2, HLA-B7, and the like, or high frequency combinations by HLA linkage. The choice of matching will be selected depending on the patient population to be treated.

In some embodiments, the $CD34^+$ hematopoietic stem cells or hematopoietic stem and progenitor cells are derived from cord blood and/or from placental blood (human cord blood or human placental blood). Such blood can be obtained by methods known in the art. See, e.g., U.S. Pat. Nos. 5,004,681 and 7,147,626 and US Patent Application Publication No. 2013/0095079 for a discussion of collecting cord and placental blood at the birth of a human. Umbilical cord blood and/or human placental blood collections are made under sterile conditions. Upon collection, cord and/or placental blood can be mixed with an anticoagulant, such as CPD (citrate-phosphate-dextrose), ACD (acid citrate-dextrose), Alsever's solution (Alsever et al., *N. Y. St. J. Med.*

41:126, 1941), De Gowin's Solution (De Gowin, et al., *J. Am. Med. Ass.* 114:850, 1940), Edglugate-Mg (Smith, et al., *J. Thorac. Cardiovasc. Surg.* 38:573, 1959), Rous-Turner Solution (Rous and Turner, *J. Exp. Med.* 23:219, 1916), other glucose mixtures, heparin, ethyl biscoumacetate, and the like. See, generally, Hum, Storage of Blood, Academic Press, New York, pp. 26-160, 1968). In one embodiment, ACD can be used.

Cord blood can preferably be obtained by direct drainage from the umbilical cord and/or by needle aspiration from the delivered placenta at the root and at distended veins. Preferably, the collected human cord blood and/or placental blood is free of contamination (e.g., bacterial or viral) and, in particular, viral contamination.

Prior to collection of the cord blood, a maternal health history can be determined to identify risks that the cord blood cells might pose, e.g., transmitting genetic or infectious diseases, such as cancer, a leukemia, immune disorders, neurological disorders, hepatitis or HIV/AIDS. The collected cord blood can have undergone testing, for example, for one or more of cell viability, HLA typing, ABO/Rh typing, $CD34^+$ cell count, and total nucleated cell count.

Once the umbilical cord blood and/or placental blood is collected from human donors at birth, the blood is processed to produce enriched HSPCs. Preferably, the HSPCs are $CD34^+$ cells or predominantly $CD34^+$ cells. The HSPCs are typically depleted of T cells and of red blood cells, resulting in enriched HSPCs. As used herein, depletion of T cells refers to the presence of less than about 2% $CD3^+$ cells, less than about 1% $CD3^+$ cells, or less than about 0.5% $CD3^+$ cells, or less than about 0.1% $CD3^+$ cells. Enrichment thus refers to a process wherein the percentage of HSPCs in the cell population is increased (relative to the percentage in the population before the enrichment procedure). Purification is one example of enrichment.

Prior to processing for enrichment, the collected cord and/or placental blood can be fresh or may have been previously cryopreserved. Any suitable technique known in the art for cell separation/selection can be used to carry out the enrichment for HSPCs. Methods which rely on differential expression of cell surface markers can be used. For example, cells expressing the cell surface marker CD34 can be positively selected using a monoclonal antibody specific to CD34, such that cells expressing CD34 are separated from cells not expressing CD34. Moreover, the separation techniques employed preferably maximize the viability of the cells to be selected. The particular technique employed depends upon the efficiency of separation, the cytotoxicity of the methodology, ease and speed of performance, and necessity for sophisticated equipment and/or technical skill.

Procedures for separation can include magnetic separation, using antibody-coated magnetic beads, affinity chromatography, and "panning" with antibody attached to a solid matrix, e.g., a plate, or another convenient technique. Techniques providing accurate separation/selection include fluorescence activated cell sorters, which can have varying degrees of sophistication, e.g., a plurality of color channels, low angle and obtuse light scattering detecting channels, impedance channels, and the like.

The antibodies used in the selection process allow for ease of separation of the particular cell type, and can be conjugated with markers, such as magnetic beads, which allow for direct separation; biotin, which enables removal by adhering to avidin or streptavidin bound to a support; fluorochromes, which can be used with a fluorescence activated cell sorter;

or the like. Any technique can be employed which is not unduly detrimental to the viability of the remaining cells.

In a preferred embodiment, fresh cord blood units or frozen and thawed cord blood units are processed to enrich for CD34$^+$ HSPCs using anti-CD34 antibodies directly or indirectly conjugated to magnetic particles in connection with a magnetic cell separator, for example, the Clini-MACS® Cell Separation System (Miltenyi Biotec, Bergisch Gladbach, Germany), which employs nano-sized super-paramagnetic particles composed of iron oxide and dextran coupled to specific monoclonal antibodies. The Clini-MACS® Cell Separator is a closed sterile system, outfitted with a single-use disposable tubing set. The disposable tubing set can be used for, and discarded after, processing a single unit of collected cord and/or placental blood to enrich for CD34$^+$ HSPCs.

In a typical embodiment, two or more, or up to at least four or more umbilical cord blood and/or placental blood units, can be pooled prior to enriching for HSPCs. In another embodiment, individual populations of CD34$^+$ HSPCs can be pooled after enriching for the HSPCs. In specific embodiments, the number of umbilical cord blood and/or placental blood units, or populations of HSPCs, that are pooled is 2, 4, 5, 6, 7, 8, 9, 10, 15, 20, 25, 30, 35, or 40, or at least any of the foregoing numbers. The number of individual populations of HSPCs pooled can depend on, for example, the number of cells in each individual populations, and/or the number of cells required for a particular patient and the immunotherapy intended. In some embodiments, the pool contains 2 to 8, 4 to 8, 2 to 10, 4 to 10, 4 to 20, or 4 to 25, and no more than 20 or 25, umbilical cord blood and/or placental blood units, or CD34$^+$ HSPC populations. In a typical embodiment the umbilical cord blood and/or placental blood units or hematopoietic stem or stem and progenitor cell populations can be pooled without regard to the HLA-type of the HSPCs. In some embodiments, the cells in the pool are combined without regard to race or ethnicity. In some embodiments, the cells in the pool are derived from the umbilical cord blood and/or placental blood of individuals of the same race, e.g., African-American, Caucasian, Asian, Hispanic, Native-American, Australian Aboriginal, Inuit, Pacific Islander, or derived from umbilical cord blood and/or placental blood of individuals of the same ethnicity, e.g., Irish, Italian, Indian, Japanese, Chinese, Russian, and the like. In less common embodiments, the cells can be from an individual cell population that has been matched or partially matched to the patient. If there are a sufficient number of matched or partially matched units available the units can be pooled; however, given the sometimes-difficult process to find units that match a particular patient, pooling is commonly not carried out for matched or mismatched units.

Typically, prior to enrichment for HSPCs, the red blood cells and white blood cells of the cord blood and/or placental blood are separated. In some embodiments, depletion of red blood cells refers to the separation of red blood cells from white blood cells. Once the separation of the red blood cells and the white blood cells has taken place, the red blood cell fraction can be discarded, and the white blood cell fraction can be processed, for example, in the magnetic cell separator as described above to enrich for CD34$^+$ HSPCs. Separation of the white and red blood cell fractions can be performed by any method known in the art, including, for example, centrifugation techniques. Other separation methods that can be used include the use of commercially available products FICOLL™ or FICOLL-PAQUE™ or PERCOLL™ (GE Healthcare, Piscataway, New Jersey). FICOLL-PAQUE™ is normally placed at the bottom of a conical tube, and the whole blood is layered above. After being centrifuged, the following layers will be visible in the conical tube, from top to bottom: plasma and other constituents, a layer of mononuclear cells, called a buffy coat, containing the mononuclear cells (white blood cells), and erythrocytes and granulocytes, which should be present in pellet form. This separation technique allows easy harvest of the mononuclear cells.

Optionally, prior to CD34$^+$ cell selection, an aliquot of the cord blood and/or placental unit can be checked for a total nucleated cell count and/or CD34$^+$ cell content. In a specific embodiment, after the CD34$^+$ cell selection, both CD34$^+$ and CD34$^-$ cell fractions are recovered. Optionally, DNA can be extracted from a sample of the CD34$^-$ cell fraction for initial HLA typing and future chimerism studies, even though HLA matching of the CD34$^+$ cells to the other cord blood and/or placental blood cells is not typically performed.

The CD34$^+$ enriched HSPCs can be subsequently processed prior to expansion, for example, by suspension in an appropriate cell culture medium for storage or transport. In a preferred embodiment, the cell culture medium is a cell culture medium suitable for the maintenance of viability of CD34$^+$ HSPCs. For example, the cell culture medium can be a serum-free, cytokine-free, hematopoietic stem cell or stem and progenitor cell culture medium to which growth factors are added, for example, at the following concentrations: 50-300 ng/ml of stem cell factor (SCF), 50-300 ng/ml of Flt-3 receptor ligand (Flt3L), 50-100 ng/ml of thrombopoietin (TPO), 50-100 ng/ml of interleukin-6 (IL-6), and 10 ng/ml of interleukin-3 (IL-3). In more specific embodiments, the cell culture medium contains 300 ng/ml of stem cell factor, 300 ng/ml of Flt-3 receptor ligand, 100 ng/ml of TPO, 100 ng/ml of IL-6 and 10 ng/ml of IL-3; or 50 ng/ml of SCF, 50 ng/ml of Flt-3L, 50 ng/ml of TPO, 50 ng/ml of IL-6 and 10 ng/ml of IL-3. In another preferred embodiment, the cell culture medium includes, or alternatively consists of, a serum free, hematopoietic stem cell or stem and progenitor cell culture medium (e.g., STEMSPAN™ Serum Free Expansion Medium or STEMSPAN™ Serum Free Expansion Medium II (StemCell Technologies, Vancouver, British Columbia)) supplemented with 10 ng/ml recombinant human Interleukin-3 (rhIL-3), 50 ng/ml recombinant human Interleukin-6 (rhIL-6), 50 ng/ml recombinant human Thrombopoietin (rhTPO), 50 ng/ml recombinant human Flt-3 Ligand (rhFlt-3L), 50 ng/ml and recombinant human stem cell factor (rhSCF). In another preferred embodiment, the cell culture medium consists of a serum-free hematopoietic stem cell or stem and progenitor cell culture medium (e.g., StemSpan Serum Free Expansion Medium II (SFEM II, StemCell Technologies, Vancouver, British Columbia)) supplemented with recombinant human rhSCF, rhFlt-3L, rhTPO, rhIL-6 (each at 50 ng/ml final concentration), and rhIL-3 (at 10 ng/ml final concentration).

In a specific embodiment, the umbilical cord blood and/or placental blood units are red blood cell depleted, and the number of CD34$^+$ cells in the red blood cell depleted fraction is determined. In some embodiments, depletion of red blood cells refers to separation of red blood cells from white blood cells or separation of red blood cells from CD34$^+$ cells. Preferably, umbilical cord blood and/or placental blood units containing more than 3.5 million CD34$^+$ cells are subject to the enrichment methods described above.

After the HSPCs have been isolated (e.g., from human cord blood and/or human placental blood collected from humans at birth) according to the enrichment methods described above or other methods known in the art, the enriched HSPCs are expanded to increase the number of HSPCs, e.g., CD34$^+$ HSPCs. The HSPCs are cultured in an expansion culture medium under cell growth conditions (e.g., promoting mitosis) such that the HSPCs grow and divide (proliferate) to obtain an expanded CD34$^+$ HSPC population. During expansion of the HSPCs, minimal differentiation of HSPCs to NK cells occurs (i.e., less than 2% or less than 1% of the resulting cells are NK cells). In one embodiment, individual populations of HSPCs each derived from umbilical cord blood and/or placental blood of a single human at birth can be pooled, without matching to the HLA type of the other HSPCs, prior to or after expansion. In another embodiment, the HSPCs are expanded prior to pooling. Preferably, the technique used for expansion is one that has been shown to result in an increase in the number of hematopoietic stem cells, or hematopoietic stem and progenitor cells, e.g., CD34$^+$ cells, in the expanded HSPCs relative to the unexpanded population of HSPCs, where the unexpanded cell population and expanded cell population are from different aliquots of the same source of HSPCs, wherein the expanded HSPCs but not the unexpanded HSPCs are subjected to the expansion technique.

Expansion techniques include, but are not limited to, those described in U.S. Pat. No. 7,399,633 B2; US Patent Application Publication No. 2013/0095079; Delaney et al., *Nature Med.* 16(2): 232-236, 2010 (incorporated herein by reference); as well as those described below.

In some embodiments, the HSPCs are cultured in vitro or ex vivo in an expansion culture medium, which is serum free and suitable for culture of hematopoietic stem cell or stem and progenitor cells, in the presence of growth factors, and are exposed to cell growth conditions (e.g., promoting mitosis) such that the HSPCs proliferate to generate an expanded population of HSPCs.

In an exemplary embodiment, the expansion culture medium, suitable for expansion of hematopoietic stem cell or stem and progenitor cells, is a serum free, culture medium such as Iscove's MDM containing non-animal sourced BSA, recombinant human insulin, human transferrin, 2-mercaptoethanol, and other supplements, with a Notch ligand and the growth factors, as described below. In other embodiments, the hematopoietic stem cell or stem and progenitor cell culture medium is STEMSPAN™ Serum Free Expansion Medium (StemCell Technologies, Vancouver, British Columbia), or STEMSPAN™ Serum Free Expansion Medium II (StemCell Technologies, Vancouver, British Columbia).

In some embodiments, the HSPCs are cultured in the presence of an amount of a Notch ligand (i.e., an agonist of Notch function effective to inhibit differentiation), typically an immobilized agonist of Notch function, in an expansion culture medium and are exposed to cell growth conditions (e.g., promoting mitosis) such that the HSPCs proliferate to generate an expanded HSPC population. Differentiation of HSPCs to NK cells is minimized during the expansion phase (i.e., less than 2% or less than 1% of the resulting cells are NK cells). In a more preferred embodiment, the expansion culture medium contains an amount of an agonist of Notch function effective to inhibit differentiation and growth factors, and the HSPCs are exposed to cell growth conditions (e.g., promoting mitosis) such that the hematopoietic stem or stem and progenitor cells proliferate to obtain an expanded hematopoietic stem or stem and progenitor cell population. The expanded hematopoietic stem or stem and progenitor cell population is typically transferred to the differentiation cell culture medium following expansion. Optionally, the Notch ligand is inactivated or removed from the expanded HSPC cell population prior to the differentiation phase (e.g., by separation or dilution).

In some embodiments, the hematopoietic stem or stem and progenitor cells are cultured for expansion for 2, 3, 4, 5, 6, 7, 8, 9, 10, 11, 12, 13, 14, 15, 16, 17, 18, 19, 20, 21, 22, 23, 24, or 25 days or more; or, preferably, the hematopoietic stem or stem and progenitor cells are cultured for expansion for at least 10 days or from about 7 to about 14 days. In some embodiments, the hematopoietic stem or stem and progenitor cells are cultured for about 7 days, about 14 days, about 13 days or about 15 days. It should be noted that the duration of the expansion would be determined by the ability to achieve either the desired or maximal cell numbers while retaining stem and progenitor cell immunophenotypic qualities/characteristics needed for the generation of the desired cell preparation. Expansion would be stopped if cell proliferation stopped, viability declined, or if the cell began to substantially lose the qualities/characteristics of HSPCs.

An exemplary ex vivo culture condition for expanding the hematopoietic stem or stem and progenitor cells includes culturing the cells for 7 to 14 days in the presence of fibronectin fragments and the extracellular domain of a Delta protein fused to the Fc domain of human IgG (Delta1$^{ext\text{-}IgG}$) in a serum free, expansion culture medium supplemented with the following human growth factors: SCF, Flt-3L, TPO, IL-6 and IL-3. Preferably, the foregoing growth factors are present at the following concentrations: 50-300 ng/ml SCF, 50-300 ng/ml Flt-3L, 50-100 ng/ml TPO, 50-100 ng/ml IL-6 and 10 ng/ml IL-3. In more specific embodiments, 300 ng/ml SCF, 300 ng/ml of Flt-3L, 100 ng/ml TPO, 100 ng/ml IL-6 and 10 ng/ml IL-3, or 50 ng/ml SCF, 50 ng/ml of Flt-3L, 50 ng/ml TPO, 50 ng/ml IL-6 and 10 ng/ml IL-3, are used. In a more preferred embodiment, the expansion culture medium (e.g., STEMSPAN™ Serum Free Expansion Medium (StemCell Technologies, Vancouver, British Columbia)) contains, or consists of, 10 ng/ml recombinant human Interleukin-3 (rhIL-3), 50 ng/ml rhIL-6, 50 ng/ml rhTPO, 50 ng/ml rhFlt-3L, 50 ng/ml and rhSCF. In another more preferred embodiment, the expansion culture medium (e.g., StemSpan™ Serum Free Expansion Medium II (SFEM II, StemCell Technologies, Vancouver, British Columbia)) contains, or consists of, rhSCF, rhFlt-3L, rhTPO, rhIL-6 (each at 50 ng/ml final concentration), and rhIL-3 (at 10 ng/ml final concentration).

In some embodiments, the Notch ligand is DXI (Delta 1$^{ext\text{-}IgG}$) and the expansion phase is performed as follows: Delta1$^{ext\text{-}IgG}$ (DXI) is immobilized on the surface of the cell culture dish(es). In a specific embodiment, the cell culture dishes are coated overnight at 4° C. (or for a minimum of 2 hours at 37° C.) with 2.5 μg/ml Delta1$^{ext\text{-}IgG}$ and 5 μg/ml RetroNectin® (a recombinant human fibronectin fragment also referred to as rFN-CH-296) in phosphate buffered saline, before adding the enriched hematopoietic stem or stem and progenitor cells. Preferably the expansion culture medium (e.g., STEMSPAN™ Serum Free Expansion Medium or StemSpan™ Serum Free Expansion Medium II (StemCell Technologies, Vancouver, British Columbia)) is supplemented with 10 ng/ml rhIL-3, 50 ng/ml rhIL-6, 50 ng/ml rhTPO, 50 ng/ml rhFlt-3L, and 50 ng/ml rhSCF.

In some embodiments, the expansion culture medium does not include growth factors other than rhIL-3, rhIL-6, rhTPO, rhFlt-3L, and rhSCF. In some embodiments, the expansion culture medium does not contain the following added growth factors or cytokines: IL-7, GM-CSF, G-CSF, LIF, MIP-1a, IL-2 or IL-15. In some embodiments, the expansion culture medium does not contain the following added growth factors or cytokines: IL-7, GM-CSF, G-CSF, LIF, MIP-1a, or IL-2. In some embodiments, the expansion culture medium does not contain an aryl hydrocarbon receptor antagonist, such as those described in U.S. Pat. No. 9,175,266 or US Patent Application Publication No. 2018/0237749; both incorporated herein by reference.

After expansion of the hematopoietic stem or stem and progenitor cells, the total number of cells and viable CD34$^+$ cells can be determined. For example, at Day 14 during expansion, a sample can be taken for determination of the total viable nucleated cell count. In addition, the total number of CD34$^+$ cells can be determined by multi-parameter flow cytometry, and thus the percentage of CD34$^+$ cells in the sample determined. Typically, cultures that have not resulted in at least a 10-fold increase in the absolute number of CD34$^+$ cells are discontinued. In a preferred embodiment, those populations containing less than 50 million CD34$^+$ viable cells can be discarded.

Viability can be determined by any method known in the art, for example, by trypan blue exclusion or 7-AAD exclusion. The percentage of viable CD34$^+$ cells can be assessed by flow cytometry and use of a stain that is excluded by viable cells. The percentage of viable CD34$^+$ cells=the number of CD34$^+$ cells that exclude 7-AAD (or other appropriate stain) in an aliquot of the sample divided by the total cell number (TNC; both viable and non-viable) of the aliquot. Viable CD34$^+$ cells in the sample can be calculated as follows: Viable CD34$^+$ cells=TNC of sample x % viable CD34$^+$ cells in the sample. The proportional increase during enrichment or expansion in viable CD34$^+$ cells can be calculated as follows: Total Viable CD34$^+$ cells Post-culture/ Total Viable CD34$^+$ cells Pre-culture.

In some embodiments, the hematopoietic stem or stem and progenitor cells are expanded by culturing the cells ex vivo in an expansion culture medium and in the presence of an agonist of Notch function and one or more growth factors or cytokines for a given period of time, as described above. An agonist of Notch function, also referred to as Notch agonist or Notch ligand, is an agent that promotes, i.e., causes or increases, activation of Notch pathway function. As used herein, "Notch function" means a function mediated by the Notch signaling (signal transduction) pathway, including but not limited to nuclear translocation of the intracellular domain of Notch, nuclear translocation of RBP-Jκ or its *Drosophila* homolog Suppressor of Hairless; activation of bHLH genes of the Enhancer of Split complex, e.g., Mastermind; activation of the HES-1 gene or the KBF2 (also called CBF1) gene; inhibition of *Drosophila* neuroblast segregation; and binding of Notch to Delta, Jagged/ Serrate, Fringe, Deltex or RBP-Jκ/Suppressor of Hairless, or homologs or analogs thereof. See generally the review article by Kopan et al., *Cell* 137:216-233, 2009 for a discussion of the Notch signal transduction pathway and its effects upon activation; see also Jarriault et al., *Mol. Cell. Biol.* 18:7423-7431, 1998.

Notch activation is carried out by exposing a cell to a Notch agonist. The agonist of Notch function can be but is not limited to a molecule immobilized on a solid phase. Exemplary Notch agonists are the extracellular binding ligands Delta and Serrate which bind to the extracellular domain of Notch and activate Notch signal transduction, or a fragment of Delta or Serrate that binds to the extracellular domain of Notch and activates Notch signal transduction. Nucleic acid and amino acid sequences of Delta and Serrate have been isolated from several species, including human, are known in the art, and are disclosed in International Patent Publication Nos. WO 93/12141, WO 96/27610, WO 97/01571, and Gray et al., *Am. J. Path.* 154:785-794, 1999. (All incorporated herein by reference in their entirety).

In a preferred embodiment, the Notch agonist is an immobilized fragment of a Delta or Serrate protein consisting of the extracellular domain of the protein fused to a myc epitope tag (Delta$^{ext-myc}$ or Serrate$^{ext-myc}$, respectively), or an immobilized fragment of a Delta or Serrate protein consisting of the extracellular domain of the protein fused to the Fc portion of IgG (Delta$^{ext-IgG}$ or Serrate$^{ext-IgG}$, respectively). Notch agonists include but are not limited to Notch proteins and analogs and derivatives (including fragments) thereof; proteins that are other elements of the Notch pathway and analogs and derivatives (including fragments) thereof; antibodies thereto and fragments or other derivatives of such antibodies containing the binding region thereof; nucleic acids encoding the proteins and derivatives or analogs; as well as proteins and derivatives and analogs thereof which bind to or otherwise interact with Notch proteins or other proteins in the Notch pathway such that Notch pathway activity is promoted. Such agonists include but are not limited to Notch proteins and derivatives thereof comprising the intracellular domain, Notch nucleic acids encoding the foregoing, and proteins comprising the Notch-interacting domain of Notch ligands (e.g., the extracellular domain of Delta or Serrate). Other agonists include but are not limited to RBPJκ/Suppressor of Hairless or Deltex. Fringe can be used to enhance Notch activity, for example in conjunction with Delta protein. These proteins, fragments and derivatives thereof can be recombinantly expressed and isolated or can be chemically synthesized.

In yet another embodiment, the agonist of Notch is a peptidomimetic or peptide analog or organic molecule that binds to a member of the Notch signaling pathway. Such an agonist can be identified by binding assays selected from those known in the art, for example the cell aggregation assays described in Rebay et al., *Cell* 67:687-699, 1991 and in International Patent Publication No. WO 92/19734. (Both incorporated herein by reference).

In a preferred embodiment the agonist is a protein consisting of at least a fragment of a protein encoded by a Notch-interacting gene which mediates binding to a Notch protein or a fragment of Notch, which fragment of Notch contains the region of Notch responsible for binding to the agonist protein, e.g., epidermal growth factor-like repeats 11 and 12 of Notch. Notch interacting genes, as used herein, shall mean the genes Notch, Delta, Serrate, RBPJκ, Suppressor of Hairless and Deltex, as well as other members of the Delta/Serrate family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g., in *Drosophila*). Exemplary fragments of Notch-binding proteins containing the region responsible for binding to Notch are described in U.S. Pat. Nos. 5,648,464; 5,849,869; and 5,856, 441. (All incorporated herein by reference).

The Notch agonists utilized by the methods described herein can be obtained commercially, produced by recombinant expression, or chemically synthesized.

In a specific embodiment, exposure of the cells to a Notch agonist is not done by incubation with other cells recombinantly expressing a Notch ligand on the cell surface (e.g., a feeder layer), but rather is by exposure to a cell-free Notch ligand, e.g., incubation with a cell-free ligand of Notch, which ligand is immobilized on the surface of a solid phase, e.g., immobilized on the surface of a tissue culture dish.

In specific embodiments, Notch activity is promoted by the binding of a Notch ligand(s) (e.g., Delta, Serrate) to the extracellular portion of the Notch receptor. Notch signaling appears to be triggered by the physical interaction between the extracellular domains of Notch and its ligands that are either membrane-bound on adjacent cells or immobilized on a solid surface. Full length ligands are agonists of Notch, as their expression on one cell triggers the activation of the pathway in the neighboring cell which expresses the Notch receptor. Soluble truncated Delta or Serrate molecules, comprising the extracellular domains of the proteins or Notch-binding portions thereof, that have been immobilized on a solid surface, such as a tissue culture plate, are particularly preferred Notch pathway agonists. Such soluble proteins can be immobilized on a solid surface by an antibody or interacting protein, for example an antibody directed to an epitope tag with which Delta or Serrate is expressed as a fusion protein (e.g., a myc epitope tag, which is recognized by the antibody 9E10) or a protein which interacts with an epitope tag with which Delta or Serrate is expressed as a fusion protein (e.g., an immunoglobulin epitope tag, which is bound by Protein A).

In another specific embodiment, and as described in U.S. Pat. No. 5,780,300 to Artavanis-Tsakonas et al., Notch agonists include reagents that promote or activate cellular processes that mediate the maturation or processing steps required for the activation of Notch or a member of the Notch signaling pathway, such as the furin-like convertase required for Notch processing, Kuzbanian, the metalloprotease-disintegrin (ADAM) thought to be required for the activation of the Notch pathway upstream or parallel to Notch (Schlondorff and Blobel, *J. Cell Sci.* 112:3603-3617, 1999), or, more generally, cellular trafficking and processing proteins such as the rab family of GTPases required for movement between cellular compartments (for a review on Rab GTPases, see Olkkonen and Stenmark, *Int. Rev. Cytol.* 176:1-185, 1997). The agonist can be any molecule that increases the activity of one of the above processes, such as a nucleic acid encoding a furin, Kuzbanian or rab protein, or a fragment or derivative or dominant active mutant thereof, or a peptidomimetic or peptide analog or organic molecule that binds to and activates the function of the above proteins.

U.S. Pat. No. 5,780,300 further discloses classes of Notch agonist molecules (and methods of their identification) which can be used to activate the Notch pathway, for example molecules that trigger the dissociation of the Notch ankyrin repeats with RBP-Jκ, thereby promoting the translocation of RBP-Jκ from the cytoplasm to the nucleus.

In some preferred embodiments, an expansion method including DXI is used. The Notch agonist DXI is an immobilized fragment of a Delta consisting of the extracellular domain of the protein fused to the Fc portion of IgG (Delta$^{ext-IgG}$ or DXI), as described in U.S. Pat. No. 7,399, 633 or an immobilized Notch-1 or Notch-2 specific antibody, as described in U.S. Pat. No. 10,208,286. Preferably, Delta1$^{ext-IgG}$ is immobilized on the surface of the cell culture dishes. In a specific embodiment, the cell culture dishes are coated overnight at 4° C. (or for a minimum of 2 hours at 37° C.) with 2.5 µg/ml Delta1$^{ext-IgG}$ and 5 µg/ml RetroNectin® (a recombinant human fibronectin fragment also referred to as rFN-CH-296) in phosphate buffered saline, before adding the hematopoietic stem or stem and progenitor cells. Preferably, the cell culture medium is a serum free hematopoietic stem cell culture medium (e.g., STEMSPAN™ Serum Free Expansion Medium or STEMSPAN™ Serum Free Expansion Medium II (StemCell Technologies, Vancouver, British Columbia)) supplemented with 10 ng/ml rhIL-3, 50 ng/ml rhIL-6, 50 ng/ml rhTPO, 50 ng/ml rhFlt-3L, and 50 ng/ml rhSCF. The hematopoietic stem or stem and progenitor cells are cultured in this embodiment for 7 to 14 days.

In certain embodiments, the increase in the number of CD34$^+$ cells as a percentage of cells in the expanded HSPCs, relative to the cell population prior to the enrichment procedure, is at least 25-, 50-, 75-, 100-, 150-, 200-, 250-, 300-, 350-, 400- or at least 350-fold, and preferably is 100-200 fold or 100-400 fold.

Once the expanded hematopoietic stem cells or stem and progenitor cells are obtained, the expanded stem or stem and progenitor cell population (expanded HSPCs) can be collected and cryopreserved or can be used directly in the second phase to produce the NK cell composition and/or preparation.

The NK cell composition and/or preparation results from differentiation of the expanded HSPCs in a second phase of the process. In the differentiation phase, the HSPCs are cultured in a differentiation culture medium that contains an amount of one or more cytokine(s) effective to induce and direct HSPC differentiation into NK cells.

In some embodiments, the cytokines in the differentiation culture medium are IL-2 and IL-15. In some embodiments, the only cytokines in the differentiation culture medium are IL-2 and IL-15. In some embodiments, the amount of IL-2 and IL-15 in the differentiation culture medium is from about 25 U/ml to about 100 U/ml for IL-2 and from about 25 ng/ml to about 50 ng/ml for IL-15. In some embodiments, the amount of IL-2 and IL-15 in the differentiation culture medium is about 50 U/ml for IL-2 and about 40 ng/ml for IL-15. In some embodiments, the cytokines in the differentiation culture comprise IL-2 and IL-15, wherein other cytokines, such as Flt-3L, FGF-2, IL-6, IL-7, IL-12, IL-3, GM-CSF, G-CSF, LIF, MIP-1α, SCF, IL-21, IL-18, and 4-1BBL (4-1BB ligand), are not added to the differentiation culture medium. In some embodiments, the differentiation culture medium does not contain added cytokines other than IL-2 and IL-15.

In an embodiment, the differentiation culture medium further includes a supplement, such as, for example, human serum or plasma, or another proteinaceous fluid that provides a broad spectrum of macromolecules, carrier proteins for lipoid substances and trace elements, attachment and spreading factors, hormones, and growth factors that promote cell growth and health. In very early cell culture methods for hematopoietic stem cells fetal bovine serum (FBS) was used as this cell culture supplement; however, bovine proteins are not acceptable in human pharmaceutical products. As such, various human biological fluids have been used including, for example, human serum, plasma, fresh frozen plasma, platelet lysate, and the like. In certain embodiments of the present methods human AB serum has been used. In a particularly preferred embodiment platelet lysate has been used. In some embodiments, between about 2.5% to about 10% human platelet lysate is included in the differentiation medium. For example, the differentiation medium can comprise about 3%, about 4%, about 5%, about 6%, about 7%, about 8%, about 9%, or more than about 9% of human platelet lysate. In embodiments comprising human platelet lysate, the human platelet lysate is produced from human platelets (e.g. from platelet-rich plasma (PRP), expired platelets collected via apheresis, and the like) by processes such as, but not limited to, freezing and thawing cycles (e.g. between 1 and 6 cycles), sonication, solvent/detergent treatment, or activation with calcium or thrombin. Human platelets can be derived from autologous collections and/or allogeneic collections from multiple different individuals. The human platelet lysates can be used with or without regard to factors which affect the composition and bioactivity, such as, but not limited to, plasma content, growth factor content, donor age and gender, platelet counts, production process, heparin or anticoagulant presence, fibrinogen-depletion, cellular component presence, metabolite presence, blood group, storage conditions (e.g. duration and/or temperature), treatment to reduce/inactivate pathogens/viruses, and the like. (Bieback, K., et al., *Transfusion* 59:3448-3460, 2019). Additionally, the human platelet lysate can be an acceptable composition procured from a commercial source which has treated the composition as described, or by any other method of producing a commercially acceptable human platelet lysate composition. In some embodiments fresh frozen plasma, or about 2.5% to about 10% human AB serum can be included in the differentiation medium instead of the platelet lysate. In some embodiments, the differentiation culture medium does not include a feeder layer or feeder cells. In some embodiments, the differentiation culture medium is free of fetal bovine serum (FBS), fetal calf serum (FCS), and other animal sourced products and does not include feeder cells or a feeder cell layer.

Although the methods disclosed herein typically and preferably do not use a feeder cell layer, the use of such a feeder cell layer does not alter the advantages of the methods described herein. As used herein, a "feeder cell layer," "feeder layer," or "feeder cells" refer to exogenous cells of one type that are co-cultured with cells of a second type (e.g., HSPCs), to provide an environment in which the cells of the second type can be maintained and differentiate or proliferate. Without being bound by any theory, feeder cells can provide, for example, peptides, polypeptides, electrical signals, organic molecules, nucleic acid molecules, growth factors, other factors (e.g., cytokines), and metabolic nutrients to the second type of cells.

In the preferred embodiments of the present methods, the NK cell composition and/or preparation does not contain exogenously added cells, such as exogenous antigen presenting cells (for example, dendritic cells). As used herein, an exogenous cell(s) refers to a cell(s) not derived from the expanded and/or differentiated HSPCs.

The HSPCs are cultured in vitro or ex vivo in the differentiation culture medium for a time period sufficient to produce the NK cell composition and/or preparation. In some embodiments, the time period for differentiation is from about 7 to 21 days, from about 7 to 14 days, from about 12 to 16 days, from about 14 to 16 days, from about 7 days or about 14 days. The time period selected can be dependent upon the temperature used when culturing, the concentration of the cytokines used and other factors.

The status of the differentiating NK cells can be monitored by flow cytometry and the determination of the development of CD56$^+$ cells by staining the cells with an anti-CD56 antibody.

The resulting NK cell composition and/or preparation can contain about 50% to about 80% CD56$^+$ cells and about 50% to about 20% endogenous CD56$^-$ cells. In some embodiments, the NK cell composition and/or preparation comprises from about 50% up to about 85% CD56$^+$ cells and about 50% to about 15% CD56$^-$, endogenous myeloid-derived cells, such as dendritic cells, macrophages, and granulocytes. In some embodiments, the NK cell composition and/or preparation comprises from about 55% up to about 65% CD56$^+$ cells and about 45% to about 35% CD56$^-$, endogenous myeloid-derived cells, such as dendritic cells, macrophages, and granulocytes. The CD56$^+$ cells are predominantly NK cells. In some embodiments, the NK cell composition and/or preparation comprises from about 70% up to about 85% CD56$^+$ cells and about 30% to about 15% CD56$^-$, endogenous myeloid-derived cells, such as dendritic cells, macrophages, and granulocytes. In addition to CD56, the CD56$^+$ cells express a high frequency of NKp30, NKp46, NKp44, NKG2A, and granzyme B; a moderate to high frequency of perforin and CD107a; a low to moderate frequency of NKG2D; and substantially no KIRs. In some embodiments the CD56$^+$ cells are KIR$^-$. (As used herein, "KIR$^-$" refers to KIR2DL1, KIR2DS1, KIR2DS3, KIR2DS5, KIR2DL2, KIR2DL3, KIR2DS2, KIR2DS4, KIR3DL1, and KIR3DS1.) CD16 is expressed at a low to moderate frequency. In some embodiments, the CD56$^-$ cells express a moderate to high frequency of granzyme B; a high frequency of CD107a, and a low frequency of perforin.

After the cells are cultured in the differentiation culture medium for a time sufficient to produce the NK cell composition and/or preparation, the resultant CD56$^+$ (mainly NK) cells in the population are typically immature but functional NK cells resembling, but distinct from, NK cells found naturally in the human body. In some embodiments, the CD56$^+$ (mainly NK) cells in the NK cell composition and/or preparation are not further differentiated prior to use or storage.

In a certain embodiment, it has been found that priming the HSPCs for NK cell differentiation with IL-15 during the expansion phase increases the number of CD56$^+$ cells obtained in the final NK cell composition and/or preparation. Typically, the IL-15 is added during the last about 4 to about 7 days of the expansion phase. Where the expansion phase is about 7 days, priming take place during the last about 4 days. The increase in the total number of CD56$^+$ cells using this method can be increased by up to 50% or more and even up to 58%, or more. The remaining steps of the expansion phase and the differentiation phase remain as described above. In this embodiment IL-15 can be added in an amount of about 40 ng/ml to about 100 ng/ml or more.

The NK cells that comprise the compositions and/or preparations produced by any of the above described methods may be genetically engineered to express a molecule or molecules of interest, such as, for example, a protein, nucleic acid, or carbohydrate. In some embodiments, the NK cells comprising the compositions and/or preparations is genetically engineered to express a protein of interest, such as a protein, polypeptide, or peptide (collectively referred to as a protein). In some embodiments, the protein is an antigen recognizing receptor, other cell surface protein(s), or an intracellular molecule. An NK cell of the composition and/or preparation can be genetically modified, prior to, or during the expansion phase and/or during or after the differentiation phase. In a typical embodiment, the NK cells are genetically engineered during the expansion phase. In some embodiments, the NK cells are genetically engineered during or subsequent to the differentiation phase.

The NK cells comprising the compositions and/or preparations can be genetically engineered to express an antigen recognizing receptor(s) that binds to an antigen of interest. In certain embodiments, the antigen recognizing receptor is a chimeric antigen receptor (CAR). In certain embodiments, the antigen recognizing receptor is a T-cell receptor (TCR). The antigen recognizing receptor can bind to, for example, a tumor specific or tumor associated antigen or a pathogen antigen.

In certain embodiments, the antigen recognizing receptor binds to a tumor associated or tumor specific antigen. Any suitable tumor associated or tumor specific antigen (e.g., an antigenic peptide) can be used in the embodiments described herein. Sources of antigen include, but are not limited to, proteins associated with cancer and/or leukemia (e.g., AML) (a tumor associated or tumor specific antigen). An antigen can be expressed as a peptide or as an intact protein or portion thereof. The intact protein or a portion thereof can be native or a variant thereof, such as a mutant form. Non-limiting examples of tumor antigens include carbonic anhydrase IX (CAIX), carcinoembryonic antigen (CEA), CD8, CD7, CD10, CD19, CD20, CD22, CD30, CD33, CLL1, CD34, CD38, CD41, CD44, CD49c, CD49f, CD56, CD66c, CD73, CD74, CD104, CD133, CD138, CD123, CD142, CD44V6, an antigen of a cytomegalovirus (CMV) infected cell (e.g., a cell surface antigen), cutaneous lymphocyte-associated antigen (CLA; a specialized glycoform of P-selectin glycoprotein ligand-1 (PSGL-1)), epithelial glycoprotein-2 (EGP-2), epithelial glycoprotein-40 (EGP-40), epithelial cell adhesion molecule (EpCAM), receptor tyrosine-protein kinases erb-B2,3,4 (erb-B2,3,4), folate-binding protein (1-BP), fetal acetylcholine receptor (AChR), folate receptor-alpha, Ganglioside G2 (GD2), Ganglioside G3 (GD3), human Epidermal Growth Factor Receptor 2 (HER2), human telomerase reverse transcriptase (hTERT), Interleukin-13 receptor subunit alpha-2 (IL-13Ralpha2), kappa-light chain, kinase insert domain receptor (KDR), Lewis Y (LeY), L1 cell adhesion molecule (L1CAM), melanoma antigen family A, 1 (MAGE-A1), Mucin 16 (MUC16), Mucin 1 (MUC1), Mesothelin (MSLN), ERBB2, MAGEA3, p53, MART1, GP100, Proteinase3 (PR1), Tyrosinase, Survivin, hTERT, EphA2, an NKG2D ligand, cancer-testis antigen NY-ES0-1, oncofetal antigen (h5T4), prostate stem cell antigen (PSCA), prostate-specific membrane antigen (PSMA), ROR1, tetraspanin 8 (TSPAN8), tumor-associated glycoprotein 72 (TAG-72), vascular endothelial growth factor R2 (VEGF-R2), Wilms tumor protein (WT-1), cytokine receptor-like factor 2 (CRLF2), BCMA, GPC3, NKCS1, EGF1R, EGFR-VIII, and ERBB.

In some embodiments, the tumor antigen is CD19, ROR1, Her2, PSMA, PSCA, mesothelin (MSLN), or CD20. In some embodiments, the tumor antigen is CD19, CD20, CD33, MSLN, or cytokine receptor-like factor 2 (CRLF2), which are expressed on leukemias or lymphomas.

In some embodiments, the antigen is associated with or specific to leukemia, such as acute lymphocytic leukemia (ALL), acute myelogenous leukemia (AML), chronic lymphocytic leukemia (CLL), or chronic myelogenous leukemia (CML). In a preferred embodiment, the target is associated with or specific to AML. In a preferred embodiment, the antigen is associated with or specific to AML. The antigen can be, but is not limited to, a protein, non-protein, neoantigen, post-translationally modified antigen, peptide-MHC antigen, and/or over-expressed antigen.

In certain embodiments, the AML specific or associated antigen is AML1-ETO, DEK-CAN, promyelocytic leukemia-retinoic acid receptor α (PML-RARα), Fms-like tyrosine kinase 3-internal tandem duplication (Flt3-ITD), Fms-like tyrosine kinase 3 (Flt3), nucleophosmin 1 (NPM1), Aurora A kinase (AurA), B-cell lymphoma-2 (Bcl-2), Bax inhibitor I (B1-1), B lymphoma Mo-MLV insertion region 1 homolog (BMI1), BRCA1-associated protein (BRAP), chronic myeloid leukemia (CML) 28 (CML28), CML66, Cyclin B1, Cyclin E, cytochrome P450 1B1 (CYP1B1), ETO/MTG8 (myeloid translocation gene on 8q), carbonic anhydrase IX (CAIX), G250/CAIX, homeobox A9 (HOXA9), human telomerase reverse transcriptase (hTERT), myeloid cell leukemia sequence 1 (Mcl-1), Mesothelin (MSLN), minor histocompatibility antigen (mHAg) (e.g., lymphoid-restricted histocompatibility antigen 1

(LRH-1)), Myeloperoxidase, M-phase phosphoprotein 11 (MPP11), mucin 1 (MUC1), nucleolar and spindle-associated protein 1 (NuSAP1), oncofetal antigen-immature laminin receptor protein (OFA/iLRP), Proteinase 3, regulator of G protein signaling 5 (RGSS), receptor for hyaluronic acid-mediated motility (RHAMM), synovial sarcoma X breakpoint 2-interacting protein (SSX2IP), Survivin, Wilms' tumor 1 protein (WT1), Cyclin A1, melanoma antigen (MAGE), Per ARNT Sim Domain containing 1 (PASD1), preferentially expressed antigen in melanoma (PRAME), renal antigen-1 (RAGE-1), heat-shock DnaJ protein homolog 2 (HSJ2), Myc-associated zinc-finger protein (MAZ), renal cell cancer antigen (NY-REN60), particularly interesting new Cys-His protein (PINCH), recombination signal-binding protein 1 for J-κ (RBPJk), Syntaxin, methyl-lysophosphatidic acid (mLPA), α-galactosylceramide (a-GalCer), Lewis Y antigen (LeY), isocitrate dehydrogenase 1 (IDH1(R132)), isocitrate dehydrogenase 2 (IDH2 (R140)), nuclophosmin 1 mutant (NPM1$^{mut}$), Notch signaling molecule isoform (Notch variants), hyaluronan receptor isoform (CD44v6), phosphorylated peptides, protein tyrosine phosphatase type Iva member 3 (PRL3), proteinase 3 peptide HLA-A2-restricted (PR1/HLA-A2), 20 Wilms' tumor peptides HLA-A2-restricted (WT1/HLA-A2), interleukin 12 receptor beta 1 (IL12RB1), and/or member of immunoglobulin superfamily (CD96). (Goswami et al., Curr. Drug Targets 18:296-303, 2017).

In certain embodiments, the antigen recognizing receptor binds to a pathogen antigen, e.g., for use in treating and/or preventing a pathogen infection or other infectious disease, for example, in an immunocompromised subject. In certain embodiments, pathogen includes a virus, bacteria, fungi, parasite or protozoa capable of causing disease.

Non-limiting examples of viruses include Retroviridae (e.g., human immunodeficiency viruses, such as HIV-1 and other isolates, such as HIV-LP; Picornaviridae (e.g., polio viruses, hepatitis A virus, enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses, zika virus); Coronoviridae (e.g., coronaviruses, including SARS-CoV and SARS-CoV-2); Rhabdoviridae (e.g., vesicular stomatitis viruses, rabies viruses); Filoviridae (e.g., Ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Naira viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

In certain embodiments, the pathogen antigen is a viral antigen present in Cytomegalovirus (CMV), Epstein Barr Virus (EBV), Human Immunodeficiency Virus (HIV), Herpes simplex virus (HSV1 or HSV2), Hepatitis virus (A, B, or C), zika virus, influenza virus, or coronavirus (SARS- CoV or SARS-CoV-2). In a preferred embodiment the viral antigen is specific to or associated with HIV, HSV 1 or 2, zika virus, Hepatitis A, B, or C, SARS-CoV, or SARS-CoV-2.

Non-limiting examples of bacteria include *Pasteurella, Staphylococci, Streptococcus, Escherichia coli, Pseudomonas species*, and *Salmonella* species. Specific examples of infectious bacteria include, but are not limited to, *Helicobacter pyloris, Borelia burgdorferi, Legionella pneumophilia, Mycobacteria* sps (e.g., *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A Streptococci), *Streptococcus agalactiae* (Group B Streptococci), Streptococci (viridans group), *Streptococcus faecalis, Streptococcus bovis*, Streptococci (anaerobic sps.), *Streptococcus pneumoniae*, pathogenic *Campylobacter* sp., *Enterococcus* sp., *Haemophilus influenzae, Bacillus antracis, Corynebacterium diphtherias, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelli*.

In certain embodiments, the antigen recognizing receptor is a TCR. A TCR is a disulfide-linked heterodimeric protein consisting of two variable chains expressed as part of a complex with the invariant CD3 chain molecules. A TCR is found on the surface of a T cell and is responsible for recognizing antigens as peptides bound to major histocompatibility complex (MHC) molecules. In certain embodiments, a TCR comprises an alpha chain and a beta chain (encoded by TRA and TRB, respectively). In certain embodiments, a TCR comprises a gamma chain and a delta chain (encoded by TRG and TRD, respectively).

Each chain of a TCR is composed of two extracellular domains: a variable (V) region and a constant (C) region. The constant region is proximal to the cell membrane, followed by a transmembrane region and a short cytoplasmic tail. The variable region binds to the peptide/MHC complex. The variable domain of both chains each have three complementarity determining regions (CDRs).

In certain embodiments, a TCR can form a receptor complex with three dimeric signaling modules: CD3delta/epsilon, CD3gamma/epsilon, and CD247zeta/zeta, or zeta/eta. When a TCR complex engages with its antigen and MHC (peptide/MHC), the T cell expressing the TCR complex is activated.

In certain embodiments, NK cells comprising the described compositions and/or preparations are genetically modified to express a recombinant TCR. In certain embodiments, the TCR is a non-naturally occurring TCR. In certain embodiments, the TCR differs from any naturally occurring TCR by at least one amino acid residue. In certain embodiments, the TCR differs from any naturally occurring TCR by at least 2, 3, 4, 5, 6, 7, 8, 9, 10, 11, 12, 13, 14, 15, 20, 25, 30, 40, 50, 60, 70, 80, 90, 100 or more amino acid residues. In certain embodiments, the TCR is modified from a naturally occurring TCR by at least one amino acid residue. In certain embodiments, the TCR is modified from a naturally occurring TCR by at least 2, 3, 4, 5, 6, 7, 8, 9, 10, 11, 12, 13, 14, 15, 20, 25, 30, 40, 50, 60, 70, 80, 90, 100 or more amino acid residues.

In some embodiments, the TCR specifically binds to an antigen of cytomegalovirus (CMV), adenovirus, human herpesvirus 6 (HHV6), BK virus, Epstein-Barr virus (EBV), HIV, or SARS (SARS-CoV or SARS-CoV-2).

In certain embodiments, the antigen recognizing receptor is a chimeric antigen receptor (CAR). A CAR is an engineered receptor which confers a specificity of interest onto a cell, such as cells of the NK cell compositions and/or preparations described herein. CARs can be used to graft the specificity of a monoclonal antibody onto an NK cell of the NK cell compositions and/or preparations described herein, with transfer of their coding sequence facilitated by, for example, a retroviral vector.

Expanded HSPCs, as described previously, can be differentiated, as described previously, to form CAR-HSPCs and CAR-NK cells. The CAR-HSPCs comprise HSPCs engineered to express the CAR receptor, and which express the engineered CAR receptor. The CAR-NK cells comprise NK cells engineered to express the CAR receptor, and which express the engineered CAR receptor.

Generations of CARs include the following. "First generation" CARs are typically composed of an extracellular antigen binding domain (e.g., a single-chain variable fragment (scFv)) fused to a transmembrane domain, fused to cytoplasmic/intracellular signaling domain of the T cell receptor chain. "First generation" CARs typically have the intracellular signaling domain from the CD3zeta-chain, which is the primary transmitter of signals from endogenous TCRs. "First generation" CARs can provide de novo antigen recognition and cause activation of cells through their CD3zeta chain signaling domain in a single fusion molecule, independent of HLA-mediated antigen presentation. "Second generation" CARs add intracellular signaling domains from various co-stimulatory molecules (e.g., CD28, 4-1BB, ICOS, OX40, or 2B4) to the cytoplasmic tail of the CAR to provide additional signals to the cell. "Second generation" CARs comprise those that provide both co-stimulation (e.g., CD28, 4-1BB or 2B4) and activation (CD3zeta). Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL). "Third generation" CARs comprise those that provide multiple co-stimulation (e.g., CD28 and 4-1BB) and activation (CD3zeta).

In some embodiments, a co-stimulatory domain can be CD27, CD28, 4-1BB (CD137), OX40 (CD134), CD30, CD40, lymphocyte function-associated antigen-1 (LFA-1), CD2, CD7, LIGHT, NKG2C, and/or B7-H3 costimulatory domains. In some embodiments, a co-stimulatory domain can be CD27, CD28, 4-1BB (CD137), OX40 (CD134), DAP10, DAP12, ICOS, and/or 2B4. In some embodiments, a co-stimulatory domain can be CD27, CD28, 4-1BB, 2B4, DAP10, DAP12, OX40, CD30, CD40, lymphocyte function-associated antigen-1 (LFA-1), CD2, CD7, LIGHT, NKG2C, and/or B7-H3 costimulatory domains. In some embodiments, an intracellular signaling domain can be a domain of CD3zeta, CD28 and/or 4-1BB.

In certain non-limiting embodiments, the extracellular antigen-binding domain of the CAR (embodied, for example, as an scFv or an analog thereof) binds to an antigen with a dissociation constant ($K_d$) of about $2 \times 10^{-7}$ M or less. In certain embodiments, the $K_d$ is about $1 \times 10^{-7}$ M or less, about $5 \times 10^{-8}$ M or less, about $1 \times 10^{-8}$ M or less, about $5 \times 10^{-9}$ M or less, or about $1 \times 10^{-9}$ M or less.

Binding of an extracellular antigen-binding domain (for example, an scFv or an analog thereof) of an antigen-targeted CAR can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or an scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March 1986, which is incorporated by reference herein). The radioactive isotope can be detected by such means as the use of a gamma counter or a scintillation counter or by autoradiography. In certain embodiments, the extracellular antigen-binding domain of the CAR is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet).

A CAR can comprise an extracellular antigen-binding domain, a transmembrane domain and an intracellular signaling domain, wherein the extracellular antigen-binding domain specifically binds to an antigen, e.g., a tumor antigen or a pathogen antigen, including for example a viral or bacterial antigen.

In certain embodiments, the extracellular antigen-binding domain specifically binds to an antigen. In certain embodiments, the extracellular antigen-binding domain is an scFv. In certain embodiments, the scFv is a human scFv. In certain embodiments, the scFv is a humanized scFv. In certain embodiments, the extracellular antigen-binding domain is a Fab, which is optionally crosslinked. In certain embodiments, the extracellular binding domain is a F(ab')₂. In certain embodiments, any of the foregoing molecules may be comprised in a fusion protein with a heterologous sequence to form the extracellular antigen-binding domain. In certain embodiments, the scFv is identified by screening scFv phage library with an antigen-Fc fusion protein. In certain embodiments, the antigen is a tumor antigen. In certain embodiments, the antigen is a pathogen antigen, including for example, a viral or a bacterial antigen.

In certain embodiments, the extracellular binding domain is an scFv that specifically binds to CD19, such as an scFv derived from the FMC63 antibody or 4G7 antibody. In some embodiments, the scFv comprises the CDRs of the FMC63 antibody: a CDRL1 sequence of RASQDISKYLN (SEQ ID NO:1), a CDRL2 sequence of SRLHSGV (SEQ ID NO:2), a CDRL3 sequence of GNTLPYTFG (SEQ ID NO:3), a CDRH1 sequence of DYGVS (SEQ ID NO:4), a CDRH2 sequence of VTWGSETTYYNSALKS (SEQ ID NO:5), and a CDRH3 sequence of YAMDYWG (SEQ ID NO:6); or a CDRL1 sequence of RASQDISKYLN (SEQ ID NO:1), a CDRL2 sequence of SRLHSGV (SEQ ID NO:2), a CDRL3 sequence of GNTLPYTFG (SEQ ID NO:3), a CDRH1 sequence of DYGVS (SEQ ID NO:4), a CDRH2 sequence of DNSKSQ (SEQ ID NO:63), and a CDRH3 sequence of YAMDYWG (SEQ ID NO:6). In some embodiments, an extracellular binding domain is an scFv derived from or comprising the heavy and light chain variable regions of antibody FMC63. The heavy and light chain variable regions of antibody FMC63 are shown in SEQ ID NO:64 and SEQ ID NO:65, respectively.

```
FMC63 heavy chain variable region
                                    SEQ ID NO: 64
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS

FMC63 light chain variable region
                                    SEQ ID NO: 65
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIT
```

In some embodiments, an scFV comprises the heavy and light chain CDRs of the CD19 monoclonal antibody 4G7, as set forth in SEQ ID NO:25 and SEQ ID NO:26 or SEQ ID NO:27. In some embodiments, the extracellular antigen binding comprises the heavy and light chain variable region CDRs set forth in SEQ ID NO:25 and 26, or in SEQ NO:25 and 27. In some embodiments, an scFV is derived from the CD19 monoclonal antibody 4G7, preferably comprises a part of the binding domains of CD19 monoclonal antibody 4G7, portions of variable region of the CD19 monoclonal antibody 4G7 immunoglobulin gamma 1 heavy chain (SEQ ID NO:25) and the variable fragments of the CD19 monoclonal antibody 4G7 immunoglobulin kappa light chain (SEQ ID NO:26 or SEQ ID NO:27) linked together by a flexible linker. In a particular embodiment, the flexible linker has the amino acid sequence set forth in SEQ ID NO:28. In some embodiments, the extracellular antigen binding comprises the heavy and light chain variable region CDRs set forth in SEQ ID NO:25 and SEQ ID NO:26, or in SEQ NO:25 and SEQ ID NO:27.

```
anti human CD 19 monoclonal antibody
4G7 heavy chain variable region:
                                    SEQ ID NO: 25
EVQLQQSGPELIKPGASVKMSCKASGYTFTSYVMHWVKQKPGQGLEWIGY

1NPYNDGTKYNEKFKGKATLTSDKSSSTAYMELSSLTSEDSAVYYCARGT

YYYGSRVFDYWGQGTTLTVSS anti-human CD19 monoclonal antibody 4G7
immunoglobulin kappa light chain variable region:
                                    SEQ ID NO: 26
DIVMTQAAPSIPVTPGESVSISCRSSKSLLNSNGNTYLYWFLQRPGQSPQ

LLIYRMSNLASGVPDRFSGSGSGTAFTLRISRVEAEDVGVYYCMQHLEYP

FTFGAGTKLELKRAD anti-human CD19 monoclonal antibody
4G7 immunoglobulin kappa light chain variable
region:
                                    SEQ ID NO: 27
DIVMTQAAPSIPVTPGESVSISCRSSKSLLNSNGNTYLYWFLQRPGQSPQ

LLIYRMSNLASGVPDRFSGSGSGTAFTLRISRVEAEDVGVYYCMQHLEYP

FTFGAGTKLELKRSDP flexible linker:
                                    SEQ ID NO: 28
GGGGSGGGGSGGGGS
```

In some embodiments, an scFV is derived from a CLA (cutaneous lymphocyte antigen) monoclonal antibody and comprises the heavy and light chain variable region of the CLA monoclonal antibody set forth in SEQ ID NO:29 and SEQ ID NO:30, respectively (see US Patent Application Publication No. 2019/0209611; incorporated herein by reference). In some embodiments, the extracellular antigen binding domain comprises the heavy and light chain variable region CDRs set forth in SEQ ID NO:29 and SEQ ID NO:30.

```
CLA VH (heavy chain variable region)
                                    SEQ ID NO: 29
EVQLVESGGGLVQPGNSLKLSCSASGFTFSSYGMHWIRQAPGEGLDWVAY

ISSSSGTVYADAVKARFTISRDNAKNTLYLQLNSLKSEDTAIYYCARAQN

WDLFDYWGQGVMVTVSS

CLA VL (light chain variable region)
                                    SEQ ID NO: 30
QIMLTQQAESLWISPGERVSITCRASQSLLYTDGKHYLSWYQQKPGQTTK

ALIYHASVRTDGVPTRFIGSGSGTEFTLSIEHVQPEDFAIYYCLQTLKSP

FTFGSGTKLEIK
```

In some embodiments, an scFV is derived from a CD142 monoclonal antibody and comprises the heavy and light chain variable region of the CD142 monoclonal antibody set forth in SEQ ID NOs:31 and 32, respectively (see US Patent Application Publication No. 2019/0209611, incorporated herein by reference). In some embodiments, the extracellular antigen binding domain comprises the heavy and light chain variable region CDRs set forth in SEQ ID NO:31 and SEQ ID NO:32.

```
CD142 VH (heavy chain variable region)
                                    SEQ ID NO: 31
QVQLKQSGPGLVQPSQSLSITCTVSGFSLSNYGVHWVRQSPGKGLEWLGV

IWSGGSTDYNVAFISRLIITKDNSKSQVFLKMNSLQADDTAIYFCARTTG

SVFNAMDHWGQGTSVTVSS

CD142 VL (light chain variable region)
                                    SEQ ID NO: 32
QIVLTQSPALMSASPGEKVTMTCSASSSVTYMYWYQQKPRSSPKPWIYLT

SNLASGVPARFSGSGSGTSYSLTISSVEAEDAATYYCQQWSSNPLTFGAG

TKLELK
```

In some embodiments, an scFV is derived from a CD73 monoclonal antibody and comprises the heavy and light chain variable region of the CD73 monoclonal antibody set forth in SEQ ID NOs:33 and 34, respectively (see US Patent Application Publication No. 2019/0209611, incorporated herein by reference). In some embodiments, the extracellular antigen binding domain comprises the heavy and light chain variable region CDRs set forth in SEQ ID NO:33 and SEQ ID NO:34.

```
CD73 VH (heavy chain variable region)
                                    SEQ ID NO: 33
EVQLQQSGAELVKPGASVKLSCTASGFNIKDTYIHWVKQRPEQGLEWIGR

IDPATGNTEYDPKFQGKATITADTSSNTAYLHLSSLTSEDTAVYYCARGY

YGSSYPPWFAYWGQGTLVTVSA
```

32

-continued

```
CD73 VL (light chain variable region)
                                    SEQ ID NO: 34
DIVMTQSHKFMSTSVGDRVSITCKASQDVGSAVAWYQQKPGQSPKLLIYW

ASTRHTGVPDRFTGSGSGTDFTLTISNVQSEDLADYFCQQYSSYPLTFGA

GTKLELK
```

In some embodiments, an scFV is derived from a CD49c monoclonal antibody and comprises the heavy and light chain variable region of the CD49c monoclonal antibody set forth in SEQ ID NOs:35 and 36, respectively (see US Patent Application Publication No. 2019/0209611; incorporated herein by reference). In some embodiments, the extracellular antigen binding domain comprises the heavy and light chain variable region CDRs set forth in SEQ ID NO:35 and SEQ ID NO:36.

```
CD49c VH (heavy chain variable region)
                                    SEQ ID NO: 35
EVQLQQSGAELVKPGASVKLSCTASGFNIKDTYMHWVKQRPEQGLEWIGR

IDPANGHTKYDPKFQGKATITADTSSNAAYLQLNSLTSEDTAVYYCARRV

AYAMDYWGQGTSVTVSS

CD49c VL (light chain variable region)
                                    SEQ ID NO: 36
ENVLTQSPAIMSASPGEKVTMTCSASSSVTYMHWYQQKSSTSPKLWIYDT

SKLASGVPGRFSGSGSGNSYSLTISSMEAEDVATYCCFQGSGYPLTFGGG

TKLEIK
```

In some embodiments, an scFV is derived from a CD66c monoclonal antibody and comprises the heavy and light chain variable region of the CD66c monoclonal antibody set forth in SEQ ID NOs:37 and 38, respectively (see US Patent Application Publication No. 2019/0209611, incorporated herein by reference). In some embodiments, the extracellular antigen binding domain comprises the heavy and light chain variable region CDRs set forth in SEQ ID NO:37 and SEQ ID NO:38.

```
CD66c VH (heavy chain variable region)
                                    SEQ ID NO: 37
QVTLKESGPGILKPSQTLSLTCSFSGFSLSTSGMGVGWIRQPSGKSLEWL

AHIWWNDERYYNPSLKNQLTISKDTSRNQVFLKITSVDTADTATYYCARS

PRGYFDYWGHGTTLTVSS

CD66c VL (light chain variable region)
                                    SEQ ID NO: 38
DIVMTQSQKFMSTSVGDRVSVTCKASQNVVTNVAWYQQTPGQSPKALIYS

ASYRYSGVPDRFSGSGSGTDFTLTISNVQSGDLAEYFCQQYNSYPLTFGA

GTKLELK
```

In some embodiments, an scFV is derived from a CD104 monoclonal antibody and comprises the heavy and light chain variable region of the CD104 monoclonal antibody set forth in SEQ ID NOs:39 and 40, respectively (see US Patent Application Publication No. 2019/0209611; incorporated herein by reference). In some embodiments, the extracellular antigen binding domain comprises the heavy and light chain variable region CDRs set forth in SEQ ID NO:39 and SEQ ID NO:40.

CD104 VH (heavy chain variable region)
SEQ ID NO: 39
QVNLLQSGAALVKPGASVKLSCKASGYTFTDYYIFWVKQSHGKSLEWIGY

INPNSGSTNYNEKFKRKATLSVDKSTNTAYMELSRLTSEDSATYYCTRRA

YYGYNPFDYWGQGVMVTVSS

CD104 VL (light chain variable region)
SEQ ID NO: 40
DIQMTQTPSSMPASLGERVTISCRASRGINNYLSWYQQNLDGTIKPLIYY

TSNLQSGVPSRFSGSGSGTDYSLTISSLEPEDFAMYYCQQYDSSPWTFGG

GTKLELK

In some embodiments, an scFV is derived from a CD318 monoclonal antibody and comprises the heavy and light chain variable region of the CD318 monoclonal antibody set forth in SEQ ID NO:41 and SEQ ID NO:42, respectively (see US Patent Application Publication No. 2019/0209611; incorporated herein by reference). In some embodiments, the extracellular antigen binding domain comprises the heavy and light chain variable region CDRs set forth in SEQ ID NO:41 and SEQ ID NO:42.

CD318 VH (heavy chain variable region)
SEQ ID NO: 41
EVQLQQSGAELVRPGALVKLSCKASGFNIKDYYIHWVKQRPEQGLEWIGW

IDPENGHTIYDPKFQGKASITADTSSNTAYLQLSSLTSEDTAVYYCARLT

GTTYAMDYWGQGTSVTVSS

CD318 VL (light chain variable region)
SEQ ID NO: 42
DIVMTQSHKFMSTSVGDRVSITCKASQDVSTAVAWYQQKSGQSPKLLIYW

ASTRHTGVPDRFTGSGSGTDYTLTISSVQAEDLALYYCQQHYSTPYTFGG

GTKLEIK

In some embodiments, an scFV is derived from a TSPAN8 monoclonal antibody and comprises the heavy and light chain variable region of the TSPAN8 monoclonal antibody set forth in SEQ ID NOs:43 and 44, respectively (see US Patent Application Publication No. 2019/0209611; incorporated herein by reference). In some embodiments, the extracellular antigen binding domain comprises the heavy and light chain variable region CDRs set forth in SEQ ID NO:43 and SEQ ID NO:44.

TSPAN8 VH (heavy chain variable region)
SEQ ID NO: 43
EVKLLESGGGLVQPGGSMRLSCAASGFTFTDFYMNWIRQPAGKAPEWLGF

IRNKASGYTTEYNPSVKGRFTISRDNTQNMLYLQMNTLRAEDTATYYCAR

AHSYYGYDYFDYWGQGVMVTVSS

TSPAN8 VL (light chain variable region)
SEQ ID NO: 44
DIQMTQSPASLSASLEEIVTITCQASQDIGNWLSWYQQKPGKSPQLLIYG

ATSLADGVPSRFSGSRSGTQYSLKISRLQVEDIRIYYCLQAYSAPWTFGG

GTKLELK

In some embodiments, an scFV to CLA has the amino acid sequence set forth in SEQ ID NO:45 or SEQ ID NO:46 (see US Patent Application Publication No. 2019/0209611; incorporated herein by reference).

CLA specific scFv VH-linker-VL
SEQ ID NO: 45
EVQLVESGGGLVQPGNSLKLSCSASGFTFSSYGMHWIRQAPGEGLDWVAY

ISSSSGTVYADAVKARFTISRDNAKNTLYLQLNSLKSEDTAIYYCARAQN

WDLFDYWGQGVMVTVSSGGGGSGGGGSGGGGSQIMLTQQAESLWISPGER

VSITCRASQSLLYTDGKHYLSWYQQKPGQTTKALIYHASVRTDGVPTRFI

GSGSGTEFTLSIEHVQPEDFAIYYCLQTLKSPFTFGSGTKLEIK

CLA specific scFv VL-linker-VH
SEQ ID NO: 46
QIMLTQQAESLWISPGERVSITCRASQSLLYTDGKHYLSWYQQKPGQTTK

ALIYHASVRTDGVPTRFIGSGSGTEFTLSIEHVQPEDFAIYYCLQTLKSP

FTFGSGTKLEIKGGGGSGGGGSGGGGSEVQLVESGGGLVQPGNSLKLSCS

ASGFTFSSYGMHWIRQAPGEGLDWVAYISSSSGTVYADAVKARFTISRDN

AKNTLYLQLNSLKSEDTAIYYCARAQNWDLFDYWGQGVMVTVSS

In some embodiments, an scFV to CD142 has the amino acid sequence set forth in SEQ ID NO:47 or SEQ ID NO:48 (see US Patent Application Publication No. 2019/0209611; incorporated herein by reference).

CD142 specific CAR sequence VH-linker-VL
SEQ ID NO: 47
QVQLKQSGPGLVQPSQSLSITCTVSGFSLSNYGVHWVRQSPGKGLEWLGV

IWSGGSTDYNVAFISRLIITKDNSKSQVFLKMNSLQADDTAIYFCARTTG

SVFNAMDHWGQGTSVTVSSGGGGSGGGGSGGGGSQIVLTQSPALMSASPG

EKVTMTCSASSSVTYMYWYQQKPRSSPKPWIYLTSNLASGVPARFSGSGS

GTSYSLTISSVEAEDAATYYCQQWSSNPLTFGAGTKLELK

CD142 specific CAR sequence VL-linker-VH
SEQ ID NO: 48
QIVLTQSPALMSASPGEKVTMTCSASSSVTYMYWYQQKPRSSPKPWIYLT

SNLASGVPARFSGSGSGTSYSLTISSVEAEDAATYYCQQWSSNPLTFGAG

TKLELKGGGGSGGGGSGGGGSQVQLKQSGPGLVQPSQSLSITCTVSGFSL

SNYGVHWVRQSPGKGLEWLGVIWSGGSTDYNVAFISRLIITKDNSKSQVF

LKMNSLQADDTAIYFCARTTGSVFNAMDHWGQGTSVTVSS

In some embodiments, an scFV to CD73 has the amino acid sequence set forth in SEQ ID NO:49 or SEQ ID NO:50 (see US Patent Application Publication No. 2019/0209611; incorporated herein by reference).

CD73 specific CAR sequence VH-linker-VL
SEQ ID NO: 49
EVQLQQSGAELVKPGASVKLSCTASGFNIKDTYIHWVKQRPEQGLEWIGR

IDPATGNTEYDPKFQGKATITADTSSNTAYLHLSSLTSEDTAVYYCARGY

YGSSYPPWFAYWGQGTLVTVSAGGGGSGGGGSGGGGSDIVMTQSHKFMST

SVGDRVSITCKASQDVGSAVAWYQQKPGQSPKLLIYWASTRHTGVPDRFT

GSGSGTDFTLTISNVQSEDLADYFCQQYSSYPLTFGAGTKLELK

CD73 specific CAR sequence VL-linker-VH
SEQ ID NO: 50
DIVMTQSHKFMSTSVGDRVSITCKASQDVGSAVAWYQQKPGQSPKLLIYW

ASTRHTGVPDRFTGSGSGTDFTLTISNVQSEDLADYFCQQYSSYPLTFGA

GTKLELKGGGGSGGGGSGGGGSEVQLQQSGAELVKPGASVKLSCTASGFN

-continued

IKDTYIHWVKQRPEQGLEWIGRIDPATGNTEYDPKFQGKATITADTSSNT

AYLHLSSLTSEDTAVYYCARGYYGSSYPPWFAYWGQGTLVTVSA

In some embodiments, an scFV to CD49c has the amino acid sequence set forth in SEQ ID NO:51 or SEQ ID NO:52 (see US Patent Application Publication No. 2019/0209611; incorporated herein by reference).

CD49c specific CAR sequence VH-linker-VL
SEQ ID NO: 51
EVQLQQSGAELVKPGASVKLSCTASGFNIKDTYMHWVKQRPEQGLEWIGR

IDPANGHTKYDPKFQGKATITADTSSNAAYLQLNSLTSEDTAVYYCARRV

AYAMDYWGQGTSVTVSSGGGGSGGGGSGGGGSENVLTQSPAIMSASPGEK

VTMTCSASSSVTYMHWYQQKSSTSPKLWIYDTSKLASGVPGRFSGSGSGN

SYSLTISSMEAEDVATYCCFQGSGYPLTFGGGTKLEIK

CD49c specific CAR sequence VL-linker-VH
SEQ ID NO: 52
ENVLTQSPAIMSASPGEKVTMTCSASSSVTYMHWYQQKSSTSPKLWIYDT

SKLASGVPGRFSGSGSGNSYSLTISSMEAEDVATYCCFQGSGYPLTFGGG

TKLEIKGGGGSGGGGSGGGGSEVQLQQSGAELVKPGASVKLSCTASGFNI

KDTYMHWVKQRPEQGLEWIGRIDPANGHTKYDPKFQGKATITADTSSNAA

YLQLNSLTSEDTAVYYCARRVAYAMDYWGQGTSVTVSS

In some embodiments, an scFV to CD66c has the amino acid sequence set forth in SEQ ID NO:53 or SEQ ID NO:54 (see US Patent Application Publication No. 2019/0209611; incorporated herein by reference).

CD66c specific CAR sequence VH-linker-VL
SEQ ID NO: 53
QVTLKESGPGILKPSQTLSLTCSFSGFSLSTSGMGVGWIRQPSGKSLEWL

AHIWWNDERYYNPSLKNQLTISKDTSRNQVFLKITSVDTADTATYYCARS

PRGYFDYWGHGTTLTVSSGGGGSGGGGSGGGGSDIVMTQSQKFMSTSVGD

RVSVTCKASQNVVTNVAWYQQTPGQSPKALIYSASYRYSGVPDRFSGSGS

GTDFTLTISNVQSGDLAEYFCQQYNSYPLTFGAGTKLELK

CD66c specific CAR sequence VL-linker-VH
SEQ ID NO: 54
DIVMTQSQKFMSTSVGDRVSVTCKASQNVVTNVAWYQQTPGQSPKALIYS

ASYRYSGVPDRFSGSGSGTDFTLTISNVQSGDLAEYFCQQYNSYPLTFGA

GTKLELKGGGGSGGGGSGGGGSQVTLKESGPGILKPSQTLSLTCSFSGFS

LSTSGMGVGWIRQPSGKSLEWLAHIWWNDERYYNPSLKNQLTISKDTSRN

QVFLKITSVDTADTATYYCARSPRGYFDYWGHGTTLTVSS

In some embodiments, an scFV to CD104 has the amino acid sequence set forth in SEQ ID NO:55 or SEQ ID NO:56 (see US Patent Application Publication No. 2019/0209611; incorporated herein by reference).

CD104 specific CAR sequence VH-linker-VL
SEQ ID NO: 55
QVNLLQSGAALVKPGASVKLSCKASGYTFTDYYIFWVKQSHGKSLEWIGY

INPNSGSTNYNEKFKRKATLSVDKSTNTAYMELSRLTSEDSATYYCTRRA

-continued
YYGYNPFDYWGQGVMVTVSSGGGGSGGGGSGGGGSDIQMTQTPSSMPASL

GERVTISCRASRGINNYLSWYQQNLDGTIKPLIYYTSNLQSGVPSRFSGS

GSGTDYSLTISSLEPEDFAMYYCQQYDSSPWTFGGGTKLELK

CD104 specific CAR sequence VL-linker-VH
SEQ ID NO: 56
DIQMTQTPSSMPASLGERVTISCRASRGINNYLSWYQQNLDGTIKPLIYY

TSNLQSGVPSRFSGSGSGTDYSLTISSLEPEDFAMYYCQQYDSSPWTFGG

GTKLELKGGGGSGGGGSGGGGSQVNLLQSGAALVKPGASVKLSCKASGYT

FTDYYIFWVKQSHGKSLEWIGYINPNSGSTNYNEKFKRKATLSVDKSTNT

AYMELSRLTSEDSATYYCTRRAYYGYNPFDYWGQGVMVTVSS

In some embodiments, an scFV to CD318 has the amino acid sequence set forth in SEQ ID NO:57 or SEQ ID NO:58 (see US Patent Application Publication No. 2019/0209611; incorporated herein by reference).

CD318 specific CAR sequence VH-linker-VL
SEQ ID NO: 57
EVQLQQSGAELVRPGALVKLSCKASGFNIKDYYIHWVKQRPEQGLEWIGW

IDPENGHTIYDPKFQGKASITADTSSNTAYLQLSSLTSEDTAVYYCARLT

GTTYAMDYWGQGTSVTVSSGGGGSGGGGSGGGGSDIVMTQSHKFMSTSVG

DRVSITCKASQDVSTAVAWYQQKSGQSPKLLIYWASTRHTGVPDRFTGSG

SGTDYTLTISSVQAEDLALYYCQQHYSTPYTFGGGTKLEIK

CD318 specific CAR sequence VL-linker-VH
SEQ ID NO: 58
DIVMTQSHKFMSTSVGDRVSITCKASQDVSTAVAWYQQKSGQSPKLLIYW

ASTRHTGVPDRFTGSGSGTDYTLTISSVQAEDLALYYCQQHYSTPYTFGG

GTKLEIKGGGGSGGGGSGGGGSEVQLQQSGAELVRPGALVKLSCKASGFN

IKDYYIHWVKQRPEQGLEWIGWIDPENGHTIYDPKFQGKASITADTSSNT

AYLQLSSLTSEDTAVYYCARLTGTTYAMDYWGQGTSVTVSS

In some embodiments, an scFV to TSPAN8 has the amino acid sequence set forth in SEQ ID NO:59 or SEQ ID NO:60 (see US Patent Application Publication No. 2019/0209611; incorporated herein by reference).

TSPAN8 specific CAR sequence VH-linker-VL
SEQ ID NO: 59
EVKLLESGGGLVQPGGSMRLSCAASGFTFTDFYMNWIRQPAGKAPEWLGF

IRNKASGYTTEYNPSVKGRFTISRDNTQNMLYLQMNTLRAEDTATYYCAR

AHSYYGYDYFDYWGQGVMVTVSSGGGGSGGGGSGGGGSDIQMTQSPASLS

ASLEEIVTITCQASQDIGNWLSWYQQKPGKSPQLLIYGATSLADGVPSRF

SGSRSGTQYSLKISRLQVEDIRIYYCLQAYSAPWTFGGGTKLELK

TSPAN8 specific CAR sequence VL-linker-VH
SEQ ID NO: 60
DIQMTQSPASLSASLEEIVTITCQASQDIGNWLSWYQQKPGKSPQLLIYG

ATSLADGVPSRFSGSRSGTQYSLKISRLQVEDIRIYYCLQAYSAPWTFGG

GTKLELKGGGGSGGGGSGGGGSEVKLLESGGGLVQPGGSMRLSCAASGFT

FTDFYMNWIRQPAGKAPEWLGFIRNKASGYTTEYNPSVKGRFTISRDNTQ

NMLYLQMNTLRAEDTATYYCARAHSYYGYDYFDYWGQGVMVTVSS

Transmembrane Domain of a CAR

In some embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. The transmembrane domain of the CAR can comprise, for example, a CD8 polypeptide, a CD28 polypeptide, a CD3zeta polypeptide, a CD4 polypeptide, a 4-1BB polypeptide, an OX40 polypeptide, an ICOS polypeptide, a NKG2D polypeptide, a synthetic peptide (not based on a protein associated with the immune response), or a combination thereof.

In certain embodiments, the transmembrane domain comprises a CD8 polypeptide. In certain embodiments, the CD8 polypeptide has an amino acid sequence that is at least about 85%, about 90%, about 95%, about 96%, about 97%, about 98%, about 99% or about 100% identical to the sequence having a NCBI Reference No: NP_001139345.1, SEQ ID NO:7, (sequence identity herein may be determined using standard software such as BLAST or FASTA), or fragments thereof, and/or may optionally comprise up to one or up to two or up to three conservative amino acid substitutions. As used herein, a "conservative amino acid substitution" means an amino acid substitution wherein an amino acid is substituted for another electronically similar amino acid. For example, an amino acid with a hydrophobic side chain can be substituted for a different amino acid also having a hydrophobic side chain (e.g., leucine substituted for isoleucine, alanine substituted for valine, and the like); an amino acid with an acidic chain can be substituted for a different amino acid also having an acidic side chain (e.g., aspartic acid substituted for glutamic acid, and the like); an amino acid with a basic chain can be substituted for a different amino acid also having a basic side chain (e.g., lysine substituted for arginine, and the like); and an amino acid with a polar side chain can be substituted for a different amino acid also having a polar side chain (e.g., serine substituted for threonine, and the like). In certain embodiments, the CD8 polypeptide can have an amino acid sequence that is a consecutive portion of SEQ ID NO:7 which is at least 20, or at least 30, or at least 40, or at least 50, and up to 235 amino acids in length. Alternatively or additionally, in non-limiting various embodiments, the CD8 polypeptide comprises or has an amino acid sequence of amino acids 1 to 235, 1 to 50, 50 to 100, 100 to 150, 150 to 200, or 200 to 235 of SEQ ID NO:7. In certain embodiments, a CAR comprises a transmembrane domain comprising a human CD8 polypeptide that comprises an amino acid sequence of amino acids 137 to 209 of SEQ ID NO:7.

SEQ ID NO: 7:
MALPVTALLLPLALLLHAARPSQFRVSPLDRTWNLGETVELKCQVLLSN

PTSGCSWLFQPRGAAASPTFLLYLSQNKPKAAEGLDTQRFSGKRLGDTF

VLTLSDFRRENEGYYFCSALSNSIMYFSHFVPVFLPAKPTTTPAPRPPT

PAPTIASQPLSLRPEACRPAAGGAVHTRGLDFACDIYIWAPLAGTCGVL

LLSLVITLYCNHRNRRRVCKCPRPVVKSGDKPSLSARYV

In certain embodiments, the CD8 polypeptide has an amino acid sequence that is at least about 85%, about 90%, about 95%, about 96%, about 97%, about 98%, about 99% or about 100% identical to the sequence having a NCBI Reference No: AAA92533.1, SEQ ID NO:8, or fragments thereof, and/or may optionally comprise up to one or up to two or up to three conservative amino acid substitutions. In certain embodiments, the CD8 polypeptide can have an amino acid sequence that is a consecutive portion of SEQ ID NO:8 which is at least about 20, or at least about 30, or at least about 40, or at least about 50, or at least about 60, or at least about 70, or at least about 100, or at least about 200, and up to 247 amino acids in length. Alternatively or additionally, in non-limiting various embodiments, the CD8 polypeptide comprises or has an amino acid sequence of amino acids 1 to 247, 1 to 50, 50 to 100, 100 to 150, 150 to 200, 151 to 219, or 200 to 247 of SEQ ID NO:8. In certain embodiments, the CAR comprises a transmembrane domain comprising a murine CD8 polypeptide that comprises an amino acid sequence of amino acids 151 to 219 of SEQ ID NO:8.

SEQ ID NO: 8:
MASPLTRELSLNLLLMGESIILGSGEAKPQAPELRIFPKKMDAELGQKVD

LVCEVLGSVSQGCSWLFQNSSSKLPQPTFVVYMASSHNKITWDEKLNSSK

LFSAVRDTNNKYVLTLNKFSKENEGYYFCSVISNSVMYFSSVVPVLQKVN

STTTKPVLRTPSPVHPTGTSQPQRPEDCRPRGSVKGTGLDFACDIYIWAP

LAGICVAPLLSLIITLICYHRSRKRVCKCPRPLVRQEGKPRPSEKIV

In certain embodiments, the CD8 polypeptide comprises or has the amino acid sequence set forth in SEQ ID NO:9.

SEQ ID NO: 9:
STTTKPVLRTPSPVHPTGTSQPQRPEDCRPRGSVKGTGLDFACDIYIWAP

LAGICVALLLSLIITLICY

In certain embodiments, the transmembrane domain of a CAR comprises a CD28 polypeptide. The CD28 polypeptide can have an amino acid sequence that is at least about 85%, about 90%, about 95%, about 96%, about 97%, about 98%, about 99% or 100% identical to the sequence having a NCBI Reference No: P10747 or NP_006130 (SEQ ID No: 10), or fragments thereof, and/or may optionally comprise up to one or up to two or up to three conservative amino acid substitutions. In non-limiting certain embodiments, the CD28 polypeptide can have an amino acid sequence that is a consecutive portion of SEQ ID NO:10 which is at least 20, or at least 30, or at least 40, or at least 50, and up to 220 amino acids in length. Alternatively or additionally, in non-limiting various embodiments, the CD28 polypeptide has an amino acid sequence of amino acids 1 to 220, 1 to 50, 50 to 100, 100 to 150, 114 to 220, 150 to 200, or 200 to 220 of SEQ ID NO:10. In certain embodiments, the CD28 polypeptide comprised in the transmembrane domain of a presently disclosed CAR has an amino acid sequence of amino acids 153 to 179 of SEQ ID NO:10.

SEQ ID NO: 10:
MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWVRSKRSRLLHSDYMNMTPRRPG

PTRKHYQPYAPPRDFAAYRS

In certain embodiments, the transmembrane domain of a CAR comprises a NKG2D polypeptide. The NKG2D polypeptide can have an amino acid sequence that is at least about 85%, about 90%, about 95%, about 96%, about 97%, about 98%, about 99% or 100% identical to the sequence having a NCBI Reference No: NP_0031386.2 (SEQ ID NO:66), or fragments thereof, and/or may optionally comprise up to one or up to two or up to three conservative amino acid substitutions. In non-limiting certain embodiments, the NKG2D polypeptide can have an amino acid sequence that is a consecutive portion of SEQ ID NO:66 which is at least 20, or at least 30, or at least 40, or at least 50, and up to 216 amino acids in length. In certain embodiments, the NKG2D polypeptide comprises the transmembrane domain of SEQ ID NO:10 (e.g., amino acids 52-72).

SEQ ID NO: 66:
MGWIRGRRSRHSWEMSEFHNYNLDLKKSDFSTRWQKQRCPVVKSKCRENA

SPHFCCFIAVAMGIRFIIMVTIWSAVFLNSLFNQEVQIPLTESYCGPCP

KNWICYKNNCYQFFDESKNWYESQASCMSQNASLLKVYSKEDQDLLKLVK

SYHWMGLVHIPTNGSWQWEDGSILSPNLLTIIEMQKGDCALYASSFKGYI

ENCSTPNTYICMQRTV

In some embodiments, the transmembrane domain of a CAR comprises a CD3zeta (CD3ζ) polypeptide. The transmembrane domain of the CD3zeta polypeptide can have an amino acid sequence that is at least about 85%, about 90%, about 95%, about 96%, about 97%, about 98%, about 99% or 100% identical to the sequence of the transmembrane domain of CD3zeta set forth in NCBI Reference No: NP_932170 (SEQ ID NO:11), SEQ ID NO:12, or SEQ ID NO:13, and/or may optionally comprise up to one or up to two or up to three conservative amino acid substitutions.

In some embodiments, the transmembrane domain of a CAR comprises a CD4 polypeptide. The transmembrane domain of the CD4 polypeptide can have an amino acid sequence that is at least about 85%, about 90%, about 95%, about 96%, about 97%, about 98%, about 99% or 100% identical to the sequence of the transmembrane domain of CD4 set forth in NCBI Reference No: NP_000607.1, NP_001181943.1 or NP_001181946.1, (each incorporated herein by reference) and/or may optionally comprise up to one or up to two or up to three conservative amino acid substitutions.

In some embodiments, the transmembrane domain of a CAR comprises a 4-1BB polypeptide. The transmembrane domain of the 4-1BB polypeptide can have an amino acid sequence that is at least about 85%, about 90%, about 95%, about 96%, about 97%, about 98%, about 99% or 100% identical to the sequence of the transmembrane domain of 4-1BB set forth in NCBI Reference No: P41273 (incorporated herein by reference) or NP_001552.2 (SEQ ID NO:18), and/or may optionally comprise up to one or up to two or up to three conservative amino acid substitutions.

In some embodiments, the transmembrane domain of a CAR comprises an OX40 polypeptide. The transmembrane domain of the OX40 polypeptide can have an amino acid sequence that is at least about 85%, about 90%, about 95%, about 96%, about 97%, about 98%, about 99% or 100% identical to the sequence of the transmembrane domain of OX40 set forth in NCBI Reference No: NP_003318.1 (incorporated herein by reference), and/or may optionally comprise up to one or up to two or up to three conservative amino acid substitutions.

In some embodiments, the transmembrane domain of a CAR comprises an ICOS polypeptide. The transmembrane domain of the ICOS polypeptide can have an amino acid sequence that is at least about 85%, about 90%, about 95%, about 96%, about 97%, about 98%, about 99% or 100% identical to the sequence of the transmembrane domain of ICOS set forth in NCBI Reference No: NP_036224.1 (incorporated herein by reference), and/or may optionally comprise up to one or up to two or up to three conservative amino acid substitutions.

Spacer Region

In certain non-limiting embodiments, a CAR can also comprise a spacer region that links the extracellular antigen-binding domain to the transmembrane domain. The spacer region can be flexible enough to allow the antigen binding domain to orient in different directions to facilitate antigen recognition. The spacer region can be the hinge region from IgG$_1$ (GenPept Ref No.: P01857.1, incorporated herein by reference), or the CH$_2$CH$_3$ region of an immunoglobulin (e.g., IgG$_4$ (GenPept Ref No.: P01861.1, incorporated herein by reference) and portions of CD3, a portion of a CD28 polypeptide (e.g., a portion of SEQ ID NO:10), a portion of a CD8 polypeptide (e.g., a portion of SEQ ID NO:7, or a portion of SEQ ID NO:8), a variation of any of the foregoing which is at least about 80%, at least about 85%, at least about 90%, or at least about 95% identical thereto, or a synthetic spacer sequence.

Intracellular Signaling Domain of a CAR

In certain non-limiting embodiments, an intracellular signaling domain of the CAR can comprise a CD3zeta (CD3ζ) polypeptide, which can activate or stimulate a cell (e.g., a cell of the lymphoid lineage, e.g., an NK cell). CD3ζ comprises 3 immunoreceptor tyrosine-based activation motifs (ITAMs), and transmits an activation signal to the cell (e.g., a cell of the lymphoid lineage, e.g., an NK cell) after antigen is bound. In certain embodiments, the CD3zeta polypeptide has an amino acid sequence that is at least about 85%, about 90%, about 95%, about 96%, about 97%, about 98%, about 99% or about 100% identical to the sequence having a NCBI Reference No: NP_932170 (SEQ ID NO:11), or fragments thereof, and/or can optionally comprise up to one or up to two or up to three conservative amino acid substitutions. In certain non-limiting embodiments, the CD3ζ polypeptide comprises or has an amino acid sequence that is a consecutive portion of SEQ ID NO:11, which is at least 20, or at least 30, or at least 40, or at least 50, and up to 164 amino acids in length. Alternatively or additionally, in non-limiting various embodiments, the CD3zeta polypeptide comprises or has an amino acid sequence of amino acids 1 to 164, 1 to 50, 50 to 100, 100 to 150, or 150 to 164 of SEQ ID NO:11. In certain embodiments, the CD3ζ polypeptide comprises or has an amino acid sequence of amino acids 52 to 164 of SEQ ID NO:11.

SEQ ID NO: 11:
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR

In certain embodiments, the CD3zeta polypeptide has an amino acid sequence that is at least about 85%, about 90%, about 95%, about 96%, about 97%, about 98%, about 99% or about 100% identical to the sequence having a NCBI Reference No: NP_001106864.2 (SEQ ID NO:12), or fragments thereof, and/or may optionally comprise up to one or up to two or up to three conservative amino acid substitutions. In certain non-limiting embodiments, the CD3zeta polypeptide can have an amino acid sequence that is a consecutive portion of SEQ ID NO:12, which is at least about 20, or at least about 30, or at least about 40, or at least about 50, or at least about 90, or at least about 100, and up to 188 amino acids in length. Alternatively or additionally, in non-limiting various embodiments, the CD3ζ polypeptide comprises or has an amino acid sequence of amino acids 1 to 164, 1 to 50, 50 to 100, 52 to 142, 100 to 150, or 150 to 188 of SEQ ID NO:12. In certain embodiments, the CD3zeta polypeptide comprises or has an amino acid sequence of amino acids 52 to 142 of SEQ ID NO:12.

SEQ ID NO: 12:
MKWKVSVLACILHVRFPGAEAQSFGLLDPKLCYLLDGILFIYGVIITALY

LRAKFSRSAETAANLQDPNQLYNELNLGRREEYDVLEKKRARDPEMGGKQ

RRRNPQEGVYNALQKDKMAEAYSEIGTKGERRRGKGHDGLYQDSHFQAVQ

FGNRREREGSELTRTLGLRARPKACRHKKPLSLPAAVS

In certain embodiments, the CD3zeta polypeptide comprises or has the amino acid sequence set forth in SEQ ID NO:13.

SEQ ID NO: 13:
RAKFSRSAETAANLQDPNQLYNELNLGRREEYDVLEKKRARDPEMGGKQQ

RRRNPQEGVYNALQKDKMAEAYSEIGTKGERRRGKGHDGLYQGLSTATKD

TYDALHMQTLAPR

In certain non-limiting embodiments, an intracellular signaling domain of the CAR further comprises at least a co-stimulatory signaling region. In certain embodiments, the co-stimulatory region comprises at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include, for example, a CD28 polypeptide, a 4-1BB polypeptide, an OX40 polypeptide, an ICOS polypeptide, a DAP-10 polypeptide, a DAP-12 polypeptide, a 2B4 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands include, but are not limited to, CD80, CD86, CD70, OX40L, and 4-1BBL. As one example, a 4-1BB ligand (i.e., 4-1BBL) may bind to 4-1BB (also known as "CD137") for providing an intracellular signal that in combination with a CAR signal induces an effector cell function of an NK cell. CARs comprising an intracellular signaling domain that comprises a co-stimulatory signaling region comprising 4-1BB, ICOS or DAP-10 are disclosed in U.S. Pat. No. 7,446,190; incorporated herein by reference (i.e., a nucleotide sequence encoding 4-1BB is set forth in SEQ ID NO:15 and the protein sequence is set forth in NP_001551.2; a nucleotide sequence encoding ICOS is set forth in SEQ ID NO:16 and the protein sequence is set forth in NP_036224.1, and a nucleotide sequence encoding DAP-10 is set forth in SEQ ID NO:17 and the protein sequence is set forth in NP_055081.1), which U.S. Pat. No. 7,446,190 and Ref Protein sequences are herein incorporated by reference in their entirety.

4-1BB

SEQ ID NO: 15
ATGGGAAACAGCTGTTACAACATAGTAGCCACTCTGTTGCTGGTCCTCAA

CTTTGAGAGGACAAGATCATTGCAGGATCCTTGTAGTAACTGCCCAGCTG

GTACATTCTGTGATAATAACAGGAATCAGATTTGCAGTCCCTGTCCTCCA

AATAGTTTCTCCAGCGCAGGTGGACAAAGGACCTGTGACATATGCAGGCA

GTGTAAAGGTGTTTTCAGGACCAGGAAGGAGTGTTCCTCCACCAGCAATG

CAGAGTGTGACTGCACTCCAGGGTTTCACTGCCTGGGGGCAGGATGCAGC

ATGTGTGAACGGATTGTAAACAAGGTCAAGAACTGACAAAAAAAGGTTG

TAAAGACTGTTGCTTTGGGACATTTAACGATCAGAAACGTGGCATCTGTC

GACCCTGGACAAACTGTTCTTTGGATGGAAAGTCTGTGCTTGTGAATGGG

ACGAAGGAGAGGGACGTGGTCTGTGGACCATCTCCAGCCGACCTCTCTCC

GGGAGCATCCTCTGTGACCCCGCCTGCCCCTGCGAGAGAGCCAGGACACT

CTCCGCAGATCATCTCCTTCTTTCTTGCGCTGACGTCGACTGCGTTGCTC

TTCCTGCTGTTCTTCCTCACGCTCCGTTTCTCTGTTGTTAAACGGGGCAG

AAAGAAACTCCTGTATATATTCAAACAACCATTTATGAGACCAGTACAAA

CTACTCAAGAGGAAGATGGCTGTAGCTGCCGATTTCCAGAAGAAGAAGAA

GGAGGATGTGAACTGTGA

ICOS

SEQ ID NO: 16
ATGAAGTCAGGCCTCTGGTATTTCTTTCTCTTCTGCTTGCGCATTAAAGT

TTTAACAGGAGAAATCAATGGTTCTGCCAATTATGAGATGTTTATATTTC

ACAACGGAGGTGTACAAATTTTATGCAAATATCCTGACATTGTCCAGCAA

TTTAAAATGCAGTTGCTGAAAAGGGGGGCAAATACTCTGCGATCTCACTA

AGACAAAAGGAAGTGGAAACACAGTGTCCATTAAGAGTCTGAAATTCTGC

CATTCTCAGTTATCCAACAACAGTGTCTCTTTTTTTCTACAACCTTGGAC

CATTCTCATGCCAACTATTACTTCTGCAACCTATCAATTTTTGATCCTCC

TCCTTTTAAAGTAACTCTTACAGGAGGATATTTGCATATTTATGAAATCA

CAACTTTGTTGCCAGCTGAAGTTCTGGTTACCCATAGGATGTGCAGCCTT

TGTTGTAGTCTGCATTTTGGGATGCATACTTATTTGTTGGCTTACAAAA

AGAAGTATTCATCCAGTGTGCACGACCCTAACGGTGAATACATGTTCATG

AGAGCAGTGAACACAGCCAAAAAATCTAGACTCACAGATGTGACCCTATA

A

DAP-10

SEQ ID NO: 17
ATGATCCATCTGGGTCACATCCTCTTCCTGCTTTTGCTCCCAGTGGCTGC

AGCTCAGACGACCCCAGGAGAGAGATCATCACTCCCTGCCTTTTACCCTG

GCACTTCAGGCTCCTGTTCCGGATGTGGGTCCCTCTCTCTGCCGCTCCTG

GCAGGCCTCGTGGCTGCTGATGCGGTGGCATCGCTGCTCATCGTGGGGGC

GGTGTTCCTGTGCGCACGCCCACGCCGCAGCCCCGCCCAAGAAGATGGCA

AAGTCTACATCAACATGCCAGGCAGGGCTGA

In certain embodiments, the intracellular signaling domain of the CAR comprises a co-stimulatory signaling region that comprises a CD28 polypeptide. The CD28 polypeptide can have an amino acid sequence that is at least about 85%, about 90%, about 95%, about 96%, about 97%, about 98%, about 99% or 100% identical to the sequence having a NCBI Reference No: P10747 (incorporated herein by reference) or NP_006130 (SEQ ID NO:10), or fragments thereof, and/or may optionally comprise up to one or up to two or up to three conservative amino acid substitutions. In non-limiting certain embodiments, the CD28 polypeptide has an amino acid sequence that is a consecutive portion of SEQ ID NO:10 which is at least 20, or at least 30, or at least 40, or at least 50, and up to 220 amino acids in length. Alternatively or additionally, in non-limiting various embodiments, the CD28 polypeptide has an amino acid sequence of amino acids 1 to 220, 1 to 50, 50 to 100, 100 to 150, 114 to 220, 150 to 200, or 200 to 220 of SEQ ID NO:10. In certain embodiments, the intracellular signaling domain of the CAR comprises a co-stimulatory signaling region that comprises a CD28 polypeptide having an amino acid sequence of amino acids 180 to 220 of SEQ ID NO:10.

In certain embodiments, the CD28 polypeptide has an amino acid sequence that is at least about 85%, about 90%, about 95%, about 96%, about 97%, about 98%, about 99% or about 100% identical to the sequence having a NCBI Reference No: NP_031668.3 (SEQ ID NO:14), or fragments thereof, and/or may optionally comprise up to one or up to two or up to three conservative amino acid substitutions. In non-limiting certain embodiments, the CD28 polypeptide has an amino acid sequence that is a consecutive portion of SEQ ID NO:14 which is at least about 20, or at least about 30, or at least about 40, or at least about 50, and up to 218 amino acids in length. Alternatively or additionally, in non-limiting various embodiments, the CD28 polypeptide has an amino acid sequence of amino acids 1 to 218, 1 to 50, 50 to 100, 100 to 150, 114 to 220, 150 to 200, 178 to 218, or 200 to 220 of SEQ ID NO:14. In certain embodiments, the co-stimulatory signaling region of a presently disclosed CAR comprises a CD28 polypeptide that comprises or has the amino acids 178 to 218 of SEQ ID NO:14.

```
SEQ ID NO: 14:
MTLRLLFLALNFFSVQVTENKILVKQSPLLVVDSNEVSLSCRYSYNLLAK

EFRASLYKGVNSDVEVCVGNGNFTYQPQFRSNAEFNCDGDFDNETVTFRL

WNLHVNHTDIYFCKIEFMYPPPYLDNERSNGTIIHIKEKHLCHTQSSPKL

FWALVVVAGVLFCYGLLVTVALCVIWTNSRRNRLLQSDYMNMTPRRPGLT

RKPYQPYAPARDFAAYRP
```

In certain embodiments, the intracellular signaling domain of the CAR comprises a co-stimulatory signaling region that comprises two co-stimulatory molecules: CD28 and 4-1BB or CD28 and OX40.

4-1BB can act as a tumor necrosis factor (TNF) ligand and have stimulatory activity. The 4-1BB polypeptide can have an amino acid sequence that is at least about 85%, about 90%, about 95%, about 96%, about 97%, about 98%, about 99% or about 100% identical to the sequence set forth in NCBI Reference No: P41273 (incorporated herein by reference) or NP_001552.2 (SEQ ID NO:18) or fragments thereof, and/or may optionally comprise up to one or up to two or up to three conservative amino acid substitutions.

```
SEQ ID NO: 18:
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS
```

-continued
```
MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL
```

An OX40 polypeptide can have an amino acid sequence that is at least about 85%, about 90%, about 95%, about 96%, about 97%, about 98%, about 99% or about 100% identical to the sequence having a NCBI Reference No: P43489 (incorporated herein by reference) or NP_003318.1 (SEQ ID NO:19), or fragments thereof, and/or may optionally comprise up to one or up to two or up to three conservative amino acid substitutions.

```
SEQ ID NO: 19:
MCVGARRLGRGPCAALLLLGLGLSTVTGLHCVGDTYPSNDRCCHECRPGN

GMVSRCSRSQNTVCRPCGPGFYNDVVSSKPCKPCTWCNLRSGSERKQLCT

ATQDTVCRCRAGTQPLDSYKPGVDCAPCPPGHFSPGDNQACKPWTNCTLA

GKHTLQPASNSSDAICEDRDPPATQPQETQGPPARPITVQPTEAWPRTSQ

GPSTRPVEVPGGRAVAAILGLGLVLGLLGPLAILLALYLLRRDQRLPPDA

HKPPGGGSFRTPIQEEQADAHSTLAKI
```

An ICOS polypeptide can have an amino acid sequence that is at least about 85%, about 90%, about 95%, about 96%, about 97%, about 98%, about 99% or about 100% identical to the sequence having a NCBI Reference No: NP_036224.1 (SEQ ID NO:20) or fragments thereof, and/or may optionally comprise up to one or up to two or up to three conservative amino acid substitutions.

```
SEQ ID NO: 20:
MKSGLWYFFLFCLRIKVLTGEINGSANYEMFIFHNGGVQILCKYPDIVQ

QFKMQLLKGGQILCDLIKTKGSGNTVSIKSLKFCHSQLSNNSVSFFLYN

LDHSHANYYFCNLSIFDPPPFKVTLIGGYLHIYESQLCCQLKFWLPIGC

AAFVVVCILGCILICWLTKKKYSSSVHDPNGEYMFMRAVNTAKKSRLTD

VTL
```

A DAP-12 polypeptide can have an amino acid sequence of a co-stimulatory region that is at least about 85%, about 90%, about 95%, about 96%, about 97%, about 98%, about 99% or about 100% identical to the sequence having a NCBI Reference No: NP_003323.1, NP_001166986.1, NP_001166985.1 or NP_937758.1 (each incorporated herein by reference) or fragments thereof, and/or may optionally comprise up to one or up to two or up to three conservative amino acid substitutions.

A 2B4 polypeptide can have an amino acid sequence of a co-stimulatory region that is at least about 85%, about 90%, about 95%, about 96%, about 97%, about 98%, about 99% or about 100% identical to the sequence having a NCBI Reference No: NP_057466.1, NP_001160135.1 or NP_001160136.1 (each incorporated herein by reference) or fragments thereof, and/or may optionally comprise up to one or up to two or up to three conservative amino acid substitutions.

Additional Genes

In some embodiments, a CAR construct further includes a gene(s) encoding an additional gene product, such as a cytokine or a transfection marker. In some embodiments, the additional gene encodes a cytokine, such as human IL-15 (U.S. Pat. No. 9,931,377; SEQ ID NO:68), IL-18 or IL-12. In some embodiments, the additional gene encodes a transfection marker or suicide gene such as truncated EGFR (tEGFR) (see WO2011/056894; SEQ ID NO:67) or iCaps9 (WO2013/040371), the sequences of which are incorporated by reference herein.

```
tEGFR
                                    SEQ ID NO: 67
RKVCNGIGIGEFKDSLSINATNIKHFKNCTSISGDLHILPVAFRGDSFT

HTPPLDPQELDILKTVKEITGFLLIQAWPENRTDLHAFENLEIIRGRTK

QHGQFSLAVVSLNITSLGLRSLKEISDGDVIISGNKNLCYANTINWKKL

FGTSGQKTKIISNRGENSCKATGQVCHALCSPEGCWGPEPRDCVSCRNV

SRGRECVDKCNLLEGEPREFVENSECIQCHPECLPQAMNITCTGRGPDN

CIQCAHYIDGPHCVKTCPAGVMGENNTLVWKYADAGHVCHLCHPNCTYG

CTGPGLEGCPTNGPKIPSIATGMVGALLLLLVVALGIGLFM

IL-15
                                    SEQ ID NO: 68
RISKPHLRSISIQCYLCLLLNSHFLTEAGIHVFILGCFSAGLPKTEANW

VNVISDLKKIEDLIQSMHIDATLYTESDVHPSCKVTAMKCFLLELQVIS

LESGDASIHDTVENLIILANNSLSSNGNVTESGCKECEELEEKNIKEFL

QSFVHIVQMFINTS
```

Exemplary CAR Constructs

In certain embodiments, a CAR comprises an extracellular antigen-binding domain that binds to CD19, a transmembrane domain comprising a CD28 polypeptide, and an intracellular signaling domain comprising a CD3zeta polypeptide and a co-stimulatory signaling region comprising a CD28 polypeptide. In certain embodiments, the CAR is designated 1928z. In certain embodiments, 1928z is a protein having at least about 85%, about 90%, about 95%, about 96%, about 97%, about 98%, about 99% or about 100% identical to the amino acid sequence set forth in SEQ ID NO:21. The protein sequence includes a CD8 leader sequence at amino acids 1-18, and is able to bind human CD19.

```
                                    SEQ ID NO: 21
MALPVTALLLPLALLLHAEVKLQQSGAELVRPGSSVKISCKASGYAFSS

YWMNWVKQRPGQGLEWIGQIYPGDGDTNYNGKFKGQATLTADKSSSTAY

MQLSGLTSEDSAVYFCARKTISSVVDFYPDYWGQGTTVTVSSGGGGSGG

GGSGGGGSDIELTQSPKFMSTSVGDRVSVTCKASQNVGTNVAWYQQKPG

QSPKPLIYSATYRNSGVPDRFTGSGSGTDFTLTITNVQSKDLADYFCQQ

YNRYPYTSGGGTKLEIKRAAAIEVMYPPPYLDNEKSNGTIIHVKGKHLC

PSPLFPGPSKPFWVLVVVGGVLACYSLLVTVAFIIFWVRSKRSRLLHSD

YMNMTPRRPGPTRKHYQPYAPPRDFAAYRSRVKFSRSAEPPAYQQGQNQ

LYNELNLGRREEYDVLDKRRGRDPEMGGKPRRKNPQEGLYNELQKDKMA

EAYSEIGMKGERRRGKGHDGLYQGLSTATKDTYDALHMQALPPR
```

In another embodiment, a CAR having an extracellular antigen-binding domain that binds to CD19, a hinge spacer from human IgG₄, a transmembrane domain comprising a CD28 transmembrane domain, a 4-1BB co-stimulatory signaling region, and a CD3ζ intracellular signaling domain is provided. In certain embodiments, the CAR is designated 1928z1. In certain embodiments, 1928z1 is a protein having at least about 85%, about 90%, about 95%, about 96%, about 97%, about 98%, about 99% or about 100% identical to the amino acid sequence set forth in SEQ ID NO:22.

```
                                    SEQ ID NO: 22
MLLLVTSLLLCELPHPAFLLIPDIQMTQTTSSLSASLGDRVTISCRASQ

DISKYLNWYQQKPDGTVKLLIYHTSRLHSGVPSRFSGSGSGTDYSLTIS

NLEQEDIATYFCQQGNTLPYTFGGGTKLEITGSTSGSGKPGSGEGSTKG

EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSESKYGPPCPPCPMFWVLVVVGGVLACY

SLLVTVAFIIFWVKRGRKKLLYIFKQPFMRPVQTTQEEDGCSCRFPEEE

EGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQG

LSTATKDTYDALHMQALPPRL
```

In certain embodiments, a CAR comprises an extracellular antigen-binding domain that binds to MUC16, a transmembrane domain comprising a CD28 polypeptide, and an intracellular signaling domain comprising a CD3zeta polypeptide and a co-stimulatory signaling region comprising a CD28 polypeptide. In certain embodiments, the CAR is designated 4H1128z. In certain embodiments, 4H1128z is a protein having at least about 85%, about 90%, about 95%, about 96%, about 97%, about 98%, about 99% or about 100% identical to the amino acid sequence set forth in SEQ ID NO:23. The protein includes a CD8 leader sequence at amino acids 1-18 and binds to the MUC-16 ectodomain.

```
                                    SEQ ID NO: 23
MALPVTALLLPLALLLHAEVKLQESGGGFVKPGGSLKVSCAASGFTFSS

YAMSWVRLSPEMRLEWVATISSAGGYIFYSDSVQGRFTISRDNAKNTLH

LQMGSLRSGDTAMYYCARQGFGNYGDYYAMDYWGQGTTVTVSSGGGGSG

GGGSGGGGSDIELTQSPSSLAVSAGEKVTMSCKSSQSLLNSRTRKNQLA

WYQQKPGQSPELLIYWASTRQSGVPDRFTGSGSGTDFTLTISSVQAEDL

AVYYCQQSYNLLTFGPGTKLEIKRAAAIEVMYPPPYLDNEKSNGTIIHV

KGKHLCPSPLFPGPSKPFWVLVVVGGVLACYSLLVTVAFIIFWVRSKRS

RLLHSDYMNMTPRRPGPTRKHYQPYAPPRDFAAYRSRVKFSRSAEPPAY

QQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPP

R
``` certain embodiments, a CAR comprises an extracellular antigen-binding domain that binds to CD19, a transmembrane domain comprising a CD8 polypeptide, and an intracellular signaling domain comprising a CD3zeta polypeptide and a co-stimulatory signaling region comprising a 4-1BB polypeptide. In certain embodiments, the CAR is 19BBz. An exemplary protein sequence of the 19BBz polypeptide is set forth in SEQ ID NO:24.

SEQ ID NO: 24:
MALPVTALLLPLALLLHAEVKLQQSGAELVRPGSSVKISCKASGYAFSS

YWMNWVKQRPGQGLEWIGQIYPGDGDTNYNGKFKGQATLTADKSSSTAY

MQLSGLTSEDSAVYFCARKTISSVVDFYFDYWGQGTTVTVSSGGGGSGG

GGSGGGGSDIELTQSPKFMSTSVGDRVSVTCKASQNVGTNVAWYQQKPG

QSPKPLIYSATYRNSGVPDRFTGSGSGTDFTLTITNVQSKDLADYFCQQ

YNRYPYTSGGGTKLEIKRAAAPTTTPAPRPPTPAPTIASQPLSLRPEAC

RPAAGGAVHTRGLDFACDIYIWAPLAGTCGVLLLSLVITLYCNKRGRKK

LLYIFKQPFMRPVQTTQEEDGCSCRFPEEEEGGCELRVKFSRSAEPPAY

QQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPP

R

In certain embodiments, a CAR having an extracellular antigen-binding domain that binds to CD19, a hinge spacer from human IgG$_4$, a transmembrane domain comprising a CD28 transmembrane domain, a 4-1BB co-stimulatory signaling region, and a CD3zeta intracellular signaling domain is provided. An exemplary CD19 CAR protein sequence, that also includes a truncated EGFR (tEGFR) polypeptide attached to the carboxy terminal portion of the CAR by a self-cleaving 2A peptide, is set forth in SEQ ID NO:61.

SEQ ID NO: 61:
MLLLVTSLLLCELPHPAFLLIPDIQMTQTTSSLSASLGDRVTISCRASQ

DISKYLNWYQQKPDGTVKLLIYHTSRLHSGVPSRFSGSGSGTDYSLTIS

NLEQEDIATYFCQQGNTLPYTFGGGTKLEITGSTSGSGKPGSGEGSTKG

EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSESKYGPPCPPCPMFWVLVVVGGVLACY

SLLVTVAFIIFWVKRGRKKLLYIFKQPFMRPVQTTQEEDGCSCRFPEEE

EGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQG

LSTATKDTYDALHMQALPPRLEGGGEGRGSLLTCGDVEENPGPRMLLLV

TSLLLCELPHPAFLLIPRKVCNGIGIGEFKDSLSINATNIKHFKNCTSI

SGDLHILPVAIRGDSFTHTPPLDPQELDILKTVKEITGFLLIQAWPENR

TDLHAFENLEIIRGRTKQHGQFSLAVVSLNITSLGLRSLKEISDGDVII

SGNKNLCYANTINWKKLFGTSGQKTKIISNRGENSCKATGQVCHALCSP

EGCWGPEPRDCVSCRNVSRGRECVDKCNLLEGEPREFVENSECIQCHPE

CLPQAMNITCTGRGPDNCIQCAHYIDGPHCVKTCPAGVMGENNTLVWKY

ADAGHVCHLCHPNCTYGCTGPGLEGCPTNGPKIPSIATGMVGALLLLLV

VALGIGLFM

In certain embodiments, a CAR having an extracellular antigen-binding domain that binds to CD19, a hinge spacer from human IgG$_4$, a transmembrane domain of a CD28 transmembrane domain, a 4-1BB co-stimulatory signaling region, and a CD3ζ intracellular signaling domain is provided. An exemplary CD19 CAR protein sequence, that also includes a human IL-15 attached to the carboxy terminal portion of the CAR by a self-cleaving 2A peptide, is set forth in SEQ ID NO:62.

SEQ ID NO: 62:
MLLLVTSLLLCELPHPAFLLIPDIQMTQTTSSLSASLGDRVTISCRASQ

DISKYLNWYQQKPDGTVKLLIYHTSRLHSGVPSRFSGSGSGTDYSLTIS

NLEQEDIATYFCQQGNTLPYTFGGGTKLEITGSTSGSGKPGSGEGSTKG

EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSESKYGPPCPPCPMFWVLVVVGGVLACY

SLLVTVAFIIFWVKRGRKKLLYIFKQPFMRPVQTTQEEDGCSCRFPEEE

EGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQG

LSTATKDTYDALHMQALPPRLEGGGEGRGSLLTCGDVEENPGPRMRISK

PHLRSISIQCYLCLLLNSHFLTEAGIHVFILGCFSAGLPKTEANWVNVI

SDLKKIEDLIQSMHIDATLYTESDVHPSCKVTAMKCFLLELQVISLESG

DASIHDTVENLIILANNSLSSNGNVTESGCKECEELEEKNIKEFLQSFV

HIVQMFINTS

The corresponding nucleic acid sequence that can encode the construct in SEQ ID NO:62 is set forth in SEQ ID NO:69.

SEQ ID NO: 69:
ATGCTGCTGCTGGTGACCAGCCTGCTGCTGTGCGAGCTGCCCCACCCCG

CCTTTCTGCTGATCCCCGACATCCAGATGACCCAGACCACCTCCAGCCT

GAGCGCCAGCCTGGGCGACCGGGTGACCATCAGCTGCCGGGCCAGCCAG

GACATCAGCAAGTACCTGAACTGGTATCAGCAGAAGCCCGACGGCACCG

TCAAGCTGCTGATCTACCACACCAGCCGGCTGCACAGCGGCGTGCCCAG

CCGGTTTAGCGGCAGCGGCTCCGGCACCGACTACAGCCTGACCATCTCC

AACCTGGAACAGGAAGATATCGCCACCTACTTTTGCCAGCAGGGCAACA

CACTGCCCTACACCTTTGGCGGCGGAACAAAGCTGGAAATCACCGGCAG

CACCTCCGGCAGCGGCAAGCCTGGCAGCGGCGAGGGCAGCACCAAGGGC

GAGGTGAAGCTGCAGGAAAGCGGCCCTGGCCTGGTGGCCCCCAGCCAGA

GCCTGAGCGTGACCTGCACCGTGAGCGGCGTGAGCCTGCCCGACTACGG

CGTGAGCTGGATCCGGCAGCCCCCCAGGAAGGGCCTGGAATGGCTGGGC

GTGATCTGGGGCAGCGAGACCACCTACTACAACAGCGCCCTGAAGAGCC

GGCTGACCATCATCAAGGACAACAGCAAGAGCCAGGTGTTCCTGAAGAT

GAACAGCCTGCAGACCGACGACACCGCCATCTACTACTGCGCCAAGCAC

TACTACTACGGCGGCAGCTACGCCATGGACTACTGGGGCCAGGGCACCA

GCGTGACCGTGAGCAGCGAATCTAAGTACGGACCGCCCTGCCCCCCTTG

CCCTATGTTCTGGGTGCTGGTGGTGGTCGGAGGCGTGCTGGCCTGCTAC

AGCCTGCTGGTCACCGTGGCCTTCATCATCTTTTGGGTGAAACGGGGCA

GAAAGAAACTCCTGTATATATTCAAACAACCATTTATGAGACCAGTACA

-continued
AACTACTCAAGAGGAAGATGGCTGTAGCTGCCGATTTCCAGAAGAAGAA

GAAGGAGGATGTGAACTGAGGGTGAAGTTCAGCAGAAGCGCCGACGCCC

CTGCCTACCAGCAGGGCCAGAATCAGCTGTACAACGAGCTGAACCTGGG

CAGAAGGGAAGAGTACGACGTCCTGGATAAGCGGAGAGGCCGGGACCCT

GAGATGGGCGGCAAGCCTCGGCGGAAGAACCCCCAGGAAGGCCTGTATA

ACGAACTGCAGAAAGACAAGATGGCCGAGGCCTACAGCGAGATCGGCAT

GAAGGGCGAGCGGAGGCGGGGCAAGGGCCACGACGGCCTGTATCAGGGC

CTGTCCACCGCCACCAAGGATACCTACGACGCCCTGCACATGCAGGCCC

TGCCCCCAAGGCTCGAGGGCGGCGGAGAGGGCAGAGGAAGTCTTCTAAC

ATGCGGTGACGTGGAGGAGAATCCCGGCCCTAGGATGCGGATTTCCAAA

CCTCACCTGCGCTCTATCTCTATCCAGTGCTATCTGTGCCTGCTGCTGA

ACTCACATTTCCTGACCGAAGCCGGCATCCACGTGTTCATCCTGGGCTG

CTTTTCCGCCGGCCTGCCAAAGACCGAGGCAAACTGGGTGAATGTGATC

TCTGACCTGAAGAAGATCGAGGATCTGATCCAGAGCATGCACATCGACG

CCACCCTGTACACAGAGTCCGATGTGCACCCTTCTTGCAAGGTGACAGC

CATGAAGTGTTTCCTGCTGGAGCTGCAGGTCATCAGCCTGGAGAGCGGC

GACGCCTCTATCCACGATACCGTGGAGAACCTGATCATCCTGGCCAACA

ATAGCCTGAGCAGCAACGGCAATGTGACAGAGTCCGGCTGCAAGGAGTG

TGAGGAGCTGGAGGAGAAGAATATCAAAGAGTTCCTGCAGTCATTCGTC

CATATCGTCCAGATGTTTATCAATACCTCCTAA

In certain embodiments, a CAR having an extracellular antigen-binding domain that binds to CD19, a hinge spacer from human IgG$_4$, a transmembrane domain of a CD28 transmembrane domain, a 2B4 co-stimulatory signaling region, and a CD3zeta intracellular signaling domain is provided. An exemplary CD19 CAR protein sequence, that also includes a human IL-15 attached to the carboxy terminal portion of the CAR by a self-cleaving 2A peptide, is set forth in SEQ ID NO:70.

SEQ ID NO: 70:
MLLLVTSLLLCELPHPAFLLIPDIQMTQTTSSLSASLGDRVTISCRASQ

DISKYLNWYQQKPDGTVKLLIYHTSRLHSGVPSRFSGSGSGTDYSLTIS

NLEQEDIATYFCQQGNTLPYTFGGGTKLEITGSTSGSGKPGSGEGSTKG

EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSESKYGPPCPPCPMFWVLVVVGGVLACY

SLLVTVAFIIFWVWRRKRKEKQSETSPKEFLTIYEDVKDLKTRRNHEQE

QTFPGGGSTIYSMIQSQSSAPTSQEPAYTLYSLIQPSRKSGSRKRNHSP

SFNSTIYEVIGKSQPKAQNPARLSRKELENFDVYSRVKFSRSADAPAYQ

QGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

LEGGGEGRGSLLTCGDVEENPGPRMRISKPHLRSISIQCYLCLLLNSHF

LTEAGIHVFILGCFSAGLPKTEANWVNVISDLKKIEDLIQSMHIDATLY

TESDVHPSCKVTAMKCFLLELQVISLESGDASIHDTVENLIILANNSLS

SNGNVTESGCKECEELEEKNIKEFLQSFVHIVQMFINTS

The corresponding nucleic acid sequence encoding the SEQ ID NO:70 construct is set forth in SEQ ID NO:71.

SEQ ID NO: 71:
ATGCTGCTGCTGGTGACCAGCCTGCTGCTGTGCGAGCTGCCCCACCCCG

CCTTTCTGCTGATCCCCGACATCCAGATGACCCAGACCACCTCCAGCCT

GAGCGCCAGCCTGGGCGACCGGGTGACCATCAGCTGCCGGGCCAGCCAG

GACATCAGCAAGTACCTGAACTGGTATCAGCAGAAGCCCGACGGCACCG

TCAAGCTGCTGATCTACCACACCAGCCGGCTGCACAGCGGCGTGCCCAG

CCGGTTTAGCGGCAGCGGCTCCGGCACCGACTACAGCCTGACCATCTCC

AACCTGGAACAGGAAGATATCGCCACCTACTTTTGCCAGCAGGGCAACA

CACTGCCCTACACCTTTGGCGGCGGAACAAAGCTGGAAATCACCGGCAG

CACCTCCGGCAGCGGCAAGCCTGGCAGCGGCGAGGGCAGCACCAAGGGC

GAGGTGAAGCTGCAGGAAAGCGGCCCTGGCCTGGTGGCCCCCAGCCAGA

GCCTGAGCGTGACCTGCACCGTGAGCGGCGTGAGCCTGCCCGACTACGG

CGTGAGCTGGATCCGGCAGCCCCCCAGGAAGGGCCTGGAATGGCTGGGC

GTGATCTGGGGCAGCGAGACCACCTACTACAACAGCGCCCTGAAGAGCC

GGCTGACCATCATCAAGGACAACAGCAAGAGCCAGGTGTTCCTGAAGAT

GAACAGCCTGCAGACCGACGACACCGCCATCTACTACTGCGCCAAGCAC

TACTACTACGGCGGCAGCTACGCCATGGACTACTGGGGCCAGGGCACCA

GCGTGACCGTGAGCAGCGAATCTAAGTACGGACCGCCCTGCCCCCCTTG

CCCTATGTTCTGGGTGCTGGTGGTGGTCGGAGGCGTGCTGGCCTGCTAC

AGCCTGCTGGTCACCGTGGCCTTCATCATCTTTTGGGTGTGGAGGAGGA

AGAGGAAGGAGAAGCAGAGCGAGACAAGCCCTAAGGAGTTTCTGACAAT

CTATGAAGACGTGAAGGACCTGAAGACACGGAGAAACCACGAGCAGGAG

CAGACCTTCCCTGGAGGAGGCAGCACAATCTACTCCATGATCCAGTCTC

AGAGCAGCGCCCCCACCTCCCAGGAGCCTGCCTACACACTGTATAGCCT

GATCCAGCCATCCCGGAAGTCTGGCAGCAGGAAGCGCAACCACTCCCCC

TCTTTTAATTCTACCATCTATGAAGTGATCGGCAAGAGCCAGCCCAAGG

CACAGAACCCCGCACGACTGAGCAGGAAGGAACTGGAGAACTTTGATGT

CTACTCTAGGGTGAAGTTCAGCAGAAGCGCCGACGCCCCTGCCTACCAG

CAGGGCCAGAATCAGCTGTACAACGAGCTGAACCTGGGCAGAAGGGAAG

AGTACGACGTCCTGGATAAGCGGAGAGGCCGGGACCCTGAGATGGGCGG

CAAGCCTCGGCGGAAGAACCCCCAGGAAGGCCTGTATAACGAACTGCAG

AAAGACAAGATGGCCGAGGCCTACAGCGAGATCGGCATGAAGGGCGAGC

GGAGGCGGGGCAAGGGCCACGACGGCCTGTATCAGGGCCTGTCCACCGC

CACCAAGGATACCTACGACGCCCTGCACATGCAGGCCCTGCCCCCAAGG

CTCGAGGGCGGCGGAGAGGGCAGAGGAAGTCTTCTAACATGCGGTGACG

-continued

```
TGGAGGAGAATCCCGGCCCTAGGATGCGGATTTCCAAACCTCACCTGCG

CTCTATCTCTATCCAGTGCTATCTGTGCCTGCTGCTGAACTCACATTTC

CTGACCGAAGCCGGCATCCACGTGTTCATCCTGGGCTGCTTTTCCGCCG

GCCTGCCAAAGACCGAGGCAAACTGGGTGAATGTGATCTCTGACCTGAA

GAAGATCGAGGATCTGATCCAGAGCATGCACATCGACGCCACCCTGTAC

ACAGAGTCCGATGTGCACCCTTCTTGCAAGGTGACAGCCATGAAGTGTT

TCCTGCTGGAGCTGCAGGTCATCAGCCTGGAGAGCGGCGACGCCTCTAT

CCACGATACCGTGGAGAACCTGATCATCCTGGCCAACAATAGCCTGAGC

AGCAACGGCAATGTGACAGAGTCCGGCTGCAAGGAGTGTGAGGAGCTGG

AGGAGAAGAATATCAAAGAGTTCCTGCAGTCATTCGTCCATATCGTCCA

GATGTTTATCAATACCTCCTAA
```

In certain embodiments, a CAR having an extracellular antigen-binding domain that binds to CD19, a hinge spacer from human IgG$_4$, a transmembrane domain of a NKG2D transmembrane domain, a 4-1BB co-stimulatory signaling region, and a CD3zeta intracellular signaling domain is provided. Use of the NKG2Ds transmembrane domain has been used previously (Xu et al., J. Hematol. Oncol. 12:49, 2019) although some suggest that because NKGD2 is a type II membrane protein it should be inserted in the opposite orientation. An exemplary CD19 CAR protein sequence, that also includes a human IL-15 attached to the carboxy terminal portion of the CAR by a self-cleaving 2A peptide, is set forth in SEQ ID NO:72.

```
SEQ ID NO: 72:
MLLLVTSLLLCELPHPAFLLIPDIQMTQTTSSLSASLGDRVTISCRASQ

DISKYLNWYQQKPDGTVKLLIYHTSRLHSGVPSRFSGSGSGTDYSLTIS

NLEQEDIATYFCQQGNTLPYTFGGGTKLEITGSTSGSGKPGSGEGSTKG

EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSESKYGPPCPPCPPFFFCCFIAVAMGIR

FIIMVTKRGRKKLLYIFKQPFMRPVQTTQEEDGCSCRFPEEEEGGCELR

VKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKD

TYDALHMQALPPRLEGGGEGRGSLLTCGDVEENPGPRMRISKPHLRSIS

IQCYLCLLLNSHFLTEAGIHVFILGCFSAGLPKTEANWVNVISDLKKIE

DLIQSMHIDATLYTESDVHPSCKVTAMKCFLLELQVISLESGDASIHDT

VENLIILANNSLSSNGNVTESGCKECEELEEKNIKEFLQSFVHIVQMFI

NTS
```

The corresponding nucleic acid sequence encoding the SEQ ID NO:72 construct is set forth in SEQ ID NO:73.

```
SEQ ID NO: 73:
ATGCTGCTGCTGGTGACCAGCCTGCTGCTGTGCGAGCTGCCCCACCCCG

CCTTTCTGCTGATCCCCGACATCCAGATGACCCAGACCACCTCCAGCCT

GAGCGCCAGCCTGGGCGACCGGGTGACCATCAGCTGCCGGGCCAGCCAG
```

-continued

```
GACATCAGCAAGTACCTGAACTGGTATCAGCAGAAGCCCGACGGCACCG

TCAAGCTGCTGATCTACCACACCAGCCGGCTGCACAGCGGCGTGCCCAG

CCGGTTTAGCGGCAGCGGCTCCGGCACCGACTACAGCCTGACCATCTCC

AACCTGGAACAGGAAGATATCGCCACCTACTTTTGCCAGCAGGGCAACA

CACTGCCCTACACCTTTGGCGGCGGAACAAAGCTGGAAATCACCGGCAG

CACCTCCGGCAGCGGCAAGCCTGGCAGCGGCGAGGGCAGCACCAAGGGC

GAGGTGAAGCTGCAGGAAAGCGGCCCTGGCCTGGTGGCCCCCAGCCAGA

GCCTGAGCGTGACCTGCACCGTGAGCGGCGTGAGCCTGCCCGACTACGG

CGTGAGCTGGATCCGGCAGCCCCCCAGGAAGGGCCTGGAATGGCTGGGC

GTGATCTGGGGCAGCGAGACCACCTACTACAACAGCGCCCTGAAGAGCC

GGCTGACCATCATCAAGGACAACAGCAAGAGCCAGGTGTTCCTGAAGAT

GAACAGCCTGCAGACCGACGACACCGCCATCTACTACTGCGCCAAGCAC

TACTACTACGGCGGCAGCTACGCCATGGACTACTGGGGCCAGGGCACCA

GCGTGACCGTGAGCAGCGAATCTAAGTACGGACCGCCCTGCCCCCCTTG

CCCTCCCTTCTTTTTCTGCTGTTTTATCGCCGTGGCTATGGGCATCCGG

TTCATCATCATGGTGACCAAACGGGGCAGAAAGAAACTCCTGTATATAT

TCAAACAACCATTTATGAGACCAGTACAAACTACTCAAGAGGAAGATGG

CTGTAGCTGCCGATTTCCAGAAGAAGAAGAAGGAGGATGTGAACTGAGG

GTGAAGTTCAGCAGAAGCGCCGACGCCCCTGCCTACCAGCAGGGCCAGA

ATCAGCTGTACAACGAGCTGAACCTGGGCAGAAGGGAAGAGTACGACGT

CCTGGATAAGCGGAGAGGCCGGGACCCTGAGATGGGCGGCAAGCCTCGG

CGGAAGAACCCCCAGGAAGGCCTGTATAACGAACTGCAGAAAGACAAGA

TGGCCGAGGCCTACAGCGAGATCGGCATGAAGGGCGAGCGGAGGCGGGG

CAAGGGCCACGACGGCCTGTATCAGGGCCTGTCCACCGCCACCAAGGAT

ACCTACGACGCCCTGCACATGCAGGCCCTGCCCCCCAAGGCTCGAGGGCG

GCGGAGAGGGCAGAGGAAGTCTTCTAACATGCGGTGACGTGGAGGAGAA

TCCCGGCCCTAGGATGCGGATTTCCAAACCTCACCTGCGCTCTATCTCT

ATCCAGTGCTATCTGTGCCTGCTGCTGAACTCACATTTCCTGACCGAAG

CCGGCATCCACGTGTTCATCCTGGGCTGCTTTTCCGCCGGCCTGCCAAA

GACCGAGGCAAACTGGGTGAATGTGATCTCTGACCTGAAGAAGATCGAG

GATCTGATCCAGAGCATGCACATCGACGCCACCCTGTACACAGAGTCCG

ATGTGCACCCTTCTTGCAAGGTGACAGCCATGAAGTGTTTCCTGCTGGA

GCTGCAGGTCATCAGCCTGGAGAGCGGCGACGCCTCTATCCACGATACC

GTGGAGAACCTGATCATCCTGGCCAACAATAGCCTGAGCAGCAACGGCA

ATGTGACAGAGTCCGGCTGCAAGGAGTGTGAGGAGCTGGAGGAGAAGAA

TATCAAAGAGTTCCTGCAGTCATTCGTCCATATCGTCCAGATGTTTATC

AATACCTCCTAA
```

In certain embodiments, a CAR having an extracellular antigen-binding domain that binds to CD19, a hinge spacer from human IgG$_4$, a transmembrane domain of a NKG2D transmembrane domain, a 2B4 co-stimulatory signaling region, and a CD3ζ intracellular signaling domain is provided. An exemplary CD19 CAR protein sequence, that also includes a human IL-15 attached to the carboxy terminal portion of the CAR by a self-cleaving 2A peptide, is set forth in SEQ ID NO:74.

SEQ ID NO: 74:
MLLLVTSLLLCELPHPAFLLIPDIQMTQTTSSLSASLGDRVTISCRASQ

DISKYLNWYQQKPDGTVKLLIYHTSRLHSGVPSRFSGSGSGTDYSLTIS

NLEQEDIATYFCQQGNTLPYTFGGGTKLEITGSTSGSGKPGSGEGSTKG

EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSESKYGPPCPPCPPFFFCCFIAVAMGIR

FIIMVTWRRKRKEKQSETSPKEFLTIYEDVKDLKTRRNHEQEQTFPGGG

STIYSMIQSQSSAPTSQEPAYTLYSLIQPSRKSGSRKRNHSPSFNSTIY

EVIGKSQPKAQNPARLSRKELENFDVYSRVKFSRSADAPAYQQGQNQLY

NELNLGRREEYDVLDKRRGRDPEMGGKPRRKNPQEGLYNELQKDKMAEA

YSEIGMKGERRRGKGHDGLYQGLSTATKDTYDALHMQALPPRLEGGGEG

RGSLLTCGDVEENPGPRMRISKPHLRSISIQCYLCLLLNSHFLTEAGIH

VFILGCFSAGLPKTEANWVNVISDLKKIEDLIQSMHIDATLYTESDVHP

SCKVTAMKCFLLELQVISLESGDASIHDTVENLIILANNSLSSNGNVTE

SGCKECEELEEKNIKEFLQSFVHIVQMFINTS

The corresponding nucleic acid sequence encoding the SEQ ID NO:74 construct is set forth in SEQ ID NO:75.

SEQ ID NO: 75:
ATGCTGCTGCTGGTGACCAGCCTGCTGCTGTGCGAGCTGCCCCACCCCG

CCTTTCTGCTGATCCCCGACATCCAGATGACCCAGACCACCTCCAGCCT

GAGCGCCAGCCTGGGCGACCGGGTGACCATCAGCTGCCGGGCCAGCCAG

GACATCAGCAAGTACCTGAACTGGTATCAGCAGAAGCCCGACGGCACCG

TCAAGCTGCTGATCTACCACACCAGCCGGCTGCACAGCGGCGTGCCCAG

CCGGTTTAGCGGCAGCGGCTCCGGCACCGACTACAGCCTGACCATCTCC

AACCTGGAACAGGAAGATATCGCCACCTACTTTTGCCAGCAGGGCAACA

CACTGCCCTACACCTTTGGCGGCGGAACAAAGCTGGAAATCACCGGCAG

CACCTCCGGCAGCGGCAAGCCTGGCAGCGGCGAGGGCAGCACCAAGGGC

GAGGTGAAGCTGCAGGAAAGCGGCCCTGGCCTGGTGGCCCCCAGCCAGA

GCCTGAGCGTGACCTGCACCGTGAGCGGCGTGAGCCTGCCCGACTACGG

CGTGAGCTGGATCCGGCAGCCCCCCAGGAAGGGCCTGGAATGGCTGGGC

GTGATCTGGGGCAGCGAGACCACCTACTACAACAGCGCCCTGAAGAGCC

GGCTGACCATCATCAAGGACAACAGCAAGAGCCAGGTGTTCCTGAAGAT

GAACAGCCTGCAGACCGACGACACCGCCATCTACTACTGCGCCAAGCAC

TACTACTACGGCGGCAGCTACGCCATGGACTACTGGGGCCAGGGCACCA

GCGTGACCGTGAGCAGCGAATCTAAGTACGGACCGCCCTGCCCCCCTTG

CCCTCCCTTCTTTTTCTGCTGTTTTATCGCCGTGGCTATGGGCATCCGG

TTCATCATCATGGTGACCTGGAGGAGGAAGAGGAAGGAGAAGCAGAGCG

AGACAAGCCCTAAGGAGTTTCTGACAATCTATGAAGACGTGAAGGACCT

*-continued*

GAAGACACGGAGAAACCACGAGCAGGAGCAGACCTTCCCTGGAGGAGGC

AGCACAATCTACTCCATGATCCAGTCTCAGAGCAGCGCCCCCACCTCCC

AGGAGCCTGCCTACACACTGTATAGCCTGATCCAGCCATCCCGGAAGTC

TGGCAGCAGGAAGCGCAACCACTCCCCCTCTTTTAATTCTACCATCTAT

GAAGTGATCGGCAAGAGCCAGCCCAAGGCACAGAACCCCGCACGACTGA

GCAGGAAGGAACTGGAGAACTTTGATGTCTACTCTAGGGTGAAGTTCAG

CAGAAGCGCCGACGCCCCTGCCTACCAGCAGGGCCAGAATCAGCTGTAC

AACGAGCTGAACCTGGGCAGAAGGGAAGAGTACGACGTCCTGGATAAGC

GGAGAGGCCGGGACCCTGAGATGGGCGGCAAGCCTCGGCGGAAGAACCC

CCAGGAAGGCCTGTATAACGAACTGCAGAAAGACAAGATGGCCGAGGCC

TACAGCGAGATCGGCATGAAGGGCGAGCGGAGGCGGGGCAAGGGCCACG

ACGGCCTGTATCAGGGCCTGTCCACCGCCACCAAGGATACCTACGACGC

CCTGCACATGCAGGCCCTGCCCCCCAAGGCTCGAGGGCGGCGGAGAGGGC

AGAGGAAGTCTTCTAACATGCGGTGACGTGGAGGAGAATCCCGGCCCTA

GGATGCGGATTTCCAAACCTCACCTGCGCTCTATCTCTATCCAGTGCTA

TCTGTGCCTGCTGCTGAACTCACATTTCCTGACCGAAGCCGGCATCCAC

GTGTTCATCCTGGGCTGCTTTTCCGCCGGCCTGCCAAAGACCGAGGCAA

ACTGGGTGAATGTGATCTCTGACCTGAAGAAGATCGAGGATCTGATCCA

GAGCATGCACATCGACGCCACCCTGTACACAGAGTCCGATGTGCACCCT

TCTTGCAAGGTGACAGCCATGAAGTGTTTCCTGCTGGAGCTGCAGGTCA

TCAGCCTGGAGAGCGGCGACGCCTCTATCCACGATACCGTGGAGAACCT

GATCATCCTGGCCAACAATAGCCTGAGCAGCAACGGCAATGTGACAGAG

TCCGGCTGCAAGGAGTGTGAGGAGCTGGAGGAGAAGAATATCAAAGAGT

TCCTGCAGTCATTCGTCCATATCGTCCAGATGTTTATCAATACCTCCTA

A

Expression Constructs

In certain embodiments, a CAR can further be expressed from a nucleic acid comprising an inducible promoter, for expressing nucleic acid sequences in human cells. Promoters for use in expressing CAR genes can be a constitutive promoter, such as promoters for ubiquitin C (UbiC), PGK, EF-1alpha, MND (a synthetic viral promoter that contains the U3 region of a modified Moloney murine leukemia virus long terminal repeat with myeloproliferative sarcoma virus enhancer), or Chicken beta actin.

Methods of preparing genetically modified NK cell compositions and/or preparations for immunotherapy comprise introducing into the CD56+ (mainly NK) cells a polynucleotide(s) encoding an antigen recognizing receptor(s), such as a CAR, into the cells. The polynucleotide(s) encoding the desired molecule can be introduced into the HSPCs, before, during, or after expansion, or into HSPCs or NK cell compositions and/or preparations before, during, or after differentiation. Some embodiments relate to a method of engineering an NK cell composition and/or preparation by transforming, transducing, or transfecting an HSPC or NK cell composition and/or preparation with at least one polynucleotide encoding a CAR, TCR, or other antigen recognizing receptor, and expressing the polynucleotide in the cell. Desired polynucleotides encoding genes can be introduced into HSPCs or other cells by any method known in the art, including transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, spheroplast fusion, using CRISPR or other rare-cutting endonuclease (e.g., TALE-nuclease or Cas9 endonuclease), and the like. Numerous techniques are known in the art for the introduction of foreign genes into cells (see e.g., Loeffler and Behr, *Meth. Enzymol.* 217:599-618, 1993; Cohen et al., *Meth. Enzymol.* 217:618-644, 1993; Cline, *Pharmac. Ther.* 29:69-92, 1985) and can be used, provided that the necessary physiological functions of the recipient cells are not disrupted. The technique should provide for the stable transfer of the gene to the cell, so that the gene is expressible by the cell and preferably heritable and expressible by its cell progeny. In some embodiments, the method of transfer includes the transfer of a selectable marker or tag sequence to the cells. The cells are then placed under selection to isolate those cells that have taken up and are expressing the transferred gene. In a preferred embodiment, the polynucleotide(s) or genes are included in lentiviral vectors in view of being stably expressed in the cells.

In an embodiment, an antigen recognizing receptor (e.g., CAR or TCR) is introduced into HSPCs during the expansion phase and prior to differentiation, to form antigen recognizing receptor-expressing HSPCs and/or antigen recognizing receptor-expressing NK cells. In a preferred embodiment, the antigen recognizing receptor CAR is introduced into HSPCs during the expansion phase and prior to differentiation, to form CAR-HSPCs and/or CAR-NK cells. In another embodiment, an antigen recognizing receptor (e.g., CAR or TCR) is introduced into isolated enriched CD56⁺ NK cells after expansion and during the differentiation phase, to form antigen recognizing receptor-expressing HSPCs and/or antigen recognizing receptor-expressing NK cells. In a preferred embodiment, the antigen recognizing receptor CAR is introduced into isolated enriched CD56⁺ NK cells after expansion and during the differentiation phase, to form CAR-HSPCs and/or CAR-NK cells. The antigen recognizing receptor introduction, CAR introduction, cell expansion, and cell differentiation mentioned above are each carried out as described above and below.

The different methods described above involve introducing CAR, or another antigen recognizing receptor into a cell. As a non-limiting example, a CAR or TCR can be introduced as a transgene(s) encoded by one plasmid vector. The plasmid vector can also contain a selection marker which provides for identification and/or selection of cells which received said vector.

Polypeptides, such as a CAR or TCR, can be synthesized in situ in the cell as a result of the introduction of polynucleotides encoding the polypeptides into the cell.

Methods for viral mediated introduction of a polynucleotide construct into cells are known in the art. and include as non-limiting examples recombinant viral vectors (e.g., retroviruses, adenoviruses).

Cryopreservation of the NK Cell Composition and/or Preparation

An NK cell composition and/or preparation, with or without genetic engineering, can be divided and frozen in one or more bags (or units). In a preferred embodiment, from about 50 to about 500 million total cells are frozen in a single bag (or unit). In another preferred embodiment, from about 100 to about 500 million cells are frozen in a single bag (or unit). In other preferred embodiments, about 50, 100, 200, 300, 400 or 400 million cells are frozen in a single bag (or unit). In some embodiments a single bag (or unit) contains about 50 million to about 2 billion viable cells per dose. In some embodiments, a single bag (or unit) contains about 100 million, about 200 million, about 300 million, about 400 million, about 500 million, about 600 million, about 750 million, about 1 billion, about 1.5 billion or about 2 billion viable cells. In some embodiments, a single bag contains about 50 million to about 2 billion viable CD56⁺ cells per dose. In some embodiments, a single bag (or unit) contains about 100 million, about 200 million, about 300 million, about 400 million, about 500 million, about 600 million, about 750 million, about 1 billion, about 1.5 billion or about 2 billion viable CD56⁺ cells.

In a preferred embodiment, the NK cell composition and/or preparation is frozen or cryopreserved. In another embodiment, the NK cell composition and/or preparation is fresh, i.e., the cells have not been previously frozen prior to expansion or cryopreservation. The terms "frozen/freezing" and "cryopreserved/cryopreserving/cryopreservation" are used interchangeably in the present application. Cryopreservation can be by any method known in the art that preserves cells in viable form. The freezing of cells is ordinarily destructive because on cooling, water within the cell freezes, leading to injury caused by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroys the cell. For a discussion, see Mazur, P., *Cryobiology* 14:251-272, 1977.

These injurious effects can be circumvented by (a) use of a cryoprotective agent, (b) control of the freezing rate, and (c) storage at a temperature sufficiently low to minimize degradative reactions.

Cryoprotective agents which can be used include, but are not limited to, dimethyl sulfoxide (DMSO) (Lovelock and Bishop, *Nature* 183:1394-1395, 1959; Ashwood-Smith, *Nature* 190:1204-1205, 1961); glycerol, polyvinylpyrrolidine (Rinfret, *Ann. N.Y. Acad. Sci.* 85:576, 1960); polyethylene glycol (Sloviter and Ravdin, *Nature* 196:548, 1962); albumin, dextran, sucrose, ethylene glycol, i-erythritol, D-ribitol, D-mannitol (Rowe et al., *Fed. Proc.* 21:157, 1962); D-sorbitol, i-inositol, D-lactose, choline chloride (Bender et al., *J. Appl. Physiol.* 15:520, 1960); amino acids (Phan The Tran and Bender, 1960, *Exp. Cell Res.* 20:651, 1960); methanol, acetamide, glycerol monoacetate (Lovelock, *Biochem. J.* 56:265, 1954); inorganic salts (Phan The Tran and Bender, *Proc. Soc. Exp. Biol. Med.* 104:388, 1960; Phan The Tran and Bender, in Radiobiology, Proceedings of the Third Australian Conference on Radiobiology, Ilbery ed., Butterworth, London, p. 59, 1961), and CryoStor® CS5 or CS10 (BioLife Solutions Inc., Bothell, WA). In a preferred embodiment, DMSO is used. For example, DMSO is used at a concentration which is nontoxic to cells. Additionally, DMSO comprises up to about 20% of the composition, up to about 15% of the composition, up to about 10% of the composition, up to about 5% of the composition, up to about 2% of the composition, up to about 1% of the composition, or up to about 0.5% of the composition. In some embodiments, addition of plasma (e.g., up to a concentration of about 20 to 25%) can augment the protective effect of DMSO. In some embodiments, addition of a human protein, such as for example, human serum albumin (e.g., up to a concentration of about 2 to 10%) can augment the protective effect of DMSO. After addition of DMSO, cells should be kept at 0° C. until freezing, since DMSO concentrations of about 1% can be toxic at temperatures above 4° C.

In another embodiment, PBS containing 20% DMSO and 8% human serum albumin (HSA), or other suitable cell freezing media is used. This mixture is then diluted 1:1 with media so that the final concentration of DMSO and HSA are 10% and 4%, respectively. The cells in this mixture are then frozen to −80° C. at a rate of 1° per minute and stored in the vapor phase of a liquid nitrogen storage tank.

A controlled slow cooling rate can be important. Different cryoprotective agents (Rapatz et al., *Cryobiology* 5(1):18-25, 1968) and different cell types have different optimal cooling rates (see e.g., Rowe and Rinfret, Blood 20:636, 1962; Rowe, *Cryobiology* 3(1):12-18, 1966; Lewis, et al., *Transfusion* 7(1):17-32, 1967; and Mazur, *Science* 168:939-949, 1970 for effects of cooling velocity on survival of marrow-stem cells and on their transplantation potential). The heat of fusion phase where water turns to ice should be kept to a minimum. The cooling procedure can be carried out by use of, e.g., a programmable freezing device or a methanol bath procedure known in the art.

A programmable freezing apparatus allows the determination of optimal cooling rates and facilitates standard reproducible cooling. A programmable controlled-rate freezer such as Cryomed or Planar permit tuning of the freezing regimen to the desired cooling rate curve. For example, for marrow cells in 10% DMSO and 20% plasma, the optimal rate is 1° C. to 3° C. per minute from 0° C. to −80° C. In a preferred embodiment, this cooling rate of 1° C. to 3° C. per minute from 0° C. to −80° C. can be used. The container holding the cells must be stable at cryogenic temperatures and allow for rapid heat transfer for effective control of both freezing and thawing. Sealed plastic vials (e.g., Nunc, the Wheaton Cryule®) or glass ampules can be used for multiple small amounts (1-2 ml) or larger amounts (e.g., 5 to 30 ml), while larger volumes (20 to 200 ml) can be frozen in polyolefin bags (e.g., Del-Med) or ethylene vinyl acetate freezer bags (e.g., OriGen) held between metal plates for better heat transfer during cooling. By way of example, bags of bone marrow cells have been successfully frozen by placing them in −80° C. freezers which gives a cooling rate of approximately 3° C./minute.

In an alternative embodiment, the methanol bath method of cooling can be used. The methanol bath method is well-suited to routine cryopreservation of multiple small items on a large scale. The method does not require manual control of the freezing rate nor a recorder to monitor the rate. In a preferred embodiment, DMSO-treated cells are pre-cooled on ice and transferred to a tray containing chilled methanol, which is placed in a mechanical refrigerator (e.g., Harris or Revco) at −80° C. Thermocouple measurements of the methanol bath and the samples indicate the desired cooling rate of 1° C. to 3° C. per minute. After at least two hours, the specimens have reached a temperature of −80° C. and can be placed directly into liquid nitrogen (−196° C.) for permanent storage.

After thorough freezing, the NK cell composition and/or preparation can be rapidly transferred to a long-term cryogenic storage vessel. In a preferred embodiment, samples are cryogenically stored in liquid nitrogen (−196° C.) or its vapor (between about −140° C. and −180° C.). In another preferred embodiment, samples are cryogenically stored in liquid nitrogen vapor phase (e.g., at about −140° C. to −180° C.). Such storage is greatly facilitated by the availability of highly efficient liquid nitrogen refrigerators, which resemble large Thermos® containers with an extremely low vacuum and internal super insulation, such that heat leakage and nitrogen losses are minimized.

Suitable racking systems are commercially available and can be used for cataloguing, storage, and retrieval of individual specimens.

Other methods of cryopreservation of viable cells, or modifications thereof, are available and envisioned for use (e.g., cold metal-mirror techniques; Livesey and Linner, *Nature* 327:255, 1987; Linner et al., *J. Histochem. Cytochem.* 34(9):1123-1135, 1986; see also U.S. Pat. No. 4,199,022 by Senkan et al., U.S. Pat. No. 3,753,357 by Schwartz, U.S. Pat. No. 4,559,298 by Fahy).

Cryopreserved or frozen cells are preferably thawed quickly (e.g., in a water bath maintained at 37° to 41° C.), and chilled immediately upon thawing. In a specific embodiment, the vial containing the frozen cells can be immersed up to its neck in a warm water bath with gentle rotation to ensure mixing of the cell suspension as it thaws and to increase heat transfer from the warm water to the internal ice mass. As soon as the ice has completely melted, the vial is immediately placed in ice.

In an embodiment, a cryopreserved NK cell composition and/or preparation is thawed, and the full preparation, or a portion thereof, is infused into a human or animal patient in need thereof (e.g., having leukemia, such as AML; another hematological malignancy; a viral infection (e.g., HIV, HSV1 or 1, Hepatitis A, B, or C, zika, SARS-CoV or SARS-CoV-2, and the like); or other infection as disclosed herein). Several procedures relating to processing of the thawed cells are available, known in the art, and can be employed if desirable.

It can be desirable to treat the cells to prevent cellular clumping upon thawing. To prevent clumping, various procedures are well known in the art and can be used in the disclosed methods, including, but not limited to, the addition of DNase before and/or after freezing (Spitzer et al., *Cancer* 45:3075-3085, 1980), low molecular weight dextran and citrate, and/or hydroxyethyl starch (Stiff et al., *Cryobiology* 20:17-24, 1983), and the like.

The cryoprotective agent, if toxic in humans, should be removed prior to therapeutic use of the thawed NK cell composition and/or preparation. In an embodiment employing DMSO as the cryopreservative, it is preferable to omit this step to avoid cell loss. However, where removal of the cryoprotective agent is desired, the removal is preferably accomplished upon thawing.

For example, removal of the cryoprotective agent can be by dilution to achieve the cryoprotective agent at an insignificant concentration. This can be accomplished by addition of medium, followed by, if necessary, one or more cycles of centrifugation to pellet cells, removal of the supernatant, and resuspension of the cells. For example, intracellular DMSO in the thawed cells can be reduced to a level (less than 1%) that will not adversely affect the recovered cells. This is preferably done slowly to minimize potentially damaging osmotic gradients that occur during DMSO removal.

After removal of the cryoprotective agent, cell count (e.g., by use of a hemocytometer) and viability testing (e.g., by trypan blue exclusion; Kuchler, Biochemical Methods in Cell Culture and Virology, Dowden, Hutchinson & Ross, Stroudsburg, Pa., pp. 18-19, 1977; Methods in Medical Research, Eisen et al., eds., Vol. 10, Year Book Medical Publishers, Inc., Chicago, pp. 39-47, 1964) can be performed to confirm cell survival. The percentage of viable antigen (e.g., CD56) positive cells can be determined by calculating the number of antigen positive cells that exclude 7-AAD (or other suitable dye excluded by viable cells) in an aliquot of the cells, divided by the total number of nucleated cells (TNC) (both viable and non-viable) in the aliquot of the cells. The number of viable antigen positive cells can then be determined by multiplying the percentage of viable antigen positive cells by the TNC.

Prior to cryopreservation and/or after thawing, the total number of nucleated cells, or in a specific embodiment, the total number of CD56$^+$ cells, can be determined. For example, total nucleated cell count can be performed by using a hemocytometer and exclusion of trypan blue dye. Specimens that are of high cellularity can be diluted to a concentration range appropriate for manual counting. Final cell counts for products are corrected for any dilution factors.

Total nucleated cell count equals viable nucleated cells per mL×volume of product in milliliters (ml). The number of CD56$^+$ positive cells in the sample can be determined, e.g., by use of flow cytometry using anti-CD56 monoclonal antibodies conjugated to a fluorochrome.

The NK cell compositions and/or preparations can be used in immunotherapy for the treatment of solid tumors, hematopoietic malignancies, viral disorders, bacterial infections and the like. In some embodiments, the NK cell compositions and/or preparations are administered to inhibit tumor growth in a subject (also referred to as a patient) in need thereof. A method according to this aspect of the present invention is affected by administering a therapeutically effective amount of an NK cell composition and/or preparation to the subject. As used herein, "treating" or "treatment" includes, but is not limited to, the administration of an NK cell composition and/or preparation to reduce or delay the onset of the symptoms, complications, or biochemical indicia of a disease, alleviating the symptoms or arresting or inhibiting further development of the disease, condition, or disorder (e.g., cancer, metastatic cancer, metastatic solid tumors, viral or bacterial symptoms). Treatment can be prophylactic, i.e., as an adjuvant (to prevent relapse or delay the onset of the disease, or to prevent the manifestation of clinical or subclinical symptoms thereof) or therapeutic suppression or alleviation of symptoms after the manifestation of the disease.

In one embodiment, an NK cell composition and/or preparation is administered in an amount effective to reduce or eliminate a cancer, such as a solid tumor or a hematologic malignancy, such as for example, leukemia or lymphoma, and the like, or prevent its occurrence or recurrence. "An amount effective to reduce or eliminate the solid tumor or hematologic malignancy or to prevent its occurrence or recurrence" or "an amount effective to reduce or eliminate the hyperproliferative disease or to prevent its occurrence or recurrence" refers to an amount of an NK cell composition and/or preparation that improves a subject's outcome or survival following treatment for the tumor disease state or hyperproliferative disease as measured by patient test data, survival data, elevation or suppression of tumor marker levels, reduced susceptibility based upon genetic profile or exposure to environmental factors. "Inhibiting tumor growth" refers to reducing the size or viability or number of cells of a tumor. "Cancer," "malignancy," "solid tumor," or "hyperproliferative disease" are used as synonymous terms and refer to any of a number of diseases that are characterized by uncontrolled, abnormal proliferation of cells; the ability of affected cells to spread locally or through the bloodstream and lymphatic system to other parts of the body (i.e., metastasize); as well as any other characteristic structural and/or molecular features. A "cancerous," "malignant cell," or "solid tumor cell" is understood as a cell having specific structural properties, lacking differentiation, and being capable of invasion and metastasis. "Cancer" refers to all types of cancer or neoplasm or malignant tumors found in mammals, including carcinomas and sarcomas. Examples are cancers of the breast, lung, non-small cell lung, stomach, brain, head and neck, medulloblastoma, bone, liver, colon, genitourinary, bladder, urinary, kidney, testes, uterus, ovary, cervix, or prostate, as well as melanoma, mesothelioma, and sarcoma, (see DeVita, et al., (eds.), Cancer Principles and Practice of Oncology, 6$^{th}$. Ed., Lippincott Williams & Wilkins, Philadelphia, Pa., 2001; this reference is herein incorporated by reference in its entirety for all purposes). "Hyperproliferative disease" refers to any disease or disorder in which the cells proliferate more rapidly than normal tissue growth. Thus, a hyperproliferating cell is a cell that is proliferating more rapidly than normal cells.

A "solid tumor" includes, but is not limited to, a sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

"Melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungual melanoma, and superficial spreading melanoma.

"Carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, mucinous carcinoma, carcinoma muciparum, carcinoma mucocellulare, choriomeningitis carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, scirrhous carcinoma, carcinoma scroti, signet-ring cell carcinoma, carcinoma simplex, small-cell carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma viflosum.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, acute myelogenous leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

In another embodiment, there is provided a method of inhibiting a viral infection in a subject in need thereof. The method is affected by administering a therapeutic amount of an NK cell composition and/or preparation to a subject. Viral infections suitable for treatment with an NK cell composition and/or preparation include, but are not limited to, HIV, lymphatic choriomeningitis virus (LCMV), cytomegalovirus (CMV), vaccinia virus, coronavirus (SARS-CoV and SARS-CoV-2), influenza and para-influenza virus, zika virus, hepatitis (including hepatitis A, hepatitis B, hepatitis C, non-A-non-B, and the like), herpes simplex virus (HSV 1 or HSV 2), herpes zoster virus, and Theiler's virus. Other infectious diseases suitable for treatment with an NK cell composition and/or preparation include, but are not limited to, parasitic infections such as *Plasmodium, Leishmania* and *Toxoplasma* infections, and bacterial infections such as mycobacteria and *Listeria* (for a review of NK cells in treatment of viral, bacterial and protozoan diseases see Zucchini et al., *Exp. Rev. Anti-Infect. Ther.* 6:867-885, 2008, which reference is incorporated by reference herein).

According to some aspects of the present invention, there are provided pharmaceutical compositions comprising an NK cell preparation for the treatment of disease. For example, the NK cell preparation is formulated together with a pharmaceutically acceptable carrier to form an NK cell composition for the treatment of e.g., metastatic cancer, solid tumors, hematological malignancy, hyperproliferative disease, any viral infection, a bacterial infection, and the like.

Therapeutic applications, compositions, or medicaments are administered to a subject suspected of, or already suffering from, such a disease, and are provided in an amount sufficient to cure or partially arrest the symptoms of the disease (biochemical, histologic and/or behavioral), including its complications and intermediate pathological phenotypes in development of the disease. An amount adequate to accomplish such therapeutic treatment is defined as a therapeutically effective dose. In therapeutic regimes, NK cell compositions and/or preparations are usually administered in several dosages until a sufficient anti-proliferative response has been achieved. Typically, the anti-proliferative response is monitored, and repeated dosages are given if the anti-proliferative response starts to wane.

Effective doses of an NK cell composition and/or preparation for the treatment of disease, e.g., metastatic cancer, solid tumors, hematologic malignancy, a hyperproliferative disease, any viral infection, a bacterial infection, and the like, as described herein, vary depending upon factors including means of administration, target site, physiological state of the patient, whether the patient is human or an animal, other medications administered, and whether treatment is prophylactic or therapeutic. Usually, the patient is a human, but nonhuman mammals including transgenic mammals can also be treated. Treatment dosages need to be titrated to optimize safety and efficacy.

For administration with a therapeutic NK cell composition and/or preparation, the dosage typically ranges from about 50 to about 500 million total cells per dose. In some embodiments, a dosage is about 50, 100, 200, 300, 400 or 400 million cells per dose. In some embodiments, a dose of the NK cell composition and/or preparation can be from about 50 million to about 2 billion viable cells per dose. In some embodiments, a dose of the NK cell composition and/or preparation contains about 100 million, about 200 million, about 300 million, about 400 million, about 500 million, about 600 million, about 750 million, about 1 billion, about 1.5 billion or about 2 billion viable cells. In some embodiments, a dose of the NK cell composition and/or preparation can be from about 50 million to about 2 billion viable CD56+ cells per dose. In some embodiments, a dose of the NK cell composition and/or preparation contains about 100 million, about 200 million, about 300 million, about 400 million, about 500 million, about 600 million, about 750 million, about 1 billion, about 1.5 billion or about 2 billion viable CD56$^+$ cells.

An exemplary treatment regimen entails administration about once, twice, or ever three times per week, once, twice or even three times per every two weeks, about once per month, about once every 3 to 6 months, or about once every 6 to 12 months. Multiple administrations of NK cell compositions and/or preparations can be provided. Intervals between single dosages can be a few days, weekly, monthly, yearly, or some combination of such time periods. Intervals can also be irregular and as indicated by measuring blood levels of the NK cell composition and/or preparation in the patient. Alternatively, the NK cell compositions and/or preparations can be administered as a sustained release formulation, in which case less frequent administration is required. Dosage and frequency vary depending on the half-life of the NK cell compositions and/or preparations in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the remainder of their lives. In therapeutic applications, a relatively high dosage at relatively short intervals is sometimes required until progression of the disease is reduced or terminated, and preferably until the patient shows partial or complete amelioration of disease symptoms or disease indication. Thereafter, the patent can be administered a prophylactic regimen.

Compositions of an NK cell composition and/or preparation for the treatment of disease, e.g., metastatic cancer, solid tumors, hematological malignancy, a hyperproliferative disease, any viral infection, a bacterial infection, and the like, can be administered by intravenous, intravesicular, intraarterial, intracranial, or intraperitoneal means.

In some embodiments, an NK cell composition and/or preparation is administered after a chemotherapy regimen. The chemotherapy regimen can be a single agent or multi-agent regimen. In some embodiments, the chemotherapy regimen is an induction regimen or a consolidation regimen. In some embodiments, the chemotherapy regimen is a salvage regimen.

In some embodiments, a fixed dose of an NK cell composition and/or preparation can be administered following chemotherapy regimen or a cycle thereof, such as an induction regimen. A fixed dose of an NK cell composition and/or preparation can also be administered following a consolidation regimen or a cycle thereof. A fixed dose of an NK cell composition and/or preparation can also be administered following a salvage regimen or a cycle thereof. In some embodiments, a fixed dose of an NK cell composition and/or preparation can be administered following a second induction regimen or cycle thereof, or a second cycle of an induction regimen, if desired or necessary. In some embodiments, a fixed dose of an NK cell composition and/or preparation can be administered following a second consolidation regimen or cycle thereof, or a second cycle of a consolidation regimen is desired or necessary. In some embodiments, a fixed dose of an NK cell composition and/or preparation can be administered following a second salvage regimen or cycle thereof, or a second cycle of a salvage regimen is desired or necessary.

EXAMPLES

The present invention is not to be limited in scope by the specific embodiments described herein. Indeed, various modifications of the invention, in addition to those described herein, will be apparent to those skilled in the art from the descriptions herein and accompanying figures. Such modifications are intended to fall within the scope of the appended claims.

Various publications, including patents, patent application publications, and scientific literature, are cited herein, the disclosures of which are incorporated by reference in their entireties for all purposes. While illustrative embodiments have been depicted and described, it will be appreciated that various changes can be made herein without departing from the spirit and scope of the invention.

Example 1: Generation of an NK Cell Composition and/or Preparation

This Example describes the production and storage of an NK cell preparation and its formulation into a NK cell composition.

Umbilical cord blood/placental blood unit(s) (CBU) were collected from human donors at birth. Typically, the CBUs are frozen after collection and the selected CBUs are donor eligible and fully qualified prior to use. The collected blood was then mixed with an anti-coagulant to prevent clotting. The blood was stored under quarantine at 4° C. in a monitored refrigerator. The received units were assessed, and the units to be processed for expansion was determined.

Phase 1 involved expansion of hematopoietic stem and progenitor cells. CD34$^+$ enriched hematopoietic stem and progenitor cells (HSPC) were seeded into tissue culture treated plastic vessels (Thermo Scientific Nunc™ EasY-Flask™). The enriched CD34$^+$ HSPCs were prepared from pooled cord blood units as described in US Patent Application Publication No. 2013/0095079 (incorporated herein by reference). Generally, CD34$^+$ cells from at least 4 cord blood units were pooled, either before or after enrichment for CD34$^+$ cells.

The tissue culture treated plastic vessels were pre-coated with a solution of recombinant human fibronectin fragment (Takara Bio, Inc.; RetroNectin® Recombinant Human Fibronectin Fragment, 5 μg/ml and 0.8 μg/cm$^2$ surface area) and a Notch agonist (Delta1$^{extIgG}$, 2.5 μg/ml and 0.4 μg/cm$^2$ surface area) in DPBS (Gibco). Culture medium consisted of a serum free cell culture medium designed and suitable for the culture and expansion of hematopoietic cells (StemSpan™ Serum-Free Expansion Medium II (SFEM II; Stem-Cell Technologies)) supplemented with 50 ng/ml each of rhSCF (Miltenyi Biotec), Flt-3L (Miltenyi Biotec), TPO (Miltenyi Biotec), and IL-6 (Miltenyi Biotec), and 10 ng/ml IL-3 (Miltenyi Biotec). Cells were cultured for 14 days, passaging the cells into larger volume culture vessels when appropriate to maintain a cell density $<2 \times 10^6$ cells/ml.

An alternate protocol for the Phase 1 expansion culture that produces the same cell preparation includes the replacement of Delta1$^{extIgG}$ as the Notch agonist with 2.5 to 10 μg/ml of a purified anti-human Notch 1 antibody (BioLegend, LEAF™ Purified, clone MHN1-519).

Phase 2 of the culturing process differentiates the expanded hematopoietic stem and progenitor cells toward an NK cell phenotype. At the end of the 14-day expansion phase (above), all cells were collected and re-plated into tissue culture treated plastic vessels without the Notch agonist (Delta1$^{extIgG}$ or RetroNectin®) coating. The culture medium comprises RPMI 1640 (Gibco) supplemented with 5 to 10% heat inactivated fetal bovine serum (FBS; Gibco), 40 ng/ml rhIL-15 (PeproTech), and 50 U/ml rhIL-2 (Pepro-Tech). Cells were cultured for up to 14 additional days, passaging the cells into larger volume culture vessels when appropriate to maintain a cell density $<2 \times 10^6$ cells/ml.

In addition to CD56, the CD56$^+$ cells expressed high a frequency of NKp30, NKp46, NKp44, NKG2A, and granzyme B, moderate to a high frequency of perforin and CD107a, a low to moderate frequency of NKG2D and substantially no KIRs. In those batches tested the CD56$^+$ cells were found to be KIR$^-$. (As used herein, "KIR$^-$" refers to KIR2DL1, KIR2DS1, KIR2DS3, KIR2DS5, KIR2DL2, KIR2DL3, KIR2DS2, KIR2DS4, KIR3DL1, and KIR3DS1.) CD16 was expressed at a low to moderate frequency. In those batches tested, the CD56$^-$ cells expressed a moderate to high frequency of granzyme B, a high frequency of CD107a and a low frequency of perforin. See Table 1 above. Table 2 also above, shows the phenotypic attributes of the CD56$^+$ cells in an exemplary NK cell preparation.

The NK cell preparation also included approximately 25% to 50% CD56$^-$ cells. These cells were largely myeloid derived and can include dendritic cells, macrophages and granulocytes. Across the CD56$^-$ cells in the NK cell preparation, the following cell surface markers were expressed at the indicated frequency: Granzyme B is expressed at intermediate frequency and CD107a is expressed at high frequency. Table 3, above, shows the phenotypic attributes of the CD56$^-$ cells in an exemplary NK cell preparation.

Figure 1B:
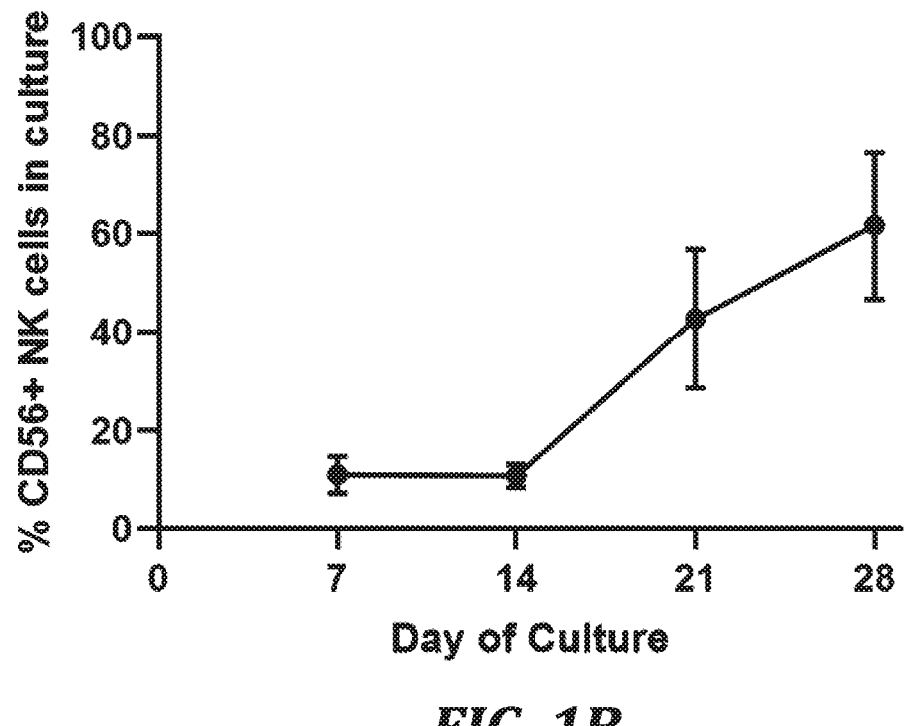

FIG. 1A shows the increase in CD56$^+$ cells/starting CD34$^+$ cells over the course of a 28-day culture (phases 1 (expansion) and 2 (differentiation)). FIG. 1B demonstrates reproducibility of CD56$^+$ cell generation over a 28-day cell culture process. FIGS. 1A and 1B show the results from 20 batches of NK cell preparations produced following the process described above.

Example 2: Production of an NK Cell Preparation without Animal Derived Serum To avoid the use of animal derived serum, an alternate protocol for the Phase 2 culture (differentiation) to produce an NK cell preparation involved the replacement of fetal bovine serum (FBS) with heat inactivated human AB serum (Valley Biomedical) or with human platelet lysate (Mill Creek Life Sciences PLTMax®). Applicant unexpectedly was able to substitute heat inactivated human AB serum or human platelet lysate in phase 2 (the differentiation phase) of the process described in Example 1.

Figure 2:
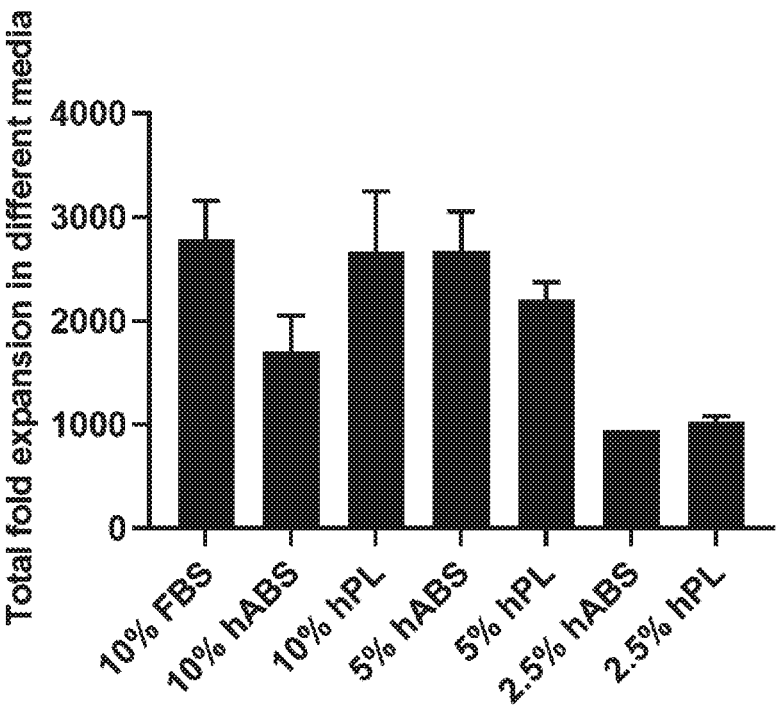
FIG. 2 shows replacement of fetal bovine serum (FBS) with human AB serum (hABS) or human platelet lysate (hPL) had minimal effects on the cell expansion during differentiation.
Figure 3:
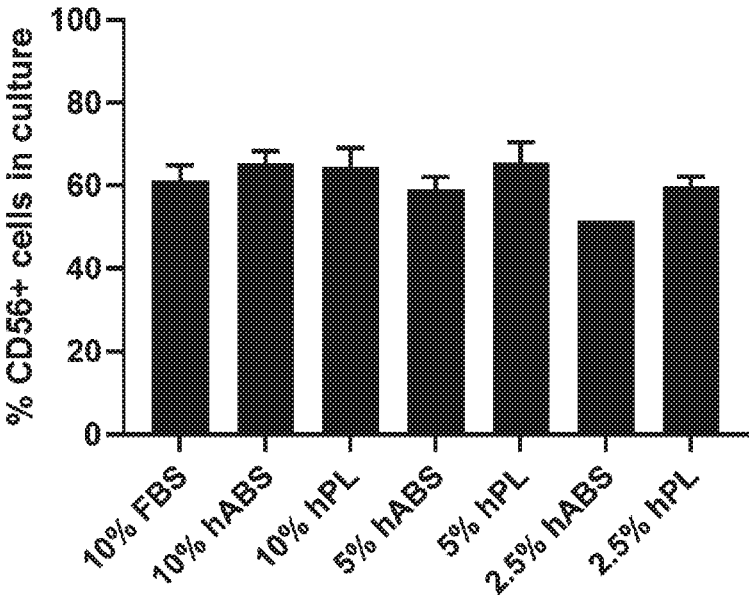
FIG. 3 shows replacement of FBS with human AB serum (hABS) or human platelet lysate (hPL) had minimal effects on the percent of $CD56^+$ cells produced.

Replacement of FBS with human AB serum (hABS) or with human platelet lysate (hPL) had minimal effects on the cell expansion during differentiation (FIG. 2) or the number of CD56$^+$ cells produced (FIG. 3). hPL maintained expansion of the culture slightly better than hABS, but the resulting cell phenotypes are very similar among the FBS, hABS, and hPL cultures.

Figure 4:
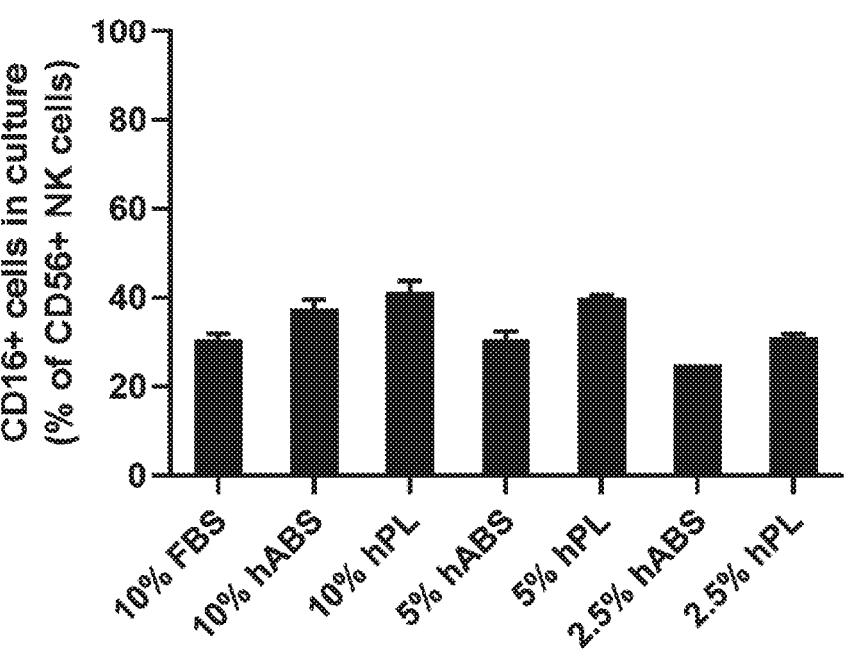
FIG. 4 shows the percent of $CD16^+$ cells relative to $CD56^+$ NK cells on day 28 of culture comparing different serum supplements used in Phase 2 (the differentiation phase) of the culture.
Figure 5:
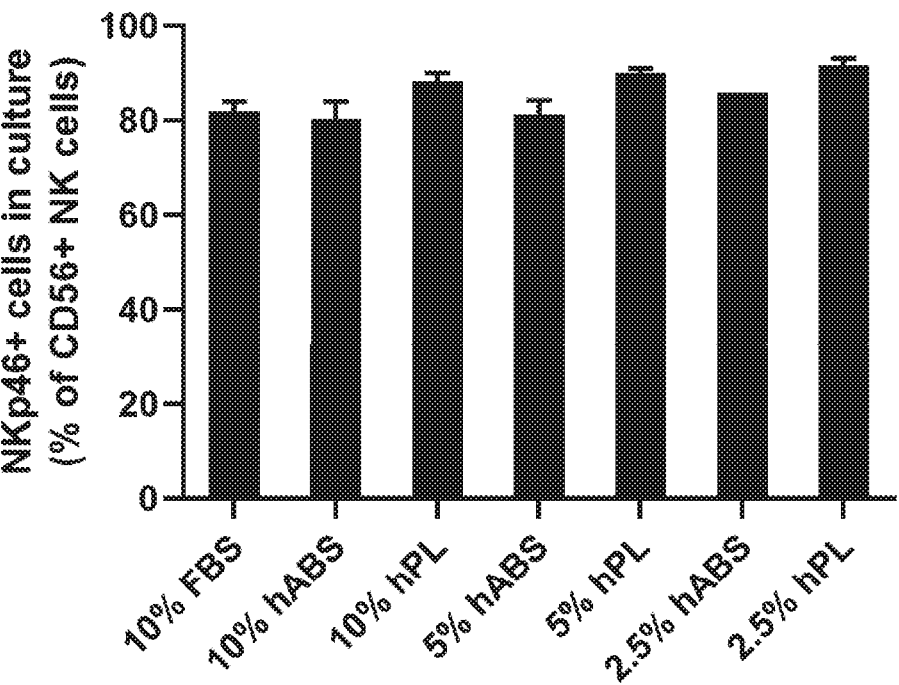
FIG. 5 shows the percent of $NKp46^+$ cells relative to $CD56^+$ NK cells on day 28 of culture comparing different serum supplements used in Phase 2 of the culture.

FIGS. 4 and 5 show the percent CD16$^+$ cells (FIG. 4) and the percent NKp46$^+$ cells (FIG. 5), both as a percent of CD56$^+$ cells, on day 28 of culture comparing different serum supplements used in Phase 2 of the culture.

Figure 6:
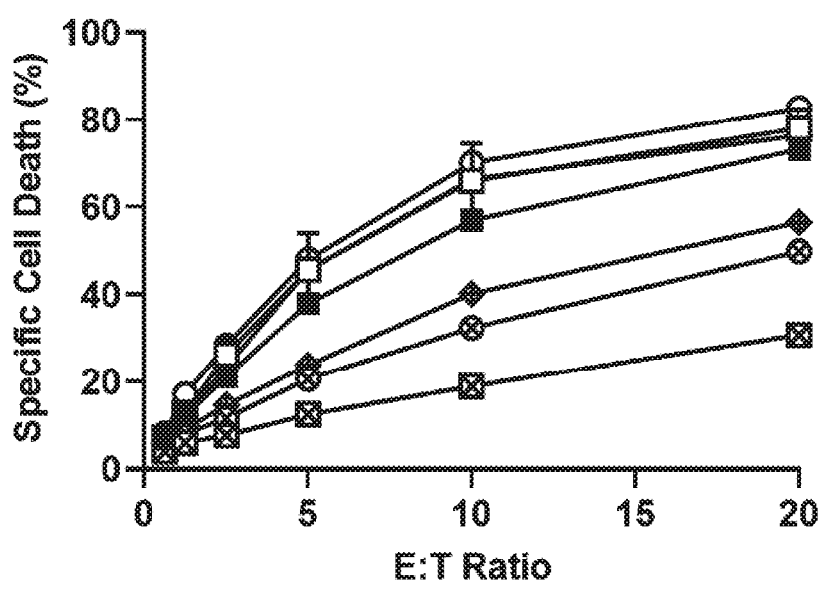
FIG. 6 shows cultures supplemented with hPL developed a more cytotoxic NK cell population than those supplemented with hABS.
Figure 7:
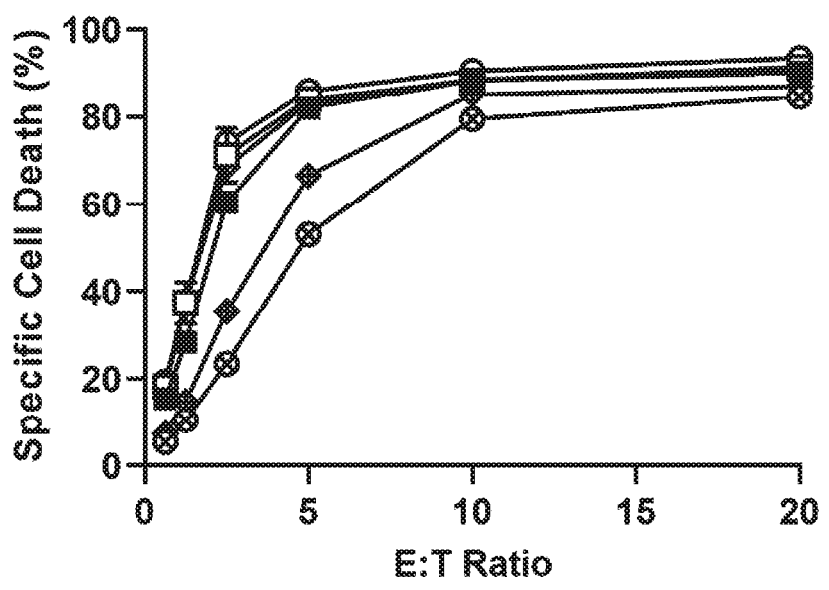
FIG. 7 shows cultures supplemented with hPL developed a more cytotoxic NK cell population than those supplemented with hABS.

In vitro cytotoxicity analysis using an NK cell preparation, and K562 target cells, was undertaken to compare NK cell preparations cultured with the various serum supplements in Phase 2 (FBS, hABS, or hPL). FIGS. 6 and 7 show cultures supplemented with hPL developed a more cytotoxic NK cell population than those supplemented with hABS.

Example 3: In Vitro Cytotoxicity Assay with an NK Cell Preparation

An in vitro cytotoxicity assay was performed using the Day 28 NK cell preparation, or K562-activated adult peripheral blood NK cells, as effector cells (E). The NK cell preparation was prepared as described above. Fluorescently labeled K562 cells (a chronic myelogenous leukemia cell line) or A549 cells (a lung carcinoma cell line) were included as target cells (T). The cells were co-incubated at the E:T ratios indicated in FIG. 8 for 4 hours at 37° C. Cells were then labeled with 4',6-diamidino-2-phenylindole (DAPI), and the fluorescent target cells that co-labeled with DAPI identified as dying and dead target cells by flow cytometric analysis.

Figure 8:
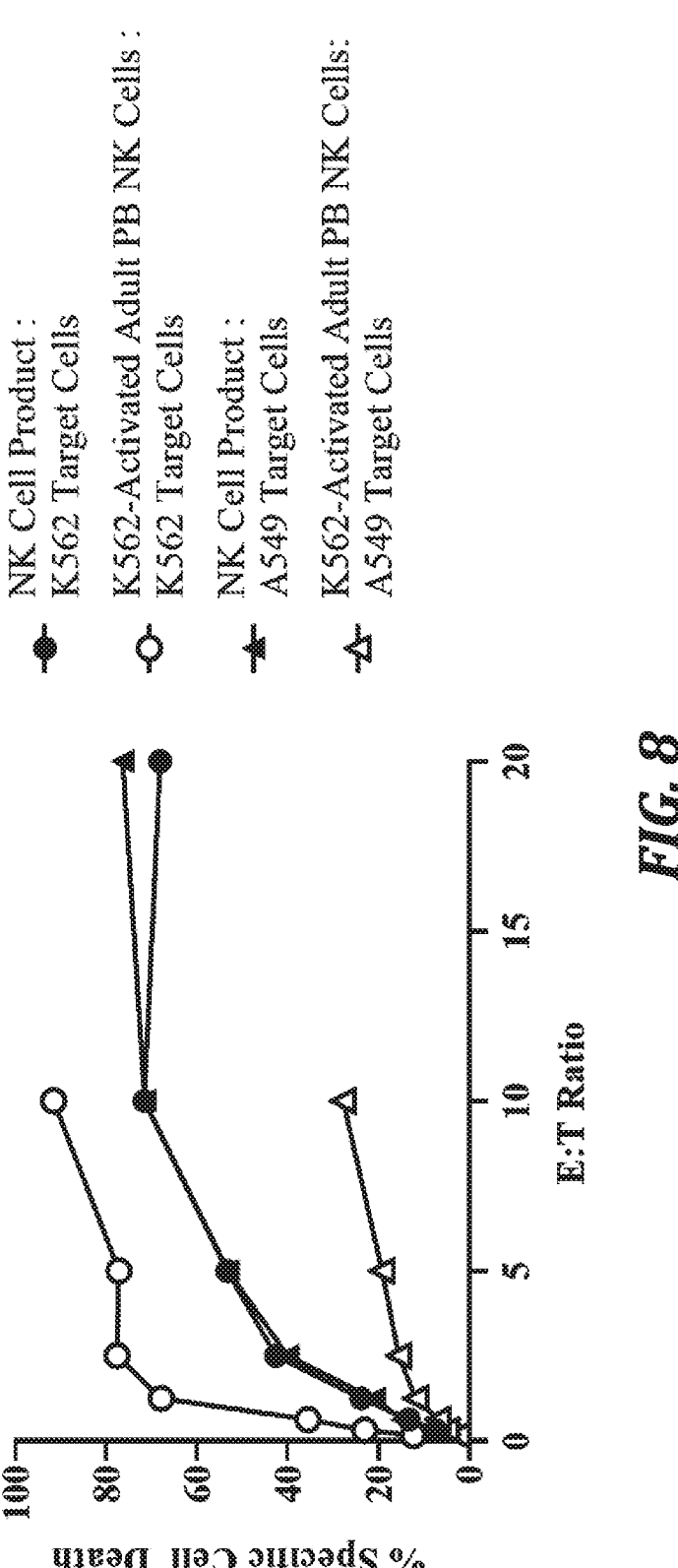
FIG. 8 shows the NK cell composition and/or preparation (referred to as NK Cell Product) was active against K562 and A549 target cells with similar activity (curves indicated with closed circles and triangles in the middle of the graph), and were more potent than activated adult NK cells against A549 target cells.

FIG. 8 shows the NK cell preparation (referred to as NK Cell Product) was active against K562 and A549 target cells with similar activity (curves indicated with filled circles and filled triangles). In contrast, adult peripheral blood NK cells, activated with K562 cells (referred to as K562-Activated Adult PB NK Cells), were active against K562 target cells (top curve with open circles), but not against A549 target cells (bottom line with open triangles). This study demonstrated the ability of the NK cell preparation to be active against various target cells.

Example 4: Additional In Vitro Assays with an NK Cell Preparation

Figure 9:
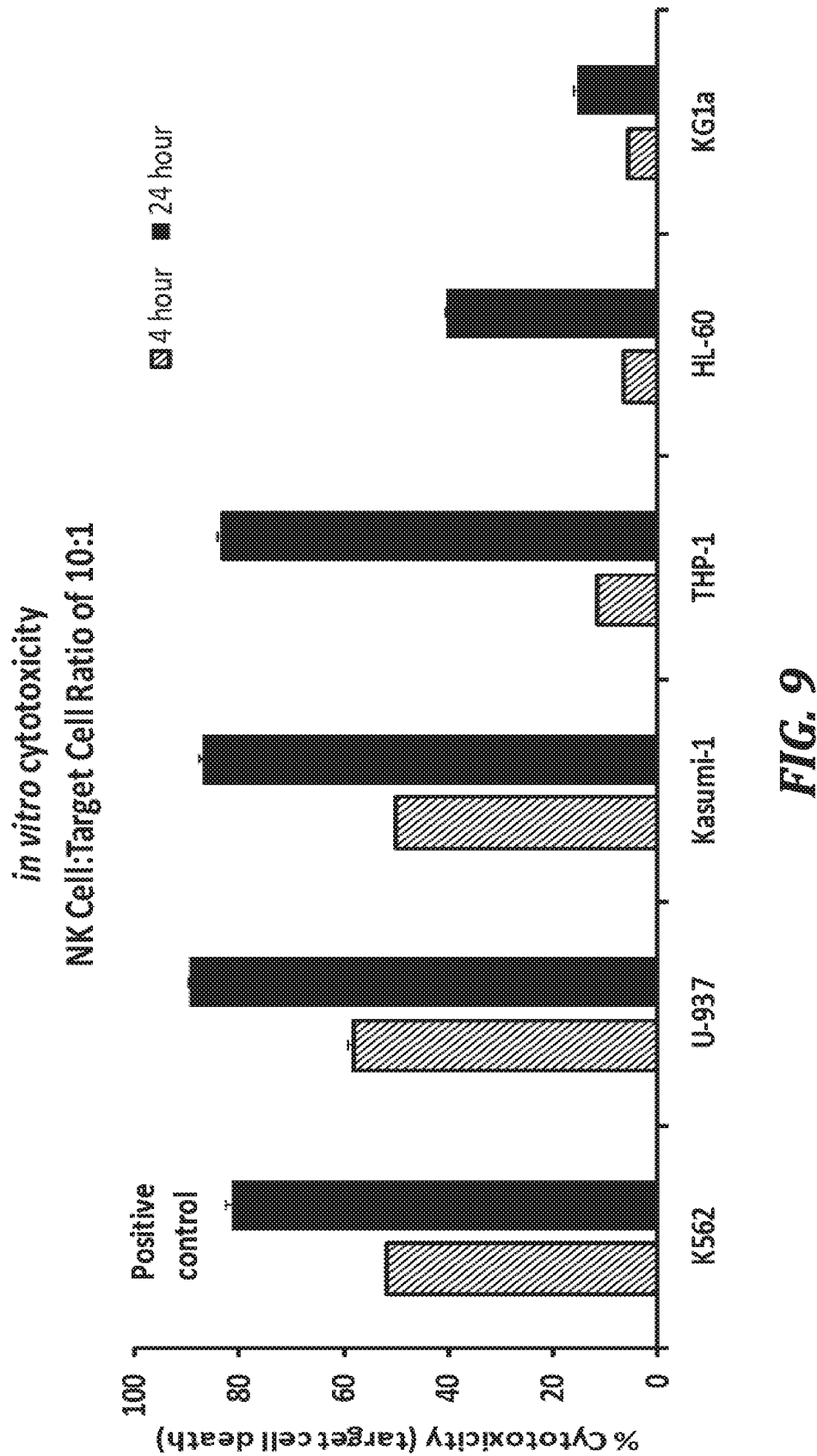
FIG. 9 shows the NK cell composition and/or preparation demonstrated cell killing against many of the tested cancer cell lines. For each cell line, the left bar indicates cytotoxicity at 4 hours and the right bar indicates cytotoxicity at 24 hours. The K562 cell line is an accepted standard for NK cell activity and serves as a positive control.

The cytotoxicity of the NK cell preparation was tested in a standard in vitro cell killing assay (as described above in Example 3) against a range of myeloid cell leukemia (similar to AML) cell lines. FIG. 9 demonstrates the NK cell preparation exhibited cell killing against many of these cancer cell lines. In FIG. 9, for each cell line, the left bar indicates cytotoxicity at 4 hours and the right bar indicates cytotoxicity at 24 hours. The K562 cell line is an accepted standard for NK cell activity and serves as a positive control.

Example 5: In Vivo Mouse Xenograft Assay with an NK Cell Preparation

Figure 10:
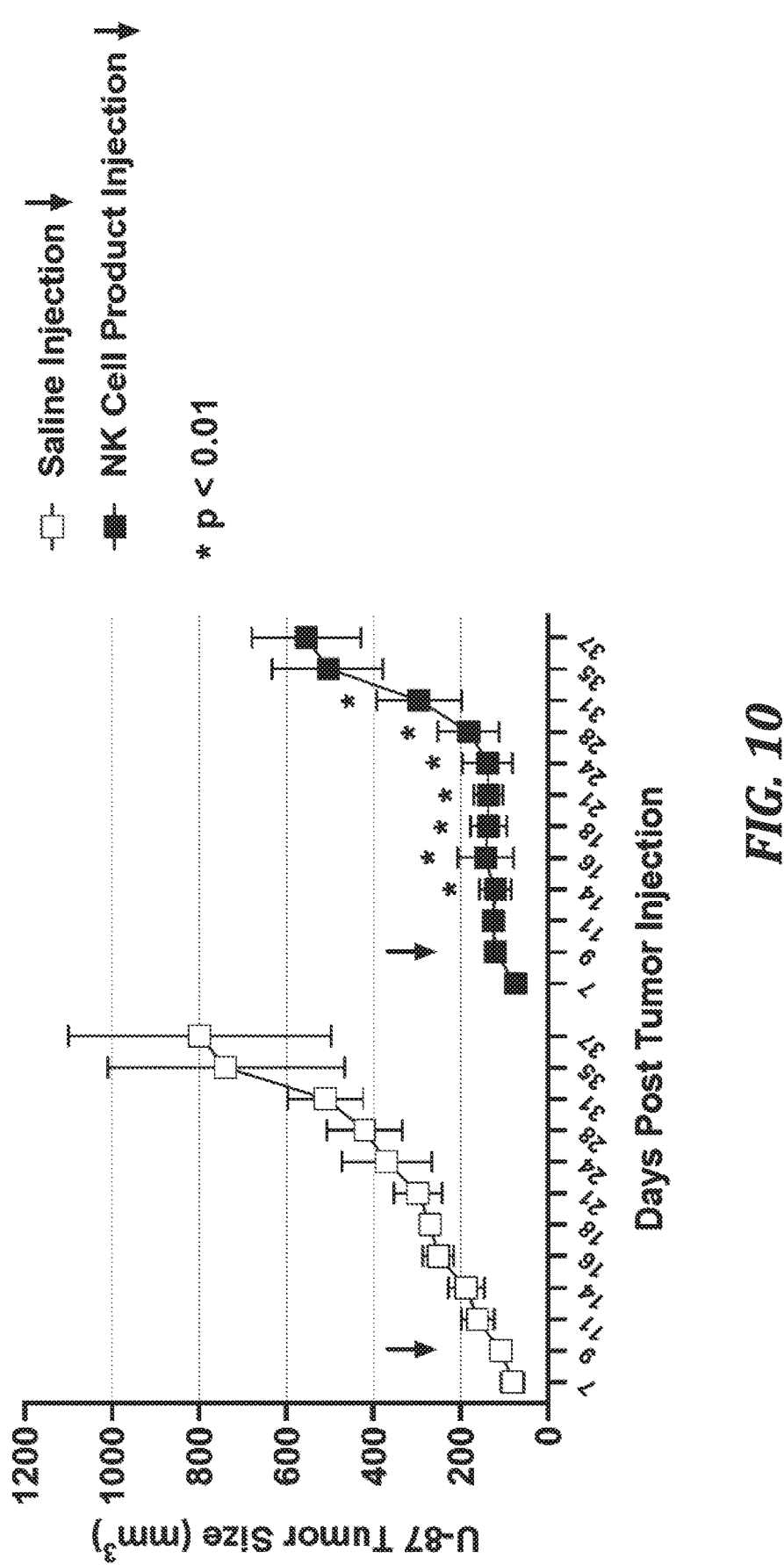
FIG. 10 demonstrates the NK Cell Product was able to reduce tumor burden, as compared to the saline injection control.

The activity of an NK cell preparation in a U-87 glioblastoma tumor model was tested in NSG mice with or without NK cell preparation treatment, by measuring U-87 tumor burden. U-87 cells were subcutaneously injected with Matrigel® (a gelatinous protein mixture secreted by Engelbreth-Holm-Swarm (EHS) mouse sarcoma cells intended to resemble the complex extracellular environment found in many tissues and as a substrate for culturing cells) into the rear flank of test NSG mice ($2 \times 10^6$ cells/mouse) and allowed to grow for 9 days to form a measurable tumor prior to intra-tumoral injection of $1 \times 10^7$ cells of an NK cell preparation per mouse (referred to as NK Cell Product or Composition). Tumor growth was assessed 2 to 3 times/week by caliper measurement. FIG. 10 demonstrates the NK Cell Product was able to reduce tumor burden, as compared to the saline injection control.

Figure 11A:
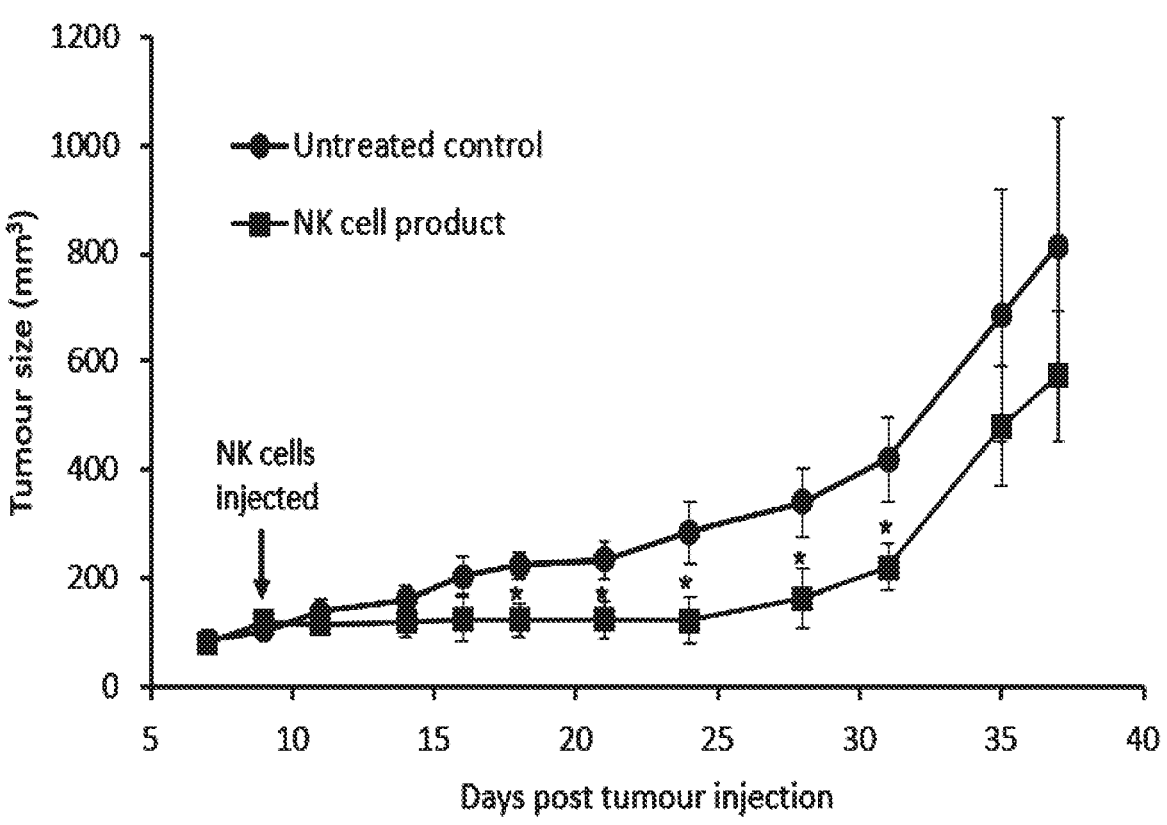
FIGS. 11A and 11B show tumor response in an in vivo mouse model.
Figure 11B:
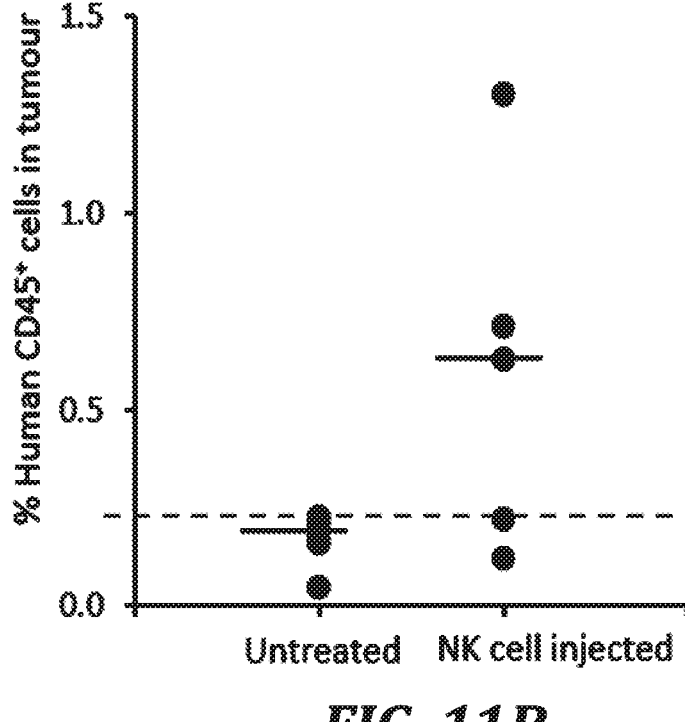
Figure 12A:
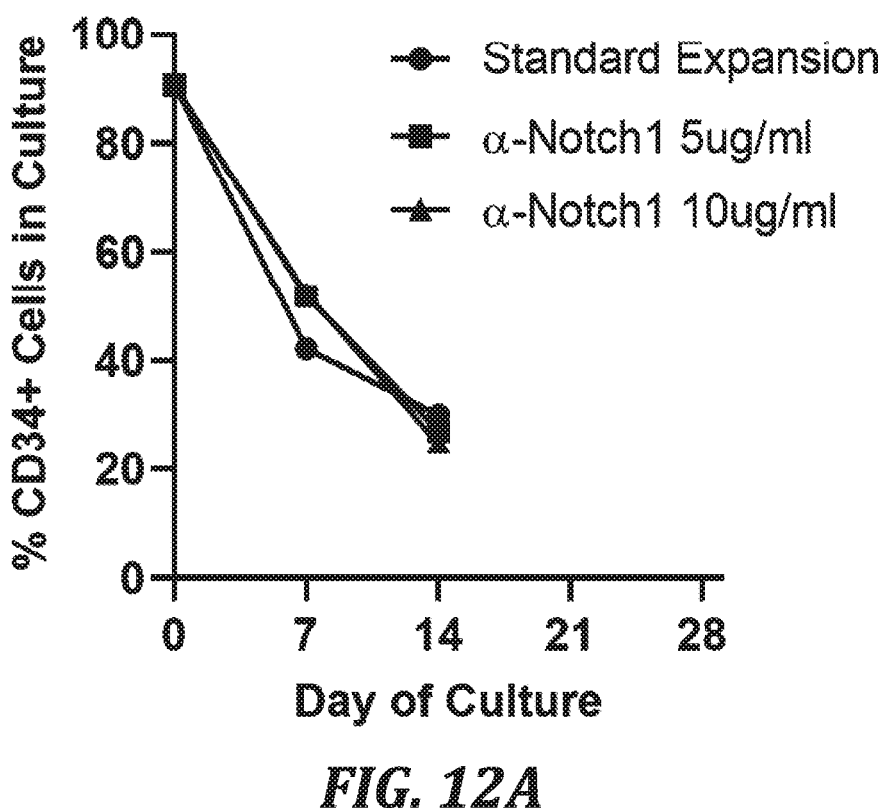
FIGS. 12A-12D show expansion of HSPCs with Notch 1 antibody (see US Patent Application Publication No. 2017/0107493, incorporated herein by reference) was comparable to expansion using DXI.
Figure 12B:
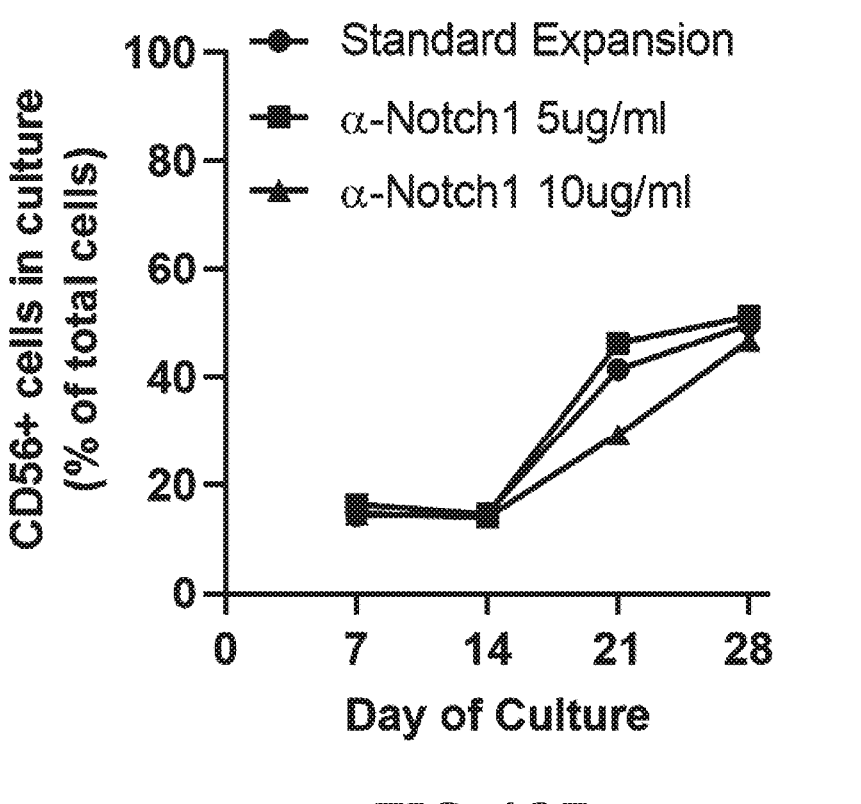
Figure 12C:
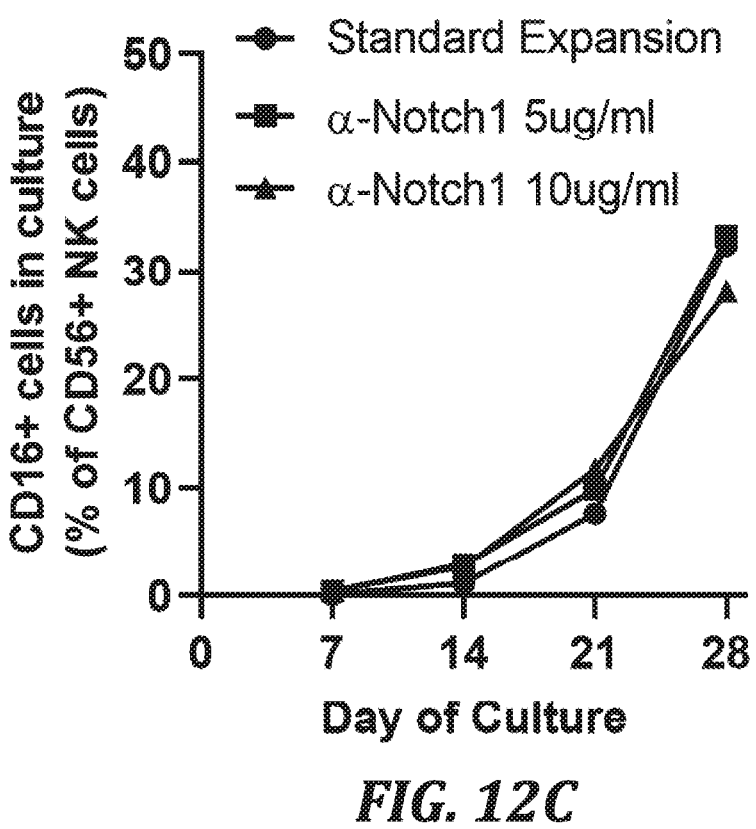
Figure 12D:
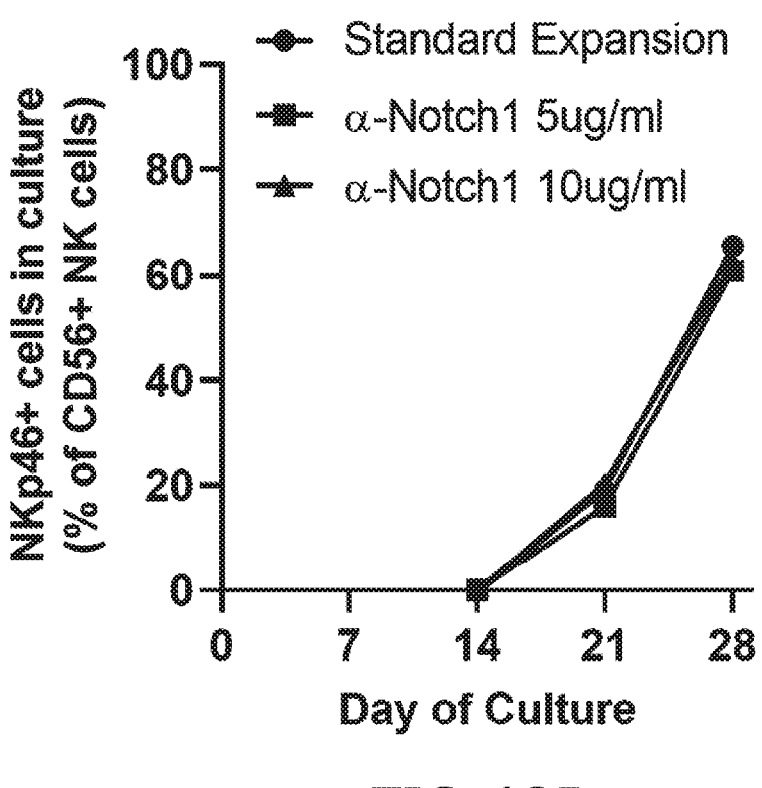

FIG. 11 shows a graph of the tumor size for the untreated control (line with circles) and for the NK cell preparation (line with squares) over time for this study. The NK cell preparation was able to cause a significant delay in tumor progression (FIG. 11). The NK cell preparation persisted and was detectable 37-days post injection, as measured by detecting human CD45$^+$ cells in the tumor (FIG. 11).

Example 6: Expansion of CD34$^+$ HSPCs Using Notch 1 or Notch 2 Specific Antibodies CD34$^+$ HSPCs were expanded as described above (Example 1) on standard substrate (5 µg/ml RetroNectin®+2.5 µg/ml DXI) or on 5 µg/ml RetroNectin®+5 µg/ml anti- Notch1 antibody (anti-Notch 1 Ab) or on 5 µg/ml RetroNec-tin®+10 µg/ml anti-Notch1 Ab. FIGS. 12A-D show expansion of HSPCs with Notch 1 or Notch 2 antibodies (see US Patent Application Publication No. 2017/0107493, incorporated herein by reference) was comparable to expansion using DXI.

Figure 13A:
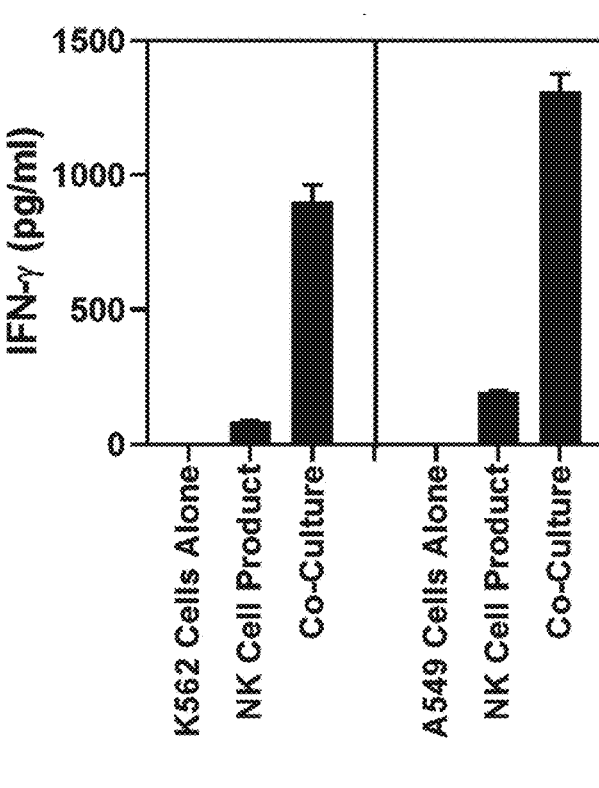
FIGS. 13A and 13B show an NK cell composition and/or preparation (referred to as an NK Cell Product), K562, or A549 tumor cells were cultured alone, or together for three days. The study was run in triplicate. After three days, cytokine levels were determined by Luminex assay. (The limit of detection of the assay used was 1 pg/ml of cytokine). Both IFNγ (FIG. 13A) and TNFα (FIG. 13B) levels increased when an NK cell composition and/or preparation was co-cultured in the presence of tumor cells. These results indicated the NK cells in the preparation became more active in the presence of tumor cells.
Figure 13B:
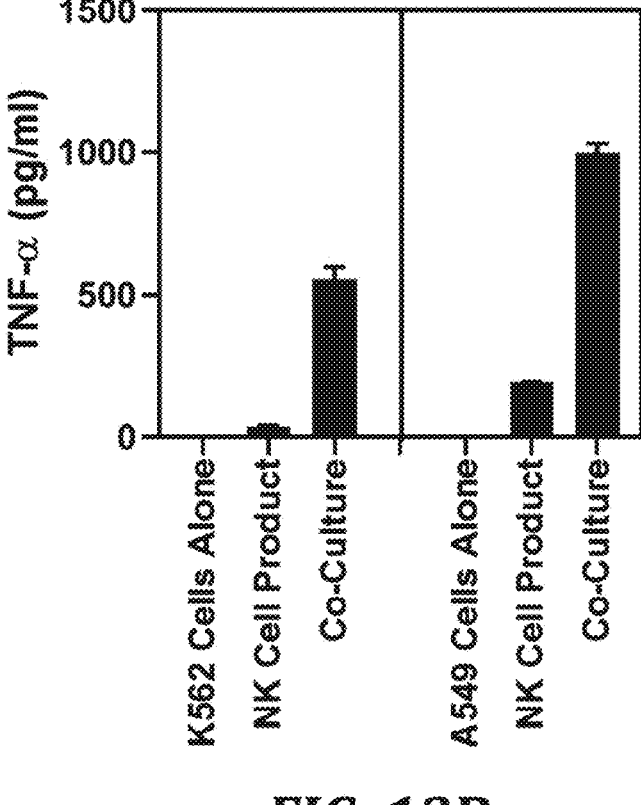
Figure 14A:
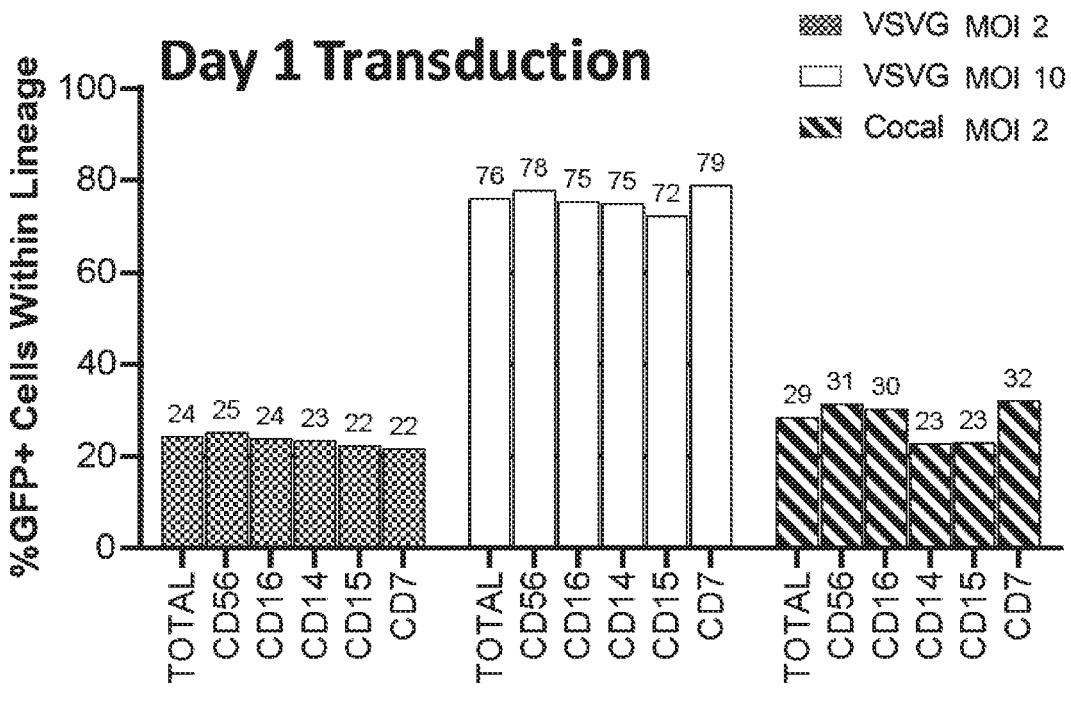
FIG. 14A-14E shows more consistent distribution of transgene expression across cell lineages was observed following transduction on Day 1, 4, 7, 14, or 21.
Figure 14B:
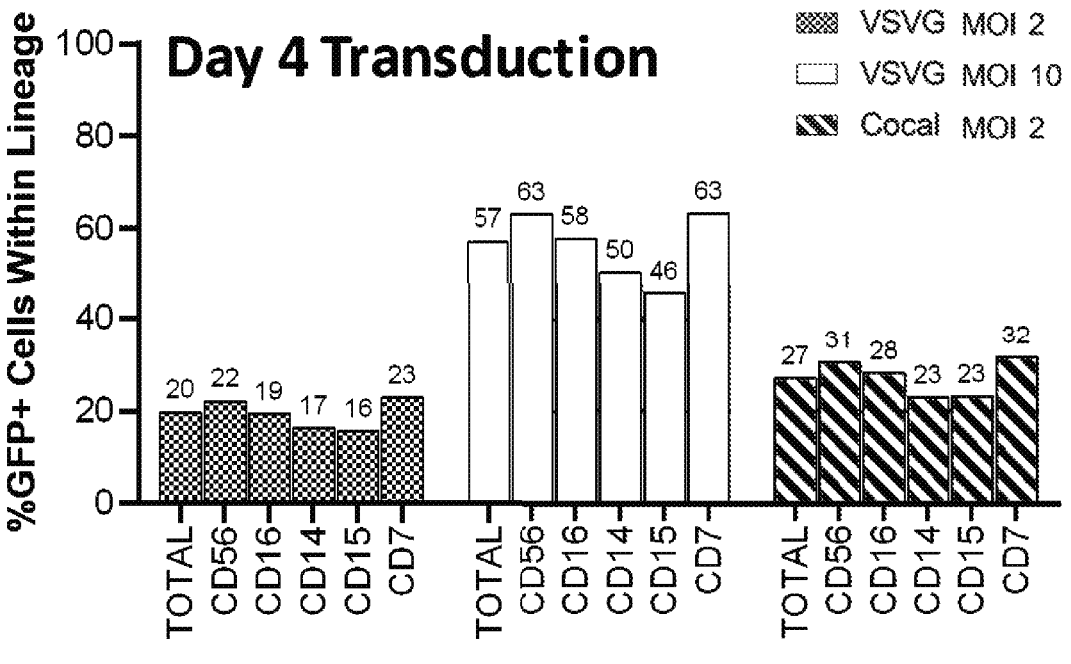
Figure 14C:
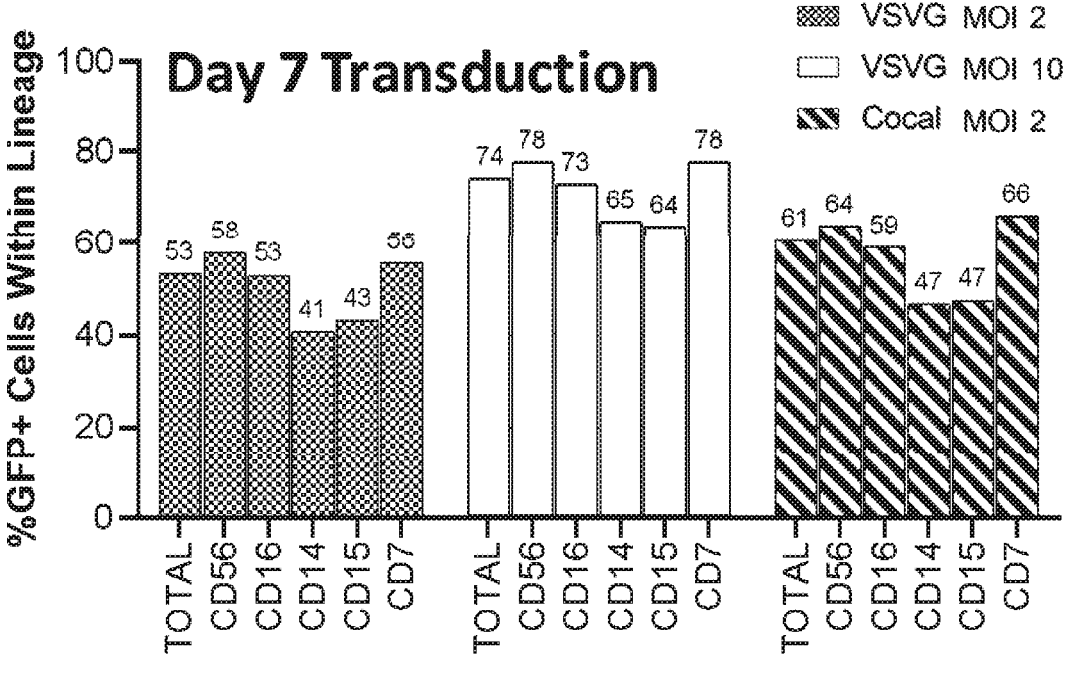
Figure 14D:
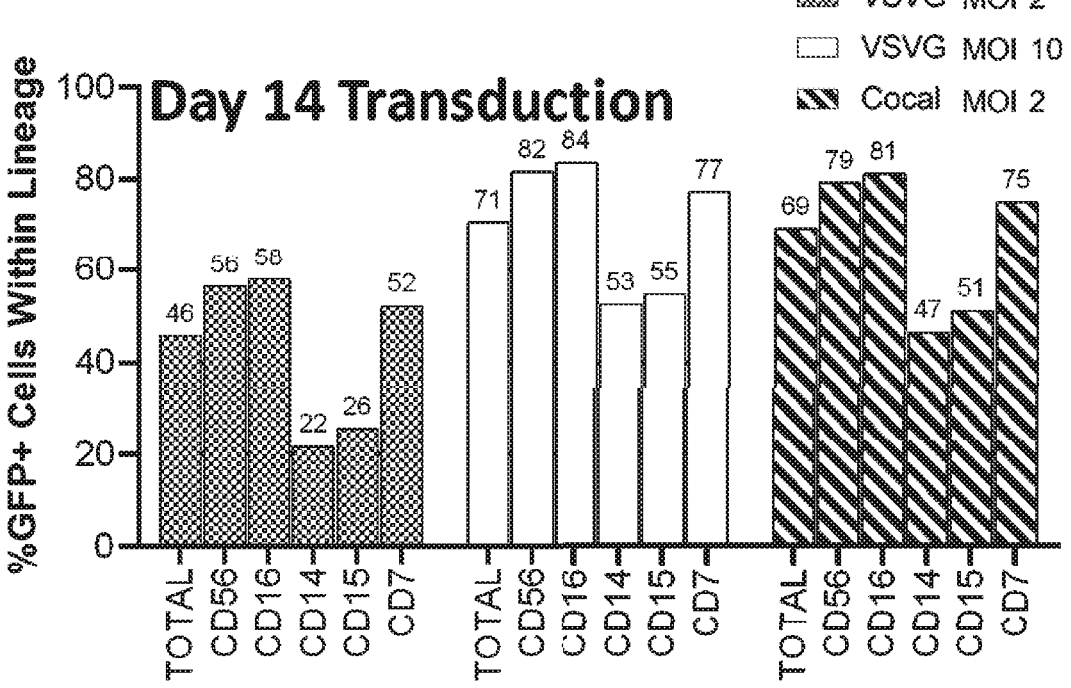
Figure 14E:
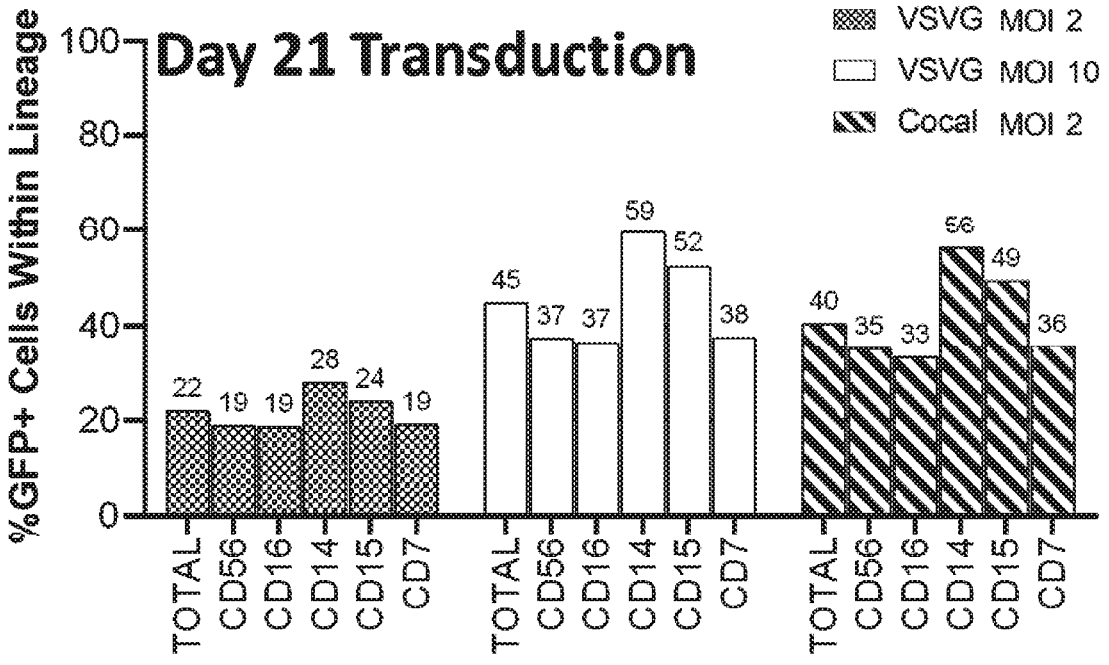

Example 7: Cytokine Release by an NK Cell Preparation in the Presence of Tumor Cells This study was performed to determine the expression of the cytokines interferon gamma (IFNγ) or tumor necrosis factor alpha (TNFα) by an NK cell preparation in the presence and absence of K562 or A549 tumor cells. FIG. 13 shows an NK cell preparation produced by the above methods (referred to as an NK Cell Product) or K562 or A549 tumor cells were cultured alone, or together for three days. The study was run in triplicate. After three days, cytokine levels were determined by Luminex assay. (The limit of detection was 1 pg/ml of cytokine.) As shown in FIG. 13, both IFNγ (FIG. 13A) and TNFα (FIG. 13B) levels increased when an NK cell preparation was co-cultured in the presence of tumor cells. These results indicated that the NK cells in the preparation became more active in the presence of tumor cells.

Example 8: Transduction Time Course for Production of Genetically Modified NK Cell Preparations This study was performed to determine suitable times during the expansion and differentiation phases for genetic modification. GFP (green fluorescent protein) lentivirus with either VSVG (vesicular stomatitis virus) or Cocal pseudo-typed virus envelope glycoprotein was used to transduce CD34$^+$ cord blood cells using 2 different multiplicities of infection (MOIs) at different time points during the expansion phase (day 1, 4, 7, or 14) or the NK differentiation phase (day 21) and continued through 28 days of the NK cell culture. On day 28 cells were immunophenotyped for different cell populations including CD56, CD16, CD14, CD15, and CD7. FIG. 14 shows more consistent distribution across cell lineages was observed following transduction on day 1, 4, or 7.

Figures 15, 16:
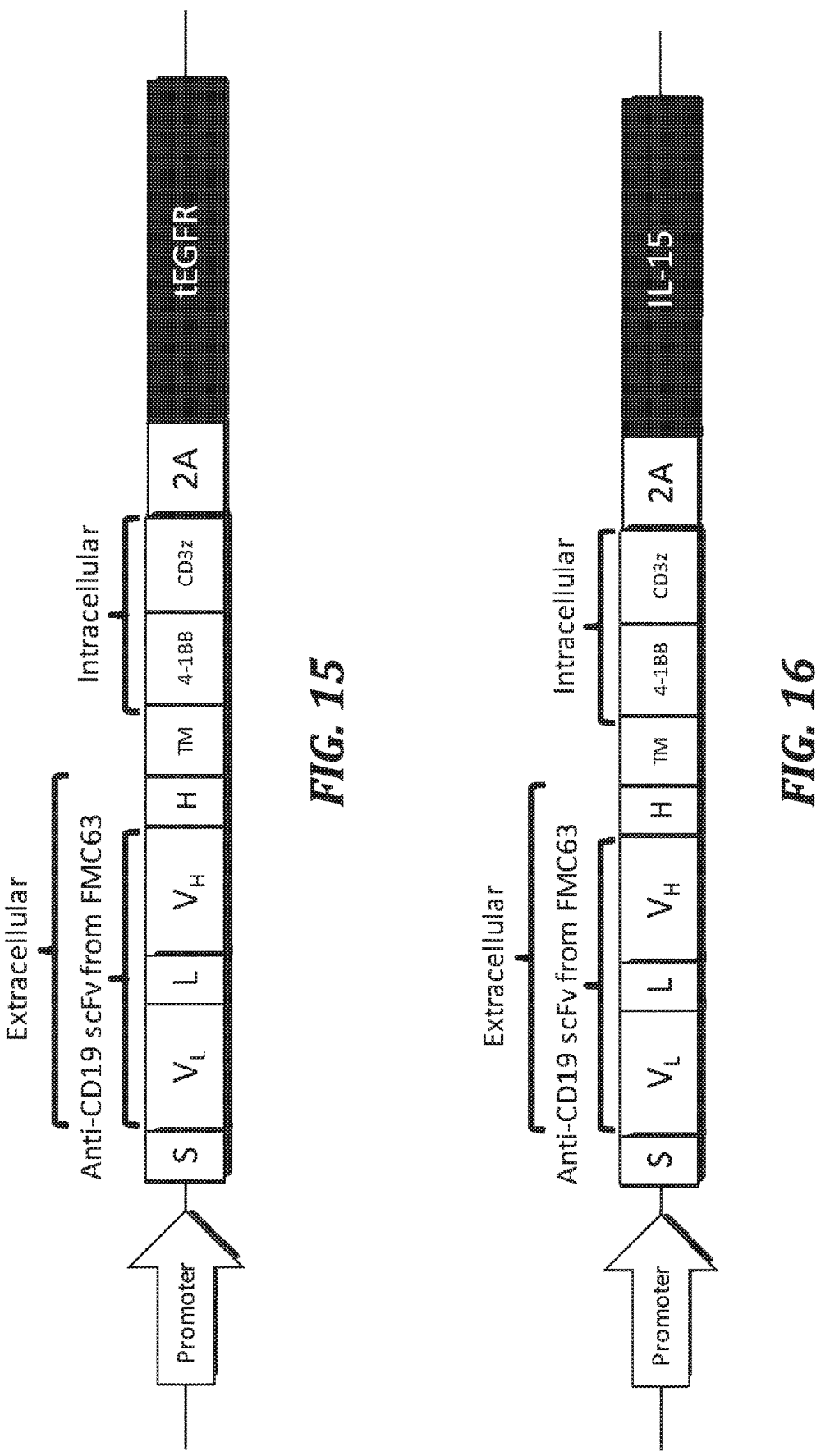
FIG. 15 shows the expression constructs included tEGFR as a selectable marker. S=Signal sequence from GM-CSF R; $V_L$=variable light chain; L=linker; $V_H$=variable heavy chain; H=Hinge spacer from human IgG$_4$; TM=CD28 or NKG2D transmembrane domain; 4-1BB=intracellular signaling domain; CD3zeta=intracellular signaling domain; 2A=self-cleaving peptide.
FIG. 16 shows the expression constructs included human IL-15 for support of NK cells. S=Signal sequence from GM-CSF R; $V_L$=variable light chain; L=linker; $V_H$=variable heavy chain; H=Hinge spacer from human IgG$_4$; TM=CD28 or NKG2D transmembrane domain; 4-1BB=intracellular signaling domain; CD3zeta=intracellular signaling domain; 2A=self-cleaving peptide.

Example 9: Preparation of CAR Constructs Targeting Human CD19 Expressing Cells CAR constructs containing an anti-CD19 scFV (FMC63), a hinge region from human IgG$_4$, a CD28 transmembrane domain, a 4-1BB co-stimulatory domain and a CD3zeta intracellular signaling domain were prepared. The expression constructs include either tEGFR as a selectable marker (FIG. 15) or human IL-15 (FIG. 16). The CAR constructs were transduced into HSPCs, generally as described in Example 8.

Example 10: Preparation and Characterization of NK Cells with IL-15 Priming During the Expansion Phase This Example describes the production and characterization of an NK cell preparation with IL-15 added during the Phase 1 expansion stage.

Phase 1 involved expansion of hematopoietic stem and progenitor cells. CD34$^+$ enriched hematopoietic stem and progenitor cells (HSPC) were seeded into tissue culture treated plastic vessels (Thermo Scientific Nunc™ EasY-Flask™). The enriched CD34$^+$ HSPCs were prepared as described above. The tissue culture treated plastic vessels were pre-coated with a solution of a recombinant human fibronectin fragment (Takara Bio, Inc.; RetroNectin® Recombinant Human Fibronectin Fragment, 5 µg/ml and 0.8 µg/cm$^2$ surface area) and a Notch agonist (Delta1$^{extIgG}$; 2.5 µg/ml and 0.4 µg/cm$^2$ surface area) in DPBS (Gibco). Culture medium comprised a cell culture medium suitable and adapted for the culture and expansion of hematopoietic cells (StemSpan™ Serum-Free Expansion Medium II (SFEM II; StemCell Technologies)) supplemented with 50 ng/ml each of rhSCF (Miltenyi Biotec), Flt-3L (Miltenyi Biotec), TPO (Miltenyi Biotec), and IL-6 (Miltenyi Biotec), and 10 ng/ml IL-3 (Miltenyi Biotec). Cells were cultured for 14 days, passaging the cells into larger volume culture vessels when appropriate to maintain a cell density <2×10$^6$ cells/ml. The expansion culture was primed by the addition of IL-15 (Pepro Tech) at 40 ng/ml from day 7 to 14 or day 10 to 14.

Phase 2 of the culturing process differentiates the expanded hematopoietic stem and progenitor cells toward an NK cell phenotype. At the end of the 14-day expansion phase (Phase 1 above), all cells were collected and re-plated at a cell density of 1×10$^6$ cells/ml in 1000 ml culture medium into culture vessels (G-Rex100M vessels, WilsonWolf) without a Notch agonist (Delta1$^{extIgG}$ or RetroNectin®) coating. The culture medium comprised RPMI 1640 (Gibco) supplemented with 5% human platelet lysate (hPL; Mill Creek Life Sciences), 40 ng/ml rhIL-15 (PeproTech), and 50 U/ml rhIL-2 (PeproTech). Cells were cultured for 10 additional days, replacing 50% of the medium in the vessel with fresh differentiation medium 7 days into differentiation.

In addition to CD56, the CD56$^+$ cells expressed a high frequency of NKp30, NKp46, NKp44, and NKG2A, and a moderate frequency of CD16, NKp44, and NKG2D.

Table 4 shows the phenotypic attributes of the CD56+ cell in an exemplary NK cell preparation produced by the method.

Table 4

| Phenotypic attributes of CD56$^+$ Cells | |
| --- | --- |
| CD56$^+$ Cells | Frequency (Mean ± SD) |
| CD56+ population | 74.03 ± 1.40 |
| Frequency within CD56$^+$ population | |
| CD16$^+$ | 35.21 ± 3.62 |
| NKp30$^+$ | 71.29 ± 23.3 |
| NKp44$^+$ | 25.39 ± 3.47 |
| NKp46$^+$ | 84.31 ± 8.16 |
| NKG2A$^+$ | 63.86 ± 4.49 |
| NKG2D$^+$ | 50.01 ± 16.78 |

The NK cell preparation also included approximately 26% CD56$^-$ cells. As with the prior method above, these cells are largely myeloid derived and can include dendritic cells, macrophages, and granulocytes. Table 5 shows the phenotypic attributes of the CD56$^-$ cells in an exemplary NK cell preparation produced by this method.

TABLE 5

| Phenotypic attributes of CD56⁻ cells | |
| --- | --- |
| CD56⁻ Cells | Frequency (Mean ± SD) |
| CD14⁻CD15⁺ | 6.46 ± 1.26 |
| CD14⁺CD15⁺ | 6.96 ± 1.19 |
| CD14⁺CD15⁻ | 0.55 ± 0.19 |
| CD14⁻CD15⁻ | (cell subsets below) |
| CD11b⁺CD11c⁺ | 3.67 ± 1.08 |
| HLA⁻DR⁺ | 4.06 ± 0.65 |
| CD7⁺ | 0.50 ± 0.14 |
| CD33⁺ | 1.83 ± 0.81 |
| CD34⁺ | 0.13 ± 0.14 |
| unidentified | 0.61 ± 0.21 |

Figure 17A:
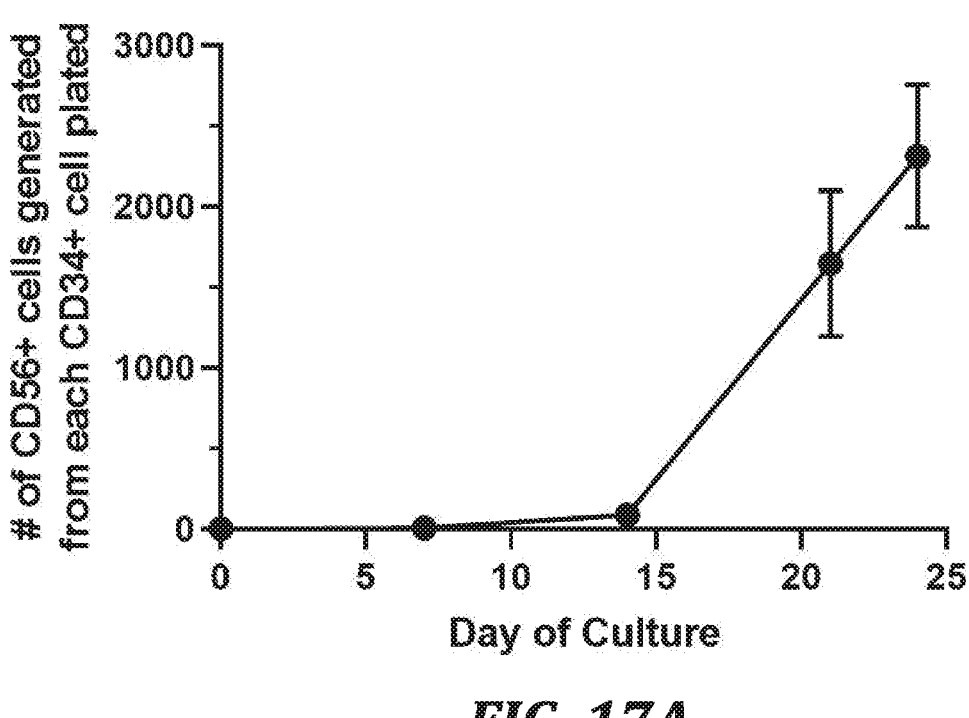
FIGS. 17A and 17B show IL-15 added during the expansion phase to prime NK cell differentiation produces significant increases in CD56$^+$ cells and that the process is reproducible. The Figures show the results from 4 batches of NK cell preparations produced at manufacturing scale.
Figure 17B:
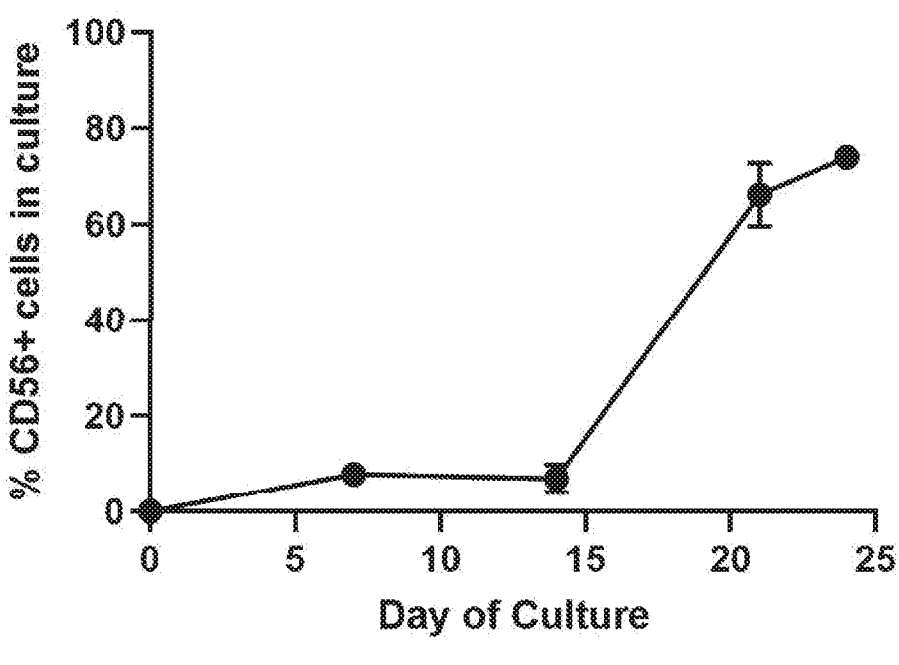

FIGS. 17A and 17B show the results of 4 batches of NK cell preparations produced at manufacturing scale following the method described above. FIG. 17A shows the increase in $CD56^+$ cells/starting $CD34^+$ cells over the course of a 24-day culture (phases 1 and 2). FIG. 17B demonstrates the reproducibility of $CD56^+$ cell generation over the 24-day cell culture process.

Figure 18A:
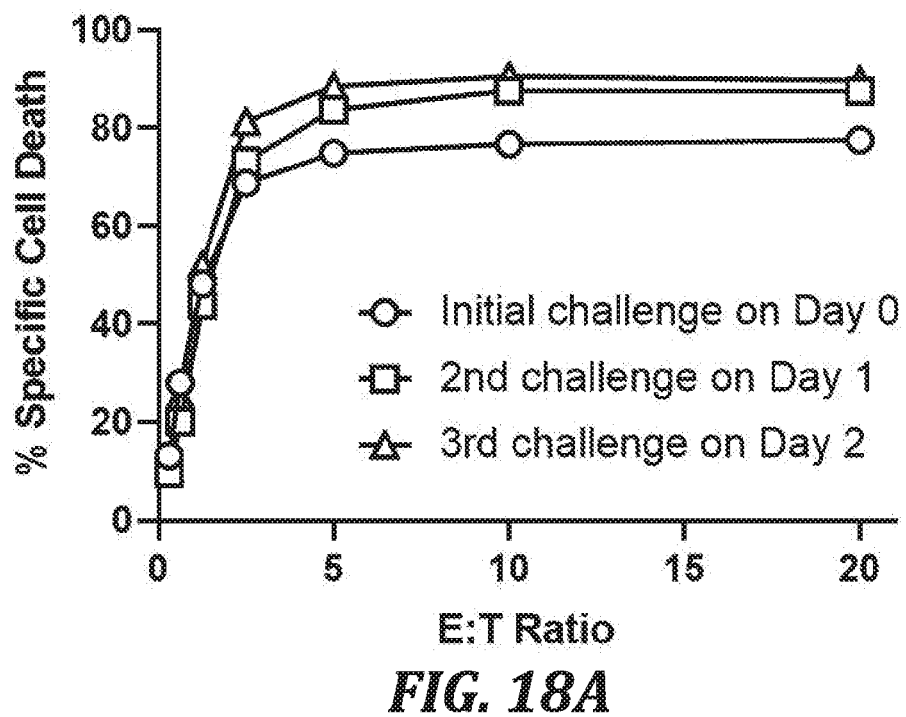
FIGS. 18A through 18C show the capacity of the NK cell preparations to serially kill repeat doses of target cells over a prolonged duration.
Figure 18B:
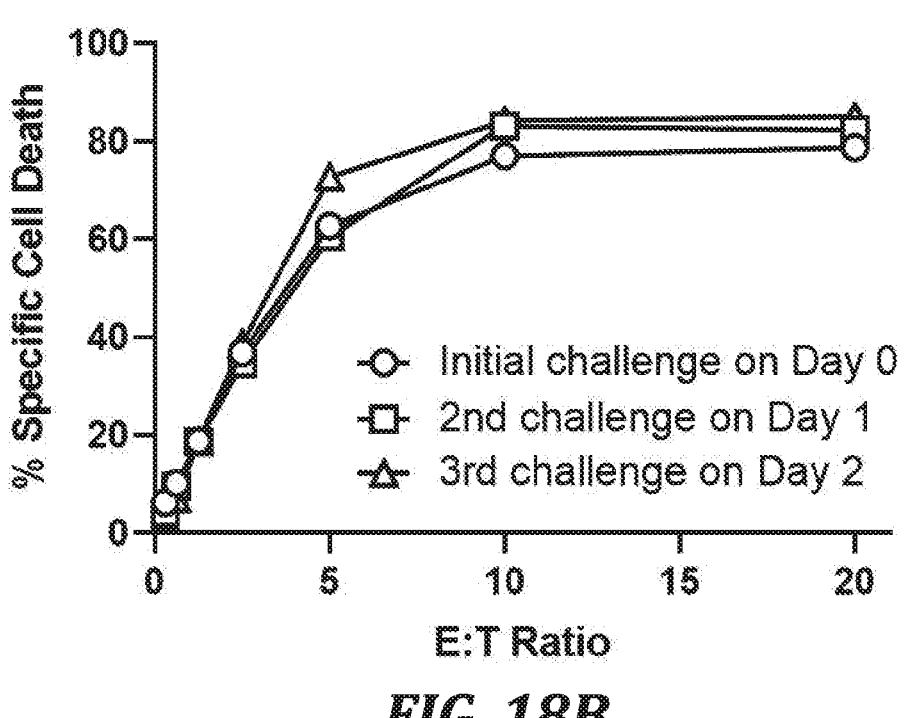
Figure 18C:
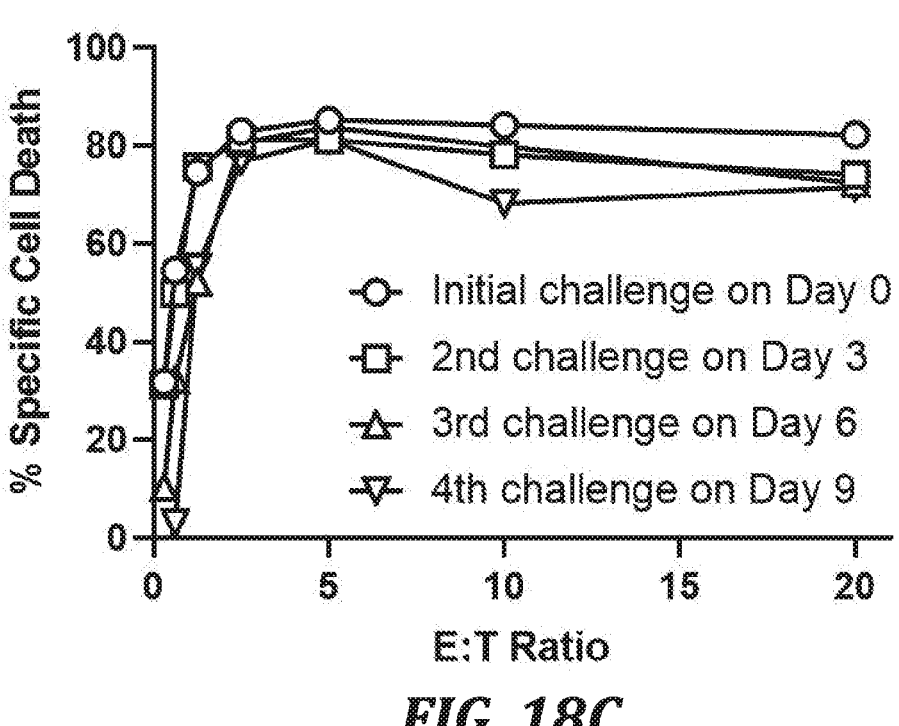

Example 11: In Vitro Cell Killing by an NK Cell Preparation Produced with IL-15 Priming In this Example the capacity of the NK cell preparations produced with IL-15 priming to serially kill repeat doses of target cells is demonstrated. The serial killing assay was run over a prolonged duration in a modification of the standard in vitro cell killing assay described in Example 3. In this example, the cell killing assay used a Kasumi-1 myeloid cell leukemia cell line (similar to AML). Fresh NK cell preparations (FIG. 18A) or cryopreserved and thawed NK cell preparations (FIG. 18B) were plated into the assay at its initiation and received repeat doses of target cells every 24 hours for a total of three days, with analysis for specific cell death of the target cells performed 24 hours after each challenge. An additional assay was plated using a fresh NK cell preparation that received repeat doses of target cells every 3 days for a total of 10 days (FIG. 18C), with analysis for specific cell death of the target cells performed 24 hours after each challenge. Both the fresh NK cell preparation and the cryopreserved and thawed NK cell preparation achieved dose-dependent cell killing against repeat target additions over the duration of each experiment, demonstrating the ability of the NK cells to serially kill target cells for at least 10 days.

Example 12: In Vivo Mouse AML Xenograft Assay with an NK Cell Preparation

Figure 19:
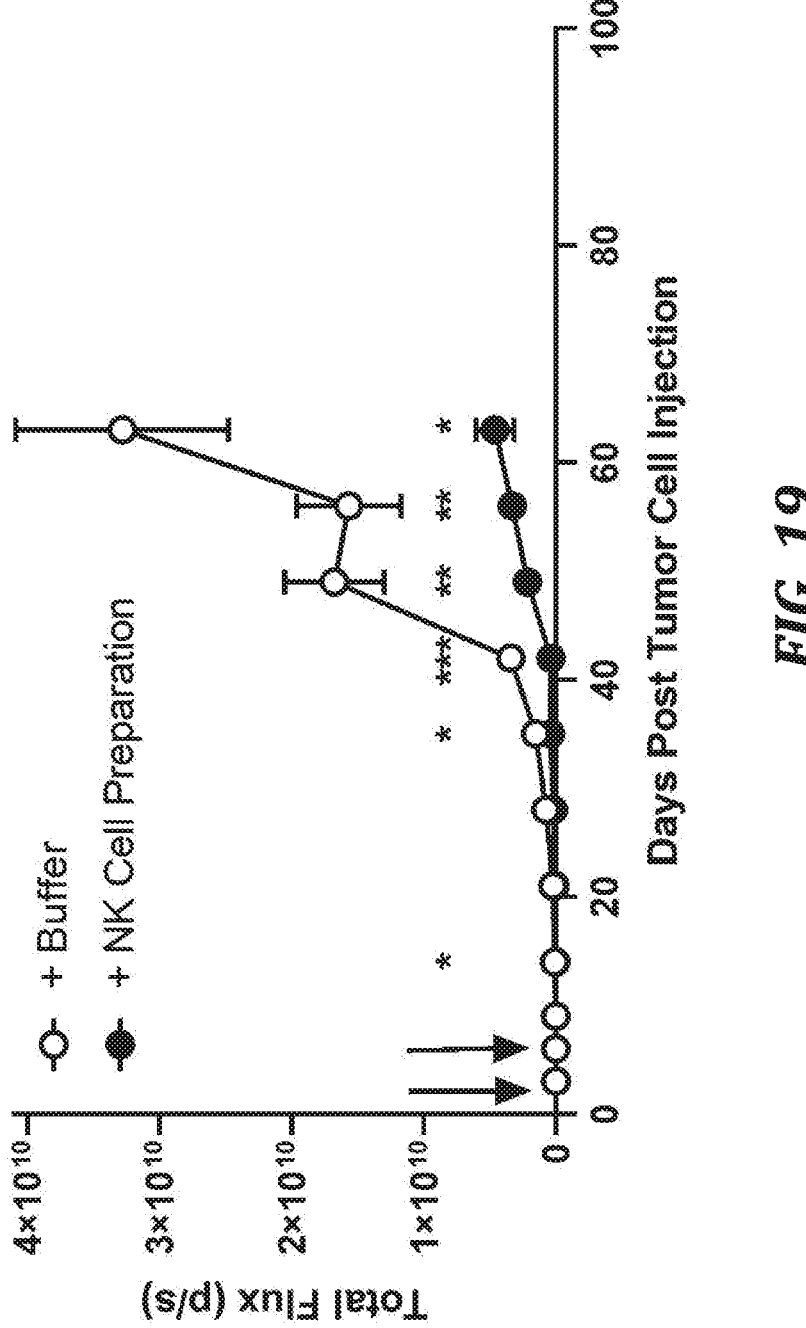
FIG. 19 shows the activity of an NK cell preparation in a Kasumi-1 AML diffuse tumor model. The model was tested in NSG mice with or without NK cell preparation treatment by measuring Kasumi-1 tumor burden via bioluminescent imaging. Compared against buffer-injected control treatment, the NK cell preparation significantly inhibited tumor progression.
Figure 20:
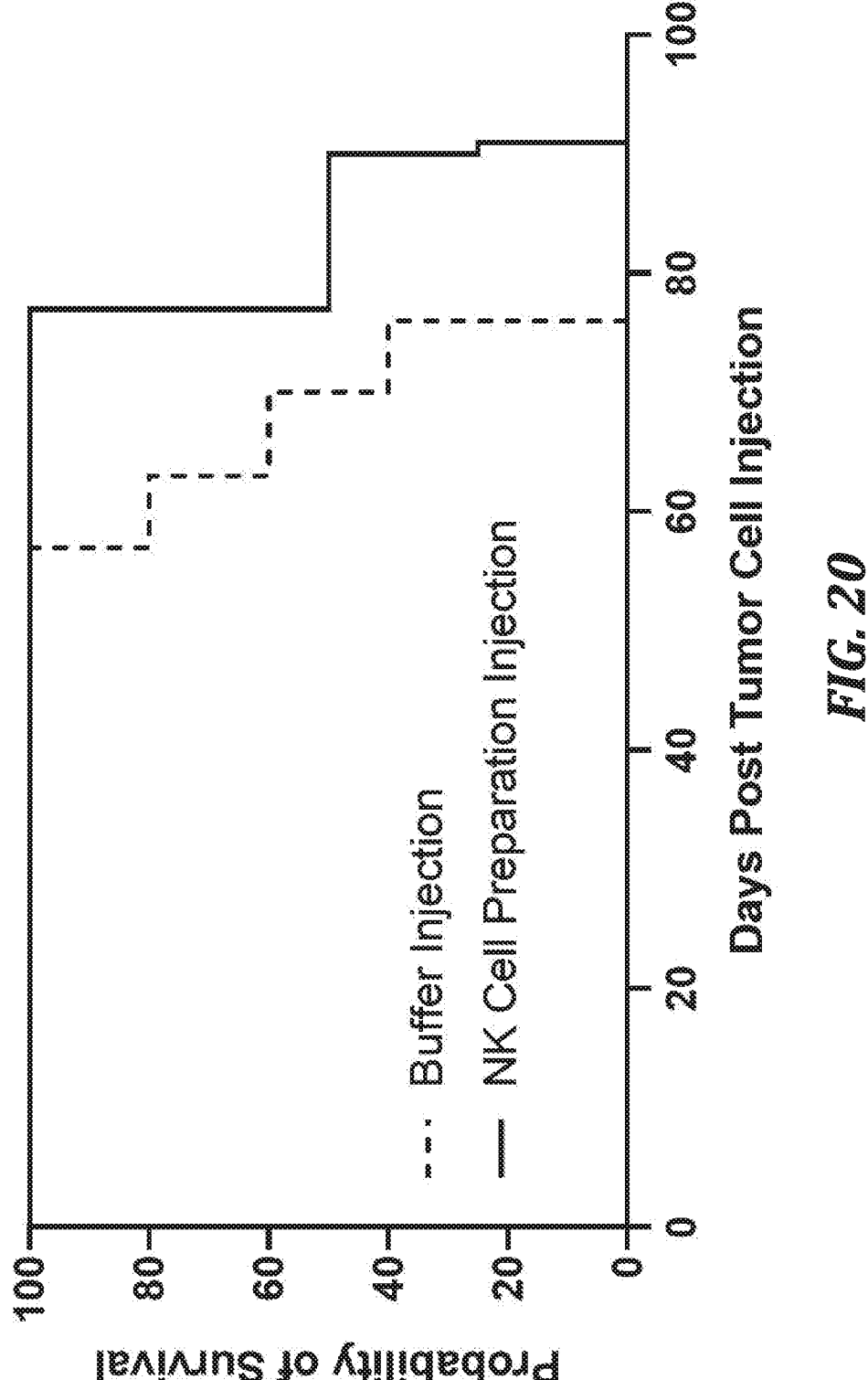
FIG. 20 shows NSG mouse survival in the Kasumi 1 AML model used in FIG. 19. The NK cell preparation significantly prolonged median survival in mice as compared with the mice injected with the buffer control.

The activity of the NK cell preparation in the Kasumi-1 AML diffuse tumor model was tested in NSG mice with or without NK cell preparation treatment by measuring Kasumi-1 tumor burden and animal survival. Firefly-luciferase expressing Kasumi-1 cells were intravenously injected into the tail vein of NSG mice ($2 \times 10^6$ cells/mouse) on Day 0 prior to intravenous injection of two doses of $2 \times 10^7$ cells of an NK cell preparation per mouse on Day 2 and Day 6. Tumor growth was assessed 1 to 2 times per week by bioluminescence imaging Compared against buffer-injected control treatment, the NK cell preparation inhibited tumor progression (FIG. 19, p values: *=<0.05, =<0.01, *=<0.001) and significantly prolonged median survival in mice. (FIG. 20; 83.5 days versus 70 days, p=<0.01 by log-rank test).

Example 13: Generation of Mesothelin CAR NK Cells—Transduction During the Expansion Phase On Day 7 of Phase 1 (the expansion phase) HSPCs were transduced with a lentivirus expressing a mesothelin targeted chimeric antigen receptor (CAR). Expression of this CAR was driven using the EF1alpha promoter. This construct also contained a truncated CD19 (tCD19) extracellular domain, expressed from the same promoter and separated from the CAR sequence by a T2A self-cleaving domain. $1 \times 10^6$ cells/ml in 0.5 ml of culture medium were plated in a 24-well plate that was precoated with a solution of recombinant human fibronectin fragment (Takara Bio, Inc.; RetroNectin® Recombinant Human Fibronectin Fragment) 5 µg/ml and 0.8 µg/cm² surface area), and a Notch agonist (Delta1$^{ext-IgG}$, 2.5 µg/ml and 0.4 µg/cm² surface area) in DPBS (Gibco). Culture medium comprised a medium suitable for the growth and expansion of hematopoietic cells (StemSpan™ Serum Free Expansion Medium II (SFEM II; StemCell Technologies)) supplemented with 50 ng/ml each recombinant human SCF (Miltenyi Biotec), Flt-3 ligand (Miltenyi Biotec), TPO (Miltenyi Biotec), and IL-6 (Miltenyi Biotec), and 10 ng/ml IL-3 (Miltenyi Biotec). 8 µg/ml protamine sulfate (Millipore Sigma) was added along with the solution of lentivirus using a multiplicity of infection (MOI) of 30. A second addition of lentivirus at MOI of 30 was added to the well 3 hours later. Cells were incubated overnight at 37° C. in a 5% $CO_2$ incubator. On day 8, cells were passaged into a larger volume vessel (6-well plate) pre coated with RetroNectin® and Delta1$^{ext-IgG}$ by diluting cells in SFEM II media plus the above 5 growth factors to maintain a cell density $<2 \times 10^6$ cells/ml. On day 14, the cells were collected and replated at a density of $1 \times 10^6$ cells/ml into tissue culture vessels (T25 tissue culture flasks) without the Delta1$^{ext-IgG}$ or Retronectin® coatings. Differentiation culture medium comprised RPMI 1640 (Gibco) supplemented with 5% human platelet lysate (hPL) (Mill Creek Life Sciences), 40 ng/ml rhIL-15 (PeproTech), and 50 U/ml rhIL-2 (PeproTech). Cells were cultured for a total of 14 additional days, replacing 50% of the medium in the vessel with fresh differentiation medium on Day 21.

On day 28, the CAR NK cell preparation was collected and evaluated for CAR expression by flow cytometry and in an in vitro cytotoxicity assay against two different green fluorescent protein- (GFP-) expressing NOMO-1 AML tumor target cells. The parental NOMO-1 cell line endogenously expresses mesothelin that the CAR is targeted against. A knockout of mesothelin was prepared in this same cell line (NOMO-1$^{MSLN-/-}$).

Figure 21:
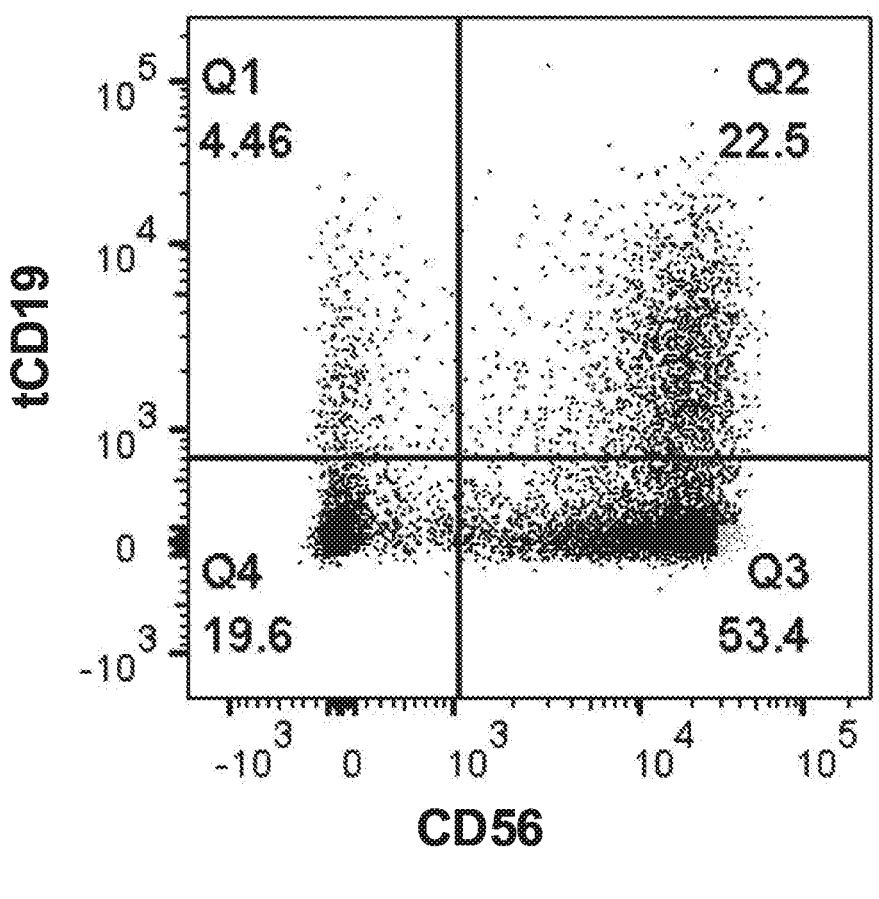
FIG. 21 shows flow cytometry-based detection of tCD19 transgene expression as an indirect measure of CAR expression in transduced CD56$^+$ and CD56$^-$ cells. Plots show the frequency of CD56 expression and tCD19 expression in cells at day 28 of culture following transduction with a lentivirus vector expressing a mesothelin targeted CAR and a truncated CD19 (tCD19) extracellular domain driven by the EF1alpha promoter. Bulk cells were transduced using an MOI of 30, two times, 3 hours apart on day 7 of expansion.

CAR expression was evaluated by indirect detection on the cell surface using an anti-CD19 antibody by flow cytometry. Cells were 76% CD56⁺ and 27% tCD19⁺ (FIG. 21).

CAR transduced and mock transduced control NK cells were tested as effector cells in an in vitro cytotoxicity assay by co-culturing with each of the two NOMO-1 target cells (parental and mesothelin knockout) in RPMI+10% FBS+40 ng/ml IL-15+50 U/ml IL-2. E:T ratios ranged between 0.3 to 20 and the assay proceeded for 24 hr. At the end of the incubation cells were labeled with a DAPI solution and analyzed by flow cytometry for GFP fluorescence of target cells and DAPI fluorescence of dead cells to determine the % specific cell death.

Figure 22:
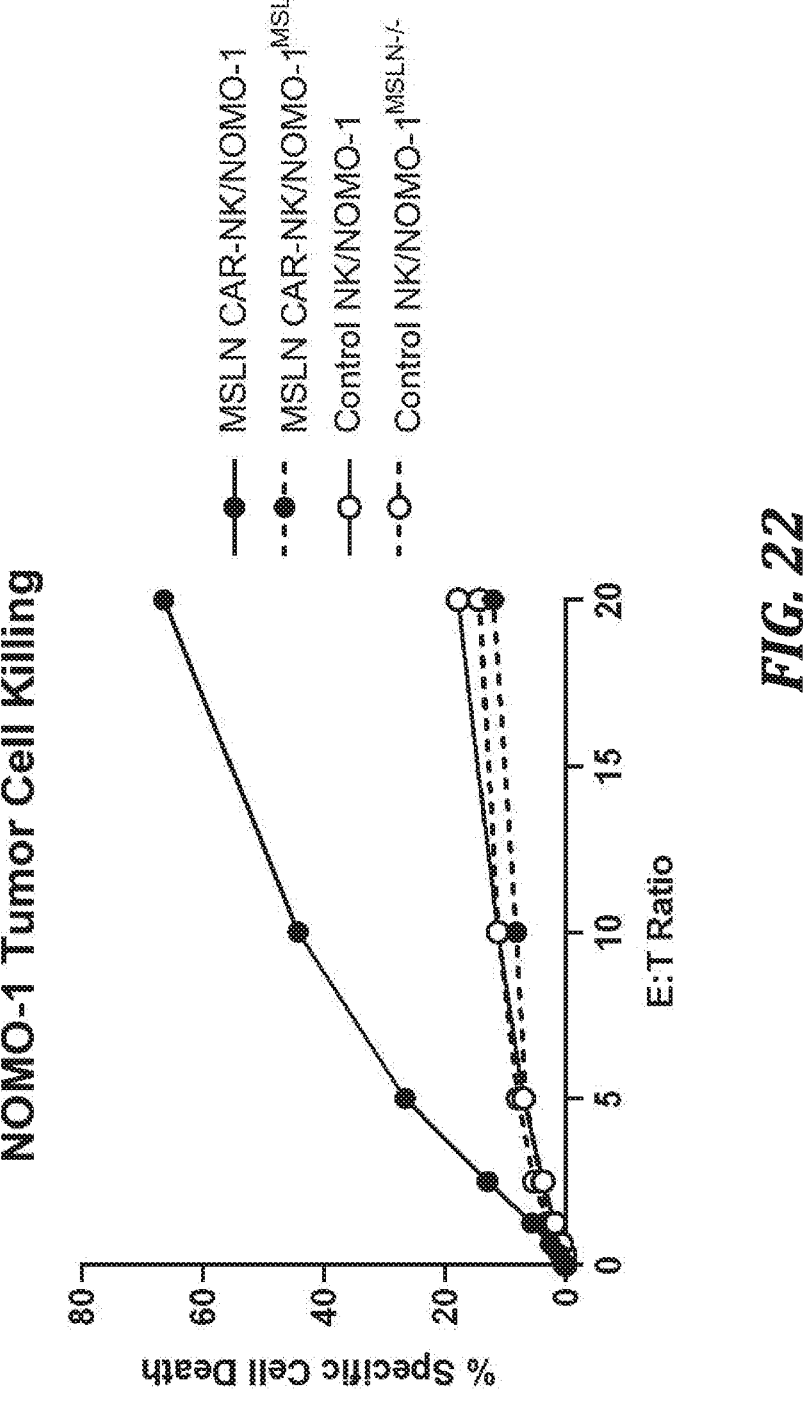
FIG. 22 shows cytotoxic activity of MSLN CAR-NK cells or control NK cells against NOMO-1 or NOMO-AML tumor cells in a 24-hour in vitro cytotoxicity assay. There is a significant and specific increase in tumor cell killing by the MSLN CAR-NK cells against the MSLN expressing NOMO-1 cells but not against the NOMO-1$^{MSLN-/-}$ tumor cells. No difference in killing was observed with the control NK cells against the NOMO-1 cells+/– MSLN knockout.

Results showed that the mesothelin CAR-NK cells demonstrated a significant and specific increase (up to 55%) in killing the parental NOMO-1 cells compared to the NOMO- $1^{MSLN-/-}$ cells. Similar low-level killing was observed with the control NK cells against either NOMO-1 cell line (FIG. 22).

Example 14: Generation of Mesothelin CAR NK Cells—Transduction after NK Cell Differentiation In this example a CD34$^+$ enriched non-immunologically matched pool of cells were processed as above through both phase 1 (expansion) and phase 2 (differentiation). Subsequent to full differentiation the NK cells were transduced with a CAR construct.

In particular, on day 23 of Phase 2 during the differentiation phase, bulk cells were enriched for human CD56$^+$ NK cells using an immunomagnetic microbead based column isolation protocol (CD56 Microbeads, human, Miltenyi Biotec). Enriched NK cells (>96% CD56$^+$) were transduced with same lentivirus described in Example 12. 1×10$^6$ cells/ml in 2 ml differentiation culture medium were plated in a 6-well plate along with 8 µg/ml protamine sulfate and lentivirus using an MOI of 40. Cells were incubated overnight at 37° C. in a 5% CO$_2$ incubator. On day 24, half the media volume was replaced with fresh culture medium.

Figure 23:
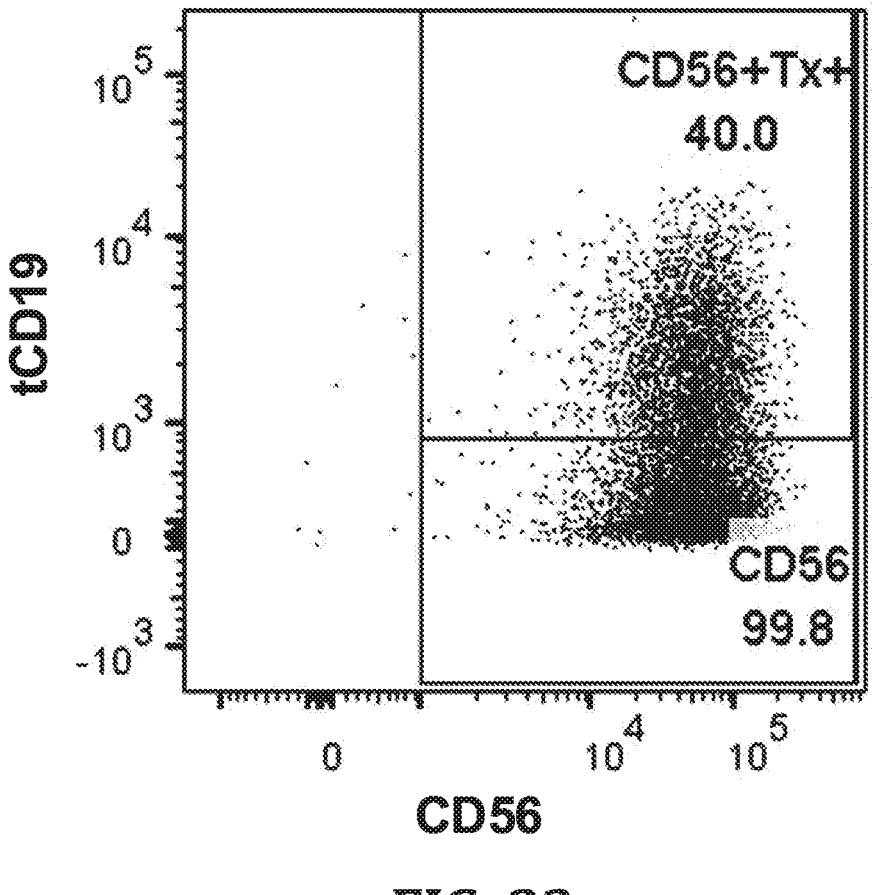
FIG. 23 shows flow cytometry-based detection of tCD19 transgene expression as an indirect measure of CAR expression in enriched CD56$^+$ cells. Plots show the frequency of CD56 expression and tCD19 expression (TO in cells at day 27 of culture following transduction with a lentivirus vector expressing a mesothelin-targeted CAR and a truncated CD19 (tCD19) extracellular domain driven by the EF1alpha promoter. CD56$^+$ cells were enriched by magnetic bead separation and transduced using an MOI of 40 on day 23 of culture in the differentiation phase.

On day 27, NK cell preparations were collected and evaluated for CAR expression by flow cytometry and in an in vitro cytotoxicity assay against the parental NOMO-1 and NOMO-1$^{MSLN-/-}$ target cells described in Example 13. CAR expression was evaluated by indirect detection on the cell surface using an anti-CD19 antibody by flow cytometry. Cells were >99% CD56$^+$ and 40% tCD19+ (FIG. 23).

CAR transduced and mock transduced control NK cells were tested as effector cells in an in vitro cytotoxicity assay by co-culturing with each of the two NOMO-1 target cells (parental and mesothelin knockout) in RPMI+10% FBS+40 ng/ml IL-15+50 U/ml IL-2. E:T ratios ranged between 0.3 to 10 and the assay proceeded for 24 hr. At the end of the incubation cells were labeled with a DAPI and analyzed by flow cytometry for GFP fluorescence of target cells and DAPI fluorescence of dead cells to determine the % specific cell death.

Figure 24:
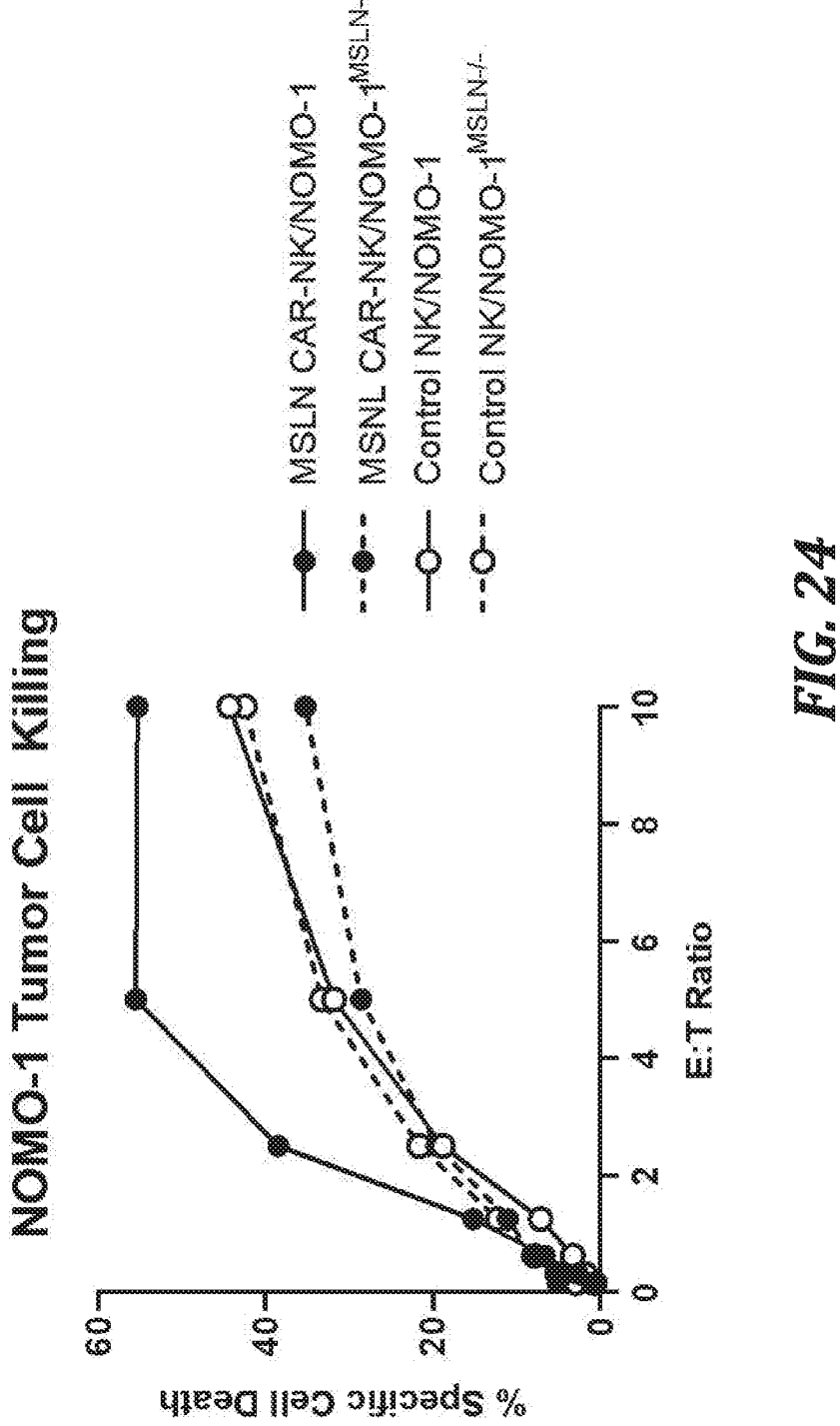
FIG. 24 shows cytotoxic activity of CAR-NK cells or control NK cells against NOMO-1 cells or NOMO-1$^{MSLN-/-}$ cells in a 24-hour in vitro cytotoxicity assay. There is a significant and specific increase in tumor cell killing by the MSLN CAR-NK cells against the MSLN expression NOMO-1 cells but not against the NOMO-1$^{MSLN-/-}$ cells. No difference in killing was observed with the control NK cells against the NOMO-1 cells+/– the MSLN knockout

Results showed that the mesothelin CAR-NK cells demonstrated a significant and specific increase (up to 27%) in killing the parental NOMO-1 target cells compared to the NOMO-1$^{MSLN-/-}$ target cells. Similar low-level killing was observed with the control NK cells against either NOMO-1 target cell line (FIG. 24).

The embodiments of the invention in which an exclusive property or privilege is claimed are defined as follows:

1. A method of preparing a natural killer (NK) cell composition or preparation, consisting of:
    selecting a plurality of umbilical cord blood or placental blood cells without immunological matching to each other;
    preparing enriched cluster of differentiation 34 positive (CD34$^+$) hematopoietic stem and progenitor cells (HSPCs) that are depleted of red blood cells and T cells;
    culturing the CD34$^+$ enriched HSPCs in an expansion culture medium comprising interleukin-3 (IL-3), interleukin-6 (IL-6), thrombopoietin (TPO), Fms-related tyrosine kinase 3 ligand (Flt-3 ligand (Flt-3L)), and stem cell factor (SCF) on a solid phase coated with a Notch ligand and recombinant human fibronectin or fragments thereof, and in the absence of exogenous feeder cells, for at least 7 days to produce expanded HSPCs, wherein the expanded HSPCs do not differentiate to produce more cluster of differentiation 56 positive (CD56$^+$) cells than CD34$^+$ cells during the expansion; and
    culturing the expanded HSPCs in a differentiation culture medium comprising effective amounts of interleukin-2 (IL-2) and interleukin-15 (IL-15), a non-animal sourced serum replacement, and in the absence of the exogenous feeder cells for at least 7 days to produce a NK cell composition or preparation comprising a population of NK cells of 50 to 80% CD56$^+$ cells and 20 to 50% endogenous CD56 negative (CD56$^-$) cells or 50 to 80% CD56$^+$ cells and 15 to 50% endogenous CD56$^-$ cells;
    wherein the CD56$^+$ cells express a high frequency of 60 to 100% of natural cytotoxicity receptor 3 (NKp30), natural cytotoxicity receptor 1 (NKp46), natural cytotoxicity receptor 2 (NKp44), immune inhibitory receptor natural killer group 2 member A (NKG2A), and granzyme B, a moderate to high frequency of 20 to 100% of perforin and lysosomal-associated membrane protein 1 (LAMP-1) or cluster of differentiation 107a (CD107a), a low to moderate frequency of 1 to 60% of cluster of differentiation 16 (CD16), and substantially no expression or less than 1% of killer-cell immunoglobulin-like receptors (KIRs); and wherein the CD56-cells express a moderate to high frequency of 20 to 100% of granzyme B, a high frequency of 60 to 100% of CD107a, and a low frequency of 1 to 20% of perforin.

2. The method of claim 1, wherein the expansion culture medium does not contain exogenous IL-15, IL-7, IL-2, granulocyte-colony stimulating factor (G-CSF), granulocyte-macrophage colony-stimulating factor (GM-CSF), leukemia inhibitory factor (LIF), macrophage inhibitory protein-1alpha (MIP-1α), or an aryl hydrocarbon receptor antagonist, and wherein the differentiation culture medium does not contain added Flt-3L, fibroblast growth factor-2 (FGF-2), IL-6, interleukin-7 (IL-7), interleukin-12 (IL-12), IL-3, GM-CSF, G-CSF, LIF, MIP-1α, SCF, interleukin-12 (IL-21), interleukin-18 (IL-18), and tumor necrosis factor ligand superfamily member 9 ligand (4-1BBL).

3. The method of claim 1, wherein IL-15 is added during the expansion of the CD34$^+$ enriched HSPCs or is added during the last 4 to 7 days of the expansion phase, and wherein IL-2 and IL-15 are the only added cytokines to the differentiation culture medium.

4. The method of claim 1, wherein the differentiation culture medium does not contain exogenous antigen presenting cells.

5. The method of claim 1, wherein the non-animal serum replacement is human AB serum, fresh frozen human plasma, or human platelet lysate.

6. The method of claim 1, wherein the NK cell composition or preparation further comprises a cryoprotective agent.

7. The method of claim 1, further comprising formulating the NK cell composition or preparation to form a NK cell composition or preparation for infusion into a subject.

8. A natural killer (NK) cell composition or preparation for use in immunotherapy, the NK cell composition or preparation comprising a population of NK cells of:
    50 to 80% CD56$^+$ cells and 20 to 50% endogenous CD56-cells, or 50 to 85% CD56$^+$ cells and 15 to 50% endogenous CD56$^-$ cells, wherein the CD56$^+$ cells express a high frequency of 60 to 100% of NKp30, NKp46, NKp44, NKG2A, NKG2D, and granzyme B, a moderate to high frequency of 20 to 100% of perforin and CD107a, a low to moderate frequency of 1 to 60% of CD16 and substantially no expression or less than 1% of KIRs; and wherein the CD56-cells express a moderate to high frequency of 60 to 100% of granzyme B, a high frequency of 60 to 100% of CD107a, and a low frequency of 1 to 20% of perforin, and a pharmaceutically acceptable carrier.

9. The NK cell composition or preparation of claim 8, wherein the composition or preparation does not contain exogenous feeder cells.

10. The NK cell composition or preparation of claim 8, wherein the NK cell composition or preparation comprises less than 2% CD3$^+$ cells, less than 2% CD19$^+$ cells, and/or less than 2% CD34$^+$ cells.

11. The NK cell composition or preparation of claim 8, wherein the CD56$^+$ cells further express a high frequency of 60 to 100% KIR2DL4.

12. The NK cell composition or preparation of claim 8, further comprising a cryoprotective agent.

13. The NK cell composition or preparation of claim 8, wherein the NK cell composition or preparation is formulated for infusion into a subject.

14. The NK cell composition or preparation of claim 13, wherein the NK cell composition or preparation comprises from 50 million to 2 billion viable cells, or wherein the NK cell composition comprises from 50 million to 2 billion viable CD56$^+$ cells.

* * * * *

SEQUENCE LISTING

```
<160> NUMBER OF SEQ ID NOS: 75

<210> SEQ ID NO 1
<211> LENGTH: 11
<212> TYPE: PRT
<213> ORGANISM: Artificial sequence
<220> FEATURE:
<223> OTHER INFORMATION: Synthetic

<400> SEQUENCE: 1

Arg Ala Ser Gln Asp Ile Ser Lys Tyr Leu Asn
1               5                   10

<210> SEQ ID NO 2
<211> LENGTH: 7
<212> TYPE: PRT
<213> ORGANISM: Artificial sequence
<220> FEATURE:
<223> OTHER INFORMATION: Synthetic

<400> SEQUENCE: 2

Ser Arg Leu His Ser Gly Val
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic

<400> SEQUENCE: 3

Gly Asn Thr Leu Pro Tyr Thr Phe Gly
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic
```

-continued

```
<400> SEQUENCE: 4

Asp Tyr Gly Val Ser
1               5

<210> SEQ ID NO 5
<211> LENGTH: 16
<212> TYPE: PRT
<213> ORGANISM: Artificial sequence
<220> FEATURE:
<223> OTHER INFORMATION: Synthetic

<400> SEQUENCE: 5

Val Thr Trp Gly Ser Glu Thr Thr Tyr Tyr Asn Ser Ala Leu Lys Ser
1               5                   10                  15

<210> SEQ ID NO 6
<211> LENGTH: 7
<212> TYPE: PRT
<213> ORGANISM: Artificial sequence
<220> FEATURE:
<223> OTHER INFORMATION: Synthetic

<400> SEQUENCE: 6

Tyr Ala Met Asp Tyr Trp Gly
1               5

<210> SEQ ID NO 7
<211> LENGTH: 235
<212> TYPE: PRT
<213> ORGANISM: Homo sapiens

<400> SEQUENCE: 7

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
```

```
              210              215              220

Gly Asp Lys Pro Ser Leu Ser Ala Arg Tyr Val
225              230              235

<210> SEQ ID NO 8
<211> LENGTH: 247
<212> TYPE: PRT
<213> ORGANISM: Homo sapiens

<400> SEQUENCE: 8

Met Ala Ser Pro Leu Thr Arg Glu Leu Ser Leu Asn Leu Leu Met
1               5              10               15

Gly Glu Ser Ile Ile Leu Gly Ser Gly Glu Ala Lys Pro Gln Ala Pro
              20              25              30

Glu Leu Arg Ile Phe Pro Lys Lys Met Asp Ala Glu Leu Gly Gln Lys
         35              40              45

Val Asp Leu Val Cys Glu Val Leu Gly Ser Val Ser Gln Gly Cys Ser
    50              55              60

Trp Leu Phe Gln Asn Ser Ser Ser Lys Leu Pro Gln Pro Thr Phe Val
65              70              75              80

Val Tyr Met Ala Ser Ser His Asn Lys Ile Thr Trp Asp Glu Lys Leu
              85              90              95

Asn Ser Ser Lys Leu Phe Ser Ala Val Arg Asp Thr Asn Asn Lys Tyr
              100              105              110

Val Leu Thr Leu Asn Lys Phe Ser Lys Glu Asn Glu Gly Tyr Tyr Phe
         115              120              125

Cys Ser Val Ile Ser Asn Ser Val Met Tyr Phe Ser Ser Val Val Pro
         130              135              140

Val Leu Gln Lys Val Asn Ser Thr Thr Thr Lys Pro Val Leu Arg Thr
145              150              155              160

Pro Ser Pro Val His Pro Thr Gly Thr Ser Gln Pro Gln Arg Pro Glu
              165              170              175

Asp Cys Arg Pro Arg Gly Ser Val Lys Gly Thr Gly Leu Asp Phe Ala
              180              185              190

Cys Asp Ile Tyr Ile Trp Ala Pro Leu Ala Gly Ile Cys Val Ala Pro
         195              200              205

Leu Leu Ser Leu Ile Ile Thr Leu Ile Cys Tyr His Arg Ser Arg Lys
         210              215              220

Arg Val Cys Lys Cys Pro Arg Pro Leu Val Arg Gln Glu Gly Lys Pro
225              230              235              240

Arg Pro Ser Glu Lys Ile Val
              245

<210> SEQ ID NO 9
<211> LENGTH: 69
<212> TYPE: PRT
<213> ORGANISM: Artificial sequence
<220> FEATURE:
<223> OTHER INFORMATION: Synthetic

<400> SEQUENCE: 9

Ser Thr Thr Thr Lys Pro Val Leu Arg Thr Pro Ser Pro Val His Pro
1               5              10               15

Thr Gly Thr Ser Gln Pro Gln Arg Pro Glu Asp Cys Arg Pro Arg Gly
              20              25              30

Ser Val Lys Gly Thr Gly Leu Asp Phe Ala Cys Asp Ile Tyr Ile Trp
         35              40              45
```

```
Ala Pro Leu Ala Gly Ile Cys Val Ala Leu Leu Leu Ser Leu Ile Ile
    50                  55                  60

Thr Leu Ile Cys Tyr
65

<210> SEQ ID NO 10
<211> LENGTH: 220
<212> TYPE: PRT
<213> ORGANISM: Homo sapiens

<400> SEQUENCE: 10

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 11
<211> LENGTH: 164
<212> TYPE: PRT
<213> ORGANISM: Artificial sequence
<220> FEATURE:
<223> OTHER INFORMATION: Synthetic

<400> SEQUENCE: 11

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
    50                  55                  60
```

```
Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
                100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
            130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 12
<211> LENGTH: 188
<212> TYPE: PRT
<213> ORGANISM: Artificial sequence
<220> FEATURE:
<223> OTHER INFORMATION: Synthetic

<400> SEQUENCE: 12

Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Ile Thr Ala
            35                  40                  45

Leu Tyr Leu Arg Ala Lys Phe Ser Arg Ser Ala Glu Thr Ala Ala Asn
        50                  55                  60

Leu Gln Asp Pro Asn Gln Leu Tyr Asn Glu Leu Asn Leu Gly Arg Arg
65                  70                  75                  80

Glu Glu Tyr Asp Val Leu Glu Lys Lys Arg Ala Arg Asp Pro Glu Met
                85                  90                  95

Gly Gly Lys Gln Arg Arg Arg Asn Pro Gln Glu Gly Val Tyr Asn Ala
                100                 105                 110

Leu Gln Lys Asp Lys Met Ala Glu Ala Tyr Ser Glu Ile Gly Thr Lys
            115                 120                 125

Gly Glu Arg Arg Arg Gly Lys Gly His Asp Gly Leu Tyr Gln Asp Ser
            130                 135                 140

His Phe Gln Ala Val Gln Phe Gly Asn Arg Arg Glu Arg Glu Gly Ser
145                 150                 155                 160

Glu Leu Thr Arg Thr Leu Gly Leu Arg Ala Arg Pro Lys Ala Cys Arg
                165                 170                 175

His Lys Lys Pro Leu Ser Leu Pro Ala Ala Val Ser
                180                 185

<210> SEQ ID NO 13
<211> LENGTH: 113
<212> TYPE: PRT
<213> ORGANISM: Artificial sequence
<220> FEATURE:
<223> OTHER INFORMATION: Synthetic

<400> SEQUENCE: 13

Arg Ala Lys Phe Ser Arg Ser Ala Glu Thr Ala Ala Asn Leu Gln Asp
1               5                   10                  15
```

-continued

```
Pro Asn Gln Leu Tyr Asn Glu Leu Asn Leu Gly Arg Arg Glu Glu Tyr
            20                  25                  30

Asp Val Leu Glu Lys Lys Arg Ala Arg Asp Pro Glu Met Gly Gly Lys
        35                  40                  45

Gln Gln Arg Arg Arg Asn Pro Gln Glu Gly Val Tyr Asn Ala Leu Gln
        50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Thr Leu Ala Pro
            100                 105                 110

Arg
```

```
<210> SEQ ID NO 14
<211> LENGTH: 218
<212> TYPE: PRT
<213> ORGANISM: Artificial sequence
<220> FEATURE:
<223> OTHER INFORMATION: Synthetic

<400> SEQUENCE: 14
```

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
        50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
        130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
            195                 200                 205

Pro Ala Arg Asp Phe Ala Ala Tyr Arg Pro
    210                 215
```

```
<210> SEQ ID NO 15
<211> LENGTH: 767
<212> TYPE: DNA
<213> ORGANISM: Homo sapiens

<400> SEQUENCE: 15
```

-continued

```
atgggaaaca gctgttacaa catagtagcc actctgttgc tggtcctcaa ctttgagagg      60
acaagatcat tgcaggatcc ttgtagtaac tgcccagctg gtacattctg tgataataac     120
aggaatcaga tttgcagtcc ctgtcctcca aatagtttct ccagcgcagg tggacaaagg     180
acctgtgaca tatgcaggca gtgtaaaggt gttttcagga ccaggaagga gtgttcctcc     240
accagcaatg cagagtgtga ctgcactcca gggtttcact gcctgggggc aggatgcagc     300
atgtgtgaac ggattgtaaa caaggtcaag aactgacaaa aaaaggttgt aaagactgtt     360
gctttgggac atttaacgat cagaaacgtg gcatctgtcg accctggaca aactgttctt     420
tggatggaaa gtctgtgctt gtgaatggga cgaaggagag ggacgtggtc tgtggaccat     480
ctccagccga cctctctccg ggagcatcct ctgtgacccc gcctgcccct gcgagagagc     540
caggacactc tccgcagatc atctccttct ttcttgcgct gacgtcgact gcgttgctct     600
tcctgctgtt cttcctcacg ctccgtttct ctgttgttaa acggggcaga aagaaactcc     660
tgtatatatt caaacaacca tttatgagac cagtacaaac tactcaagag gaagatggct     720
gtagctgccg atttccagaa gaagaagaag gaggatgtga actgtga                   767
```

<210> SEQ ID NO 16
<211> LENGTH: 601
<212> TYPE: DNA
<213> ORGANISM: Homo sapiens

<400> SEQUENCE: 16

```
atgaagtcag gcctctggta tttctttctc ttctgcttgc gcattaaagt tttaacagga      60
gaaatcaatg gttctgccaa ttatgagatg tttatatttc acaacggagg tgtacaaatt     120
ttatgcaaat atcctgacat tgtccagcaa tttaaaatgc agttgctgaa aaggggggca     180
aatactctgc gatctcacta agacaaaagg aagtggaaac acagtgtcca ttaagagtct     240
gaaattctgc cattctcagt tatccaacaa cagtgtctct tttttttctac aaccttggac     300 cattctcatg ccaactatta cttctgcaac ctatcaattt ttgatcctcc tccttttaaa     360
gtaactctta caggaggata tttgcatatt tatgaaatca caactttgtt gccagctgaa     420
gttctggtta cccataggat gtgcagcctt tgttgtagtc tgcattttgg gatgcatact     480
tatttgttgg cttacaaaaa agaagtattc atccagtgtg cacgaccccta acggtgaata     540 catgttcatg agagcagtga acacagccaa aaaatctaga ctcacagatg tgaccctata     600
a                                                                     601
```

<210> SEQ ID NO 17
<211> LENGTH: 282
<212> TYPE: DNA
<213> ORGANISM: Homo sapiens

<400> SEQUENCE: 17

```
atgatccatc tgggtcacat cctcttcctg cttttgctcc cagtggctgc agctcagacg      60 acccccaggag agagatcatc actccctgcc ttttaccctg gcacttcagg ctcctgttcc     120
ggatgtgggt ccctctctct gccgctcctg gcaggcctcg tggctgctga tgcggtggca     180
tcgctgctca tcgtggggggc ggtgttcctg tgcgcacgcc cacgccgcag ccccgcccaa     240
gaagatggca aagtctacat caacatgcca ggcaggggct ga                        282
```

<210> SEQ ID NO 18
<211> LENGTH: 255
<212> TYPE: PRT

-continued

```
<213> ORGANISM: Artificial sequence
<220> FEATURE:
<223> OTHER INFORMATION: Synthetic

<400> SEQUENCE: 18

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 19
<211> LENGTH: 277
<212> TYPE: PRT
<213> ORGANISM: Artificial sequence
<220> FEATURE:
<223> OTHER INFORMATION: Synthetic

<400> SEQUENCE: 19

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80
```

```
Cys Lys Pro Cys Thr Trp Cys Asn Leu Arg Ser Gly Ser Glu Arg Lys
                85              90              95

Gln Leu Cys Thr Ala Thr Gln Asp Thr Val Cys Arg Cys Arg Ala Gly
        100             105             110

Thr Gln Pro Leu Asp Ser Tyr Lys Pro Gly Val Asp Cys Ala Pro Cys
        115             120             125

Pro Pro Gly His Phe Ser Pro Gly Asp Asn Gln Ala Cys Lys Pro Trp
    130             135             140

Thr Asn Cys Thr Leu Ala Gly Lys His Thr Leu Gln Pro Ala Ser Asn
145             150             155             160

Ser Ser Asp Ala Ile Cys Glu Asp Arg Asp Pro Pro Ala Thr Gln Pro
                165             170             175

Gln Glu Thr Gln Gly Pro Pro Ala Arg Pro Ile Thr Val Gln Pro Thr
                180             185             190

Glu Ala Trp Pro Arg Thr Ser Gln Gly Pro Ser Thr Arg Pro Val Glu
                195             200             205

Val Pro Gly Gly Arg Ala Val Ala Ala Ile Leu Gly Leu Gly Leu Val
    210             215             220

Leu Gly Leu Leu Gly Pro Leu Ala Ile Leu Leu Ala Leu Tyr Leu Leu
225             230             235             240

Arg Arg Asp Gln Arg Leu Pro Pro Asp Ala His Lys Pro Pro Gly Gly
                245             250             255

Gly Ser Phe Arg Thr Pro Ile Gln Glu Glu Gln Ala Asp Ala His Ser
                260             265             270

Thr Leu Ala Lys Ile
                275

<210> SEQ ID NO 20
<211> LENGTH: 199
<212> TYPE: PRT
<213> ORGANISM: Artificial sequence
<220> FEATURE:
<223> OTHER INFORMATION: Synthetic

<400> SEQUENCE: 20

Met Lys Ser Gly Leu Trp Tyr Phe Phe Leu Phe Cys Leu Arg Ile Lys
1               5               10              15

Val Leu Thr Gly Glu Ile Asn Gly Ser Ala Asn Tyr Glu Met Phe Ile
                20              25              30

Phe His Asn Gly Gly Val Gln Ile Leu Cys Lys Tyr Pro Asp Ile Val
        35              40              45

Gln Gln Phe Lys Met Gln Leu Leu Lys Gly Gly Gln Ile Leu Cys Asp
        50              55              60

Leu Ile Lys Thr Lys Gly Ser Gly Asn Thr Val Ser Ile Lys Ser Leu
65              70              75              80

Lys Phe Cys His Ser Gln Leu Ser Asn Asn Ser Val Ser Phe Phe Leu
                85              90              95

Tyr Asn Leu Asp His Ser His Ala Asn Tyr Tyr Phe Cys Asn Leu Ser
        100             105             110

Ile Phe Asp Pro Pro Pro Phe Lys Val Thr Leu Ile Gly Gly Tyr Leu
        115             120             125

His Ile Tyr Glu Ser Gln Leu Cys Cys Gln Leu Lys Phe Trp Leu Pro
    130             135             140

Ile Gly Cys Ala Ala Phe Val Val Val Cys Ile Leu Gly Cys Ile Leu
145             150             155             160
```

-continued

```
Ile Cys Trp Leu Thr Lys Lys Lys Tyr Ser Ser Ser Val His Asp Pro
            165                 170                 175

Asn Gly Glu Tyr Met Phe Met Arg Ala Val Asn Thr Ala Lys Lys Ser
            180                 185                 190

Arg Leu Thr Asp Val Thr Leu
            195

<210> SEQ ID NO 21
<211> LENGTH: 485
<212> TYPE: PRT
<213> ORGANISM: Artificial sequence
<220> FEATURE:
<223> OTHER INFORMATION: Synthetic

<400> SEQUENCE: 21

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
            35                  40                  45

Ser Tyr Trp Met Asn Trp Val Lys Gln Arg Pro Gly Gln Gly Leu Glu
        50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
            115                 120                 125

Tyr Trp Gly Gln Gly Thr Thr Val Thr Val Ser Ser Gly Gly Gly Gly
        130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
            195                 200                 205

Arg Asn Ser Gly Val Pro Asp Arg Phe Thr Gly Ser Gly Ser Gly Thr
        210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
            260                 265                 270

Pro Pro Tyr Leu Asp Asn Glu Lys Ser Asn Gly Thr Ile Ile His Val
            275                 280                 285

Lys Gly Lys His Leu Cys Pro Ser Pro Leu Phe Pro Gly Pro Ser Lys
        290                 295                 300

Pro Phe Trp Val Leu Val Val Val Gly Gly Val Leu Ala Cys Tyr Ser
305                 310                 315                 320
```

-continued

```
Leu Leu Val Thr Val Ala Phe Ile Ile Phe Trp Val Arg Ser Lys Arg
            325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
            355                 360                 365

Ala Ala Tyr Arg Ser Arg Val Lys Phe Ser Arg Ser Ala Glu Pro Pro
        370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
        450                 455                 460

Gly Leu Ser Thr Ala Thr Lys Asp Thr Tyr Asp Ala Leu His Met Gln
465                 470                 475                 480

Ala Leu Pro Pro Arg
                485
```

```
<210> SEQ ID NO 22
<211> LENGTH: 462
<212> TYPE: PRT
<213> ORGANISM: Artificial sequence
<220> FEATURE:
<223> OTHER INFORMATION: Synthetic

<400> SEQUENCE: 22
```

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
        50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
            115                 120                 125

Thr Gly Ser Thr Ser Gly Ser Gly Lys Pro Gly Ser Gly Glu Gly Ser
        130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190
```

-continued

```
Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
        210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Glu Ser Lys Tyr Gly
                260                 265                 270

Pro Pro Cys Pro Pro Cys Pro Met Phe Trp Val Leu Val Val Val Gly
        275                 280                 285

Gly Val Leu Ala Cys Tyr Ser Leu Leu Val Thr Val Ala Phe Ile Ile
        290                 295                 300

Phe Trp Val Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
                340                 345                 350

Phe Ser Arg Ser Ala Asp Ala Pro Ala Tyr Gln Gln Gly Gln Asn Gln
                355                 360                 365

Leu Tyr Asn Glu Leu Asn Leu Gly Arg Arg Glu Glu Tyr Asp Val Leu
        370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
                420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg Leu
        450                 455                 460
```

```
<210> SEQ ID NO 23
<211> LENGTH: 491
<212> TYPE: PRT
<213> ORGANISM: Artificial sequence
<220> FEATURE:
<223> OTHER INFORMATION: Synthetic

<400> SEQUENCE: 23
```

```
Met Ala Leu Pro Val Thr Ala Leu Leu Leu Pro Leu Ala Leu Leu Leu
1               5                   10                  15

His Ala Glu Val Lys Leu Gln Glu Ser Gly Gly Gly Phe Val Lys Pro
                20                  25                  30

Gly Gly Ser Leu Lys Val Ser Cys Ala Ala Ser Gly Phe Thr Phe Ser
        35                  40                  45

Ser Tyr Ala Met Ser Trp Val Arg Leu Ser Pro Glu Met Arg Leu Glu
        50                  55                  60

Trp Val Ala Thr Ile Ser Ser Ala Gly Gly Tyr Ile Phe Tyr Ser Asp
65                  70                  75                  80

Ser Val Gln Gly Arg Phe Thr Ile Ser Arg Asp Asn Ala Lys Asn Thr
                85                  90                  95
```

-continued

```
Leu His Leu Gln Met Gly Ser Leu Arg Ser Gly Asp Thr Ala Met Tyr
            100                 105                 110

Tyr Cys Ala Arg Gln Gly Phe Gly Asn Tyr Gly Asp Tyr Tyr Ala Met
            115                 120                 125

Asp Tyr Trp Gly Gln Gly Thr Thr Val Thr Val Ser Ser Gly Gly Gly
    130                 135                 140

Gly Ser Gly Gly Gly Gly Ser Gly Gly Gly Gly Ser Asp Ile Glu Leu
145                 150                 155                 160

Thr Gln Ser Pro Ser Ser Leu Ala Val Ser Ala Gly Glu Lys Val Thr
                165                 170                 175

Met Ser Cys Lys Ser Ser Gln Ser Leu Leu Asn Ser Arg Thr Arg Lys
            180                 185                 190

Asn Gln Leu Ala Trp Tyr Gln Gln Lys Pro Gly Gln Ser Pro Glu Leu
            195                 200                 205

Leu Ile Tyr Trp Ala Ser Thr Arg Gln Ser Gly Val Pro Asp Arg Phe
    210                 215                 220

Thr Gly Ser Gly Ser Gly Thr Asp Phe Thr Leu Thr Ile Ser Ser Val
225                 230                 235                 240

Gln Ala Glu Asp Leu Ala Val Tyr Tyr Cys Gln Gln Ser Tyr Asn Leu
                245                 250                 255

Leu Thr Phe Gly Pro Gly Thr Lys Leu Glu Ile Lys Arg Ala Ala Ala
            260                 265                 270

Ile Glu Val Met Tyr Pro Pro Pro Tyr Leu Asp Asn Glu Lys Ser Asn
            275                 280                 285

Gly Thr Ile Ile His Val Lys Gly Lys His Leu Cys Pro Ser Pro Leu
    290                 295                 300

Phe Pro Gly Pro Ser Lys Pro Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser Arg Leu Leu His Ser Asp Tyr Met Asn
            340                 345                 350

Met Thr Pro Arg Arg Pro Gly Pro Thr Arg Lys His Tyr Gln Pro Tyr
            355                 360                 365

Ala Pro Pro Arg Asp Phe Ala Ala Tyr Arg Ser Arg Val Lys Phe Ser
    370                 375                 380

Arg Ser Ala Glu Pro Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 24
<211> LENGTH: 491
<212> TYPE: PRT

```
<213> ORGANISM: Artificial sequence
<220> FEATURE:
<223> OTHER INFORMATION: Synthetic

<400> SEQUENCE: 24

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
                20                  25                  30

Gly Ser Ser Val Lys Ile Ser Cys Lys Ala Ser Gly Tyr Ala Phe Ser
            35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
                100                 105                 110

Phe Cys Ala Arg Lys Thr Ile Ser Ser Val Val Asp Phe Tyr Phe Asp
            115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
            245                 250                 255

Thr Lys Leu Glu Ile Lys Arg Ala Ala Ala Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
            325                 330                 335

Asn Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
    370                 375                 380

Arg Ser Ala Glu Pro Pro Ala Tyr Gln Gln Gly Gln Asn Gln Leu Tyr
```

```
385                   390                    395                    400

Asn Glu Leu Asn Leu Gly Arg Arg Glu Glu Tyr Asp Val Leu Asp Lys
                405                    410                    415

Arg Arg Gly Arg Asp Pro Glu Met Gly Gly Lys Pro Arg Arg Lys Asn
                420                    425                    430

Pro Gln Glu Gly Leu Tyr Asn Glu Leu Gln Lys Asp Lys Met Ala Glu
                435                    440                    445

Ala Tyr Ser Glu Ile Gly Met Lys Gly Glu Arg Arg Arg Gly Lys Gly
        450                    455                    460

His Asp Gly Leu Tyr Gln Gly Leu Ser Thr Ala Thr Lys Asp Thr Tyr
465                    470                    475                    480

Asp Ala Leu His Met Gln Ala Leu Pro Pro Arg
                485                    490
```

<210> SEQ ID NO 25
<211> LENGTH: 121
<212> TYPE: PRT
<213> ORGANISM: Artificial sequence
<220> FEATURE:
<223> OTHER INFORMATION: Synthetic

<400> SEQUENCE: 25

```
Glu Val Gln Leu Gln Gln Ser Gly Pro Glu Leu Ile Lys Pro Gly Ala
1                   5                    10                    15

Ser Val Lys Met Ser Cys Lys Ala Ser Gly Tyr Thr Phe Thr Ser Tyr
                20                    25                    30

Val Met His Trp Val Lys Gln Lys Pro Gly Gln Gly Leu Glu Trp Ile
        35                    40                    45

Gly Tyr Ile Asn Pro Tyr Asn Asp Gly Thr Lys Tyr Asn Glu Lys Phe
        50                    55                    60

Lys Gly Lys Ala Thr Leu Thr Ser Asp Lys Ser Ser Ser Thr Ala Tyr
65                    70                    75                    80

Met Glu Leu Ser Ser Leu Thr Ser Glu Asp Ser Ala Val Tyr Tyr Cys
                85                    90                    95

Ala Arg Gly Thr Tyr Tyr Tyr Gly Ser Arg Val Phe Asp Tyr Trp Gly
                100                    105                    110

Gln Gly Thr Thr Leu Thr Val Ser Ser
        115                    120
```

<210> SEQ ID NO 26
<211> LENGTH: 115
<212> TYPE: PRT
<213> ORGANISM: Artificial sequence
<220> FEATURE:
<223> OTHER INFORMATION: Synthetic

<400> SEQUENCE: 26

```
Asp Ile Val Met Thr Gln Ala Ala Pro Ser Ile Pro Val Thr Pro Gly
1                   5                    10                    15

Glu Ser Val Ser Ile Ser Cys Arg Ser Ser Lys Ser Leu Leu Asn Ser
                20                    25                    30

Asn Gly Asn Thr Tyr Leu Tyr Trp Phe Leu Gln Arg Pro Gly Gln Ser
        35                    40                    45

Pro Gln Leu Leu Ile Tyr Arg Met Ser Asn Leu Ala Ser Gly Val Pro
        50                    55                    60

Asp Arg Phe Ser Gly Ser Gly Ser Gly Thr Ala Phe Thr Leu Arg Ile
65                    70                    75                    80
```

```
Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ala Asp
        115

<210> SEQ ID NO 27
<211> LENGTH: 116
<212> TYPE: PRT
<213> ORGANISM: Artificial sequence
<220> FEATURE:
<223> OTHER INFORMATION: Synthetic

<400> SEQUENCE: 27

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ser Asp Pro
        115

<210> SEQ ID NO 28
<211> LENGTH: 15
<212> TYPE: PRT
<213> ORGANISM: Artificial sequence
<220> FEATURE:
<223> OTHER INFORMATION: Synthetic

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 117
<212> TYPE: PRT
<213> ORGANISM: Artificial sequence
<220> FEATURE:
<223> OTHER INFORMATION: Synthetic

<400> SEQUENCE: 29

Glu Val Gln Leu Val Glu Ser Gly Gly Gly Leu Val Gln Pro Gly Asn
1               5                   10                  15

Ser Leu Lys Leu Ser Cys Ser Ala Ser Gly Phe Thr Phe Ser Ser Tyr
                20                  25                  30

Gly Met His Trp Ile Arg Gln Ala Pro Gly Glu Gly Leu Asp Trp Val
            35                  40                  45

Ala Tyr Ile Ser Ser Ser Ser Gly Thr Val Tyr Ala Asp Ala Val Lys
        50                  55                  60

Ala Arg Phe Thr Ile Ser Arg Asp Asn Ala Lys Asn Thr Leu Tyr Leu
```

-continued

```
65                  70                  75                  80

Gln Leu Asn Ser Leu Lys Ser Glu Asp Thr Ala Ile Tyr Tyr Cys Ala
                85                  90                  95

Arg Ala Gln Asn Trp Asp Leu Phe Asp Tyr Trp Gly Gln Gly Val Met
                100                 105                 110

Val Thr Val Ser Ser
        115
```

<210> SEQ ID NO 30
<211> LENGTH: 112
<212> TYPE: PRT
<213> ORGANISM: Artificial sequence
<220> FEATURE:
<223> OTHER INFORMATION: Synthetic

<400> SEQUENCE: 30

```
Gln Ile Met Leu Thr Gln Gln Ala Glu Ser Leu Trp Ile Ser Pro Gly
1               5                   10                  15

Glu Arg Val Ser Ile Thr Cys Arg Ala Ser Gln Ser Leu Leu Tyr Thr
                20                  25                  30

Asp Gly Lys His Tyr Leu Ser Trp Tyr Gln Gln Lys Pro Gly Gln Thr
        35                  40                  45

Thr Lys Ala Leu Ile Tyr His Ala Ser Val Arg Thr Asp Gly Val Pro
    50                  55                  60

Thr Arg Phe Ile Gly Ser Gly Ser Gly Thr Glu Phe Thr Leu Ser Ile
65                  70                  75                  80

Glu His Val Gln Pro Glu Asp Phe Ala Ile Tyr Tyr Cys Leu Gln Thr
                85                  90                  95

Leu Lys Ser Pro Phe Thr Phe Gly Ser Gly Thr Lys Leu Glu Ile Lys
                100                 105                 110
```

<210> SEQ ID NO 31
<211> LENGTH: 119
<212> TYPE: PRT
<213> ORGANISM: Artificial sequence
<220> FEATURE:
<223> OTHER INFORMATION: Synthetic

<400> SEQUENCE: 31

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Asn Tyr
                20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Val Ala Phe Ile
    50                  55                  60

Ser Arg Leu Ile Ile Thr Lys Asp Asn Ser Lys Ser Gln Val Phe Leu
65                  70                  75                  80

Lys Met Asn Ser Leu Gln Ala Asp Asp Thr Ala Ile Tyr Phe Cys Ala
                85                  90                  95

Arg Thr Thr Gly Ser Val Phe Asn Ala Met Asp His Trp Gly Gln Gly
                100                 105                 110

Thr Ser Val Thr Val Ser Ser
        115
```

<210> SEQ ID NO 32
<211> LENGTH: 106

-continued

```
<212> TYPE: PRT
<213> ORGANISM: Artificial sequence
<220> FEATURE:
<223> OTHER INFORMATION: Synthetic

<400> SEQUENCE: 32

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Thr Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 33
<211> LENGTH: 120
<212> TYPE: PRT
<213> ORGANISM: Artificial sequence
<220> FEATURE:
<223> OTHER INFORMATION: Synthetic

<400> SEQUENCE: 33

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Thr Gly Asn Thr Glu Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Gly Tyr Tyr Gly Ser Ser Tyr Pro Pro Trp Phe Ala Tyr Trp
            100                 105                 110

Gly Gln Gly Thr Leu Val Thr Val
        115                 120

<210> SEQ ID NO 34
<211> LENGTH: 107
<212> TYPE: PRT
<213> ORGANISM: Artificial sequence
<220> FEATURE:
<223> OTHER INFORMATION: Synthetic

<400> SEQUENCE: 34

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ser Ala
            20                  25                  30

Val Ala Trp Tyr Gln Gln Lys Pro Gly Gln Ser Pro Lys Leu Leu Ile
```

```
              35                    40                    45

Tyr Trp Ala Ser Thr Arg His Thr Gly Val Pro Asp Arg Phe Thr Gly
    50                    55                    60

Ser Gly Ser Gly Thr Asp Phe Thr Leu Thr Ile Ser Asn Val Gln Ser
65                    70                    75                    80

Glu Asp Leu Ala Asp Tyr Phe Cys Gln Gln Tyr Ser Ser Tyr Pro Leu
              85                    90                    95

Thr Phe Gly Ala Gly Thr Lys Leu Glu Leu Lys
              100                   105

<210> SEQ ID NO 35
<211> LENGTH: 117
<212> TYPE: PRT
<213> ORGANISM: Artificial sequence
<220> FEATURE:
<223> OTHER INFORMATION: Synthetic

<400> SEQUENCE: 35

Glu Val Gln Leu Gln Gln Ser Gly Ala Glu Leu Val Lys Pro Gly Ala
1                     5                     10                    15

Ser Val Lys Leu Ser Cys Thr Ala Ser Gly Phe Asn Ile Lys Asp Thr
              20                    25                    30

Tyr Met His Trp Val Lys Gln Arg Pro Glu Gln Gly Leu Glu Trp Ile
              35                    40                    45

Gly Arg Ile Asp Pro Ala Asn Gly His Thr Lys Tyr Asp Pro Lys Phe
              50                    55                    60

Gln Gly Lys Ala Thr Ile Thr Ala Asp Thr Ser Ser Asn Ala Ala Tyr
65                    70                    75                    80

Leu Gln Leu Asn Ser Leu Thr Ser Glu Asp Thr Ala Val Tyr Tyr Cys
              85                    90                    95

Ala Arg Arg Val Ala Tyr Ala Met Asp Tyr Trp Gly Gln Gly Thr Ser
              100                   105                   110

Val Thr Val Ser Ser
              115

<210> SEQ ID NO 36
<211> LENGTH: 106
<212> TYPE: PRT
<213> ORGANISM: Artificial sequence
<220> FEATURE:
<223> OTHER INFORMATION: Synthetic

<400> SEQUENCE: 36

Glu Asn Val Leu Thr Gln Ser Pro Ala Ile Met Ser Ala Ser Pro Gly
1                     5                     10                    15

Glu Lys Val Thr Met Thr Cys Ser Ala Ser Ser Ser Val Thr Tyr Met
              20                    25                    30

His Trp Tyr Gln Gln Lys Ser Ser Thr Ser Pro Lys Leu Trp Ile Tyr
              35                    40                    45

Asp Thr Ser Lys Leu Ala Ser Gly Val Pro Gly Arg Phe Ser Gly Ser
              50                    55                    60

Gly Ser Gly Asn Ser Tyr Ser Leu Thr Ile Ser Ser Met Glu Ala Glu
65                    70                    75                    80

Asp Val Ala Thr Tyr Cys Cys Phe Gln Gly Ser Gly Tyr Pro Leu Thr
              85                    90                    95

Phe Gly Gly Gly Thr Lys Leu Glu Ile Lys
              100                   105
```

<210> SEQ ID NO 37
<211> LENGTH: 118
<212> TYPE: PRT
<213> ORGANISM: Artificial sequence
<220> FEATURE:
<223> OTHER INFORMATION: Synthetic

<400> SEQUENCE: 37

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
                20                  25                  30

Gly Met Gly Val Gly Trp Ile Arg Gln Pro Ser Gly Lys Ser Leu Glu
            35                  40                  45

Trp Leu Ala His Ile Trp Trp Asn Asp Glu Arg Tyr Tyr Asn Pro Ser
        50                  55                  60

Leu Lys Asn Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                    85                  90                  95

Cys Ala Arg Ser Pro Arg Gly Tyr Phe Asp Tyr Trp Gly His Gly Thr
                100                 105                 110

Thr Leu Thr Val Ser Ser
            115

<210> SEQ ID NO 38
<211> LENGTH: 107
<212> TYPE: PRT
<213> ORGANISM: Artificial sequence
<220> FEATURE:
<223> OTHER INFORMATION: Synthetic

<400> SEQUENCE: 38

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Val Thr Asn
                20                  25                  30

Val Ala Trp Tyr Gln Gln Thr Pro Gly Gln Ser Pro Lys Ala Leu Ile
            35                  40                  45

Tyr Ser Ala Ser Tyr Arg Tyr Ser Gly Val Pro Asp Arg Phe Ser Gly
        50                  55                  60

Ser Gly Ser Gly Thr Asp Phe Thr Leu Thr Ile Ser Asn Val Gln Ser
65                  70                  75                  80

Gly Asp Leu Ala Glu Tyr Phe Cys Gln Gln Tyr Asn Ser Tyr Pro Leu
                    85                  90                  95

Thr Phe Gly Ala Gly Thr Lys Leu Glu Leu Lys
                100                 105

<210> SEQ ID NO 39
<211> LENGTH: 120
<212> TYPE: PRT
<213> ORGANISM: Artificial sequence
<220> FEATURE:
<223> OTHER INFORMATION: Synthetic

<400> SEQUENCE: 39

Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr

-continued

```
                20                  25                  30

Tyr Ile Phe Trp Val Lys Gln Ser His Gly Lys Ser Leu Glu Trp Ile
            35                  40                  45

Gly Tyr Ile Asn Pro Asn Ser Gly Ser Thr Asn Tyr Asn Glu Lys Phe
        50                  55                  60

Lys Arg Lys Ala Thr Leu Ser Val Asp Lys Ser Thr Asn Thr Ala Tyr
65                  70                  75                  80

Met Glu Leu Ser Arg Leu Thr Ser Glu Asp Ser Ala Thr Tyr Tyr Cys
                85                  90                  95

Thr Arg Arg Ala Tyr Tyr Gly Tyr Asn Pro Phe Asp Tyr Trp Gly Gln
                100                 105                 110

Gly Val Met Val Thr Val Ser Ser
            115                 120

<210> SEQ ID NO 40
<211> LENGTH: 107
<212> TYPE: PRT
<213> ORGANISM: Artificial sequence
<220> FEATURE:
<223> OTHER INFORMATION: Synthetic

<400> SEQUENCE: 40

Asp Ile Gln Met Thr Gln Thr Pro Ser Ser Met Pro Ala Ser Leu Gly
1               5                   10                  15

Glu Arg Val Thr Ile Ser Cys Arg Ala Ser Arg Gly Ile Asn Asn Tyr
                20                  25                  30

Leu Ser Trp Tyr Gln Gln Asn Leu Asp Gly Thr Ile Lys Pro Leu Ile
            35                  40                  45

Tyr Tyr Thr Ser Asn Leu Gln Ser Gly Val Pro Ser Arg Phe Ser Gly
        50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Tyr Asp Ser Ser Pro Trp
                85                  90                  95

Thr Phe Gly Gly Gly Thr Lys Leu Glu Leu Lys
            100                 105

<210> SEQ ID NO 41
<211> LENGTH: 119
<212> TYPE: PRT
<213> ORGANISM: Artificial sequence
<220> FEATURE:
<223> OTHER INFORMATION: Synthetic

<400> SEQUENCE: 41

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
                20                  25                  30

Tyr Ile His Trp Val Lys Gln Arg Pro Glu Gln Gly Leu Glu Trp Ile
            35                  40                  45

Gly Trp Ile Asp Pro Glu Asn Gly His Thr Ile Tyr Asp Pro Lys Phe
        50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95
```

Ala Arg Leu Thr Gly Thr Thr Tyr Ala Met Asp Tyr Trp Gly Gln Gly
                100                 105                 110

Thr Ser Val Thr Val Ser Ser
        115

<210> SEQ ID NO 42
<211> LENGTH: 107
<212> TYPE: PRT
<213> ORGANISM: Artificial sequence
<220> FEATURE:
<223> OTHER INFORMATION: Synthetic

<400> SEQUENCE: 42

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Ser Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 43
<211> LENGTH: 123
<212> TYPE: PRT
<213> ORGANISM: Artificial sequence
<220> FEATURE:
<223> OTHER INFORMATION: Synthetic

<400> SEQUENCE: 43

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Phe Ile Arg Asn Lys Ala Ser Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Ala His Ser Tyr Tyr Gly Tyr Asp Tyr Phe Asp Tyr
            100                 105                 110

Trp Gly Gln Gly Val Met Val Thr Val Ser Ser
        115                 120

<210> SEQ ID NO 44
<211> LENGTH: 107
<212> TYPE: PRT
<213> ORGANISM: Artificial sequence
<220> FEATURE:
<223> OTHER INFORMATION: Synthetic

<400> SEQUENCE: 44

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
                20                  25                  30

Leu Ser Trp Tyr Gln Gln Lys Pro Gly Lys Ser Pro Gln Leu Leu Ile
            35                  40                  45

Tyr Gly Ala Thr Ser Leu Ala Asp Gly Val Pro Ser Arg Phe Ser Gly
        50                  55                  60

Ser Arg Ser Gly Thr Gln Tyr Ser Leu Lys Ile Ser Arg Leu Gln Val
65                  70                  75                  80

Glu Asp Ile Arg Ile Tyr Tyr Cys Leu Gln Ala Tyr Ser Ala Pro Trp
                85                  90                  95

Thr Phe Gly Gly Gly Thr Lys Leu Glu Leu Lys
            100                 105

<210> SEQ ID NO 45
<211> LENGTH: 244
<212> TYPE: PRT
<213> ORGANISM: Artificial sequence
<220> FEATURE:
<223> OTHER INFORMATION: Synthetic

<400> SEQUENCE: 45

Glu Val Gln Leu Val Glu Ser Gly Gly Gly Leu Val Gln Pro Gly Asn
1               5                   10                  15

Ser Leu Lys Leu Ser Cys Ser Ala Ser Gly Phe Thr Phe Ser Ser Tyr
                20                  25                  30

Gly Met His Trp Ile Arg Gln Ala Pro Gly Glu Gly Leu Asp Trp Val
        35                  40                  45

Ala Tyr Ile Ser Ser Ser Ser Gly Thr Val Tyr Ala Asp Ala Val Lys
        50                  55                  60

Ala Arg Phe Thr Ile Ser Arg Asp Asn Ala Lys Asn Thr Leu Tyr Leu
65                  70                  75                  80

Gln Leu Asn Ser Leu Lys Ser Glu Asp Thr Ala Ile Tyr Tyr Cys Ala
                85                  90                  95

Arg Ala Gln Asn Trp Asp Leu Phe Asp Tyr Trp Gly Gln Gly Val Met
            100                 105                 110

Val Thr Val Ser Ser Gly Gly Gly Gly Ser Gly Gly Gly Gly Ser Gly
            115                 120                 125

Gly Gly Gly Ser Gln Ile Met Leu Thr Gln Gln Ala Glu Ser Leu Trp
        130                 135                 140

Ile Ser Pro Gly Glu Arg Val Ser Ile Thr Cys Arg Ala Ser Gln Ser
145                 150                 155                 160

Leu Leu Tyr Thr Asp Gly Lys His Tyr Leu Ser Trp Tyr Gln Gln Lys
            165                 170                 175

Pro Gly Gln Thr Thr Lys Ala Leu Ile Tyr His Ala Ser Val Arg Thr
            180                 185                 190

Asp Gly Val Pro Thr Arg Phe Ile Gly Ser Gly Ser Gly Thr Glu Phe
            195                 200                 205

Thr Leu Ser Ile Glu His Val Gln Pro Glu Asp Phe Ala Ile Tyr Tyr
        210                 215                 220

Cys Leu Gln Thr Leu Lys Ser Pro Phe Thr Phe Gly Ser Gly Thr Lys
225                 230                 235                 240

Leu Glu Ile Lys

-continued

```
<210> SEQ ID NO 46
<211> LENGTH: 244
<212> TYPE: PRT
<213> ORGANISM: Artificial sequence
<220> FEATURE:
<223> OTHER INFORMATION: Synthetic

<400> SEQUENCE: 46

Gln Ile Met Leu Thr Gln Gln Ala Glu Ser Leu Trp Ile Ser Pro Gly
1               5                   10                  15

Glu Arg Val Ser Ile Thr Cys Arg Ala Ser Gln Ser Leu Leu Tyr Thr
                20                  25                  30

Asp Gly Lys His Tyr Leu Ser Trp Tyr Gln Gln Lys Pro Gly Gln Thr
            35                  40                  45

Thr Lys Ala Leu Ile Tyr His Ala Ser Val Arg Thr Asp Gly Val Pro
        50                  55                  60

Thr Arg Phe Ile Gly Ser Gly Ser Gly Thr Glu Phe Thr Leu Ser Ile
65                  70                  75                  80

Glu His Val Gln Pro Glu Asp Phe Ala Ile Tyr Tyr Cys Leu Gln Thr
                85                  90                  95

Leu Lys Ser Pro Phe Thr Phe Gly Ser Gly Thr Lys Leu Glu Ile Lys
                100                 105                 110

Gly Gly Gly Gly Ser Gly Gly Gly Gly Ser Gly Gly Gly Gly Ser Glu
            115                 120                 125

Val Gln Leu Val Glu Ser Gly Gly Gly Leu Val Gln Pro Gly Asn Ser
        130                 135                 140

Leu Lys Leu Ser Cys Ser Ala Ser Gly Phe Thr Phe Ser Ser Tyr Gly
145                 150                 155                 160

Met His Trp Ile Arg Gln Ala Pro Gly Glu Gly Leu Asp Trp Val Ala
                165                 170                 175

Tyr Ile Ser Ser Ser Ser Gly Thr Val Tyr Ala Asp Ala Val Lys Ala
                180                 185                 190

Arg Phe Thr Ile Ser Arg Asp Asn Ala Lys Asn Thr Leu Tyr Leu Gln
                195                 200                 205

Leu Asn Ser Leu Lys Ser Glu Asp Thr Ala Ile Tyr Tyr Cys Ala Arg
        210                 215                 220

Ala Gln Asn Trp Asp Leu Phe Asp Tyr Trp Gly Gln Gly Val Met Val
225                 230                 235                 240

Thr Val Ser Ser

<210> SEQ ID NO 47
<211> LENGTH: 240
<212> TYPE: PRT
<213> ORGANISM: Artificial sequence
<220> FEATURE:
<223> OTHER INFORMATION: Synthetic

<400> SEQUENCE: 47

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Ser Thr Asp Tyr Asn Val Ala Phe Ile
        50                  55                  60
```

-continued

```
Ser Arg Leu Ile Ile Thr Lys Asp Asn Ser Lys Ser Gln Val Phe Leu
65              70                  75                  80

Lys Met Asn Ser Leu Gln Ala Asp Asp Thr Ala Ile Tyr Phe Cys Ala
                85                  90                  95

Arg Thr Thr Gly Ser Val Phe Asn Ala Met Asp His Trp Gly Gln Gly
            100                 105                 110

Thr Ser Val Thr Val Ser Ser Gly Gly Gly Gly Ser Gly Gly Gly Gly
            115                 120                 125

Ser Gly Gly Gly Gly Ser Gln Ile Val Leu Thr Gln Ser Pro Ala Leu
        130                 135                 140

Met Ser Ala Ser Pro Gly Glu Lys Val Thr Met Thr Cys Ser Ala Ser
145                 150                 155                 160

Ser Ser Val Thr Tyr Met Tyr Trp Tyr Gln Gln Lys Pro Arg Ser Ser
                165                 170                 175

Pro Lys Pro Trp Ile Tyr Leu Thr Ser Asn Leu Ala Ser Gly Val Pro
                180                 185                 190

Ala Arg Phe Ser Gly Ser Gly Ser Gly Thr Ser Tyr Ser Leu Thr Ile
            195                 200                 205

Ser Ser Val Glu Ala Glu Asp Ala Ala Thr Tyr Tyr Cys Gln Gln Trp
        210                 215                 220

Ser Ser Asn Pro Leu Thr Phe Gly Ala Gly Thr Lys Leu Glu Leu Lys
225                 230                 235                 240
```

<210> SEQ ID NO 48
<211> LENGTH: 240
<212> TYPE: PRT
<213> ORGANISM: Artificial sequence
<220> FEATURE:
<223> OTHER INFORMATION: Synthetic

<400> SEQUENCE: 48

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Thr Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Val Glu Ala Glu
65              70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Gly Ser Gln Val Gln Leu Lys Gln Ser
            115                 120                 125

Gly Pro Gly Leu Val Gln Pro Ser Gln Ser Leu Ser Ile Thr Cys Thr
        130                 135                 140

Val Ser Gly Phe Ser Leu Ser Asn Tyr Gly Val His Trp Val Arg Gln
145                 150                 155                 160

Ser Pro Gly Lys Gly Leu Glu Trp Leu Gly Val Ile Trp Ser Gly Gly
                165                 170                 175

Ser Thr Asp Tyr Asn Val Ala Phe Ile Ser Arg Leu Ile Ile Thr Lys
                180                 185                 190
```

-continued

Asp Asn Ser Lys Ser Gln Val Phe Leu Lys Met Asn Ser Leu Gln Ala
        195                 200                 205

Asp Asp Thr Ala Ile Tyr Phe Cys Ala Arg Thr Thr Gly Ser Val Phe
    210                 215                 220

Asn Ala Met Asp His Trp Gly Gln Gly Thr Ser Val Thr Val Ser Ser
225                 230                 235                 240

<210> SEQ ID NO 49
<211> LENGTH: 244
<212> TYPE: PRT
<213> ORGANISM: Artificial sequence
<220> FEATURE:
<223> OTHER INFORMATION: Synthetic

<400> SEQUENCE: 49

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
        20                  25                  30

Tyr Ile His Trp Val Lys Gln Arg Pro Glu Gln Gly Leu Glu Trp Ile
        35                  40                  45

Gly Arg Ile Asp Pro Ala Thr Gly Asn Thr Glu Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Gly Tyr Tyr Gly Ser Ser Tyr Pro Pro Trp Phe Ala Tyr Trp
            100                 105                 110

Gly Gln Gly Thr Leu Val Thr Val Ser Ala Gly Gly Gly Gly Ser Gly
        115                 120                 125

Gly Gly Gly Ser Gly Gly Gly Gly Ser Asp Ile Val Met Thr Gln Ser
    130                 135                 140

His Lys Phe Met Ser Thr Ser Val Gly Asp Arg Val Ser Ile Thr Cys
145                 150                 155                 160

Lys Ala Ser Gln Asp Val Gly Ser Ala Val Ala Trp Tyr Gln Gln Lys
                165                 170                 175

Pro Gly Gln Ser Pro Lys Leu Leu Ile Tyr Trp Ala Ser Thr Arg His
            180                 185                 190

Thr Gly Val Pro Asp Arg Phe Thr Gly Ser Gly Ser Gly Thr Asp Phe
        195                 200                 205

Thr Leu Thr Ile Ser Asn Val Gln Ser Glu Asp Leu Ala Asp Tyr Phe
    210                 215                 220

Cys Gln Gln Tyr Ser Ser Tyr Pro Leu Thr Phe Gly Ala Gly Thr Lys
225                 230                 235                 240

Leu Glu Leu Lys

<210> SEQ ID NO 50
<211> LENGTH: 244
<212> TYPE: PRT
<213> ORGANISM: Artificial sequence
<220> FEATURE:
<223> OTHER INFORMATION: Synthetic

<400> SEQUENCE: 50

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ser Ala
        20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Gly Ser Glu Val Gln Leu Gln Gln
            115                 120                 125

Ser Gly Ala Glu Leu Val Lys Pro Gly Ala Ser Val Lys Leu Ser Cys
    130                 135                 140

Thr Ala Ser Gly Phe Asn Ile Lys Asp Thr Tyr Ile His Trp Val Lys
145                 150                 155                 160

Gln Arg Pro Glu Gln Gly Leu Glu Trp Ile Gly Arg Ile Asp Pro Ala
                165                 170                 175

Thr Gly Asn Thr Glu Tyr Asp Pro Lys Phe Gln Gly Lys Ala Thr Ile
                180                 185                 190

Thr Ala Asp Thr Ser Ser Asn Thr Ala Tyr Leu His Leu Ser Ser Leu
            195                 200                 205

Thr Ser Glu Asp Thr Ala Val Tyr Tyr Cys Ala Arg Gly Tyr Tyr Gly
    210                 215                 220

Ser Ser Tyr Pro Pro Trp Phe Ala Tyr Trp Gly Gln Gly Thr Leu Val
225                 230                 235                 240

Thr Val Ser Ala

<210> SEQ ID NO 51
<211> LENGTH: 238
<212> TYPE: PRT
<213> ORGANISM: Artificial sequence
<220> FEATURE:
<223> OTHER INFORMATION: Synthetic

<400> SEQUENCE: 51

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly His Thr Lys Tyr Asp Pro Lys Phe
    50                  55                  60

Gln Gly Lys Ala Thr Ile Thr Ala Asp Thr Ser Ser Asn Ala Ala Tyr
65                  70                  75                  80

Leu Gln Leu Asn Ser Leu Thr Ser Glu Asp Thr Ala Val Tyr Tyr Cys
                85                  90                  95

Ala Arg Arg Val Ala Tyr Ala Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

-continued

```
Gly Gly Gly Ser Glu Asn Val Leu Thr Gln Ser Pro Ala Ile Met Ser
    130             135             140

Ala Ser Pro Gly Glu Lys Val Thr Met Thr Cys Ser Ala Ser Ser Ser
145             150             155             160

Val Thr Tyr Met His Trp Tyr Gln Gln Lys Ser Ser Thr Ser Pro Lys
                165             170             175

Leu Trp Ile Tyr Asp Thr Ser Lys Leu Ala Ser Gly Val Pro Gly Arg
            180             185             190

Phe Ser Gly Ser Gly Ser Gly Asn Ser Tyr Ser Leu Thr Ile Ser Ser
            195             200             205

Met Glu Ala Glu Asp Val Ala Thr Tyr Cys Cys Phe Gln Gly Ser Gly
    210             215             220

Tyr Pro Leu Thr Phe Gly Gly Gly Thr Lys Leu Glu Ile Lys
225             230             235
```

```
<210> SEQ ID NO 52
<211> LENGTH: 238
<212> TYPE: PRT
<213> ORGANISM: Artificial sequence
<220> FEATURE:
<223> OTHER INFORMATION: Synthetic

<400> SEQUENCE: 52
```

```
Glu Asn Val Leu Thr Gln Ser Pro Ala Ile Met Ser Ala Ser Pro Gly
1               5               10              15

Glu Lys Val Thr Met Thr Cys Ser Ala Ser Ser Ser Val Thr Tyr Met
                20              25              30

His Trp Tyr Gln Gln Lys Ser Ser Thr Ser Pro Lys Leu Trp Ile Tyr
            35              40              45

Asp Thr Ser Lys Leu Ala Ser Gly Val Pro Gly Arg Phe Ser Gly Ser
    50              55              60

Gly Ser Gly Asn Ser Tyr Ser Leu Thr Ile Ser Ser Met Glu Ala Glu
65              70              75              80

Asp Val Ala Thr Tyr Cys Cys Phe Gln Gly Ser Gly Tyr Pro Leu Thr
                85              90              95

Phe Gly Gly Gly Thr Lys Leu Glu Ile Lys Gly Gly Gly Gly Ser Gly
            100             105             110

Gly Gly Gly Ser Gly Gly Gly Gly Ser Glu Val Gln Leu Gln Gln Ser
            115             120             125

Gly Ala Glu Leu Val Lys Pro Gly Ala Ser Val Lys Leu Ser Cys Thr
    130             135             140

Ala Ser Gly Phe Asn Ile Lys Asp Thr Tyr Met His Trp Val Lys Gln
145             150             155             160

Arg Pro Glu Gln Gly Leu Glu Trp Ile Gly Arg Ile Asp Pro Ala Asn
                165             170             175

Gly His Thr Lys Tyr Asp Pro Lys Phe Gln Gly Lys Ala Thr Ile Thr
            180             185             190

Ala Asp Thr Ser Ser Asn Ala Ala Tyr Leu Gln Leu Asn Ser Leu Thr
            195             200             205

Ser Glu Asp Thr Ala Val Tyr Tyr Cys Ala Arg Arg Val Ala Tyr Ala
    210             215             220

Met Asp Tyr Trp Gly Gln Gly Thr Ser Val Thr Val Ser Ser
225             230             235
```

```
<210> SEQ ID NO 53
<211> LENGTH: 240
```

<212> TYPE: PRT
<213> ORGANISM: Artificial sequence
<220> FEATURE:
<223> OTHER INFORMATION: Synthetic

<400> SEQUENCE: 53

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Ser Leu Glu
        35                  40                  45

Trp Leu Ala His Ile Trp Trp Asn Asp Glu Arg Tyr Tyr Asn Pro Ser
    50                  55                  60

Leu Lys Asn Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Pro Arg Gly Tyr Phe Asp Tyr Trp Gly His Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Thr Gln Ser Gln Lys Phe Met
    130                 135                 140

Ser Thr Ser Val Gly Asp Arg Val Ser Val Thr Cys Lys Ala Ser Gln
145                 150                 155                 160

Asn Val Val Thr Asn Val Ala Trp Tyr Gln Gln Thr Pro Gly Gln Ser
                165                 170                 175

Pro Lys Ala Leu Ile Tyr Ser Ala Ser Tyr Arg Tyr Ser Gly Val Pro
            180                 185                 190

Asp Arg Phe Ser Gly Ser Gly Ser Gly Thr Asp Phe Thr Leu Thr Ile
            195                 200                 205

Ser Asn Val Gln Ser Gly Asp Leu Ala Glu Tyr Phe Cys Gln Gln Tyr
    210                 215                 220

Asn Ser Tyr Pro Leu Thr Phe Gly Ala Gly Thr Lys Leu Glu Leu Lys
225                 230                 235                 240

<210> SEQ ID NO 54
<211> LENGTH: 240
<212> TYPE: PRT
<213> ORGANISM: Artificial sequence
<220> FEATURE:
<223> OTHER INFORMATION: Synthetic

<400> SEQUENCE: 54

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Val Thr Asn
            20                  25                  30

Val Ala Trp Tyr Gln Gln Thr Pro Gly Gln Ser Pro Lys Ala Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Asn Val Gln Ser
65                  70                  75                  80

Gly Asp Leu Ala Glu Tyr Phe Cys Gln Gln Tyr Asn Ser Tyr Pro Leu
                85                  90                  95

-continued

```
Thr Phe Gly Ala Gly Thr Lys Leu Glu Leu Lys Gly Gly Gly Gly Ser
            100                 105                 110

Gly Gly Gly Gly Ser Gly Gly Gly Ser Gln Val Thr Leu Lys Glu
            115                 120                 125

Ser Gly Pro Gly Ile Leu Lys Pro Ser Gln Thr Leu Ser Leu Thr Cys
    130                 135                 140

Ser Phe Ser Gly Phe Ser Leu Ser Thr Ser Gly Met Gly Val Gly Trp
145                 150                 155                 160

Ile Arg Gln Pro Ser Gly Lys Ser Leu Glu Trp Leu Ala His Ile Trp
                165                 170                 175

Trp Asn Asp Glu Arg Tyr Tyr Asn Pro Ser Leu Lys Asn Gln Leu Thr
            180                 185                 190

Ile Ser Lys Asp Thr Ser Arg Asn Gln Val Phe Leu Lys Ile Thr Ser
            195                 200                 205

Val Asp Thr Ala Asp Thr Ala Thr Tyr Tyr Cys Ala Arg Ser Pro Arg
    210                 215                 220

Gly Tyr Phe Asp Tyr Trp Gly His Gly Thr Thr Leu Thr Val Ser Ser
225                 230                 235                 240
```

```
<210> SEQ ID NO 55
<211> LENGTH: 242
<212> TYPE: PRT
<213> ORGANISM: Artificial sequence
<220> FEATURE:
<223> OTHER INFORMATION: Synthetic

<400> SEQUENCE: 55
```

```
Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Ile Phe Trp Val Lys Gln Ser His Gly Lys Ser Leu Glu Trp Ile
        35                  40                  45

Gly Tyr Ile Asn Pro Asn Ser Gly Ser Thr Asn Tyr Asn Glu Lys Phe
    50                  55                  60

Lys Arg Lys Ala Thr Leu Ser Val Asp Lys Ser Thr Asn Thr Ala Tyr
65                  70                  75                  80

Met Glu Leu Ser Arg Leu Thr Ser Glu Asp Ser Ala Thr Tyr Tyr Cys
                85                  90                  95

Thr Arg Arg Ala Tyr Tyr Gly Tyr Asn Pro Phe Asp Tyr Trp Gly Gln
            100                 105                 110

Gly Val Met Val Thr Val Ser Ser Gly Gly Gly Ser Gly Gly Gly
            115                 120                 125

Gly Ser Gly Gly Gly Gly Ser Asp Ile Gln Met Thr Gln Thr Pro Ser
    130                 135                 140

Ser Met Pro Ala Ser Leu Gly Glu Arg Val Thr Ile Ser Cys Arg Ala
145                 150                 155                 160

Ser Arg Gly Ile Asn Asn Tyr Leu Ser Trp Tyr Gln Gln Asn Leu Asp
                165                 170                 175

Gly Thr Ile Lys Pro Leu Ile Tyr Tyr Thr Ser Asn Leu Gln Ser Gly
            180                 185                 190

Val Pro Ser Arg Phe Ser Gly Ser Gly Ser Gly Thr Asp Tyr Ser Leu
            195                 200                 205

Thr Ile Ser Ser Leu Glu Pro Glu Asp Phe Ala Met Tyr Tyr Cys Gln
    210                 215                 220
```

-continued

```
Gln Tyr Asp Ser Ser Pro Trp Thr Phe Gly Gly Gly Thr Lys Leu Glu
225                 230                 235                 240

Leu Lys

<210> SEQ ID NO 56
<211> LENGTH: 242
<212> TYPE: PRT
<213> ORGANISM: Artificial sequence
<220> FEATURE:
<223> OTHER INFORMATION: Synthetic

<400> SEQUENCE: 56

Asp Ile Gln Met Thr Gln Thr Pro Ser Ser Met Pro Ala Ser Leu Gly
1               5                   10                  15

Glu Arg Val Thr Ile Ser Cys Arg Ala Ser Arg Gly Ile Asn Asn Tyr
                20                  25                  30

Leu Ser Trp Tyr Gln Gln Asn Leu Asp Gly Thr Ile Lys Pro Leu Ile
            35                  40                  45

Tyr Tyr Thr Ser Asn Leu Gln Ser Gly Val Pro Ser Arg Phe Ser Gly
        50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Tyr Asp Ser Ser Pro Trp
                85                  90                  95

Thr Phe Gly Gly Gly Thr Lys Leu Glu Leu Lys Gly Gly Gly Gly Ser
            100                 105                 110

Gly Gly Gly Gly Ser Gly Gly Gly Ser Gln Val Asn Leu Leu Gln
            115                 120                 125

Ser Gly Ala Ala Leu Val Lys Pro Gly Ala Ser Val Lys Leu Ser Cys
        130                 135                 140

Lys Ala Ser Gly Tyr Thr Phe Thr Asp Tyr Tyr Ile Phe Trp Val Lys
145                 150                 155                 160

Gln Ser His Gly Lys Ser Leu Glu Trp Ile Gly Tyr Ile Asn Pro Asn
                165                 170                 175

Ser Gly Ser Thr Asn Tyr Asn Glu Lys Phe Lys Arg Lys Ala Thr Leu
            180                 185                 190

Ser Val Asp Lys Ser Thr Asn Thr Ala Tyr Met Glu Leu Ser Arg Leu
            195                 200                 205

Thr Ser Glu Asp Ser Ala Thr Tyr Tyr Cys Thr Arg Arg Ala Tyr Tyr
        210                 215                 220

Gly Tyr Asn Pro Phe Asp Tyr Trp Gly Gln Gly Val Met Val Thr Val
225                 230                 235                 240

Ser Ser

<210> SEQ ID NO 57
<211> LENGTH: 241
<212> TYPE: PRT
<213> ORGANISM: Artificial sequence
<220> FEATURE:
<223> OTHER INFORMATION: Synthetic

<400> SEQUENCE: 57

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
                20                  25                  30
```

-continued

```
Tyr Ile His Trp Val Lys Gln Arg Pro Glu Gln Gly Leu Glu Trp Ile
        35                  40                  45

Gly Trp Ile Asp Pro Glu Asn Gly His Thr Ile Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Leu Thr Gly Thr Thr Tyr Ala Met Asp Tyr Trp Gly Gln Gly
            100                 105                 110

Thr Ser Val Thr Val Ser Ser Gly Gly Gly Gly Ser Gly Gly Gly Gly
            115                 120                 125

Ser Gly Gly Gly Gly Ser Asp Ile Val Met Thr Gln Ser His Lys Phe
    130                 135                 140

Met Ser Thr Ser Val Gly Asp Arg Val Ser Ile Thr Cys Lys Ala Ser
145                 150                 155                 160

Gln Asp Val Ser Thr Ala Val Ala Trp Tyr Gln Gln Lys Ser Gly Gln
                165                 170                 175

Ser Pro Lys Leu Leu Ile Tyr Trp Ala Ser Thr Arg His Thr Gly Val
            180                 185                 190

Pro Asp Arg Phe Thr Gly Ser Gly Ser Gly Thr Asp Tyr Thr Leu Thr
            195                 200                 205

Ile Ser Ser Val Gln Ala Glu Asp Leu Ala Leu Tyr Tyr Cys Gln Gln
    210                 215                 220

His Tyr Ser Thr Pro Tyr Thr Phe Gly Gly Gly Thr Lys Leu Glu Ile
225                 230                 235                 240

Lys

<210> SEQ ID NO 58
<211> LENGTH: 241
<212> TYPE: PRT
<213> ORGANISM: Artificial sequence
<220> FEATURE:
<223> OTHER INFORMATION: Synthetic

<400> SEQUENCE: 58

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Ser Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Glu Val Gln Leu Gln Gln
            115                 120                 125

Ser Gly Ala Glu Leu Val Arg Pro Gly Ala Leu Val Lys Leu Ser Cys
    130                 135                 140

Lys Ala Ser Gly Phe Asn Ile Lys Asp Tyr Tyr Ile His Trp Val Lys
```

-continued

```
145              150              155              160

Gln Arg Pro Glu Gln Gly Leu Glu Trp Ile Gly Trp Ile Asp Pro Glu
             165              170              175

Asn Gly His Thr Ile Tyr Asp Pro Lys Phe Gln Gly Lys Ala Ser Ile
             180              185              190

Thr Ala Asp Thr Ser Ser Asn Thr Ala Tyr Leu Gln Leu Ser Ser Leu
             195              200              205

Thr Ser Glu Asp Thr Ala Val Tyr Tyr Cys Ala Arg Leu Thr Gly Thr
     210              215              220

Thr Tyr Ala Met Asp Tyr Trp Gly Gln Gly Thr Ser Val Thr Val Ser
225              230              235              240

Ser
```

```
<210> SEQ ID NO 59
<211> LENGTH: 245
<212> TYPE: PRT
<213> ORGANISM: Artificial sequence
<220> FEATURE:
<223> OTHER INFORMATION: Synthetic
```

```
<400> SEQUENCE: 59

Glu Val Lys Leu Leu Glu Ser Gly Gly Gly Leu Val Gln Pro Gly Gly
1               5               10              15

Ser Met Arg Leu Ser Cys Ala Ala Ser Gly Phe Thr Phe Thr Asp Phe
             20              25              30

Tyr Met Asn Trp Ile Arg Gln Pro Ala Gly Lys Ala Pro Glu Trp Leu
             35              40              45

Gly Phe Ile Arg Asn Lys Ala Ser Gly Tyr Thr Thr Glu Tyr Asn Pro
     50              55              60

Ser Val Lys Gly Arg Phe Thr Ile Ser Arg Asp Asn Thr Gln Asn Met
65              70              75              80

Leu Tyr Leu Gln Met Asn Thr Leu Arg Ala Glu Asp Thr Ala Thr Tyr
             85              90              95

Tyr Cys Ala Arg Ala His Ser Tyr Tyr Gly Tyr Asp Tyr Phe Asp Tyr
             100             105             110

Trp Gly Gln Gly Val Met Val Thr Val Ser Ser Gly Gly Gly Gly Ser
             115             120             125

Gly Gly Gly Gly Ser Gly Gly Gly Gly Ser Asp Ile Gln Met Thr Gln
     130             135             140

Ser Pro Ala Ser Leu Ser Ala Ser Leu Glu Glu Ile Val Thr Ile Thr
145             150             155             160

Cys Gln Ala Ser Gln Asp Ile Gly Asn Trp Leu Ser Trp Tyr Gln Gln
             165             170             175

Lys Pro Gly Lys Ser Pro Gln Leu Leu Ile Tyr Gly Ala Thr Ser Leu
             180             185             190

Ala Asp Gly Val Pro Ser Arg Phe Ser Gly Ser Arg Ser Gly Thr Gln
             195             200             205

Tyr Ser Leu Lys Ile Ser Arg Leu Gln Val Glu Asp Ile Arg Ile Tyr
     210             215             220

Tyr Cys Leu Gln Ala Tyr Ser Ala Pro Trp Thr Phe Gly Gly Gly Thr
225             230             235             240

Lys Leu Glu Leu Lys
             245
```

```
<210> SEQ ID NO 60
```

-continued

```
<211> LENGTH: 245
<212> TYPE: PRT
<213> ORGANISM: Artificial sequence
<220> FEATURE:
<223> OTHER INFORMATION: Synthetic

<400> SEQUENCE: 60

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Tyr Ser Leu Lys Ile Ser Arg Leu Gln Val
65                  70                  75                  80

Glu Asp Ile Arg Ile Tyr Tyr Cys Leu Gln Ala Tyr Ser Ala Pro Trp
                85                  90                  95

Thr Phe Gly Gly Gly Thr Lys Leu Glu Leu Lys Gly Gly Gly Gly Ser
            100                 105                 110

Gly Gly Gly Gly Ser Gly Gly Gly Ser Glu Val Lys Leu Leu Glu
        115                 120                 125

Ser Gly Gly Gly Leu Val Gln Pro Gly Gly Ser Met Arg Leu Ser Cys
    130                 135                 140

Ala Ala Ser Gly Phe Thr Phe Thr Asp Phe Tyr Met Asn Trp Ile Arg
145                 150                 155                 160

Gln Pro Ala Gly Lys Ala Pro Glu Trp Leu Gly Phe Ile Arg Asn Lys
                165                 170                 175

Ala Ser Gly Tyr Thr Thr Glu Tyr Asn Pro Ser Val Lys Gly Arg Phe
            180                 185                 190

Thr Ile Ser Arg Asp Asn Thr Gln Asn Met Leu Tyr Leu Gln Met Asn
        195                 200                 205

Thr Leu Arg Ala Glu Asp Thr Ala Thr Tyr Tyr Cys Ala Arg Ala His
    210                 215                 220

Ser Tyr Tyr Gly Tyr Asp Tyr Phe Asp Tyr Trp Gly Gln Gly Val Met
225                 230                 235                 240

Val Thr Val Ser Ser
                245

<210> SEQ ID NO 61
<211> LENGTH: 842
<212> TYPE: PRT
<213> ORGANISM: Artificial sequence
<220> FEATURE:
<223> OTHER INFORMATION: Synthetic

<400> SEQUENCE: 61

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
```

```
65                    70                    75                    80

Pro Ser Arg Phe Ser Gly Ser Gly Ser Gly Thr Asp Tyr Ser Leu Thr
                85                    90                    95

Ile Ser Asn Leu Glu Gln Glu Asp Ile Ala Thr Tyr Phe Cys Gln Gln
            100                   105                   110

Gly Asn Thr Leu Pro Tyr Thr Phe Gly Gly Gly Thr Lys Leu Glu Ile
            115                   120                   125

Thr Gly Ser Thr Ser Gly Ser Gly Lys Pro Gly Ser Gly Glu Gly Ser
        130                   135                   140

Thr Lys Gly Glu Val Lys Leu Gln Glu Ser Gly Pro Gly Leu Val Ala
145                   150                   155                   160

Pro Ser Gln Ser Leu Ser Val Thr Cys Thr Val Ser Gly Val Ser Leu
                165                   170                   175

Pro Asp Tyr Gly Val Ser Trp Ile Arg Gln Pro Pro Arg Lys Gly Leu
            180                   185                   190

Glu Trp Leu Gly Val Ile Trp Gly Ser Glu Thr Thr Tyr Tyr Asn Ser
            195                   200                   205

Ala Leu Lys Ser Arg Leu Thr Ile Ile Lys Asp Asn Ser Lys Ser Gln
        210                   215                   220

Val Phe Leu Lys Met Asn Ser Leu Gln Thr Asp Asp Thr Ala Ile Tyr
225                   230                   235                   240

Tyr Cys Ala Lys His Tyr Tyr Tyr Gly Gly Ser Tyr Ala Met Asp Tyr
                245                   250                   255

Trp Gly Gln Gly Thr Ser Val Thr Val Ser Ser Glu Ser Lys Tyr Gly
            260                   265                   270

Pro Pro Cys Pro Pro Cys Pro Met Phe Trp Val Leu Val Val Val Gly
            275                   280                   285

Gly Val Leu Ala Cys Tyr Ser Leu Leu Val Thr Val Ala Phe Ile Ile
        290                   295                   300

Phe Trp Val Lys Arg Gly Arg Lys Lys Leu Leu Tyr Ile Phe Lys Gln
305                   310                   315                   320

Pro Phe Met Arg Pro Val Gln Thr Thr Gln Glu Glu Asp Gly Cys Ser
                325                   330                   335

Cys Arg Phe Pro Glu Glu Glu Glu Gly Gly Cys Glu Leu Arg Val Lys
                340                   345                   350

Phe Ser Arg Ser Ala Asp Ala Pro Ala Tyr Gln Gln Gly Gln Asn Gln
            355                   360                   365

Leu Tyr Asn Glu Leu Asn Leu Gly Arg Arg Glu Glu Tyr Asp Val Leu
        370                   375                   380

Asp Lys Arg Arg Gly Arg Asp Pro Glu Met Gly Gly Lys Pro Arg Arg
385                   390                   395                   400

Lys Asn Pro Gln Glu Gly Leu Tyr Asn Glu Leu Gln Lys Asp Lys Met
            405                   410                   415

Ala Glu Ala Tyr Ser Glu Ile Gly Met Lys Gly Glu Arg Arg Arg Gly
            420                   425                   430

Lys Gly His Asp Gly Leu Tyr Gln Gly Leu Ser Thr Ala Thr Lys Asp
        435                   440                   445

Thr Tyr Asp Ala Leu His Met Gln Ala Leu Pro Pro Arg Leu Glu Gly
        450                   455                   460

Gly Gly Glu Gly Arg Gly Ser Leu Leu Thr Cys Gly Asp Val Glu Glu
465                   470                   475                   480

Asn Pro Gly Pro Arg Met Leu Leu Leu Val Thr Ser Leu Leu Leu Cys
                485                   490                   495
```

-continued

```
Glu Leu Pro His Pro Ala Phe Leu Leu Ile Pro Arg Lys Val Cys Asn
            500             505             510

Gly Ile Gly Ile Gly Glu Phe Lys Asp Ser Leu Ser Ile Asn Ala Thr
            515             520             525

Asn Ile Lys His Phe Lys Asn Cys Thr Ser Ile Ser Gly Asp Leu His
            530             535             540

Ile Leu Pro Val Ala Phe Arg Gly Asp Ser Phe Thr His Thr Pro Pro
545             550             555             560

Leu Asp Pro Gln Glu Leu Asp Ile Leu Lys Thr Val Lys Glu Ile Thr
            565             570             575

Gly Phe Leu Leu Ile Gln Ala Trp Pro Glu Asn Arg Thr Asp Leu His
            580             585             590

Ala Phe Glu Asn Leu Glu Ile Ile Arg Gly Arg Thr Lys Gln His Gly
            595             600             605

Gln Phe Ser Leu Ala Val Val Ser Leu Asn Ile Thr Ser Leu Gly Leu
            610             615             620

Arg Ser Leu Lys Glu Ile Ser Asp Gly Asp Val Ile Ile Ser Gly Asn
625             630             635             640

Lys Asn Leu Cys Tyr Ala Asn Thr Ile Asn Trp Lys Lys Leu Phe Gly
            645             650             655

Thr Ser Gly Gln Lys Thr Lys Ile Ile Ser Asn Arg Gly Glu Asn Ser
            660             665             670

Cys Lys Ala Thr Gly Gln Val Cys His Ala Leu Cys Ser Pro Glu Gly
            675             680             685

Cys Trp Gly Pro Glu Pro Arg Asp Cys Val Ser Cys Arg Asn Val Ser
            690             695             700

Arg Gly Arg Glu Cys Val Asp Lys Cys Asn Leu Leu Glu Gly Glu Pro
705             710             715             720

Arg Glu Phe Val Glu Asn Ser Glu Cys Ile Gln Cys His Pro Glu Cys
            725             730             735

Leu Pro Gln Ala Met Asn Ile Thr Cys Thr Gly Arg Gly Pro Asp Asn
            740             745             750

Cys Ile Gln Cys Ala His Tyr Ile Asp Gly Pro His Cys Val Lys Thr
            755             760             765

Cys Pro Ala Gly Val Met Gly Glu Asn Asn Thr Leu Val Trp Lys Tyr
            770             775             780

Ala Asp Ala Gly His Val Cys His Leu Cys His Pro Asn Cys Thr Tyr
785             790             795             800

Gly Cys Thr Gly Pro Gly Leu Glu Gly Cys Pro Thr Asn Gly Pro Lys
            805             810             815

Ile Pro Ser Ile Ala Thr Gly Met Val Gly Ala Leu Leu Leu Leu Leu
            820             825             830

Val Val Ala Leu Gly Ile Gly Leu Phe Met
            835             840
```

```
<210> SEQ ID NO 62
<211> LENGTH: 647
<212> TYPE: PRT
<213> ORGANISM: Artificial sequence
<220> FEATURE:
<223> OTHER INFORMATION: Synthetic

<400> SEQUENCE: 62

Met Leu Leu Leu Val Thr Ser Leu Leu Leu Cys Glu Leu Pro His Pro
1               5               10              15
```

-continued

```
Ala Phe Leu Leu Ile Pro Asp Ile Gln Met Thr Gln Thr Thr Ser Ser
         20              25              30

Leu Ser Ala Ser Leu Gly Asp Arg Val Thr Ile Ser Cys Arg Ala Ser
         35              40              45

Gln Asp Ile Ser Lys Tyr Leu Asn Trp Tyr Gln Gln Lys Pro Asp Gly
     50              55              60

Thr Val Lys Leu Leu Ile Tyr His Thr Ser Arg Leu His Ser Gly Val
65              70              75              80

Pro Ser Arg Phe Ser Gly Ser Gly Ser Gly Thr Asp Tyr Ser Leu Thr
             85              90              95

Ile Ser Asn Leu Glu Gln Glu Asp Ile Ala Thr Tyr Phe Cys Gln Gln
             100             105             110

Gly Asn Thr Leu Pro Tyr Thr Phe Gly Gly Gly Thr Lys Leu Glu Ile
         115             120             125

Thr Gly Ser Thr Ser Gly Ser Gly Lys Pro Gly Ser Gly Glu Gly Ser
     130             135             140

Thr Lys Gly Glu Val Lys Leu Gln Glu Ser Gly Pro Gly Leu Val Ala
145             150             155             160

Pro Ser Gln Ser Leu Ser Val Thr Cys Thr Val Ser Gly Val Ser Leu
             165             170             175

Pro Asp Tyr Gly Val Ser Trp Ile Arg Gln Pro Pro Arg Lys Gly Leu
             180             185             190

Glu Trp Leu Gly Val Ile Trp Gly Ser Glu Thr Thr Tyr Tyr Asn Ser
         195             200             205

Ala Leu Lys Ser Arg Leu Thr Ile Ile Lys Asp Asn Ser Lys Ser Gln
     210             215             220

Val Phe Leu Lys Met Asn Ser Leu Gln Thr Asp Asp Thr Ala Ile Tyr
225             230             235             240

Tyr Cys Ala Lys His Tyr Tyr Tyr Gly Gly Ser Tyr Ala Met Asp Tyr
             245             250             255

Trp Gly Gln Gly Thr Ser Val Thr Val Ser Ser Glu Ser Lys Tyr Gly
         260             265             270

Pro Pro Cys Pro Pro Cys Pro Met Phe Trp Val Leu Val Val Val Gly
         275             280             285

Gly Val Leu Ala Cys Tyr Ser Leu Leu Val Thr Val Ala Phe Ile Ile
     290             295             300

Phe Trp Val Lys Arg Gly Arg Lys Lys Leu Leu Tyr Ile Phe Lys Gln
305             310             315             320

Pro Phe Met Arg Pro Val Gln Thr Thr Gln Glu Glu Asp Gly Cys Ser
             325             330             335

Cys Arg Phe Pro Glu Glu Glu Glu Gly Gly Cys Glu Leu Arg Val Lys
             340             345             350

Phe Ser Arg Ser Ala Asp Ala Pro Ala Tyr Gln Gln Gly Gln Asn Gln
         355             360             365

Leu Tyr Asn Glu Leu Asn Leu Gly Arg Arg Glu Glu Tyr Asp Val Leu
     370             375             380

Asp Lys Arg Arg Gly Arg Asp Pro Glu Met Gly Gly Lys Pro Arg Arg
385             390             395             400

Lys Asn Pro Gln Glu Gly Leu Tyr Asn Glu Leu Gln Lys Asp Lys Met
             405             410             415

Ala Glu Ala Tyr Ser Glu Ile Gly Met Lys Gly Glu Arg Arg Arg Gly
             420             425             430
```

```
Lys Gly His Asp Gly Leu Tyr Gln Gly Leu Ser Thr Ala Thr Lys Asp
        435             440             445

Thr Tyr Asp Ala Leu His Met Gln Ala Leu Pro Pro Arg Leu Glu Gly
        450             455             460

Gly Gly Glu Gly Arg Gly Ser Leu Leu Thr Cys Gly Asp Val Glu Glu
465             470             475             480

Asn Pro Gly Pro Arg Met Arg Ile Ser Lys Pro His Leu Arg Ser Ile
                485             490             495

Ser Ile Gln Cys Tyr Leu Cys Leu Leu Leu Asn Ser His Phe Leu Thr
            500             505             510

Glu Ala Gly Ile His Val Phe Ile Leu Gly Cys Phe Ser Ala Gly Leu
            515             520             525

Pro Lys Thr Glu Ala Asn Trp Val Asn Val Ile Ser Asp Leu Lys Lys
        530             535             540

Ile Glu Asp Leu Ile Gln Ser Met His Ile Asp Ala Thr Leu Tyr Thr
545             550             555             560

Glu Ser Asp Val His Pro Ser Cys Lys Val Thr Ala Met Lys Cys Phe
                565             570             575

Leu Leu Glu Leu Gln Val Ile Ser Leu Glu Ser Gly Asp Ala Ser Ile
            580             585             590

His Asp Thr Val Glu Asn Leu Ile Ile Leu Ala Asn Asn Ser Leu Ser
            595             600             605

Ser Asn Gly Asn Val Thr Glu Ser Gly Cys Lys Glu Cys Glu Glu Leu
        610             615             620

Glu Glu Lys Asn Ile Lys Glu Phe Leu Gln Ser Phe Val His Ile Val
625             630             635             640

Gln Met Phe Ile Asn Thr Ser
                645
```

<210> SEQ ID NO 63
<211> LENGTH: 6
<212> TYPE: PRT
<213> ORGANISM: Artificial sequence
<220> FEATURE:
<223> OTHER INFORMATION: Synthetic

<400> SEQUENCE: 63

```
Asp Asn Ser Lys Ser Gln
1               5
```

<210> SEQ ID NO 64
<211> LENGTH: 120
<212> TYPE: PRT
<213> ORGANISM: Artificial sequence
<220> FEATURE:
<223> OTHER INFORMATION: Synthetic

<400> SEQUENCE: 64

```
Glu Val Lys Leu Gln Glu Ser Gly Pro Gly Leu Val Ala Pro Ser Gln
1               5               10              15

Ser Leu Ser Val Thr Cys Thr Val Ser Gly Val Ser Leu Pro Asp Tyr
                20              25              30

Gly Val Ser Trp Ile Arg Gln Pro Pro Arg Lys Gly Leu Glu Trp Leu
            35              40              45

Gly Val Ile Trp Gly Ser Glu Thr Thr Tyr Tyr Asn Ser Ala Leu Lys
        50              55              60

Ser Arg Leu Thr Ile Ile Lys Asp Asn Ser Lys Ser Gln Val Phe Leu
65              70              75              80
```

-continued

```
Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 65
<211> LENGTH: 107
<212> TYPE: PRT
<213> ORGANISM: Artificial sequence
<220> FEATURE:
<223> OTHER INFORMATION: Synthetic

<400> SEQUENCE: 65

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 66
<211> LENGTH: 216
<212> TYPE: PRT
<213> ORGANISM: Artificial sequence
<220> FEATURE:
<223> OTHER INFORMATION: Synthetic

<400> SEQUENCE: 66

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Phe Cys Cys Phe Ile Ala Val Ala Met Gly
    50                  55                  60

Ile Arg Phe Ile Ile Met Val Thr Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
            115                 120                 125

Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
```

```
145                150                155                160

Pro Thr Asn Gly Ser Trp Gln Trp Glu Asp Gly Ser Ile Leu Ser Pro
            165                170                175

Asn Leu Leu Thr Ile Ile Glu Met Gln Lys Gly Asp Cys Ala Leu Tyr
            180                185                190

Ala Ser Ser Phe Lys Gly Tyr Ile Glu Asn Cys Ser Thr Pro Asn Thr
            195                200                205

Tyr Ile Cys Met Gln Arg Thr Val
        210                215

<210> SEQ ID NO 67
<211> LENGTH: 335
<212> TYPE: PRT
<213> ORGANISM: Artificial sequence
<220> FEATURE:
<223> OTHER INFORMATION: Synthetic

<400> SEQUENCE: 67

Arg Lys Val Cys Asn Gly Ile Gly Ile Gly Glu Phe Lys Asp Ser Leu
1                5                10                15

Ser Ile Asn Ala Thr Asn Ile Lys His Phe Lys Asn Cys Thr Ser Ile
            20                25                30

Ser Gly Asp Leu His Ile Leu Pro Val Ala Phe Arg Gly Asp Ser Phe
            35                40                45

Thr His Thr Pro Pro Leu Asp Pro Gln Glu Leu Asp Ile Leu Lys Thr
        50                55                60

Val Lys Glu Ile Thr Gly Phe Leu Leu Ile Gln Ala Trp Pro Glu Asn
65                70                75                80

Arg Thr Asp Leu His Ala Phe Glu Asn Leu Glu Ile Ile Arg Gly Arg
            85                90                95

Thr Lys Gln His Gly Gln Phe Ser Leu Ala Val Val Ser Leu Asn Ile
            100                105                110

Thr Ser Leu Gly Leu Arg Ser Leu Lys Glu Ile Ser Asp Gly Asp Val
            115                120                125

Ile Ile Ser Gly Asn Lys Asn Leu Cys Tyr Ala Asn Thr Ile Asn Trp
        130                135                140

Lys Lys Leu Phe Gly Thr Ser Gly Gln Lys Thr Lys Ile Ile Ser Asn
145                150                155                160

Arg Gly Glu Asn Ser Cys Lys Ala Thr Gly Gln Val Cys His Ala Leu
            165                170                175

Cys Ser Pro Glu Gly Cys Trp Gly Pro Glu Pro Arg Asp Cys Val Ser
            180                185                190

Cys Arg Asn Val Ser Arg Gly Arg Glu Cys Val Asp Lys Cys Asn Leu
            195                200                205

Leu Glu Gly Glu Pro Arg Glu Phe Val Glu Asn Ser Glu Cys Ile Gln
        210                215                220

Cys His Pro Glu Cys Leu Pro Gln Ala Met Asn Ile Thr Cys Thr Gly
225                230                235                240

Arg Gly Pro Asp Asn Cys Ile Gln Cys Ala His Tyr Ile Asp Gly Pro
            245                250                255

His Cys Val Lys Thr Cys Pro Ala Gly Val Met Gly Glu Asn Asn Thr
            260                265                270

Leu Val Trp Lys Tyr Ala Asp Ala Gly His Val Cys His Leu Cys His
        275                280                285

Pro Asn Cys Thr Tyr Gly Cys Thr Gly Pro Gly Leu Glu Gly Cys Pro
```

-continued

```
             290                 295                 300
Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 68
<211> LENGTH: 161
<212> TYPE: PRT
<213> ORGANISM: Artificial sequence
<220> FEATURE:
<223> OTHER INFORMATION: Synthetic

<400> SEQUENCE: 68

Arg Ile Ser Lys Pro His Leu Arg Ser Ile Ser Ile Gln Cys Tyr Leu
1               5                   10                  15

Cys Leu Leu Leu Asn Ser His Phe Leu Thr Glu Ala Gly Ile His Val
                20                  25                  30

Phe Ile Leu Gly Cys Phe Ser Ala Gly Leu Pro Lys Thr Glu Ala Asn
        35                  40                  45

Trp Val Asn Val Ile Ser Asp Leu Lys Lys Ile Glu Asp Leu Ile Gln
    50                  55                  60

Ser Met His Ile Asp Ala Thr Leu Tyr Thr Glu Ser Asp Val His Pro
65                  70                  75                  80

Ser Cys Lys Val Thr Ala Met Lys Cys Phe Leu Leu Glu Leu Gln Val
                85                  90                  95

Ile Ser Leu Glu Ser Gly Asp Ala Ser Ile His Asp Thr Val Glu Asn
            100                 105                 110

Leu Ile Ile Leu Ala Asn Asn Ser Leu Ser Ser Asn Gly Asn Val Thr
        115                 120                 125

Glu Ser Gly Cys Lys Glu Cys Glu Glu Leu Glu Glu Lys Asn Ile Lys
    130                 135                 140

Glu Phe Leu Gln Ser Phe Val His Ile Val Gln Met Phe Ile Asn Thr
145                 150                 155                 160

Ser

<210> SEQ ID NO 69
<211> LENGTH: 1944
<212> TYPE: DNA
<213> ORGANISM: Artificial sequence
<220> FEATURE:
<223> OTHER INFORMATION: Synthetic

<400> SEQUENCE: 69
atgctgctgc tggtgaccag cctgctgctg tgcgagctgc cccaccccgc ctttctgctg      60
atccccgaca tccagatgac ccagaccacc tccagcctga gcgccagcct gggcgaccgg     120
gtgaccatca gctgccgggc cagccaggac atcagcaagt acctgaactg gtatcagcag     180
aagcccgacg gcaccgtcaa gctgctgatc taccacacca gccggctgca cagcggcgtg     240
cccagccggt ttagcggcag cggctccggc accgactaca gcctgaccat ctccaacctg     300
gaacaggaag atatcgccac ctactttttgc cagcagggca cacactgcc ctacaccttt     360 ggcggcggaa caaagctgga aatcaccggc agcacctccg gcagcggcaa gcctggcagc     420
ggcgagggca gcaccaaggg cgaggtgaag ctgcaggaaa gcggccctgg cctggtggcc     480
cccagccaga gcctgagcgt gacctgcacc gtgagcggcg tgagcctgcc cgactacggc     540
gtgagctgga tccggcagcc ccccaggaag ggcctggaat ggctgggcgt gatctggggc     600
```

-continued

```
agcgagacca cctactacaa cagcgccctg aagagccggc tgaccatcat caaggacaac    660
agcaagagcc aggtgttcct gaagatgaac agcctgcaga ccgacgacac cgccatctac    720
tactgcgcca agcactacta ctacggcggc agctacgcca tggactactg gggccagggc    780
accagcgtga ccgtgagcag cgaatctaag tacggaccgc cctgcccccc ttgccctatg    840
ttctgggtgc tggtggtggt cggaggcgtg ctggcctgct acagcctgct ggtcaccgtg    900
gccttcatca tctttttggt gaaacggggc agaaagaaac tcctgtatat attcaaacaa    960
ccatttatga gaccagtaca aactactcaa gaggaagatg gctgtagctg ccgatttcca   1020
gaagaagaag aaggaggatg tgaactgagg gtgaagttca gcagaagcgc cgacgcccct   1080
gcctaccagc agggccagaa tcagctgtac aacgagctga acctgggcag aagggaagag   1140
tacgacgtcc tggataagcg gagaggccgg gaccctgaga tgggcggcaa gcctcggcgg   1200 aagaacccc  aggaaggcct gtataacgaa ctgcagaaag acaagatggc cgaggcctac   1260
agcgagatcg gcatgaaggg cgagcggagg cggggcaagg ccacgacgg  cctgtatcag   1320 ggcctgtcca ccgccaccaa ggatacctac gacgccctgc acatgcaggc cctgccccca   1380
aggctcgagg gcgcggagaga gggcagagga agtcttctaa catgcggtga cgtggaggag   1440
aatcccggcc ctaggatgcg gatttccaaa cctcacctgc gctctatctc tatccagtgc   1500
tatctgtgcc tgctgctgaa ctcacatttc ctgaccgaag ccggcatcca cgtgttcatc   1560
ctgggctgct tttccgccgg cctgccaaag accgaggcaa actgggtgaa tgtgatctct   1620
gacctgaaga gatcgagga  tctgatccag agcatgcaca tcgacgccac cctgtacaca   1680
gagtccgatg tgcacccttc ttgcaaggtg acagccatga agtgtttcct gctggagctg   1740
caggtcatca gcctggagag cggcgacgcc tctatccacg ataccgtgga gaacctgatc   1800
atcctggcca acaatagcct gagcagcaac ggcaatgtga cagagtccgg ctgcaaggag   1860
tgtgaggagc tggaggagaa gaatatcaaa gagttcctgc agtcattcgt ccatatcgtc   1920
cagatgttta tcaataccct ctaa                                        1944
```

<210> SEQ ID NO 70
<211> LENGTH: 725
<212> TYPE: PRT
<213> ORGANISM: Artificial sequence
<220> FEATURE:
<223> OTHER INFORMATION: Synthetic

<400> SEQUENCE: 70

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
```

```
                115                    120                    125

Thr Gly Ser Thr Ser Gly Ser Gly Lys Pro Gly Ser Gly Glu Gly Ser
    130                    135                    140

Thr Lys Gly Glu Val Lys Leu Gln Glu Ser Gly Pro Gly Leu Val Ala
145                    150                    155                    160

Pro Ser Gln Ser Leu Ser Val Thr Cys Thr Val Ser Gly Val Ser Leu
                    165                    170                    175

Pro Asp Tyr Gly Val Ser Trp Ile Arg Gln Pro Pro Arg Lys Gly Leu
                180                    185                    190

Glu Trp Leu Gly Val Ile Trp Gly Ser Glu Thr Thr Tyr Tyr Asn Ser
                195                    200                    205

Ala Leu Lys Ser Arg Leu Thr Ile Ile Lys Asp Asn Ser Lys Ser Gln
    210                    215                    220

Val Phe Leu Lys Met Asn Ser Leu Gln Thr Asp Asp Thr Ala Ile Tyr
225                    230                    235                    240

Tyr Cys Ala Lys His Tyr Tyr Tyr Gly Gly Ser Tyr Ala Met Asp Tyr
                    245                    250                    255

Trp Gly Gln Gly Thr Ser Val Thr Val Ser Ser Glu Ser Lys Tyr Gly
                260                    265                    270

Pro Pro Cys Pro Pro Cys Pro Met Phe Trp Val Leu Val Val Val Gly
            275                    280                    285

Gly Val Leu Ala Cys Tyr Ser Leu Leu Val Thr Val Ala Phe Ile Ile
    290                    295                    300

Phe Trp Val Trp Arg Arg Lys Arg Lys Glu Lys Gln Ser Glu Thr Ser
305                    310                    315                    320

Pro Lys Glu Phe Leu Thr Ile Tyr Glu Asp Val Lys Asp Leu Lys Thr
                325                    330                    335

Arg Arg Asn His Glu Gln Glu Gln Thr Phe Pro Gly Gly Gly Ser Thr
                340                    345                    350

Ile Tyr Ser Met Ile Gln Ser Gln Ser Ser Ala Pro Thr Ser Gln Glu
                355                    360                    365

Pro Ala Tyr Thr Leu Tyr Ser Leu Ile Gln Pro Ser Arg Lys Ser Gly
    370                    375                    380

Ser Arg Lys Arg Asn His Ser Pro Ser Phe Asn Ser Thr Ile Tyr Glu
385                    390                    395                    400

Val Ile Gly Lys Ser Gln Pro Lys Ala Gln Asn Pro Ala Arg Leu Ser
                405                    410                    415

Arg Lys Glu Leu Glu Asn Phe Asp Val Tyr Ser Arg Val Lys Phe Ser
                420                    425                    430

Arg Ser Ala Asp Ala Pro Ala Tyr Gln Gln Gly Gln Asn Gln Leu Tyr
            435                    440                    445

Asn Glu Leu Asn Leu Gly Arg Arg Glu Glu Tyr Asp Val Leu Asp Lys
    450                    455                    460

Arg Arg Gly Arg Asp Pro Glu Met Gly Gly Lys Pro Arg Arg Lys Asn
465                    470                    475                    480

Pro Gln Glu Gly Leu Tyr Asn Glu Leu Gln Lys Asp Lys Met Ala Glu
                485                    490                    495

Ala Tyr Ser Glu Ile Gly Met Lys Gly Glu Arg Arg Arg Gly Lys Gly
                500                    505                    510

His Asp Gly Leu Tyr Gln Gly Leu Ser Thr Ala Thr Lys Asp Thr Tyr
                515                    520                    525

Asp Ala Leu His Met Gln Ala Leu Pro Pro Arg Leu Glu Gly Gly Gly
    530                    535                    540
```

```
Glu Gly Arg Gly Ser Leu Leu Thr Cys Gly Asp Val Glu Glu Asn Pro
545                 550                 555                 560

Gly Pro Arg Met Arg Ile Ser Lys Pro His Leu Arg Ser Ile Ser Ile
                565                 570                 575

Gln Cys Tyr Leu Cys Leu Leu Leu Asn Ser His Phe Leu Thr Glu Ala
            580                 585                 590

Gly Ile His Val Phe Ile Leu Gly Cys Phe Ser Ala Gly Leu Pro Lys
            595                 600                 605

Thr Glu Ala Asn Trp Val Asn Val Ile Ser Asp Leu Lys Lys Ile Glu
    610                 615                 620

Asp Leu Ile Gln Ser Met His Ile Asp Ala Thr Leu Tyr Thr Glu Ser
625                 630                 635                 640

Asp Val His Pro Ser Cys Lys Val Thr Ala Met Lys Cys Phe Leu Leu
            645                 650                 655

Glu Leu Gln Val Ile Ser Leu Glu Ser Gly Asp Ala Ser Ile His Asp
            660                 665                 670

Thr Val Glu Asn Leu Ile Ile Leu Ala Asn Asn Ser Leu Ser Ser Asn
            675                 680                 685

Gly Asn Val Thr Glu Ser Gly Cys Lys Glu Cys Glu Glu Leu Glu Glu
    690                 695                 700

Lys Asn Ile Lys Glu Phe Leu Gln Ser Phe Val His Ile Val Gln Met
705                 710                 715                 720

Phe Ile Asn Thr Ser
                725

<210> SEQ ID NO 71
<211> LENGTH: 2177
<212> TYPE: DNA
<213> ORGANISM: Artificial sequence
<220> FEATURE:
<223> OTHER INFORMATION: Synthetic

<400> SEQUENCE: 71
atgctgctgc tggtgaccag cctgctgctg tgcgagctgc cccacccgc ctttctgctg      60 atccccgaca tccagatgac ccagaccacc tccagcctga gcgccagcct gggcgaccgg     120
gtgaccatca gctgccgggc cagccaggac atcagcaagt acctgaactg gtatcagcag     180
aagcccgacg gcaccgtcaa gctgctgatc taccacacca gccggctgca cagcggcgtg     240
cccagccggt ttagcggcag cggctccggc accgactaca gcctgaccat ctccaacctg     300
gaacaggaag atatcgccac ctacttttgc cagcagggca cacactgcc ctacaccttt      360 ggcggcggaa caaagctgga aatcaccggc agcacctccg gcagcggcaa gcctggcagc     420
ggcgagggca gcaccaaggg cgaggtgaag ctgcaggaaa gcggccctgg cctggtggcc     480
cccagccaga gcctgagcgt gacctgcacc gtgagcggcg tgagcctgcc cgactacggc     540
gtgagctgga tccggcagcc ccccaggaag ggcctggaat ggctgggcgt gatctggggc     600
agcgagacca cctactacaa cagcgccctg aagagccggc tgaccatcat caaggacaac     660
agcaagagcc aggtgttcct gaagatgaac agcctgcaga ccgacgacac cgccatctac     720
tactgcgcca gcactacta ctacggcggc agctacgcca tggactactg gggccagggc     780
accagcgtga ccgtgagcag cgaatctaag tacggaccgc cctgcccccc ttgccctatg     840
ttctgggtgc tggtggtggt cggaggcgtg ctggcctgct acagcctgct ggtcaccgtg     900
gccttcatca tctttttgggt gtggaggagg aagaggaagg agaagcagag cgagacaagc     960
```

-continued

```
cctaaggagt ttctgacaat ctatgaagac gtgaaggacc tgaagacacg gagaaaccac    1020
gagcaggagc agaccttccc tggaggaggc agcacaatct actccatgat ccagtctcag    1080
agcagcgccc ccacctccca ggagcctgcc tacacactgt atagcctgat ccagccatcc    1140
cggaagtctg gcagcaggaa gcgcaaccac tccccctctt ttaattctac catctatgaa    1200
gtgatcggca agagccagcc caaggcacag aaccccgcac gactgagcag gaaggaactg    1260
gagaactttg atgtctactc tagggtgaag ttcagcagaa gcgccgacgc ccctgcctac    1320
cagcagggcc agaatcagct gtacaacgag ctgaacctgg gcagaaggga gagtacgac     1380 gtcctggata gcggagagg ccgggaccct gagatgggcg gcaagcctcg gcggaagaac     1440
ccccaggaag gcctgtataa cgaactgcag aaagacaaga tggccgaggc ctacagcgag    1500
atcggcatga agggcgagcg gaggcggggc aagggccacg acggcctgta tcagggcctg    1560
tccaccgcca ccaaggatac ctacgacgcc ctgcacatgc aggccctgcc cccaaggctc    1620
gagggcggcg gagagggcag aggaagtctt ctaacatgcg gtgacgtgga gagaatcccg    1680
gccctaggat gcggatttcc aaacctcacc tgcgctctat ctctatccag tgctatctgt    1740
gcctgctgct gaactcacat ttcctgaccg aagccggcat ccacgtgttc atcctgggct    1800
gcttttccgc cggcctgcca aagaccgagg caaactgggt gaatgtgatc tctgacctga    1860
agaagatcga ggatctgatc cagagcatgc acatcgacgc caccctgtac acagagtccg    1920
atgtgcaccc ttcttgcaag gtgacagcca tgaagtgttt cctgctggag ctgcaggtca    1980
tcagcctgga gagcggcgac gcctctatcc acgataccgt ggagaacctg atcatcctgg    2040
ccaacaatag cctgagcagc aacggcaatg tgacagagtc cggctgcaag gagtgtgagg    2100
agctggagga gaagaatatc aaagagttcc tgcagtcatt cgtccatatc gtccagatgt    2160
ttatcaatac ctcctaa                                                    2177
```

```
<210> SEQ ID NO 72
<211> LENGTH: 640
<212> TYPE: PRT
<213> ORGANISM: Artificial sequence
<220> FEATURE:
<223> OTHER INFORMATION: Synthetic

<400> SEQUENCE: 72

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140
```

```
Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Glu Ser Lys Tyr Gly
                260                 265                 270

Pro Pro Cys Pro Pro Cys Pro Pro Phe Phe Phe Cys Cys Phe Ile Ala
            275                 280                 285

Val Ala Met Gly Ile Arg Phe Ile Ile Met Val Thr Lys Arg Gly Arg
    290                 295                 300

Lys Lys Leu Leu Tyr Ile Phe Lys Gln Pro Phe Met Arg Pro Val Gln
305                 310                 315                 320

Thr Thr Gln Glu Glu Asp Gly Cys Ser Cys Arg Phe Pro Glu Glu Glu
                325                 330                 335

Glu Gly Gly Cys Glu Leu Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
            355                 360                 365

Gly Arg Arg Glu Glu Tyr Asp Val Leu Asp Lys Arg Arg Gly Arg Asp
    370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg Leu Glu Gly Gly Gly Glu Gly Arg Gly Ser
    450                 455                 460

Leu Leu Thr Cys Gly Asp Val Glu Glu Asn Pro Gly Pro Arg Met Arg
465                 470                 475                 480

Ile Ser Lys Pro His Leu Arg Ser Ile Ser Ile Gln Cys Tyr Leu Cys
                485                 490                 495

Leu Leu Leu Asn Ser His Phe Leu Thr Glu Ala Gly Ile His Val Phe
            500                 505                 510

Ile Leu Gly Cys Phe Ser Ala Gly Leu Pro Lys Thr Glu Ala Asn Trp
        515                 520                 525

Val Asn Val Ile Ser Asp Leu Lys Lys Ile Glu Asp Leu Ile Gln Ser
    530                 535                 540

Met His Ile Asp Ala Thr Leu Tyr Thr Glu Ser Asp Val His Pro Ser
545                 550                 555                 560

Cys Lys Val Thr Ala Met Lys Cys Phe Leu Leu Glu Leu Gln Val Ile
```

```
                565                    570                    575
Ser Leu Glu Ser Gly Asp Ala Ser Ile His Asp Thr Val Glu Asn Leu
            580                    585                    590

Ile Ile Leu Ala Asn Asn Ser Leu Ser Ser Asn Gly Asn Val Thr Glu
        595                    600                    605

Ser Gly Cys Lys Glu Cys Glu Glu Leu Glu Glu Lys Asn Ile Lys Glu
    610                    615                    620

Phe Leu Gln Ser Phe Val His Ile Val Gln Met Phe Ile Asn Thr Ser
625                    630                    635                    640
```

<210> SEQ ID NO 73
<211> LENGTH: 1923
<212> TYPE: DNA
<213> ORGANISM: Artificial sequence
<220> FEATURE:
<223> OTHER INFORMATION: Synthetic

<400> SEQUENCE: 73

```
atgctgctgc tggtgaccag cctgctgctg tgcgagctgc cccaccccgc ctttctgctg      60
atccccgaca tccagatgac ccagaccacc tccagcctga gcgccagcct gggcgaccgg     120
gtgaccatca gctgccgggc cagccaggac atcagcaagt acctgaactg gtatcagcag     180
aagcccgacg gcaccgtcaa gctgctgatc taccacacca gccggctgca cagcggcgtg     240
cccagccggt ttagcggcag cggctccggc accgactaca gcctgaccat ctccaacctg     300
gaacaggaag atatcgccac ctacttttgc cagcagggca cacactgcc ctacaccttt     360 ggcggcggaa caaagctgga aatcaccggc agcacctccg gcagcggcaa gcctggcagc     420
ggcgagggca gcaccaaggg cgaggtgaag ctgcaggaaa gcggccctgg cctggtggcc     480
cccagccaga gcctgagcgt gacctgcacc gtgagcggcg tgagcctgcc cgactacggc     540
gtgagctgga tccggcagcc ccccaggaag ggcctggaat ggctgggcgt gatctggggc     600
agcgagacca cctactacaa cagcgccctg aagagccggc tgaccatcat caaggacaac     660
agcaagagcc aggtgttcct gaagatgaac agcctgcaga ccgacgacac cgccatctac     720
tactgcgcca gcactacta ctacggcggc agctacgcca tggactactg gggccagggc     780
accagcgtga ccgtgagcag cgaatctaag tacggaccgc cctgcccccc ttgccctccc     840
ttctttttct gcgtgtttat cgccgtggct atgggcatcc ggttcatcat catggtgacc     900
aaacggggca gaaagaaact cctgtatata ttcaaacaac catttatgag accagtacaa     960
actactcaag aggaagatgg ctgtagctgc cgatttccag aagaagaaga aggaggatgt    1020
gaactgaggg tgaagttcag cagaagcgcc gacgcccctg cctaccagca gggccagaat    1080
cagctgtaca cgagctgaa cctgggcaga agggaagagt acgacgtcct ggataagcgg    1140
agaggccggg accctgagat gggcggcaag cctcggcgga agaacccca ggaaggcctg    1200 tataacgaac tgcagaaaga caagatggcc gaggcctaca gcgagatcgg catgaagggc    1260
gagcggaggc ggggcaaggg ccacgacggc ctgtatcagg gcctgtccac cgccaccaag    1320
gatacctacg acgccctgca catgcaggcc ctgccccca ggctcgaggg cggcggagag    1380
ggcagaggaa gtcttctaac atgcggtgac gtggaggaga tcccggccc taggatgcgg    1440 atttccaaac tcacctgcg ctctatctct atccagtgct atctgtgcct gctgctgaac    1500
tcacatttcc tgaccgaagc cggcatccac gtgttcatcc tgggctgctt ttccgccggc    1560
ctgccaaaga ccgaggcaaa ctgggtgaat gtgatctctg acctgaagaa gatcgaggat    1620
ctgatccaga gcatgcacat cgacgccacc ctgtacacag agtccgatgt gcaccttct    1680
```

```
tgcaaggtga cagccatgaa gtgtttcctg ctggagctgc aggtcatcag cctggagagc      1740
ggcgacgcct ctatccacga taccgtggag aacctgatca tcctggccaa caatagcctg      1800
agcagcaacg gcaatgtgac agagtccggc tgcaaggagt gtgaggagct ggaggagaag      1860
aatatcaaag agttcctgca gtcattcgtc catatcgtcc agatgtttat caatacctcc      1920
taa                                                                    1923
```

```
<210> SEQ ID NO 74
<211> LENGTH: 718
<212> TYPE: PRT
<213> ORGANISM: Artificial sequence
<220> FEATURE:
<223> OTHER INFORMATION: Synthetic

<400> SEQUENCE: 74

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
                180                 185                 190

Glu Trp Leu Gly Val Ile Trp Gly Ser Glu Thr Thr Tyr Tyr Asn Ser
            195                 200                 205

Ala Leu Lys Ser Arg Leu Thr Ile Ile Lys Asp Asn Ser Lys Ser Gln
        210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Glu Ser Lys Tyr Gly
            260                 265                 270

Pro Pro Cys Pro Pro Cys Pro Pro Phe Phe Phe Cys Cys Phe Ile Ala
        275                 280                 285

Val Ala Met Gly Ile Arg Phe Ile Ile Met Val Thr Trp Arg Arg Lys
    290                 295                 300

Arg Lys Glu Lys Gln Ser Glu Thr Ser Pro Lys Glu Phe Leu Thr Ile
```

-continued

```
305                    310                    315                    320

Tyr Glu Asp Val Lys Asp Leu Lys Thr Arg Arg Asn His Glu Gln Glu
                325                    330                    335

Gln Thr Phe Pro Gly Gly Gly Ser Thr Ile Tyr Ser Met Ile Gln Ser
                340                    345                    350

Gln Ser Ser Ala Pro Thr Ser Gln Glu Pro Ala Tyr Thr Leu Tyr Ser
                355                    360                    365

Leu Ile Gln Pro Ser Arg Lys Ser Gly Ser Arg Lys Arg Asn His Ser
        370                    375                    380

Pro Ser Phe Asn Ser Thr Ile Tyr Glu Val Ile Gly Lys Ser Gln Pro
385                    390                    395                    400

Lys Ala Gln Asn Pro Ala Arg Leu Ser Arg Lys Glu Leu Glu Asn Phe
                405                    410                    415

Asp Val Tyr Ser Arg Val Lys Phe Ser Arg Ser Ala Asp Ala Pro Ala
                420                    425                    430

Tyr Gln Gln Gly Gln Asn Gln Leu Tyr Asn Glu Leu Asn Leu Gly Arg
                435                    440                    445

Arg Glu Glu Tyr Asp Val Leu Asp Lys Arg Arg Gly Arg Asp Pro Glu
        450                    455                    460

Met Gly Gly Lys Pro Arg Arg Lys Asn Pro Gln Glu Gly Leu Tyr Asn
465                    470                    475                    480

Glu Leu Gln Lys Asp Lys Met Ala Glu Ala Tyr Ser Glu Ile Gly Met
                485                    490                    495

Lys Gly Glu Arg Arg Arg Gly Lys Gly His Asp Gly Leu Tyr Gln Gly
                500                    505                    510

Leu Ser Thr Ala Thr Lys Asp Thr Tyr Asp Ala Leu His Met Gln Ala
                515                    520                    525

Leu Pro Pro Arg Leu Glu Gly Gly Gly Glu Gly Arg Gly Ser Leu Leu
        530                    535                    540

Thr Cys Gly Asp Val Glu Glu Asn Pro Gly Pro Arg Met Arg Ile Ser
545                    550                    555                    560

Lys Pro His Leu Arg Ser Ile Ser Ile Gln Cys Tyr Leu Cys Leu Leu
                565                    570                    575

Leu Asn Ser His Phe Leu Thr Glu Ala Gly Ile His Val Phe Ile Leu
                580                    585                    590

Gly Cys Phe Ser Ala Gly Leu Pro Lys Thr Glu Ala Asn Trp Val Asn
                595                    600                    605

Val Ile Ser Asp Leu Lys Lys Ile Glu Asp Leu Ile Gln Ser Met His
        610                    615                    620

Ile Asp Ala Thr Leu Tyr Thr Glu Ser Asp Val His Pro Ser Cys Lys
625                    630                    635                    640

Val Thr Ala Met Lys Cys Phe Leu Leu Glu Leu Gln Val Ile Ser Leu
                645                    650                    655

Glu Ser Gly Asp Ala Ser Ile His Asp Thr Val Glu Asn Leu Ile Ile
                660                    665                    670

Leu Ala Asn Asn Ser Leu Ser Ser Asn Gly Asn Val Thr Glu Ser Gly
        675                    680                    685

Cys Lys Glu Cys Glu Glu Leu Glu Glu Lys Asn Ile Lys Glu Phe Leu
        690                    695                    700

Gln Ser Phe Val His Ile Val Gln Met Phe Ile Asn Thr Ser
705                    710                    715
```

<210> SEQ ID NO 75

```
<211> LENGTH: 2157
<212> TYPE: DNA
<213> ORGANISM: Artificial sequence
<220> FEATURE:
<223> OTHER INFORMATION: Synthetic

<400> SEQUENCE: 75
atgctgctgc tggtgaccag cctgctgctg tgcgagctgc cccaccccgc ctttctgctg      60
atccccgaca tccagatgac ccagaccacc tccagcctga gcgccagcct gggcgaccgg     120
gtgaccatca gctgccgggc cagccaggac atcagcaagt acctgaactg gtatcagcag     180
aagcccgacg gcaccgtcaa gctgctgatc taccacacca gccggctgca cagcggcgtg     240
cccagccggt ttagcggcag cggctccggc accgactaca gcctgaccat ctccaacctg     300
gaacaggaag atatcgccac ctacttttgc cagcagggca cacactgcc ctacaccttt      360 ggcggcggaa caaagctgga aatcaccggc agcacctccg gcagcggcaa gcctggcagc     420
ggcgagggca gcaccaaggg cgaggtgaag ctgcaggaaa gcggccctgg cctggtggcc     480
cccagccaga gcctgagcgt gacctgcacc gtgagcggcg tgagcctgcc cgactacggc     540
gtgagctgga tccggcagcc ccccaggaag ggcctggaat ggctgggcgt gatctggggc     600
agcgagacca cctactacaa cagcgccctg aagagccggc tgaccatcat caaggacaac     660
agcaagagcc aggtgttcct gaagatgaac agcctgcaga ccgacgacac cgccatctac     720
tactgcgcca gcactacta ctacggcggc agctacgcca tggactactg gggccagggc      780
accagcgtga ccgtgagcag cgaatctaag tacggaccgc cctgcccccc ttgccctccc     840
ttctttttct gctgttttat cgccgtggct atgggcatcc ggttcatcat catggtgacc     900
tggaggagga gaggaagga gaagcagagc gagacaagcc ctaaggagtt tctgacaatc      960
tatgaagacg tgaaggacct gaagacacgg agaaaccacg agcaggagca gaccttccct    1020
ggaggaggca gcacaatcta ctccatgatc cagtctcaga gcagcgcccc cacctcccag    1080
gagcctgcct acacactgta tagcctgatc cagccatccc ggaagtctgg cagcaggaag    1140
cgcaaccact cccctctttt taattctacc atctatgaag tgatcggcaa gagccagccc    1200
aaggcacaga acccgcacg actgagcagg aaggaactgg agaactttga tgtctactct     1260
agggtgaagt tcagcagaag cgccgacgcc cctgcctacc agcagggcca gaatcagctg    1320
tacaacgagc tgaacctggg cagaaggaa gagtacgacg tcctggataa gcggagaggc     1380
cgggaccctg agatgggcgg caagcctcgg cggaagaacc cccaggaagg cctgtataac    1440
gaactgcaga agacaagat ggccgaggcc tacagcgaga tcggcatgaa gggcgagcgg     1500
aggcggggca agggccacga cggcctgtat cagggcctgt ccaccgccac caaggatacc    1560
tacgacgccc tgcacatgca ggccctgccc ccaaggctcg agggcggcgg agagggcaga    1620
ggaagtcttc taacatgcgg tgacgtggag gagaatcccg ccctaggat gcggatttcc      1680 aaacctcacc tgcgctctat ctctatccag tgctatctgt gcctgctgct gaactcacat    1740
ttcctgaccg aagccggcat ccacgtgttc atcctgggct gctttttccgc cggcctgcca    1800 aagaccgagg caaactgggt gaatgtgatc tctgacctga agaagatcga ggatctgatc    1860
cagagcatgc acatcgacgc caccctgtac acagagtccg atgtgcaccc ttcttgcaag    1920
gtgacagcca tgaagtgttt cctgctggag ctgcaggtca tcagcctgga gagcggcgac    1980
```

-continued

```
gcctctatcc acgataccgt ggagaacctg atcatcctgg ccaacaatag cctgagcagc    2040
aacggcaatg tgacagagtc cggctgcaag gagtgtgagg agctggagga gaagaatatc    2100
aaagagttcc tgcagtcatt cgtccatatc gtccagatgt ttatcaatac ctcctaa       2157
```